(12) United States Patent
Izumimoto et al.

(10) Patent No.: US 7,320,984 B2
(45) Date of Patent: Jan. 22, 2008

(54) REMEDIES OR PREVENTIVES FOR URINARY FREQUENCY OR URINARY INCONTINENCE AND MORPHINAN DERIVATIVES HAVING NITROGEN-CONTAINING HETEROCYCLIC GROUP

(75) Inventors: Naoki Izumimoto, Kamakura (JP); Koji Kawai, Oiso-machi (JP); Kuniaki Kawamura, Kamakura (JP); Morihiro Fujimura, Yokohama (JP); Toshikazu Komagata, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 10/530,664

(22) PCT Filed: Oct. 8, 2003

(86) PCT No.: PCT/JP03/12890

§ 371 (c)(1),
(2), (4) Date: Apr. 6, 2005

(87) PCT Pub. No.: WO2004/033457

PCT Pub. Date: Apr. 22, 2004

(65) Prior Publication Data

US 2006/0040970 A1    Feb. 23, 2006

(30) Foreign Application Priority Data

Oct. 9, 2002    (JP) ............................. 2002-295616

(51) Int. Cl.
*A61K 31/485* (2006.01)
*C07D 489/00* (2006.01)

(52) U.S. Cl. .......................... 514/282; 546/46; 546/44; 546/74; 544/56; 544/125; 544/361; 514/289; 514/254; 514/232.8; 514/228.2

(58) Field of Classification Search ................ 514/282, 514/289, 254, 232.8, 228.2; 546/46, 44, 546/74; 544/56, 125, 361
See application file for complete search history.

(56) References Cited

U.S. PATENT DOCUMENTS 3,318,885 A * 5/1967 Brown et al. ................ 544/125

FOREIGN PATENT DOCUMENTS

| EP | 0 846 694 A1 | 6/1998 |
|----|---|---|
| JP | 11-501627 A | 2/1999 |
| WO | WO 95/03308 | 2/1995 |
| WO | WO 01/05795 A | 1/2001 |
| WO | WO 02/080918 A | 10/2002 |

OTHER PUBLICATIONS

Simon, C. et al.: Stereoselective synthesis of beta-naltrexol, beta-naloxol, beta-naloxamine, beta-naltrexamine and related compounds. Tetrahedron, vol. 50, pp. 9757-9768, 1994.*

Csaba Simon et al, "Stereoselective Synthesis of β-Naltrexol, β-Naloxol, β-Naloxamine, β-Naltrexamine and Related Compounds by the Application of the Mitsunobu Reaction", *Tetrahedron*, vol. 50, No. 32, pp. 9757-9768, 1994.

László Szilágyi et al, "Substituent-Dependent Conformational Changes in 6 β-Substituted Codeine Derivatives", *Magnetic Resonance in Chemistry*, vol. 30, pp. 552-557 (1992).

Csaba Simon et al, "Mitsunobu Reaction for Morphine Compounds. Preparation of 6β-Aminomorphine and Codeine Derivatives", *Synthetic Communications*, vol. 22, No. 6, pp. 913-921 (1992).

L. M. Sayre, et al, "Design and Synthesis of Naltrexone-Derived Affinity Labels with Nonequilibrium Opioid Agonist and Antagonist Activities. Evidence for the Existence of Different μ Receptor Subtypes in Different Tissues", *Journal of Medicinal Chemistry*. vol. 27, No. 10, pp. 1325-1335 (1984).

Issei Iwai, "14-Hydroxy-6.alpha.-aminodihydrocorsides", retrieved from STN, Abstract and JP 41 018826 B4 (Sankyo Co., Ltd.) (Oct. 31, 1964).

Issei Iwai, "6-Aminodihydromorphides", retrieved from STN, Abstract and JP 41 018824 B4 (Sankyo Co., Ltd) (Oct. 31, 1964).

(Continued)

*Primary Examiner*—Charanjit S. Aulakh
(74) *Attorney, Agent, or Firm*—DLA Piper US LLP

(57) ABSTRACT

The invention provides a morphinan derivative of the Formula (I):

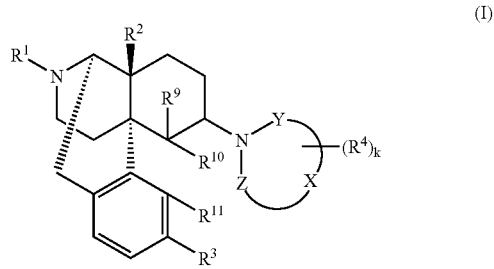

wherein $R^1$ is methyl, cyclopropylmethyl or the like; $R^2$ and $R^3$ are hydroxy, methoxy, acetoxy or the like; both Y and Z are valence bonds, —C(=O)— or the like; X is $C_2$-$C_5$ carbon chain (one of the carbon atoms may be substituted by oxygen, sulfur or nitrogen) constituting a part of the ring structure, or the like; $(R^4)k$ is substituted or non-substituted benzene fused ring, carbonyl group or the like; $R^9$ is hydrogen or the like; $R^{10}$ and $R^{11}$ are bound to represent —O—, or the like, and $R^6$ is hydrogen or the like or a pharmaceutically acceptable acid addition salt thereof. The invention also provides a therapeutic or prophylactic agent for urinary frequency or urinary incontinence, comprising as an effective ingredient the morphinan derivative or the pharmaceutically acceptable acid addition salt thereof; a method for therapy or prophylaxis of the diseases.

14 Claims, No Drawings

OTHER PUBLICATIONS

Isao Seki, "Morpholine alkaloids. IX. Aminomorphide compounds. 1. The formation of enamines and the additionof amine to .alpha., .beta.-unsaturated ketones", retrieved from STN, Abstract and Yagugaku Zasshi, 84(7), 621-5 (1964).

Isao Seki, "Morpholine alkaloids. X. Aminomorpholide compounds. 2. The reduction of enamines and the catalytic reductive amination of C-6 ketones", retrieved from STN, Abstract and Yagugaku Zasshi, 84(7), 626-31 (1964).

Isao Seki, "Morpholine alkaloids. XI. Aminomorphde compounds. 3. The steric aspects of the amino group", retrieved from STN, Abstract and Yagugaku Zasshi, 84(7) (1964).

A. G. Hayes et al, "Evaluation of the Receptor Selectivities of Opioid Drugs by Investigating the Block of Their Effect on Urine Output by β-Funaltrexamine", *Journal of Pharmacology and Experimental Therapeutics*, vol. 240, No. 3, pp. 984-988 (1987).

A Dray et al., "Morphine and the Centrally-Mediated Inhibition of Urinary Bladder Motility in the Rat", *Brain Research*. vol. 297, No. 1, pp. 191-195 (1984)).

A. Dray et al., "Opioids and Central Inhibition of Urinary Bladder Motility", *European Journal of Pharmacology*, vol. 98, No. 1, pp. 155-156 (1984)).

* cited by examiner

REMEDIES OR PREVENTIVES FOR URINARY FREQUENCY OR URINARY INCONTINENCE AND MORPHINAN DERIVATIVES HAVING NITROGEN-CONTAINING HETEROCYCLIC GROUP

TECHNICAL FIELD

This disclosure relates to a therapeutic or prophylactic agent for urinary frequency or urinary incontinence, and to a morphinan derivative having a nitrogen-containing hetrocyclic group or a pharmaceutically acceptable acid addition salt thereof.

BACKGROUND

Recently, with coming of an aging society, the number of patients suffering from urinary frequency or urinary incontinence is increasing year by year. At present, as therapeutic drugs for urinary frequency or urinary incontinence, anticholinergic drugs such as propiverine hydrochloride, oxybutynin hydrochloride and flavoxate hydrochloride are used. However, it has been reported that these existing drugs have side effects, that is, dry mouth, gastrointestinal system symptoms such as constipation, cardiovascular symptoms such as orthostatic hypotension, urinary retention and residual urine. In addition, it is concerned that by administering the existing drugs having anticholinergic activities for the therapy of urinary frequency or urinary incontinence accompanied by cerebrovascular dysfunction or dementia, cholinergic system activity in the brain is inhibited, so that the cerebrovascular dysfunction or dementiaper se progress. On the other hand, from the view point of improving quality of life (QOL) of patients, which is recently regarded as important, urinary frequency and urinary incontinence are attracting attention as symptoms which should be positively cured. Thus, development of a therapeutic or prophylactic agent for urinary frequency or urinary incontinence without side effects is strongly demanded.

Morphinan derivatives having a nitrogen-containing heterocyclic group are described in Japanese Patent Publication Nos. 41-18824 and 41-18826 together with their uses as analgesics and antitussives, and in Tetrahedron. 50, 9757 (1994), Synth. Commun. 22, 913 (1992), J. Med. Chem. 27, 1325 (1984) which is silent about their uses. These patents and reference are silent about the use as a therapeutic or prophylactic agent for urinary frequency or urinary incontinence. Although it is known that morphine which is similar to the compounds of the present invention in the respect that it has morphinan structure although it does not contain a nitrogen-containing heterocyclic group has an activity to inhibit micturition reflex (J. Pharm. Exp. Ther. 254(1984) etc.), it has strong side effects such as drug dependence, constipation and so on, so that it is not used as a therapeutic or prophylactic agent for urinary frequency or urinary incontinence.

SUMMARY

We provide a novel therapeutic or prophylactic agent for urinary frequency or urinary incontinence, which has a high therapeutic or prophylactic effect and of which side effects are improved, as well as to provide a method for therapy or prophylaxis of the disease, use for the disease, and a novel compound useful for therapy or prophylaxis of the disease.

We provide a therapeutic or prophylactic agent for urinary frequency or urinary incontinence, comprising as an effective ingredient a morphinan derivative having a nitrogen-containing heterocyclic group of the Formula (I):

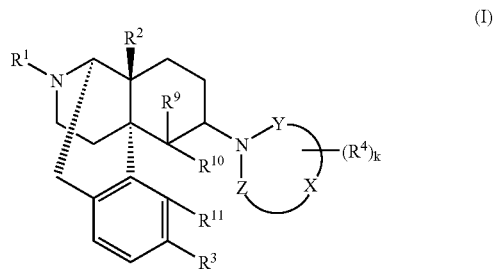

[wherein $R^1$ is hydrogen, $C_1$-$C_5$ alkyl, $C_4$-$C_7$ cycloalkenylalkyl, $C_6$-$C_8$ cycloallcenylalkyl, $C_6$-$C_{12}$ $C_7$-$C_{13}$ aralkyl, $C_3$-$C_7$ alkenyl, furanylalkyl (wherein the number of carbon atoms in the alkyl moiety is 1 to 5), thienylalkyl (wherein the number of carbon atoms in the alkyl moiety is 1 to 5) or pyndylalkyl (wherein the number of carbon atoms in the alkyl moiety is 1 to 5), $R^2$ and $R^3$ independently are hyrdrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy; Y and Z independently represent valence bond or —C(=O)—; —X— represents a C2-C7 carbon chain (one or more of the carbon atoms therein may be replaced by nitrogen, oxygen or sulfur atom(s), and the carbon chain may contain an unsaturated bond) constituting a part of the ring structure, k is an integer of 0 to 8; $R^4$ is(are) (a) substituent(s) in the number of k on the nitrogen-containing ring, which independently represent(s) fluorine, chlorine, bromine, iodine, nitro, hydroxy, $C_1$-$C_5$ alkyl, $C_7$-$C_{13}$ cycloalkylalkyl, $C_6$-$C_{12}$ aryl, $C_7$-$C_{13}$ aralkyl, $C_7$-$C_{13}$ aralkyloxy, $C_1$-$C_5$ alkoxy, trifluoromethyl, trifluoromethoxy, cyano, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$, or among the $R^4$s in the number of k, two $R^4$s bound to the same carbon atom or to the same sulfur atom cooperatively represent one oxygen atom to form carbonyl or sulfoxide, or two $R^4$s bound to the same carbon atom cooperatively represent one sulfur atom to form thiocarbonyl, or four $R^4$s bound to the same sulfur atom cooperatively represent two oxygen atoms to form sulfone, or among the $R^4$s in the number of k, two $R^4$s bound to adjacent carbon atoms, respectively, cooperatively form beuzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of said fused rings is non-substituted or substituted by 1 or more $R^5$s, wherein $R^5$(s) independently represent(s) fluorine chlorine, bromine, iodine, nitro, hydroxy, $C_1$-$C_5$ alkyl, $C_1$-$C_5$ alkoxy, trifluoromethyl, trifluoromethoxy, cyano, $C_6$-$C_{12}$ aryl, isothiocyanato, $SR^6$, $SOR^6$, $SO_2R^6$, $(CH_2)_pOR_6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$; $R^9$ is hydrogen, $C_1$-$C_5$ alkyl, $C_1$-$C_5$ alkenyl, $C_7$-C13 aralkyl, $C_1$-$C_3$ hydroxyalkyl, $(CH_2)_pOR^6$ or $(CH_2)_pCO_2R^6$; $R^{10}$ and $R^{11}$ are bound to form —O—, —S— or —CH_2—, or $R^{10}$ is hydrogen and $R^{11}$ is hydrogen, hydroxy, $C_1$-$C_5$ alkoxy or C1-C5 alkanoyloxy; p is an integer of 0 to 5; $R^6$ is hydrogen, $C_1$-$C_5$ alkyl, $C_3$-$C_7$ alkenyl, $C_6$-$C_{12}$ aryl or $C_7$-$C_{13}$ aralkyl; and $R^7$ and $R^8$ independently are hydrogen, $C_1$-$C_5$ alkyl or $C_7$-$C_{13}$ aralkyl]

or a pharmaceutically acceptable acid addition salt thereof, as well as a method for therapy or prophylaxis of the diseases, and uses thereof for the diseases.

In the present specification, substituent groups are interpreted as follows: The alkyl moieties of alkyl, alkoxy, cycloalkylalkyl, aralkyl and aralkyloxy contain straight or branched chain, may be substituted by hydroxy, and may contain unsaturated bonds. The aromatic moieties of aryl, aralkyl, aralkyloxy, furanylalkyl, thienylalkyl and pyridylalkyl may be substituted by at least one substituent group selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy.

We also provide a morphinan derivative having a nitrogen-containing heterocyclic group of the Formula (II):

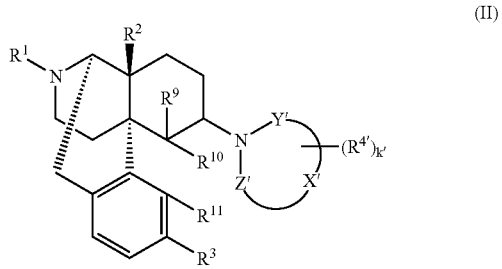

(II)

[wherein $R^1$, $R^2$, $R^3$, $R^9$, $R^{10}$ and $R^{11}$ represent the same meanings as described above, $R^{4'}$, X', Y', Z' and k' represent the same meanings as said $R^4$, X, Y, Z and k within the proviso that in cases where Y' and Z' are simultaneously valence bonds and X' is —(CH$_2$)$_4$—, —(CH$_2$)$_5$— or —(CH$_2$)$_2$—O—(CH$_2$)$_2$—, k' must be not less than 1, in cases where Y' and Z' are simultaneously —C(=O)— and X' is a chain comprising two carbon atoms constituting the ring structure, k' must be not less than 1, and in particular, in cases where (R$^{4'}$)k' is a benzene fused ring, the benzene ring must be substituted by the $R^{5'}$]

or a pharmaceutically acceptable acid addition salt thereof, as well as a pharmaceutical or pharmaceutical composition containing the compound.

DETAILED DESCRIPTION

The compounds represented by Formula (I) are preferably used. Among the compounds of Formula (I), those having the following substituent groups are preferred. In the present specification, "therapeutic or prophylactic agent" includes not only those which are used for one of therapy and prophylaxis, but also those aiming at attaining both therapy and prophylaxis simultaneously.

As for Y and Z, it is preferred that both Y and Z are —C(=O)— or both Y and Z are valence bonds.

In cases where both Y and Z are —C(=O)—, $R^1$ is preferably hydrogen, $C_4$-$C_7$ cycloalkylalkyl, $C_6$-$C_8$ cycloalkenylalkyl, $C_6$-$C_{12}$ aryl or $C_3$-$C_7$ alkenyl, more preferably hydrogen, cyclopropylmethyl, 2-cyclopropylethyl, 3-cyclopropylpropyl, 4-cyclopropylbutyl, cyclobutylmethyl, cyclopentylmethyl, cyclohexylmethyl, 2-cyclobutenylethyl, 3-cyclobutenylpropyl, phenyl, naphthyl, tolyl, allyl or prenyl. Among these, especially preferred are hydrogen, cyclopropylmethyl, cyclobutylmethyl, cyclopentylmethyl, cyclohexylmethyl, allyl and prenyl. $R^2$ is preferably hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy. Among these, hydroxy, methoxy, ethoxy, allyloxy, benzyloxy, acetoxy and propionoxy are preferred, and hydrogen, hydroxy, methoxy and acetoxy are especially preferred. $R^3$ is preferably hydrogen, hydroxy, $C_1$-$C_5$ alkoxy, $C_7$-$C_{13}$ aralkyloxy or $C_1$-$C_5$ alkanoyloxy, more preferably, hydrogen, hydroxy, methoxy, ethoxy, benzyloxy, acetoxy or propionoxy. Among these, hydrogen, hydroxy, methoxy and acetoxy are especially preferred. The "—X—" is preferably $C_2$-$C_4$ carbon chain constituting a part of the ring structure, more preferably a carbon chain having two carbon atoms constituting a part of the ring structure. The "k" is preferably an integer of 0 to 6. $R^4$ is preferably $C_1$-$C_5$ alkyl, $C_7$-$C_{13}$ aralkyl, $C_7$-$C_{13}$ aralkyloxy, or two $R^4$s bound to adjacent carbon atoms, respectively, cooperatively form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of the fused rings is non-substituted or substituted by 1 or more $R^5$s. More preferably, $R^4$ is methyl, ethyl, ethylidene, propyl, propylidene, butyl, butylidene, benzyl, benzylidene, methylbenzyl, methylbenzylidene, fluorobenzyl, fluorobenzylidene, trifluoromethoxybenzyl, trifluoromethoxybenzylidene, phenethyl, phenethylidene, cyclohexylmethyl, cyclohexylmethylidene, phenoxy, chlorophenoxy or to form benzene fused ring. Especially preferably, two $R^4$s bound to adjacent carbon atoms, respectively, cooperatively form benzene fused ring substituted by 1 or more, preferably 1 to 4 $R^5$s. Although the benzene fused ring which is not substituted is also preferred, the substituent(s) $R^5$(s) is(are) preferably and independently fluorine, chlorine, bromine, iodine, nitro, $C_1$-$C_5$ alkyl (especially methyl, ethyl or propyl), $C_7$-$C_{13}$ aralkyl (especially benzyl), hydroxy, $C_1$-$C_5$ alkoxy (especially methoxy or ethoxy), trifluoromethyl, trifluoromethoxy, cyano, phenyl, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH^2)_pN(R^7)COR^8$ (wherein p is an integer of 0 to 5; $R^6$ is hydrogen, $C_1$-$C_5$ alkyl (especially methyl, ethyl or propyl), $C_3$-$C_7$ alkenyl or $C_6$-$C_{12}$ aryl (especially phenyl); $R^7$ and $R^8$ independently are hydrogen, $C_1$-$C_5$ alkyl (especially methyl, ethyl or propyl), or $C_7$-$C_{13}$ aralkyl (especially benzyl)). The benzene fused ring is more preferably non-substituted, or substituted by one or more substituents selected from the group consisting of fluorine, chlorine, bromine, iodine, nitro, methyl, ethyl, propyl, benzyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, acetoxy, phenyloxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl and amino. $R^9$ is preferably hydrogen, $C_1$-$C_5$ alkyl, allyl or benzyl, more preferably hydrogen or methyl. $R^{10}$ and $R^{11}$ are preferably bound to form —O—, or $R^{10}$ is preferably hydrogen and $R^{11}$ is preferably hydrogen, hydroxy or methoxy. Especially preferably, $R^{10}$ and $R^{11}$ are bound to form —O—.

On the other hand, in cases where both Y and Z are valence bonds, $R^1$ is preferably hydrogen, $C_1$-$C_5$ aralkyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5), more preferably hydrogen, methyl, ethyl, propyl, benzyl, phenethyl, phenylpropyl, 2- or 3-furanylmethyl, 2- or 3-furanylethel, 2- or 3-furanylpropyl, 2- or 3-thiophenyl-methyl, 2- or 3-thiophenylethyl, 2- or 3-thiophenylpropyl, 2-, 3- or 4-pyridinylmethyl, 2-, 3- or 4-pyridinylethyl, or 2-, 3- or 4-pyridinylpropyl. Among these, hydrogen, methyl, phenethyl, furanylethyl, thiophenylethyl and pyridinylethyl are especially preferred. $R^2$ is preferably hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy. Among these, hydrogen, hydroxy, methoxy, ethoxy, allyloxy, benzyloxy, acetoxy and propionoxy are preferred, and hydrogen, hydroxy, methoxy and acetoxy are preferred. $R^3$ is preferably hydrogen, hydroxy, $C_{1-5}$ alkoxy, $C_7$-$C_{13}$ aralkyloxy or C1-C5 alkanoyloxy, more preferably, hydrogen, hydroxy, methoxy, ethoxy, benzyloxy, acetoxy or propionoxy. Among these, hydrogen hydroxy, methoxy and acetoxy are especially preferred. The "—X—" is preferably $C_4$-$C_6$ carbon chain constituting a part of the ring structure, or the above-mentioned carbon chain in which one or two carbon atoms is (are) replaced by oxygen, sulfur or nitrogen atom(s). Among these, especially preferred are carbon chain having 5 carbon atoms constituting a part of the ring structure and the carbon chain just mentioned above in which one carbon atom is replaced by oxygen, sulfur or nitrogen atom. The "k" is preferably an integer of 0 to 6. $R^4$ is preferably $CONR^7R^8$ (wherein $R^7$ and $R^8$ are independently hydrogen, methyl, ethyl, propyl or benzyl), or two $R^4$s preferably bound to adjacent carbon atoms, respectively, cooperatively form benzene fused ring, pyridine fused ring, naphthalene fused ring, cyclopropane fused ring, cyclobutane fused ring, cyclopentane fused ring, cyclopentene fused rign, cyclohexane fused ring, cyclohexene fused ring, cycloheptane fused ring or cycloheptene fused ring, each of the fused rings is non-substituted or substituted by 1 or more, especially 1 to 4 $R^5$s. $R^4$ is more preferably dimethylamide or diethylamide, or to form the benzene fused ring. Other $R^4$(s) is (are) preferably and independently methyl, ethyl, propyl or benzyl, or two $R^4$s bound to the same carbon atom preferably represent one oxygen atom to form carbonyl. Especially preferably, the carbon atom adjacent to the above-mentioned carbonyl group is replaced by nitrogen atom to form amide bond. Although the benzene fused ring which is not substituted is also preferred, the substituent(s) $R^5$(s) is (are) preferably and independently fluorine, chlorine, bromine, iodine, nitro, $C_1$-$C_5$ alkyl (especially methyl, ethyl or propyl), $C_7$-$C_{13}$ aralkyl (especially benzyl), hydroxy, $C_1$-$C_5$ alkoxy (especially methoxy or ethoxy), trifluoromethyl, trifluoromethoxy, cyano, phenyl, isothiocyanato, $SR^6$, $SOR^6$, $SO^2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$ (wherein p is an integer of 0 to 5; $R^6$ is hydrogen, $C_1$-$C_5$ alkyl (especially methyl, ethyl or propyl), $C_3$-$C_7$ alkenyl or $C_6$-$C_{12}$ aryl (especially phenyl); $R^7$ and $R^8$ independently are hydrogen, $C_1$-$C_5$ alkyl (especially methyl, ethyl or propyl), or $C_7$-$C_{13}$ aralkyl (especially benzyl)). The benzene fused ring is more preferably non-substituted, or substituted by one or more substituents selected from the group consisting of fluorine, chlorine, bromine, iodine, nitro, methyl, ethyl, propyl, benzyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, acetoxy, phenyloxy, methoxycarbonyl, ethoxycarbonyl, methoxycarbonylmethyl, ethoxycarbonyl-methyl, sulfamoyl, dimethylsulfamoyl, dimethylcarbamoyl, dimethylamino, dimethylaminomehtyl, dimethylaminoethyl and amino. $R^9$ preferably hydrogen, $C_1$-$C_5$ alkyl, allyl or benzyl, more preferably hydrogen or methyl, $R^{10}$ $R^{11}$ are preferably bound to form —O—, or $R^{10}$ is preferably hydrogen and $R^{11}$ is preferably hydrogen, hydroxy or methoxy. Especially preferably, R10 and R11 are bound to form —O—.

We also provide the morphinan derivatives having a nitrogen-containing heterocyclic group represented by the above-described Formula (II) and pharmaceutically acid addition salts thereof.

As for Y' and Z', it is preferred that both Y' and Z' are —C(═O)— or both Y' and Z' are valence bonds.

In cases where both Y' and Z' are —C(═O)—, $R^1$ is preferably hydrogen, $C_4$-$C_7$ cycloalkylalkyl, $C_6$-$C_8$ cycloalkenylalkyl, $C_6$-$C_{12}$ aryl or $C_3$-$C_7$ alkenyl, more preferably hydrogen, cyclopropylmethyl, 2-cyclopropylethyl, 3-cyclopropylpropyl, 4-cyclopropylbutyl, cyclobutylmethyl, cyclopentylmethyl, cyclohexylmethyl, 2-cyclobutenylethyl, 3-cyclobutenylpropyl, phenyl, naphthyl, tolyl, allyl or prenyl. Among these, especially preferred are hydrogen, cyclopropylmethyl, cyclobutylmethyl, cyclopentylmethyl, cyclohexylmethyl, allyl and prenyl. $R^2$ is preferably hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy. Among these, hydroxy, methoxy, ethoxy, allyloxy, benzyloxy and acetoxy are preferred, and hydrogen, hydroxy, methoxy and acetoxy are especially preferred. $R^3$ is preferably hydrogen, hydroxy, $C_1$-$C_5$ alkoxy, $C_7$-$C_{13}$ aralkyloxy or $C_1$-$C_5$ alkanoyloxy, more preferably, hydrogen, hydroxy, methoxy, ethoxy, benzyloxy, acetoxy or propionoxy. Among these, hydrogen, hydroxy, methoxy and acetoxy are especially preferred. The k' is preferably an integer of 0 to 6. The "—X'—" is preferably $C_2$-$C_4$ carbon chain constituting a part of the ring structure, more preferably a carbon chain having two carbon atoms constituting a part of the ring structure. $R^{4'}$ is preferably $C_1$-$C_5$ alkyl, $C_7$-$C_{13}$ aralkyl, $C_7$-$C_{13}$ aralkyloxy, or two $R^4$s bound to adjacent carbon atoms, respectively, cooperatively form benzene fused ring, pyridine fused ring, naphthalene fused ring, cyclopropane fused ring, cyclobutane fused ring, cyclopentane fused ring, cyclopentene fused ring, cyclohexane condensed ring, cyclohexene condensed ring, cycloheptane fused ring or cycloheptene fused ring, each of the fused rings is non-substituted or substituted by 1 or more, especially 1 to 4 $R^5$s. More preferably, $R^{4'}$ is ethyl, ethylidene, propyl, propylidene, butyl, butylidene, benzyl, benzylidene, methylbenzyl, methylbenzylidene, fluorobenzyl, fluorobenzylidene, trifluoromethoxybenzyl, trifluoromethoxybenzylidene, phenethyl, phenethylidene, cyclohexylmethyl, cyclohexylmethylidene, phenoxy, chlorophenoxy or to form benzene fused ring. Especially preferably, two $R^4$s bound to adjacent carbon atoms, respectively, cooperatively form benzene fused ring. Although the benzene fused ring which is not substituted is also preferred, the substituent(s) $R^5$(s) is(are) preferably and independently fluorine, chlorine, bromine, iodine, nitro, $C_1$-$C_5$ alkyl (especially methyl, ethyl or propyl), $C_7$-$C_{13}$ aralkyl (especially benzyl), hydroxy, $C_1$-$C_5$ alkoxy (especially methoxy or ethoxy), trifluoromethyl, trifluoromethoxy, cyano, phenyl, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$ (wherein p is an integer of 0 to 5; $R^6$ is hydrogen, $C_1$-$C_5$ alkyl (especially methyl, ethyl or propyl), $C_3$-$C_7$ alkenyl or $C_6$-$C_{12}$ aryl (especially phenyl); $R^7$ and $R^8$ independently are hydrogen, $C_1$-$C_5$ alkyl (especially methyl, ethyl or propyl), or $C_7$-$C_{13}$ aralkyl (especially benzyl)). The benzene fused ring is more preferably non-substituted, or substituted by one or more substituents selected from the group consisting of fluorine, chlorine, bromine, iodine, nitro, methyl, ethyl, propyl, benzyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, acetoxy, phenyloxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl and amino. $R^9$ is preferably hydrogen, $C_1$-$C_5$ alkyl, allyl or benzyl, more preferably hydrogen or methyl. $R^{10}$ and $R^{11}$ are preferably bound to form —O—, or $R^{10}$ is preferably hydrogen and $R^{11}$ is preferably hydrogen, hydroxy or methoxy. Especially preferably, $R^{10}$ and $R^{11}$ are bound to form —O—.

On the other hand, in cases where both Y' and Z'0 are valence bonds, $R^1$ is preferably hydrogen $C_1$-$C_5$ alkyl, $C_7$-$C_{13}$ aralkyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5), more preferably hydrogen, methyl, ethyl, propyl, benzyl, phenethyl, phenylpropyl, 2- or 3-furanylniethyl, 2- or 3- furanylethyl, 2- or 3-furanylpropyl, 2- or 3-thiophenylmethyl, 2- or 3-thiophenylethyl, 2- or 3-thiophenylpropyl, 2-, 3- or 4-pyridinylmethyl, 2-, 3- or 4-pyridinylethyl, or 2-, 3- or 4-pyridinyipropyl. Among these, hydrogen, methyl, phenethyl, furanylethyl, thiophenylethyl and pyridinylethyl are especially preferred. $R^2$ is preferably hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy. Among these, hydrogen, hydroxy, methoxy, ethoxy, allyloxy, benzyloxy, acetoxy and propionoxy are preferred, and hydrogen, hydroxy, methoxy and acetoxy are preferred. $R^3$ is preferably hydrogen, hydroxy, $C_1$-$C_5$ alkoxy, $C_7$-$C_{13}$ aralkyloxy or $C_1$-$C_5$ alkanoyloxy, more preferably, hydrogen, hydroxy, methoxy, ethoxy, benzyloxy, acetoxy or propionoxy. Among these, hydrogen, hydroxy, methoxy and acetoxy are especially preferred. The "—X'—" is preferably $C_4$-$C_6$ carbon chain constituting a part of the ring structure, or the above-mentioned carbon chain in which one or two carbon atoms is(are) replaced by oxygen, sulfur or nitrogen atom(s). Among these, especially preferred are carbon chain having 5 carbon atoms constituting a part of the ring structure and the carbon chain just mentioned above in which one carbon atom is replaced by oxygen, sulfur or nitrogen atom. The k' is preferably an integer of 0 to 6. $R^{4'}$ is preferably $CONR^7R^8$ (wherein $R^7$ and $R^8$ are independently hydrogen, methyl, ethyl, propyl, or benzyl), or two $R^4$s preferably bound to adjacent carbon atoms, respectively, cooperatively form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of the fused rings is non-substituted or substituted by 1 or more, especially 1 to 4 $R^5$s. $R^{4'}$ is more preferably dimethylamide or diethylamide, or to form the benzene fused ring. Other $R^{4'}$(s) is(are) preferably and independently methyl, ethyl, propyl or benzyl, or two $R^4$s bound to the same carbon atom preferably represent one oxygen atom to form carbonyl. Especially preferably, the carbon atom adjacent to the above-mentioned carbonyl group is replaced by nitrogen atom to form amide bond. Although the benzene fused ring which is not substituted is also preferred, the substituent(s) $R^5$(s) is(are) preferably and independently fluorine, chlorine, bromine, iodine, nitro, $C_1$-$C_5$ alkyl (especially methyl, ethyl or propyl), $C_7$-$C_{13}$ aralkyl (especially benzyl), hydroxy, $C_1$-$C_5$ alkoxy (especially methoxy or ethoxy), trifluoromethyl, trifluoromethoxy, cyano, phenyl, isothiocyanato, $SR^6$, $SOR^6$, $SO^2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$ (wherein p is an integer of 0 to 5; $R^6$ is hydrogen, $C_1$-$C_5$ alkyl (especially methyl, ethyl orpropyl), $C_3$-$C_7$ alkenyl or $C_6$-$C_{12}$ aryl (especiallyphenyl); $R^7$ and $R^8$ independently are hydrogen, $C_1$-$C_5$ alkyl (especially methyl, ethyl or propyl), or $C_7$-$C_{13}$ aralkyl (especially benzyl)). The benzene fused ring is more preferably non-substituted, or substituted by one or more substituents selected from the group consisting of fluorine, chlorine, bromine, iodine, nitro, methyl, ethyl, propyl, benzyl, hydroxy, methoxy, trifluoromethyl, trifluoromethoxy, cyano, phenyl, hydroxymethyl, hydroxyethyl, isothiocyanato, mercapto, methylthio, methylsulfinyl, methylsulfonyl, methoxymethyl, ethoxymethyl, methoxyethyl, acetoxy, phenyloxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylcaminoethyl and amino. $R^9$ is preferably hydrogen, $C_1$-$C_5$ alkyl, allyl or benzyl, more preferably hydrogen or methyl. $R^{10}$ and $R^{11}$ are preferably bound to form —O—, or $R^{10}$ is preferably hydrogen and $R^{11}$ is preferably hydrogen, hydroxy or methoxy. Especially preferably $R^{10}$ and $R^{11}$ are bound to form —O—.

Among the compounds represented by Formula (II), in cases where Y' and Z' are simultaneously valence bonds and X' is —(CH$_2$)$_4$—, —(CH$_2$)$_5$— or —(CH$_2$)$_2$—O—(CH$_2$)$_2$—, k' must be not less than 1; in cases where Y' and Z' are simultaneously —C(=O)— and X' is a chain comprising two carbon atoms constituting the ring structure, k' must be not less than 1; and in particular, in cases where $(R^{4'})k'$ is a benzene fused ring, the benzene ring must be substituted by the $R^5$.

However, this disclosure is not restricted to those described above.

Preferred examples of the pharmaceutically acceptable acid addition salts include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt and the like are preferred, but the acid addition salt is not restricted thereto.

Among the compounds of the Formula (I), specific examples of those wherein —X— is a carbon chain having two carbon atoms constituting a part of the ring structure; Y and Z are —C(=O)—; two R4s form benzene fused ring which is not substituted or substituted by one or more R5s; r9 is hydrogen; R10 and R11 are bound to represent —O—, that is, those represented by the Formula (Ia) below are shown in Table 1. In the tables described below, CPM means cyclopropylmethyl, and the bond at 6-position is α or β.

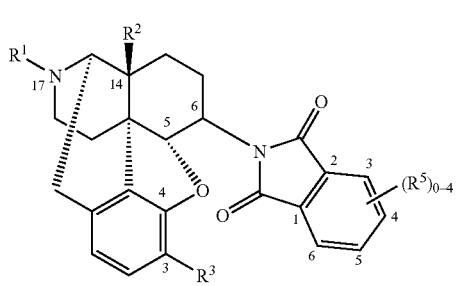

(Ia)

Among the compounds represented by Formula (Ia), the compound wherein $R^1$ is cyclopropylmethyl, $R^2$ and $R^3$ are hydroxy, $R^5$ is 4-fluoro, and the configuration of the bond at the 6-position is β, that is, Compound 16 of the following formula is named N-[17-(cyclopropylmethyl)-4,5α-epoxy-3,14-dihydroxymorphinan-6β-yl]-4-fluorophthalimide.

TABLE 1

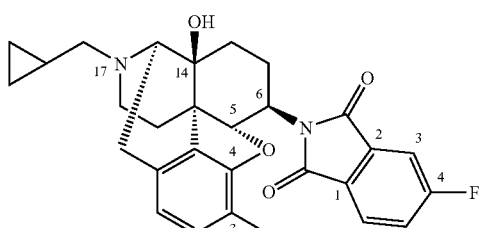

16

| $R^1$ | $R^2$ | $R^3$ | $R^5$ |
|---|---|---|---|
| CPM | OH | OH | (non-substituted) |
| CPM | OH | OH | 3-F |
| CPM | OH | OH | 4-F |
| CPM | OH | OH | 3,6-F |
| CPM | OH | OH | 4,5-F |
| CPM | OH | OH | 3,4,5,6-F |
| CPM | OH | OH | 3-Cl |
| CPM | OH | OH | 4-Cl |
| CPM | OH | OH | 3,6-Cl |
| CPM | OH | OH | 4,5-Cl |
| CPM | OH | OH | 3-Br |
| CPM | OH | OH | 4-Br |
| CPM | OH | OH | 3,6-Br |
| CPM | OH | OH | 4,5-Br |
| CPM | OH | OH | 3-Me |
| CPM | OH | OH | 4-Me |
| CPM | OH | OH | 3,6-Me |
| CPM | OH | OH | 4,5-Me |
| CPM | OH | OH | 3-OMe |
| CPM | OH | OH | 4-OMe |
| CPM | OH | OH | 3,6-OMe |
| CPM | OH | OH | 4,5-OMe |
| CPM | OH | OH | 3-OH |
| CPM | OH | OH | 4-OH |
| CPM | OH | OH | 3,6-OH |
| CPM | OH | OH | 4,5-OH |
| CPM | OH | OH | 3-NO$_2$ |
| CPM | OH | OH | 4-NO$_2$ |
| CPM | OH | OH | 3,6-NO$_2$ |
| CPM | OH | OH | 4,5-NO$_2$ |
| CPM | OH | OH | 3-NH$_2$ |
| CPM | OH | OH | 4-NH$_2$ |
| CPM | OH | OH | 3,6-NH$_2$ |
| CPM | OH | OH | 4,5-NH$_2$ |
| Allyl | OH | OH | (non-substituted) |
| Allyl | OH | OH | 3-F |
| Allyl | OH | OH | 4-F |
| Allyl | OH | OH | 3,6-F |
| Allyl | OH | OH | 4,5-F |
| Allyl | OH | OH | 3,4,5,6-F |
| Allyl | OH | OH | 3-Cl |
| Allyl | OH | OH | 4-Cl |
| Allyl | OH | OH | 3,6-Cl |
| Allyl | OH | OH | 4,5-Cl |
| Allyl | OH | OH | 3-Br |
| Allyl | OH | OH | 4-Br |
| Allyl | OH | OH | 3,6-Br |
| Allyl | OH | OH | 4,5-Br |
| Allyl | OH | OH | 3-Me |
| Allyl | OH | OH | 4-Me |
| Allyl | OH | OH | 3,6-Me |
| Allyl | OH | OH | 4,5-Me |
| Allyl | OH | OH | 3-OMe |
| Allyl | OH | OH | 4-OMe |
| Allyl | OH | OH | 3,6-OMe |
| Allyl | OH | OH | 4,5-OMe |
| Allyl | OH | OH | 3-OH |
| Allyl | OH | OH | 4-OH |
| Allyl | OH | OH | 3,6-OH |
| Allyl | OH | OH | 4,5-OH |
| Allyl | OH | OH | 3-NO$_2$ |
| Allyl | OH | OH | 4-NO$_2$ |
| Allyl | OH | OH | 3,6-NO$_2$ |
| Allyl | OH | OH | 4,5-NO$_2$ |
| Allyl | OH | OH | 3-NH$_2$ |
| Allyl | OH | OH | 4-NH$_2$ |
| Allyl | OH | OH | 3,6-NH$_2$ |
| Allyl | OH | OH | 4,5-NH$_2$ |
| CPM | H | OH | (non-substituted) |
| CPM | H | OH | 3-F |
| CPM | H | OH | 4-F |
| CPM | H | OH | 3,6-F |
| CPM | H | OH | 4,5-F |
| CPM | H | OH | 3,4,5,6-F |
| CPM | H | OH | 3-Cl |
| CPM | H | OH | 4-Cl |
| CPM | H | OH | 3,6-Cl |
| CPM | H | OH | 4,5-Cl |
| CPM | H | OH | 3-Br |
| CPM | H | OH | 4-Br |
| CPM | H | OH | 3,6-Br |
| CPM | H | OH | 4,5-Br |
| CPM | H | OH | 3-Me |
| CPM | H | OH | 4-Me |
| CPM | H | OH | 3,6-Me |
| CPM | H | OH | 4,5-Me |
| CPM | H | OH | 3-OMe |
| CPM | H | OH | 4-OMe |
| CPM | H | OH | 3,6-OMe |
| CPM | H | OH | 4,5-OMe |
| CPM | H | OH | 3-OH |
| CPM | H | OH | 4-OH |
| CPM | H | OH | 3,6-OH |
| CPM | H | OH | 4,5-OH |
| CPM | H | OH | 3-NO$_2$ |
| CPM | H | OH | 4-NO$_2$ |
| CPM | H | OH | 3,6-NO$_2$ |
| CPM | H | OH | 4,5-NO$_2$ |
| CPM | H | OH | 3-NH$_2$ |
| CPM | H | OH | 4-NH$_2$ |
| CPM | H | OH | 3,6-NH$_2$ |

TABLE 1-continued

16

[Structure shown: compound with OH, N-CPM (cyclopropylmethyl) at position 17, N-14, positions 4,5,6, phenol with 3-OH, and phthalimide-type ring with F at position 4]

| R¹ | R² | R³ | R⁵ |
|---|---|---|---|
| CPM | H | OH | 4,5-NH₂ |
| Allyl | H | OH | (non-substituted) |
| Allyl | H | OH | 3-F |
| Allyl | H | OH | 4-F |
| Allyl | H | OH | 3,6-F |
| Allyl | H | OH | 4,5-F |
| Allyl | H | OH | 3,4,5,6-F |
| Allyl | H | OH | 3-Cl |
| Allyl | H | OH | 4-Cl |
| Allyl | H | OH | 3,6-Cl |
| Allyl | H | OH | 4,5-Cl |
| Allyl | H | OH | 3-Br |
| Allyl | H | OH | 4-Br |
| Allyl | H | OH | 3,6-Br |
| Allyl | H | OH | 4,5-Br |
| Allyl | H | OH | 3-Me |
| Allyl | H | OH | 4-Me |
| Allyl | H | OH | 3,6-Me |
| Allyl | H | OH | 4,5-Me |
| Allyl | H | OH | 3-OMe |
| Allyl | H | OH | 4-OMe |
| Allyl | H | OH | 3,6-OMe |
| Allyl | H | OH | 4,5-OMe |
| Allyl | H | OH | 3-OH |
| Allyl | H | OH | 4-OH |
| Allyl | H | OH | 3,6-OH |
| Allyl | H | OH | 4,5-OH |
| Allyl | H | OH | 3-NO₂ |
| Allyl | H | OH | 4-NO₂ |
| Allyl | H | OH | 3,6-NO₂ |
| Allyl | H | OH | 4,5-NO₂ |
| Allyl | H | OH | 3-NH₂ |
| Allyl | H | OH | 4-NH₂ |
| Allyl | H | OH | 3,6-NH₂ |
| Allyl | H | OH | 4,5-NH₂ |
| CPM | OAc | OH | (non-substituted) |
| CPM | OAc | OH | 3-F |
| CPM | OAc | OH | 4-F |
| CPM | OAc | OH | 3,6-F |
| CPM | OAc | OH | 4,5-F |
| CPM | OAc | OH | 3,4,5,6-F |
| CPM | OAc | OH | 3-Cl |
| CPM | OAc | OH | 4-Cl |
| CPM | OAc | OH | 3,6-Cl |
| CPM | OAc | OH | 4,5-Cl |
| CPM | OAc | OH | 3-Br |
| CPM | OAc | OH | 4-Br |
| CPM | OAc | OH | 3,6-Br |
| CPM | OAc | OH | 4,5-Br |
| CPM | OAc | OH | 3-Me |
| CPM | OAc | OH | 4-Me |
| CPM | OAc | OH | 3,6-Me |
| CPM | OAc | OH | 4,5-Me |
| CPM | OAc | OH | 3-OMe |
| CPM | OAc | OH | 4-OMe |
| CPM | OAc | OH | 3,6-OMe |
| CPM | OAc | OH | 4,5-OMe |
| CPM | OAc | OH | 3-OH |
| CPM | OAc | OH | 4-OH |
| CPM | OAc | OH | 3,6-OH |
| CPM | OAc | OH | 4,5-OH |
| CPM | OAc | OH | 3-NO₂ |
| CPM | OAc | OH | 4-NO₂ |
| CPM | OAc | OH | 3,6-NO₂ |
| CPM | OAc | OH | 4,5-NO₂ |
| CPM | OAc | OH | 3-NH₂ |
| CPM | OAc | OH | 4-NH₂ |
| CPM | OAc | OH | 3,6-NH₂ |
| CPM | OAc | OH | 4,5-NH₂ |
| Allyl | OAc | OH | (non-substituted) |
| Allyl | OAc | OH | 3-F |
| Allyl | OAc | OH | 4-F |
| Allyl | OAc | OH | 3,6-F |
| Allyl | OAc | OH | 4,5-F |
| Allyl | OAc | OH | 3,4,5,6-F |
| Allyl | OAc | OH | 3-Cl |
| Allyl | OAc | OH | 4-Cl |
| Allyl | OAc | OH | 3,6-Cl |
| Allyl | OAc | OH | 4,5-Cl |
| Allyl | OAc | OH | 3-Br |
| Allyl | OAc | OH | 4-Br |
| Allyl | OAc | OH | 3,6-Br |
| Allyl | OAc | OH | 4,5-Br |
| Allyl | OAc | OH | 3-Me |
| Allyl | OAc | OH | 4-Me |
| Allyl | OAc | OH | 3,6-Me |
| Allyl | OAc | OH | 4,5-Me |
| Allyl | OAc | OH | 3-OMe |
| Allyl | OAc | OH | 4-OMe |
| Allyl | OAc | OH | 3,6-OMe |
| Allyl | OAc | OH | 4,5-OMe |
| Allyl | OAc | OH | 3-OH |
| Allyl | OAc | OH | 4-OH |
| Allyl | OAc | OH | 3,6-OH |
| Allyl | OAc | OH | 4,5-OH |
| Allyl | OAc | OH | 3-NO₂ |
| Allyl | OAc | OH | 4-NO₂ |
| Allyl | OAc | OH | 3,6-NO₂ |
| Allyl | OAc | OH | 4,5-NO₂ |
| Allyl | OAc | OH | 3-NH₂ |
| Allyl | OAc | OH | 4-NH₂ |
| Allyl | OAc | OH | 3,6-NH₂ |
| Allyl | OAc | OH | 4,5-NH₂ |

Among the compounds of the Formula (I), specific examples of those wherein —X— is a carbon chain having three carbon atoms constituting a part of the ring structure; Y is —C(=O)— and Z is valence bond; two $R^4$s form benzene fused ring which is not substituted or substituted by one or more $R^5$s; $R^9$ is hydrogen; $R^{10}$ and $R^{11}$ are bound to represent —O—, that is, those represented by the Formula (Ib) below are shown in Table 2.

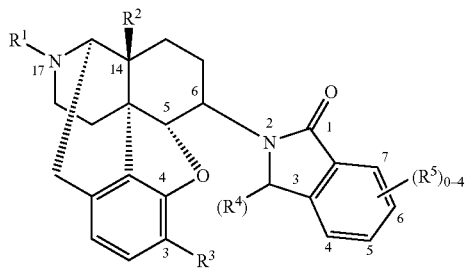

(Ib)

Among the compounds represented by Formula (Ib), the compound wherein $R^1$ is cyclopropylmethyl, $R^2$ and $R^3$ are hydroxy, which does not have $R^4$ other than a benzene fused ring, $R^5$ is 6-fluoro, and the configuration of the bond at the 6-position is β, that is, Compound 82 of the following formula is named 2-[17-(cyclopropylmethyl)-4,5α-epoxy-3,14-dihydroxymorphinan-6β-yl]-6-fluoro-2,3-dihydro-isoindol-1-one.

TABLE 2

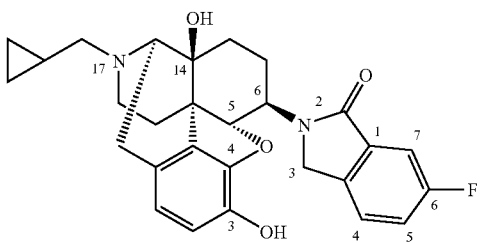

82

| $R^1$ | $R^2$ | $R^3$ | $R^4$ | $R^5$ |
|---|---|---|---|---|
| CPM | OH | OH | — | (non-substituted) |
| CPM | OH | OH | — | 4-F |
| CPM | OH | OH | — | 5-F |
| CPM | OH | OH | — | 6-F |
| CPM | OH | OH | — | 7-F |
| CPM | OH | OH | — | 5,6-F |
| CPM | OH | OH | — | 4,5,6,7-F |
| CPM | OH | OH | — | 4-Cl |
| CPM | OH | OH | — | 5-Cl |
| CPM | OH | OH | — | 6-Cl |
| CPM | OH | OH | — | 7-Cl |
| CPM | OH | OH | — | 5,6-Cl |
| CPM | OH | OH | — | 4-Me |
| CPM | OH | OH | — | 5-Me |
| CPM | OH | OH | — | 6-Me |
| CPM | OH | OH | — | 7-Me |
| CPM | OH | OH | — | 5,6-Me |
| CPM | OH | OH | — | 4-OMe |
| CPM | OH | OH | — | 5-OMe |
| CPM | OH | OH | — | 6-OMe |
| CPM | OH | OH | — | 7-OMe |
| CPM | OH | OH | — | 5,6-OMe |
| Allyl | OH | OH | — | (non-substituted) |
| Allyl | OH | OH | — | 4-F |
| Allyl | OH | OH | — | 5-F |
| Allyl | OH | OH | — | 6-F |
| Allyl | OH | OH | — | 7-F |
| Allyl | OH | OH | — | 5,6-F |
| Allyl | OH | OH | — | 4,5,6,7-F |
| Allyl | OH | OH | — | 4-Cl |
| Allyl | OH | OH | — | 5-Cl |
| Allyl | OH | OH | — | 6-Cl |
| Allyl | OH | OH | — | 7-Cl |
| Allyl | OH | OH | — | 5,6-Cl |
| Allyl | OH | OH | — | 4-Me |
| Allyl | OH | OH | — | 5-Me |
| Allyl | OH | OH | — | 6-Me |
| Allyl | OH | OH | — | 7-Me |
| Allyl | OH | OH | — | 5,6-Me |
| Allyl | OH | OH | — | 4-OMe |
| Allyl | OH | OH | — | 5-OMe |
| Allyl | OH | OH | — | 6-OMe |
| Allyl | OH | OH | — | 7-OMe |
| Allyl | OH | OH | — | 5,6-OMe |
| CPM | H | OH | — | (non-substituted) |
| CPM | H | OH | — | 4-F |
| CPM | H | OH | — | 5-F |
| CPM | H | OH | — | 6-F |
| CPM | H | OH | — | 7-F |
| CPM | H | OH | — | 5,6-F |
| CPM | H | OH | — | 4,5,6,7-F |
| CPM | H | OH | — | 4-Cl |
| CPM | H | OH | — | 5-Cl |
| CPM | H | OH | — | 6-Cl |
| CPM | H | OH | — | 7-Cl |
| CPM | H | OH | — | 5,6-Cl |
| CPM | H | OH | — | 4-Me |
| CPM | H | OH | — | 5-Me |
| CPM | H | OH | — | 6-Me |
| CPM | H | OH | — | 7-Me |
| CPM | H | OH | — | 5,6-Me |
| CPM | H | OH | — | 4-OMe |
| CPM | H | OH | — | 5-OMe |
| CPM | H | OH | — | 6-OMe |
| CPM | H | OH | — | 7-OMe |
| CPM | H | OH | — | 5,6-OMe |
| Allyl | H | OH | — | (non-substituted) |
| Allyl | H | OH | — | 4-F |
| Allyl | H | OH | — | 5-F |
| Allyl | H | OH | — | 6-F |
| Allyl | H | OH | — | 7-F |
| Allyl | H | OH | — | 5,6-F |
| Allyl | H | OH | — | 4,5,6,7-F |
| Allyl | H | OH | — | 4-Cl |
| Allyl | H | OH | — | 5-Cl |
| Allyl | H | OH | — | 6-Cl |
| Allyl | H | OH | — | 7-Cl |
| Allyl | H | OH | — | 5,6-Cl |
| Allyl | H | OH | — | 4-Me |
| Allyl | H | OH | — | 5-Me |
| Allyl | H | OH | — | 6-Me |
| Allyl | H | OH | — | 7-Me |
| Allyl | H | OH | — | 5,6-Me |
| Allyl | H | OH | — | 4-OMe |
| Allyl | H | OH | — | 5-OMe |
| Allyl | H | OH | — | 6-OMe |
| Allyl | H | OH | — | 7-OMe |
| Allyl | H | OH | — | 5,6-OMe |
| CPM | OH | OH | OH | (non-substituted) |
| CPM | OH | OH | OH | 4-F |
| CPM | OH | OH | OH | 5-F |
| CPM | OH | OH | OH | 6-F |
| CPM | OH | OH | OH | 7-F |
| CPM | OH | OH | OH | 5,6-F |
| CPM | OH | OH | OH | 4,5,6,7-F |
| CPM | OH | OH | OH | 4-Cl |
| CPM | OH | OH | OH | 5-Cl |
| CPM | OH | OH | OH | 6-Cl |

TABLE 2-continued

82

| R¹ | R² | R³ | R⁴ | R⁵ |
|---|---|---|---|---|
| CPM | OH | OH | OH | 7-Cl |
| CPM | OH | OH | OH | 5,6-Cl |
| CPM | OH | OH | OH | 4-Me |
| CPM | OH | OH | OH | 5-Me |
| CPM | OH | OH | OH | 6-Me |
| CPM | OH | OH | OH | 7-Me |
| CPM | OH | OH | OH | 5,6-Me |
| CPM | OH | OH | OH | 4-OMe |
| CPM | OH | OH | OH | 5-OMe |
| CPM | OH | OH | OH | 6-OMe |
| CPM | OH | OH | OH | 7-OMe |
| CPM | OH | OH | OH | 5,6-OMe |
| Allyl | OH | OH | OH | (non-substituted) |
| Allyl | OH | OH | OH | 4-F |
| Allyl | OH | OH | OH | 5-F |
| Allyl | OH | OH | OH | 6-F |
| Allyl | OH | OH | OH | 7-F |
| Allyl | OH | OH | OH | 5,6-F |
| Allyl | OH | OH | OH | 4,5,6,7-F |
| Allyl | OH | OH | OH | 4-Cl |
| Allyl | OH | OH | OH | 5-Cl |
| Allyl | OH | OH | OH | 6-Cl |
| Allyl | OH | OH | OH | 7-Cl |
| Allyl | OH | OH | OH | 5,6-Cl |
| Allyl | OH | OH | OH | 4-Me |
| Allyl | OH | OH | OH | 5-Me |
| Allyl | OH | OH | OH | 6-Me |
| Allyl | OH | OH | OH | 7-Me |
| Allyl | OH | OH | OH | 5,6-Me |
| Allyl | OH | OH | OH | 4-OMe |
| Allyl | OH | OH | OH | 5-OMe |
| Allyl | OH | OH | OH | 6-OMe |
| Allyl | OH | OH | OH | 7-OMe |
| Allyl | OH | OH | OH | 5,6-OMe |
| CPM | H | OH | OH | (non-substituted) |
| CPM | H | OH | OH | 4-F |
| CPM | H | OH | OH | 5-F |
| CPM | H | OH | OH | 6-F |
| CPM | H | OH | OH | 7-F |
| CPM | H | OH | OH | 5,6-F |
| CPM | H | OH | OH | 4,5,6,7-F |
| CPM | H | OH | OH | 4-Cl |
| CPM | H | OH | OH | 5-Cl |
| CPM | H | OH | OH | 6-Cl |
| CPM | H | OH | OH | 7-Cl |
| CPM | H | OH | OH | 5,6-Cl |
| CPM | H | OH | OH | 4-Me |
| CPM | H | OH | OH | 5-Me |
| CPM | H | OH | OH | 6-Me |
| CPM | H | OH | OH | 7-Me |
| CPM | H | OH | OH | 5,6-Me |
| CPM | H | OH | OH | 4-OMe |
| CPM | H | OH | OH | 5-OMe |
| CPM | H | OH | OH | 6-OMe |
| CPM | H | OH | OH | 7-OMe |
| CPM | H | OH | OH | 5,6-OMe |
| Allyl | H | OH | OH | (non-substituted) |
| Allyl | H | OH | OH | 4-F |
| Allyl | H | OH | OH | 5-F |
| Allyl | H | OH | OH | 6-F |
| Allyl | H | OH | OH | 7-F |
| Allyl | H | OH | OH | 5,6-F |
| Allyl | H | OH | OH | 4,5,6,7-F |
| Allyl | H | OH | OH | 4-Cl |
| Allyl | H | OH | OH | 5-Cl |
| Allyl | H | OH | OH | 6-Cl |
| Allyl | H | OH | OH | 7-Cl |
| Allyl | H | OH | OH | 5,6-Cl |
| Allyl | H | OH | OH | 4-Me |
| Allyl | H | OH | OH | 5-Me |
| Allyl | H | OH | OH | 6-Me |
| Allyl | H | OH | OH | 7-Me |
| Allyl | H | OH | OH | 5,6-Me |
| Allyl | H | OH | OH | 4-OMe |
| Allyl | H | OH | OH | 5-OMe |
| Allyl | H | OH | OH | 6-OMe |
| Allyl | H | OH | OH | 7-OMe |
| Allyl | H | OH | OH | 5,6-OMe |
| CPM | OH | OH | CH₂COOMe | (non-substituted) |
| CPM | OH | OH | CH₂COOMe | 4-F |
| CPM | OH | OH | CH₂COOMe | 5-F |
| CPM | OH | OH | CH₂COOMe | 6-F |
| CPM | OH | OH | CH₂COOMe | 7-F |
| CPM | OH | OH | CH₂COOMe | 5,6-F |
| CPM | OH | OH | CH₂COOMe | 4,5,6,7-F |
| CPM | OH | OH | CH₂COOMe | 4-Cl |
| CPM | OH | OH | CH₂COOMe | 5-Cl |
| CPM | OH | OH | CH₂COOMe | 6-Cl |
| CPM | OH | OH | CH₂COOMe | 7-Cl |
| CPM | OH | OH | CH₂COOMe | 5,6-Cl |
| CPM | OH | OH | CH₂COOMe | 4-Me |
| CPM | OH | OH | CH₂COOMe | 5-Me |
| CPM | OH | OH | CH₂COOMe | 6-Me |
| CPM | OH | OH | CH₂COOMe | 7-Me |
| CPM | OH | OH | CH₂COOMe | 5,6-Me |
| CPM | OH | OH | CH₂COOMe | 4-OMe |
| CPM | OH | OH | CH₂COOMe | 5-OMe |
| CPM | OH | OH | CH₂COOMe | 6-OMe |
| CPM | OH | OH | CH₂COOMe | 7-OMe |
| CPM | OH | OH | CH₂COOMe | 5,6-OMe |
| Allyl | OH | OH | CH₂COOMe | (non-substituted) |
| Allyl | OH | OH | CH₂COOMe | 4-F |
| Allyl | OH | OH | CH₂COOMe | 5-F |
| Allyl | OH | OH | CH₂COOMe | 6-F |
| Allyl | OH | OH | CH₂COOMe | 7-F |
| Allyl | OH | OH | CH₂COOMe | 5,6-F |
| Allyl | OH | OH | CH₂COOMe | 4,5,6,7-F |
| Allyl | OH | OH | CH₂COOMe | 4-Cl |
| Allyl | OH | OH | CH₂COOMe | 5-Cl |
| Allyl | OH | OH | CH₂COOMe | 6-Cl |
| Allyl | OH | OH | CH₂COOMe | 7-Cl |
| Allyl | OH | OH | CH₂COOMe | 5,6-Cl |
| Allyl | OH | OH | CH₂COOMe | 4-Me |
| Allyl | OH | OH | CH₂COOMe | 5-Me |
| Allyl | OH | OH | CH₂COOMe | 6-Me |
| Allyl | OH | OH | CH₂COOMe | 7-Me |
| Allyl | OH | OH | CH₂COOMe | 5,6-Me |
| Allyl | OH | OH | CH₂COOMe | 4-OMe |
| Allyl | OH | OH | CH₂COOMe | 5-OMe |
| Allyl | OH | OH | CH₂COOMe | 6-OMe |
| Allyl | OH | OH | CH₂COOMe | 7-OMe |
| Allyl | OH | OH | CH₂COOMe | 5,6-OMe |
| CPM | H | OH | CH₂COOMe | (non-substituted) |
| CPM | H | OH | CH₂COOMe | 4-F |
| CPM | H | OH | CH₂COOMe | 5-F |
| CPM | H | OH | CH₂COOMe | 6-F |

TABLE 2-continued

82

[Structure 82: morphinan with OH at 14, CPM at N17, and 7-F isoindolinone at 6β position]

| R¹ | R² | R³ | R⁴ | R⁵ |
|---|---|---|---|---|
| CPM | H | OH | CH₂COOMe | 7-F |
| CPM | H | OH | CH₂COOMe | 5,6-F |
| CPM | H | OH | CH₂COOMe | 4,5,6,7-F |
| CPM | H | OH | CH₂COOMe | 4-Cl |
| CPM | H | OH | CH₂COOMe | 5-Cl |
| CPM | H | OH | CH₂COOMe | 6-Cl |
| CPM | H | OH | CH₂COOMe | 7-Cl |
| CPM | H | OH | CH₂COOMe | 5,6-Cl |
| CPM | H | OH | CH₂COOMe | 4-Me |
| CPM | H | OH | CH₂COOMe | 5-Me |
| CPM | H | OH | CH₂COOMe | 6-Me |
| CPM | H | OH | CH₂COOMe | 7-Me |
| CPM | H | OH | CH₂COOMe | 5,6-Me |
| CPM | H | OH | CH₂COOMe | 4-OMe |
| CPM | H | OH | CH₂COOMe | 5-OMe |
| CPM | H | OH | CH₂COOMe | 6-OMe |
| CPM | H | OH | CH₂COOMe | 7-OMe |
| CPM | H | OH | CH₂COOMe | 5,6-OMe |
| Allyl | H | OH | CH₂COOMe | (non-substituted) |
| Allyl | H | OH | CH₂COOMe | 4-F |
| Allyl | H | OH | CH₂COOMe | 5-F |
| Allyl | H | OH | CH₂COOMe | 6-F |
| Allyl | H | OH | CH₂COOMe | 7-F |
| Allyl | H | OH | CH₂COOMe | 5,6-F |
| Allyl | H | OH | CH₂COOMe | 4,5,6,7-F |
| Allyl | H | OH | CH₂COOMe | 4-Cl |
| Allyl | H | OH | CH₂COOMe | 5-Cl |
| Allyl | H | OH | CH₂COOMe | 6-Cl |
| Allyl | H | OH | CH₂COOMe | 7-Cl |
| Allyl | H | OH | CH₂COOMe | 5,6-Cl |
| Allyl | H | OH | CH₂COOMe | 4-Me |
| Allyl | H | OH | CH₂COOMe | 5-Me |
| Allyl | H | OH | CH₂COOMe | 6-Me |
| Allyl | H | OH | CH₂COOMe | 7-Me |
| Allyl | H | OH | CH₂COOMe | 5,6-Me |
| Allyl | H | OH | CH₂COOMe | 4-OMe |
| Allyl | H | OH | CH₂COOMe | 5-OMe |
| Allyl | H | OH | CH₂COOMe | 6-OMe |
| Allyl | H | OH | CH₂COOMe | 7-OMe |
| Allyl | H | OH | CH₂COOMe | 5,6-OMe |

Among the compounds of the Formula (I), specific examples of those wherein —X— is a carbon chain (single bond or unsaturated bond) having two carbon atoms constituting a part of the ring structure; Y and Z are —C(═O)—; R⁹ hydrogen; R¹⁰ and R¹¹ are bound to represent —O—, that is, those represented by the Formula (Ic) below are shown in Table 3.

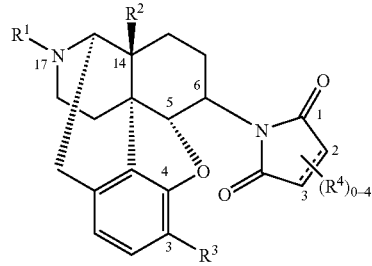

(Ic)

Among the compounds represented by Formula (Ic), the compound wherein R¹ is cyclopropylmethyl, R² and R³ are hydroxy, R⁴ is 2-ethylidene, and the configuration of the bond at the 6-position is β, that is, Compound 22 of the following formula is named N-[17-(cyclopropylmethyl)-4,5α-epoxy-3,14-dihydroxymorphinan-6β-yl]-2-ethylidene-succinic imide.

TABLE 3

22

[Structure 22: morphinan with 2-ethylidene succinimide substituent]

| R¹ | R² | R³ | 2-3 bond | R⁴ |
|---|---|---|---|---|
| CPM | OH | OH | single bond | (non-substituted) |
| CPM | OH | OH | single bond | 2-methylene |
| CPM | OH | OH | single bond | 2-ethylidene |
| CPM | OH | OH | single bond | 2-propylidene |
| CPM | OH | OH | single bond | 2-butylidene |
| CPM | OH | OH | single bond | 2-cyclohexylmethylene |
| CPM | OH | OH | single bond | 2-Benzylidene |
| CPM | OH | OH | single bond | 2-phenethylidene |
| CPM | OH | OH | single bond | 2-metyl |
| CPM | OH | OH | single bond | 2-ethyl |
| CPM | OH | OH | single bond | 2-propyl |
| CPM | OH | OH | single bond | 2-butyl |
| CPM | OH | OH | single bond | 2-cyclohexylmethyl |
| CPM | OH | OH | single bond | 2-benzyl |
| CPM | OH | OH | single bond | 2-(4-methyl-benzyl) |
| CPM | OH | OH | single bond | 2-(4-fluoro-benzyl) |
| CPM | OH | OH | single bond | 2-(4-Chloro-benzyl) |
| CPM | OH | OH | single bond | 2-(4-trifluoromethoxy-benzyl) |
| CPM | OH | OH | single bond | 2-phenetyl |
| CPM | OH | OH | single bond | 2-phenoxy |
| CPM | OH | OH | single bond | 2-(4-methyl-phenoxy) |
| CPM | OH | OH | single bond | 2-(4-fluoro-phenoxy) |
| CPM | OH | OH | single bond | 2-(4-chloro-phenoxy) |
| CPM | OH | OH | single bond | Cyclopropano |
| CPM | OH | OH | single bond | Cyclopentano |
| CPM | OH | OH | single bond | Cyclohexano |
| CPM | OH | OH | single bond | Cyclohexeno |
| CPM | OH | OH | single bond | 2-Ph |
| CPM | OH | OH | single bond | 2,3-Ph |
| CPM | OH | OH | double bond | (non-substituted) |
| CPM | OH | OH | double bond | 2-Ph |
| CPM | OH | OH | double bond | 2,3-Ph |
| CPM | OH | OH | double bond | Cyclohexeno |
| CPM | OH | OH | double bond | Pyrido |
| Allyl | OH | OH | single bond | (non-substituted) |
| Allyl | OH | OH | single bond | 2-methylene |
| Allyl | OH | OH | single bond | 2-ethylidene |

TABLE 3-continued

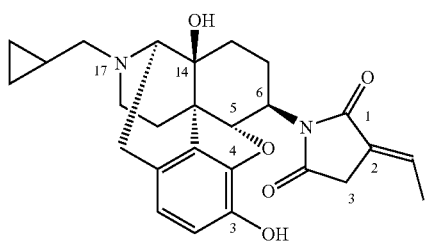

22

| R¹ | R² | R³ | 2-3 bond | R⁴ |
|---|---|---|---|---|
| Allyl | OH | OH | single bond | 2-propylidene |
| Allyl | OH | OH | single bond | 2-butylidene |
| Allyl | OH | OH | single bond | 2-cyclohexylmethylene |
| Allyl | OH | OH | single bond | 2-Benzylidene |
| Allyl | OH | OH | single bond | 2-phenethylidene |
| Allyl | OH | OH | single bond | 2-metyl |
| Allyl | OH | OH | single bond | 2-ethyl |
| Allyl | OH | OH | single bond | 2-propyl |
| Allyl | OH | OH | single bond | 2-butyl |
| Allyl | OH | OH | single bond | 2-cyclohexylmethyl |
| Allyl | OH | OH | single bond | 2-benzyl |
| Allyl | OH | OH | single bond | 2-(4-methyl-benzyl) |
| Allyl | OH | OH | single bond | 2-(4-fluoro-benzyl) |
| Allyl | OH | OH | single bond | 2-(4-chloro-benzyl) |
| Allyl | OH | OH | single bond | 2-(4-trifluoromethoxy-benzyl) |
| Allyl | OH | OH | single bond | 2-phenetyl |
| Allyl | OH | OH | single bond | 2-phenoxy |
| Allyl | OH | OH | single bond | 2-(4-methyl-phenoxy) |
| Allyl | OH | OH | single bond | 2-(4-fluoro-phenoxy) |
| Allyl | OH | OH | single bond | 2-(4-chloro-phenoxy) |
| Allyl | OH | OH | single bond | Cyclopropano |
| Allyl | OH | OH | single bond | Cyclopentano |
| Allyl | OH | OH | single bond | Cyclohexano |
| Allyl | OH | OH | single bond | Cyclohexeno |
| Allyl | OH | OH | single bond | 2-Ph |
| Allyl | OH | OH | single bond | 2,3-Ph |
| Allyl | OH | OH | double bond | (non-substituted) |
| Allyl | OH | OH | double bond | 2-Ph |
| Allyl | OH | OH | double bond | 2,3-Ph |
| Allyl | OH | OH | double bond | Cyclohexeno |
| Allyl | OH | OH | double bond | Pyridino |

Among the compounds of the Formula (I), specific examples of those wherein —X— is a carbon chain having three carbon atoms constituting a part of the ring structure; Y is —C(=O)— and Z is valence bond; R⁹ is hydrogen; R¹⁰ and R¹¹ are bound to represent —O—, that is, those represented by the Formula (1d) below are shown in Table 4.

(Id)

Among the compounds represented by Formula (Id), the compound wherein R¹ is cyclopropylmethyl, R² and R³ are hydroxy, R⁴ is 3-benzyl, and the configuration of the bond at the 6-position is β, that is, Compound 47 of the following formula is named 3-benzyl-1-[17-(cyclopropylmethyl)-4,5α-epoxy-3,14-dihydroxymorphinan-6β-yl]-pyrrolidin-2-one.

TABLE 4

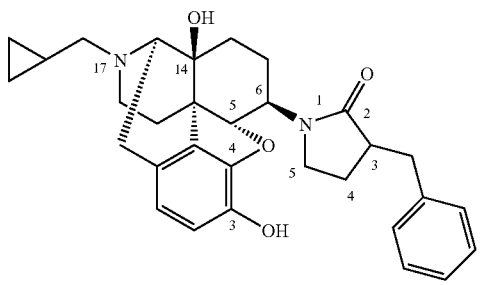

47

| R¹ | R² | R³ | 3-4 bond | R⁴ |
|---|---|---|---|---|
| CPM | OH | OH | single bond | (non-substituted) |
| CPM | OH | OH | single bond | 3-methylene |
| CPM | OH | OH | single bond | 3-ethylidene |
| CPM | OH | OH | single bond | 3-propylidene |
| CPM | OH | OH | single bond | 3-butylidene |
| CPM | OH | OH | single bond | 3-cyclohexylmethylene |
| CPM | OH | OH | single bond | 3-Benzylidene |
| CPM | OH | OH | single bond | 3-phenethylidene |
| CPM | OH | OH | single bond | 3-metyl |
| CPM | OH | OH | single bond | 3-ethyl |
| CPM | OH | OH | single bond | 3-propyl |
| CPM | OH | OH | single bond | 3-butyl |
| CPM | OH | OH | single bond | 3-cyclohexylmethyl |
| CPM | OH | OH | single bond | 3-benzyl |
| CPM | OH | OH | single bond | 3-(4-methyl-benzyl) |
| CPM | OH | OH | single bond | 3-(4-fluoro-benzyl) |
| CPM | OH | OH | single bond | 3-(4-Chloro-benzyl) |
| CPM | OH | OH | single bond | 3-(4-trifluoromethoxy-benzyl) |
| CPM | OH | OH | single bond | 3-phenetyl |
| CPM | OH | OH | single bond | 3-phenoxy |
| CPM | OH | OH | single bond | 3-(4-methyl-phenoxy) |
| CPM | OH | OH | single bond | 3-(4-fluoro-phenoxy) |
| CPM | OH | OH | single bond | 3-(4-chloro-phenoxy) |
| CPM | OH | OH | single bond | Cyclopropano |
| CPM | OH | OH | single bond | Cyclopentano |
| CPM | OH | OH | single bond | Cyclohexano |
| CPM | OH | OH | single bond | Cyclohexeno |
| CPM | OH | OH | single bond | 3-Ph |
| CPM | OH | OH | single bond | 3,4-Ph |
| CPM | OH | OH | double bond | (non-substituted) |
| CPM | OH | OH | double bond | 3-Ph |
| CPM | OH | OH | double bond | 3,4-Ph |
| CPM | OH | OH | double bond | Cyclohexeno |
| CPM | OH | OH | double bond | Pyrido |
| Allyl | OH | OH | single bond | (non-substituted) |
| Allyl | OH | OH | single bond | 3-methylene |
| Allyl | OH | OH | single bond | 3-ethylidene |
| Allyl | OH | OH | single bond | 3-propylidene |
| Allyl | OH | OH | single bond | 3-butylidene |
| Allyl | OH | OH | single bond | 3-cyclohexylmethylene |
| Allyl | OH | OH | single bond | 3-Benzylidene |
| Allyl | OH | OH | single bond | 3-phenethylidene |
| Allyl | OH | OH | single bond | 3-metyl |
| Allyl | OH | OH | single bond | 3-ethyl |
| Allyl | OH | OH | single bond | 3-propyl |
| Allyl | OH | OH | single bond | 3-butyl |
| Allyl | OH | OH | single bond | 3-cyclohexylmethyl |
| Allyl | OH | OH | single bond | 3-benzyl |
| Allyl | OH | OH | single bond | 3-(4-methyl-benzyl) |
| Allyl | OH | OH | single bond | 3-(4-fluoro-benzyl) |
| Allyl | OH | OH | single bond | 3-(4-Chloro-benzyl) |
| Allyl | OH | OH | single bond | 3-(4-trifluoromethoxy-benzyl) |
| Allyl | OH | OH | single bond | 3-phenetyl |
| Allyl | OH | OH | single bond | 3-phenoxy |
| Allyl | OH | OH | single bond | 3-(4-methyl-phenoxy) |
| Allyl | OH | OH | single bond | 3-(4-fluoro-phenoxy) |
| Allyl | OH | OH | single bond | 3-(4-chloro-phenoxy) |
| Allyl | OH | OH | single bond | Cyclopropano |

TABLE 4-continued

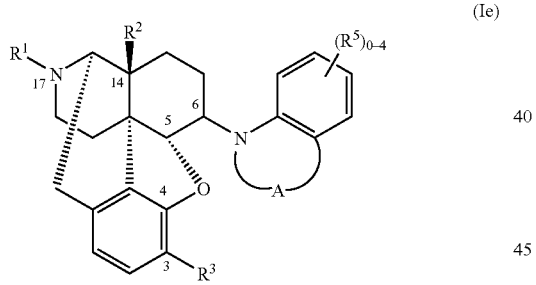

47

| R¹ | R² | R³ | 3-4 bond | R⁴ |
|---|---|---|---|---|
| Allyl | OH | OH | single bond | Cyclopentano |
| Allyl | OH | OH | single bond | Cyclohexano |
| Allyl | OH | OH | single bond | Cyclohexeno |
| Allyl | OH | OH | single bond | 3-Ph |
| Allyl | OH | OH | single bond | 3,4-Ph |
| Allyl | OH | OH | double bond | (non-substituted) |
| Allyl | OH | OH | double bond | 3-Ph |
| Allyl | OH | OH | double bond | 3,4-Ph |
| Allyl | OH | OH | double bond | Cyclohexeno |
| Allyl | OH | OH | double bond | Pyrido |

Among the compounds of the Formula (I), specific examples of those wherein —X(R⁴)$_{k-2}$— is -A-; Y and Z are valence bonds; two R⁴s form benzene fused ring which is not substituted or substituted by one or more R⁵s; R⁹ is hydrogen; R¹⁰ and R¹¹ are bound to represent —O—, that is, those represented by the Formula (Ie) below are shown in Table 5.

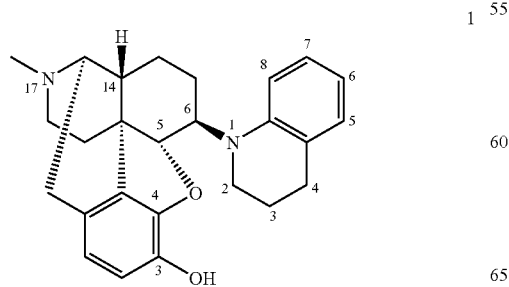

(Ie)

Among the compounds represented by Formula (Ie), the compound wherein R¹ is methyl, R² is hydrogen, R³ is hydroxy, -A- is —(CH₂)₃—, that is, Compound 1 of the following formula is named 4,5α-epoxy-6β-tetrahydro-quinolino-17-methyl-morphinan-3-ol.

1

Among the compounds represented by Formula (Ie), the compound wherein R¹ is methyl, R² is hydrogen, R³ is hydroxy, -A- is —(CH₂)₂—O—, that is, Compound 4 of the following formula is named 4,5α-epoxy-6β-(3,4-dihydro-2H-benzo[1,4]oxadino)-17-methyl-morphinan-3-ol.

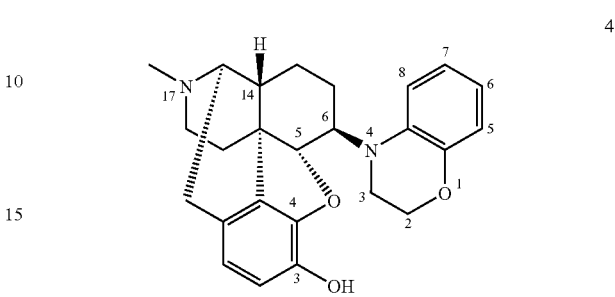

4

Among the compounds represented by Formula (Ie), the compound wherein R¹ is methyl, R² and R³ are hydroxy, -A- is —CH₂—CO—NMe-, that is, Compound 8 of the following formula is named 4-[4,5α-epoxy-3,14-dihydroxy 17-methylmorphinan-6β-yl]-1-methyl-3,4-dihydro-1H-quinoxalin-2-one.

8

Among the compounds represented by Formula (Ie), the compound wherein R¹ is methyl, R² is hydrogen, R³ is hydroxy, -A- is —(CH₂)₂—O—CH₂—, that is, Compound 10 of the following formula is named 4,5α-epoxy-6β-(1,2,3,5-tetrahydro-benzo[e][1,4]oxazepino)-17-methyl-morphinan-3-ol.

TABLE 5

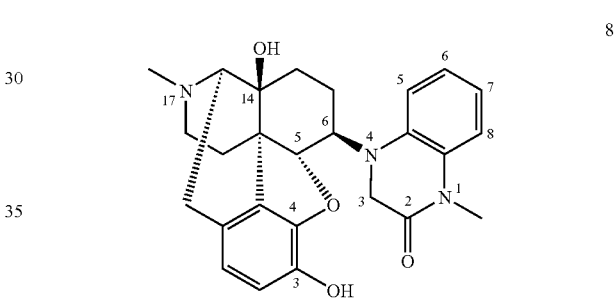

10

| R¹ | R² | R³ | -A- | R⁵ |
|---|---|---|---|---|
| Me | H | OH | —(CH₂)₂— | (non-substituted) |
| Me | H | OH | —(CH₂)₂— | 4-F |
| Me | H | OH | —(CH₂)₂— | 5-F |
| Me | H | OH | —(CH₂)₂— | 6-F |
| Me | H | OH | —(CH₂)₂— | 7-F |
| Me | H | OH | —(CH₂)₂— | 4-Cl |
| Me | H | OH | —(CH₂)₂— | 5-Cl |

TABLE 5-continued

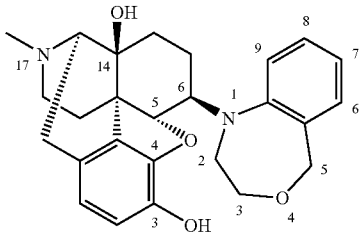

| R¹ | R² | R³ | -A- | R⁵ |
|---|---|---|---|---|
| Me | H | OH | —(CH$_2$)$_2$— | 6-Cl |
| Me | H | OH | —(CH$_2$)$_2$— | 7-Cl |
| Me | H | OH | —(CH$_2$)$_2$— | 4-Me |
| Me | H | OH | —(CH$_2$)$_2$— | 5-Me |
| Me | H | OH | —(CH$_2$)$_2$— | 6-Me |
| Me | H | OH | —(CH$_2$)$_2$— | 7-Me |
| Me | H | OH | —(CH$_2$)$_2$— | 4-OMe |
| Me | H | OH | —(CH$_2$)$_2$— | 5-OMe |
| Me | H | OH | —(CH$_2$)$_2$— | 6-OMe |
| Me | H | OH | —(CH$_2$)$_2$— | 7-OMe |
| phenethyl | H | OH | —(CH$_2$)$_2$— | (non-substituted) |
| phenethyl | H | OH | —(CH$_2$)$_2$— | 4-F |
| phenethyl | H | OH | —(CH$_2$)$_2$— | 5-F |
| phenethyl | H | OH | —(CH$_2$)$_2$— | 6-F |
| phenethyl | H | OH | —(CH$_2$)$_2$— | 7-F |
| phenethyl | H | OH | —(CH$_2$)$_2$— | 4-Cl |
| phenethyl | H | OH | —(CH$_2$)$_2$— | 5-Cl |
| phenethyl | H | OH | —(CH$_2$)$_2$— | 6-Cl |
| phenethyl | H | OH | —(CH$_2$)$_2$— | 7-Cl |
| phenethyl | H | OH | —(CH$_2$)$_2$— | 4-Me |
| phenethyl | H | OH | —(CH$_2$)$_2$— | 5-Me |
| phenethyl | H | OH | —(CH$_2$)$_2$— | 6-Me |
| phenethyl | H | OH | —(CH$_2$)$_2$— | 7-Me |
| phenethyl | H | OH | —(CH$_2$)$_2$— | 4-OMe |
| phenethyl | H | OH | —(CH$_2$)$_2$— | 5-OMe |
| phenethyl | H | OH | —(CH$_2$)$_2$— | 6-OMe |
| phenethyl | H | OH | —(CH$_2$)$_2$— | 7-OMe |
| Me | OH | OH | —(CH$_2$)$_2$— | (non-substituted) |
| Me | OH | OH | —(CH$_2$)$_2$— | 4-F |
| Me | OH | OH | —(CH$_2$)$_2$— | 5-F |
| Me | OH | OH | —(CH$_2$)$_2$— | 6-F |
| Me | OH | OH | —(CH$_2$)$_2$— | 7-F |
| Me | OH | OH | —(CH$_2$)$_2$— | 4-Cl |
| Me | OH | OH | —(CH$_2$)$_2$— | 5-Cl |
| Me | OH | OH | —(CH$_2$)$_2$— | 6-Cl |
| Me | OH | OH | —(CH$_2$)$_2$— | 7-Cl |
| Me | OH | OH | —(CH$_2$)$_2$— | 4-Me |
| Me | OH | OH | —(CH$_2$)$_2$— | 5-Me |
| Me | OH | OH | —(CH$_2$)$_2$— | 6-Me |
| Me | OH | OH | —(CH$_2$)$_2$— | 7-Me |
| Me | OH | OH | —(CH$_2$)$_2$— | 4-OMe |
| Me | OH | OH | —(CH$_2$)$_2$— | 5-OMe |
| Me | OH | OH | —(CH$_2$)$_2$— | 6-OMe |
| Me | OH | OH | —(CH$_2$)$_2$— | 7-OMe |
| phenethyl | OH | OH | —(CH$_2$)$_2$— | (non-substituted) |
| phenethyl | OH | OH | —(CH$_2$)$_2$— | 4-F |
| phenethyl | OH | OH | —(CH$_2$)$_2$— | 5-F |
| phenethyl | OH | OH | —(CH$_2$)$_2$— | 6-F |
| phenethyl | OH | OH | —(CH$_2$)$_2$— | 7-F |
| phenethyl | OH | OH | —(CH$_2$)$_2$— | 4-Cl |
| phenethyl | OH | OH | —(CH$_2$)$_2$— | 5-Cl |
| phenethyl | OH | OH | —(CH$_2$)$_2$— | 6-Cl |
| phenethyl | OH | OH | —(CH$_2$)$_2$— | 7-Cl |
| phenethyl | OH | OH | —(CH$_2$)$_2$— | 4-Me |
| phenethyl | OH | OH | —(CH$_2$)$_2$— | 5-Me |
| phenethyl | OH | OH | —(CH$_2$)$_2$— | 6-Me |
| phenethyl | OH | OH | —(CH$_2$)$_2$— | 7-Me |
| phenethyl | OH | OH | —(CH$_2$)$_2$— | 4-OMe |
| phenethyl | OH | OH | —(CH$_2$)$_2$— | 5-OMe |
| phenethyl | OH | OH | —(CH$_2$)$_2$— | 6-OMe |
| phenethyl | OH | OH | —(CH$_2$)$_2$— | 7-OMe |
| Me | H | OH | —(CH$_2$)$_3$— | (non-substituted) |
| Me | H | OH | —(CH$_2$)$_3$— | 5-F |

TABLE 5-continued

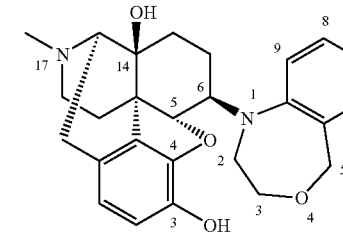

| R¹ | R² | R³ | -A- | R⁵ |
|---|---|---|---|---|
| Me | H | OH | —(CH$_2$)$_3$— | 6-F |
| Me | H | OH | —(CH$_2$)$_3$— | 7-F |
| Me | H | OH | —(CH$_2$)$_3$— | 8-F |
| Me | H | OH | —(CH$_2$)$_3$— | 5-Cl |
| Me | H | OH | —(CH$_2$)$_3$— | 6-Cl |
| Me | H | OH | —(CH$_2$)$_3$— | 7-Cl |
| Me | H | OH | —(CH$_2$)$_3$— | 8-Cl |
| Me | H | OH | —(CH$_2$)$_3$— | 5-Me |
| Me | H | OH | —(CH$_2$)$_3$— | 6-Me |
| Me | H | OH | —(CH$_2$)$_3$— | 7-Me |
| Me | H | OH | —(CH$_2$)$_3$— | 8-Me |
| Me | H | OH | —(CH$_2$)$_3$— | 5-OMe |
| Me | H | OH | —(CH$_2$)$_3$— | 6-OMe |
| Me | H | OH | —(CH$_2$)$_3$— | 7-OMe |
| Me | H | OH | —(CH$_2$)$_3$— | 8-OMe |
| phenethyl | H | OH | —(CH$_2$)$_3$— | (non-substituted) |
| phenethyl | H | OH | —(CH$_2$)$_3$— | 5-F |
| phenethyl | H | OH | —(CH$_2$)$_3$— | 6-F |
| phenethyl | H | OH | —(CH$_2$)$_3$— | 7-F |
| phenethyl | H | OH | —(CH$_2$)$_3$— | 8-F |
| phenethyl | H | OH | —(CH$_2$)$_3$— | 5-Cl |
| phenethyl | H | OH | —(CH$_2$)$_3$— | 6-Cl |
| phenethyl | H | OH | —(CH$_2$)$_3$— | 7-Cl |
| phenethyl | H | OH | —(CH$_2$)$_3$— | 8-Cl |
| phenethyl | H | OH | —(CH$_2$)$_3$— | 5-Me |
| phenethyl | H | OH | —(CH$_2$)$_3$— | 6-Me |
| phenethyl | H | OH | —(CH$_2$)$_3$— | 7-Me |
| phenethyl | H | OH | —(CH$_2$)$_3$— | 8-Me |
| phenethyl | H | OH | —(CH$_2$)$_3$— | 5-OMe |
| phenethyl | H | OH | —(CH$_2$)$_3$— | 6-OMe |
| phenethyl | H | OH | —(CH$_2$)$_3$— | 7-OMe |
| phenethyl | H | OH | —(CH$_2$)$_3$— | 8-OMe |
| Me | OH | OH | —(CH$_2$)$_3$— | (non-substituted) |
| Me | OH | OH | —(CH$_2$)$_3$— | 5-F |
| Me | OH | OH | —(CH$_2$)$_3$— | 6-F |
| Me | OH | OH | —(CH$_2$)$_3$— | 7-F |
| Me | OH | OH | —(CH$_2$)$_3$— | 8-F |
| Me | OH | OH | —(CH$_2$)$_3$— | 5-Cl |
| Me | OH | OH | —(CH$_2$)$_3$— | 6-Cl |
| Me | OH | OH | —(CH$_2$)$_3$— | 7-Cl |
| Me | OH | OH | —(CH$_2$)$_3$— | 8-Cl |
| Me | OH | OH | —(CH$_2$)$_3$— | 5-Me |
| Me | OH | OH | —(CH$_2$)$_3$— | 6-Me |
| Me | OH | OH | —(CH$_2$)$_3$— | 7-Me |
| Me | OH | OH | —(CH$_2$)$_3$— | 8-Me |
| Me | OH | OH | —(CH$_2$)$_3$— | 5-OMe |
| Me | OH | OH | —(CH$_2$)$_3$— | 6-OMe |
| Me | OH | OH | —(CH$_2$)$_3$— | 7-OMe |
| Me | OH | OH | —(CH$_2$)$_3$— | 8-OMe |
| phenethyl | OH | OH | —(CH$_2$)$_3$— | (non-substituted) |
| phenethyl | OH | OH | —(CH$_2$)$_3$— | 5-F |
| phenethyl | OH | OH | —(CH$_2$)$_3$— | 6-F |
| phenethyl | OH | OH | —(CH$_2$)$_3$— | 7-F |
| phenethyl | OH | OH | —(CH$_2$)$_3$— | 8-F |
| phenethyl | OH | OH | —(CH$_2$)$_3$— | 5-Cl |
| phenethyl | OH | OH | —(CH$_2$)$_3$— | 6-Cl |
| phenethyl | OH | OH | —(CH$_2$)$_3$— | 7-Cl |
| phenethyl | OH | OH | —(CH$_2$)$_3$— | 8-Cl |
| phenethyl | OH | OH | —(CH$_2$)$_3$— | 5-Me |
| phenethyl | OH | OH | —(CH$_2$)$_3$— | 6-Me |
| phenethyl | OH | OH | —(CH$_2$)$_3$— | 7-Me |
| phenethyl | OH | OH | —(CH$_2$)$_3$— | 8-Me |
| phenethyl | OH | OH | —(CH$_2$)$_3$— | 5-OMe |

TABLE 5-continued

| R¹ | R² | R³ | -A- | R⁵ |
|---|---|---|---|---|
| phenethyl | OH | OH | —(CH₂)₃— | 6-OMe |
| phenethyl | OH | OH | —(CH₂)₃— | 7-OMe |
| phenethyl | OH | OH | —(CH₂)₃— | 8-OMe |
| Me | H | OH | —(CH₂)₄— | (non-substituted) |
| Me | H | OH | —(CH₂)₄— | 6-F |
| Me | H | OH | —(CH₂)₄— | 7-F |
| Me | H | OH | —(CH₂)₄— | 8-F |
| Me | H | OH | —(CH₂)₄— | 9-F |
| Me | H | OH | —(CH₂)₄— | 6-Cl |
| Me | H | OH | —(CH₂)₄— | 7-Cl |
| Me | H | OH | —(CH₂)₄— | 8-Cl |
| Me | H | OH | —(CH₂)₄— | 9-Cl |
| Me | H | OH | —(CH₂)₄— | 6-Me |
| Me | H | OH | —(CH₂)₄— | 7-Me |
| Me | H | OH | —(CH₂)₄— | 8-Me |
| Me | H | OH | —(CH₂)₄— | 9-Me |
| Me | H | OH | —(CH₂)₄— | 6-OMe |
| Me | H | OH | —(CH₂)₄— | 7-OMe |
| Me | H | OH | —(CH₂)₄— | 8-OMe |
| Me | H | OH | —(CH₂)₄— | 9-OMe |
| phenethyl | H | OH | —(CH₂)₄— | (non-substituted) |
| phenethyl | H | OH | —(CH₂)₄— | 6-F |
| phenethyl | H | OH | —(CH₂)₄— | 7-F |
| phenethyl | H | OH | —(CH₂)₄— | 8-F |
| phenethyl | H | OH | —(CH₂)₄— | 9-F |
| phenethyl | H | OH | —(CH₂)₄— | 6-Cl |
| phenethyl | H | OH | —(CH₂)₄— | 7-Cl |
| phenethyl | H | OH | —(CH₂)₄— | 8-Cl |
| phenethyl | H | OH | —(CH₂)₄— | 9-Cl |
| phenethyl | H | OH | —(CH₂)₄— | 6-Me |
| phenethyl | H | OH | —(CH₂)₄— | 7-Me |
| phenethyl | H | OH | —(CH₂)₄— | 8-Me |
| phenethyl | H | OH | —(CH₂)₄— | 9-Me |
| phenethyl | H | OH | —(CH₂)₄— | 6-OMe |
| phenethyl | H | OH | —(CH₂)₄— | 7-OMe |
| phenethyl | H | OH | —(CH₂)₄— | 8-OMe |
| phenethyl | H | OH | —(CH₂)₄— | 9-OMe |
| Me | OH | OH | —(CH₂)₄— | (non-substituted) |
| Me | OH | OH | —(CH₂)₄— | 6-F |
| Me | OH | OH | —(CH₂)₄— | 7-F |
| Me | OH | OH | —(CH₂)₄— | 8-F |
| Me | OH | OH | —(CH₂)₄— | 9-F |
| Me | OH | OH | —(CH₂)₄— | 6-Cl |
| Me | OH | OH | —(CH₂)₄— | 7-Cl |
| Me | OH | OH | —(CH₂)₄— | 8-Cl |
| Me | OH | OH | —(CH₂)₄— | 9-Cl |
| Me | OH | OH | —(CH₂)₄— | 6-Me |
| Me | OH | OH | —(CH₂)₄— | 7-Me |
| Me | OH | OH | —(CH₂)₄— | 8-Me |
| Me | OH | OH | —(CH₂)₄— | 9-Me |
| Me | OH | OH | —(CH₂)₄— | 6-OMe |
| Me | OH | OH | —(CH₂)₄— | 7-OMe |
| Me | OH | OH | —(CH₂)₄— | 8-OMe |
| Me | OH | OH | —(CH₂)₄— | 9-OMe |
| phenethyl | OH | OH | —(CH₂)₄— | (non-substituted) |
| phenethyl | OH | OH | —(CH₂)₄— | 6-F |
| phenethyl | OH | OH | —(CH₂)₄— | 7-F |
| phenethyl | OH | OH | —(CH₂)₄— | 8-F |
| phenethyl | OH | OH | —(CH₂)₄— | 9-F |
| phenethyl | OH | OH | —(CH₂)₄— | 6-Cl |
| phenethyl | OH | OH | —(CH₂)₄— | 7-Cl |
| phenethyl | OH | OH | —(CH₂)₄— | 8-Cl |
| phenethyl | OH | OH | —(CH₂)₄— | 9-Cl |
| phenethyl | OH | OH | —(CH₂)₄— | 6-Me |
| phenethyl | OH | OH | —(CH₂)₄— | 7-Me |
| phenethyl | OH | OH | —(CH₂)₄— | 8-Me |
| phenethyl | OH | OH | —(CH₂)₄— | 9-Me |
| phenethyl | OH | OH | —(CH₂)₄— | 6-OMe |
| phenethyl | OH | OH | —(CH₂)₄— | 7-OMe |
| phenethyl | OH | OH | —(CH₂)₄— | 8-OMe |
| phenethyl | OH | OH | —(CH₂)₄— | 9-OMe |
| Me | H | OH | —(CH₂)₂—O— | (non-substituted) |
| Me | H | OH | —(CH₂)₂—O— | 5-F |
| Me | H | OH | —(CH₂)₂—O— | 6-F |
| Me | H | OH | —(CH₂)₂—O— | 7-F |
| Me | H | OH | —(CH₂)₂—O— | 8-F |
| Me | H | OH | —(CH₂)₂—O— | 5-Cl |
| Me | H | OH | —(CH₂)₂—O— | 6-Cl |
| Me | H | OH | —(CH₂)₂—O— | 7-Cl |
| Me | H | OH | —(CH₂)₂—O— | 8-Cl |
| Me | H | OH | —(CH₂)₂—O— | 5-Me |
| Me | H | OH | —(CH₂)₂—O— | 6-Me |
| Me | H | OH | —(CH₂)₂—O— | 7-Me |
| Me | H | OH | —(CH₂)₂—O— | 8-Me |
| Me | H | OH | —(CH₂)₂—O— | 5-OMe |
| Me | H | OH | —(CH₂)₂—O— | 6-OMe |
| Me | H | OH | —(CH₂)₂—O— | 7-OMe |
| Me | H | OH | —(CH₂)₂—O— | 8-OMe |
| phenethyl | H | OH | —(CH₂)₂—O— | (non-substituted) |
| phenethyl | H | OH | —(CH₂)₂—O— | 5-F |
| phenethyl | H | OH | —(CH₂)₂—O— | 6-F |
| phenethyl | H | OH | —(CH₂)₂—O— | 7-F |
| phenethyl | H | OH | —(CH₂)₂—O— | 8-F |
| phenethyl | H | OH | —(CH₂)₂—O— | 5-Cl |
| phenethyl | H | OH | —(CH₂)₂—O— | 6-Cl |
| phenethyl | H | OH | —(CH₂)₂—O— | 7-Cl |
| phenethyl | H | OH | —(CH₂)₂—O— | 8-Cl |
| phenethyl | H | OH | —(CH₂)₂—O— | 5-Me |
| phenethyl | H | OH | —(CH₂)₂—O— | 6-Me |
| phenethyl | H | OH | —(CH₂)₂—O— | 7-Me |
| phenethyl | H | OH | —(CH₂)₂—O— | 8-Me |
| phenethyl | H | OH | —(CH₂)₂—O— | 5-OMe |
| phenethyl | H | OH | —(CH₂)₂—O— | 6-OMe |
| phenethyl | H | OH | —(CH₂)₂—O— | 7-OMe |
| phenethyl | H | OH | —(CH₂)₂—O— | 8-OMe |
| Me | OH | OH | —(CH₂)₂—O— | (non-substituted) |
| Me | OH | OH | —(CH₂)₂—O— | 5-F |
| Me | OH | OH | —(CH₂)₂—O— | 6-F |
| Me | OH | OH | —(CH₂)₂—O— | 7-F |
| Me | OH | OH | —(CH₂)₂—O— | 8-F |
| Me | OH | OH | —(CH₂)₂—O— | 5-Cl |
| Me | OH | OH | —(CH₂)₂—O— | 6-Cl |
| Me | OH | OH | —(CH₂)₂—O— | 7-Cl |
| Me | OH | OH | —(CH₂)₂—O— | 8-Cl |
| Me | OH | OH | —(CH₂)₂—O— | 5-Me |
| Me | OH | OH | —(CH₂)₂—O— | 6-Me |
| Me | OH | OH | —(CH₂)₂—O— | 7-Me |
| Me | OH | OH | —(CH₂)₂—O— | 8-Me |
| Me | OH | OH | —(CH₂)₂—O— | 5-OMe |
| Me | OH | OH | —(CH₂)₂—O— | 6-OMe |
| Me | OH | OH | —(CH₂)₂—O— | 7-OMe |
| Me | OH | OH | —(CH₂)₂—O— | 8-OMe |
| phenethyl | OH | OH | —(CH₂)₂—O— | (non-substituted) |
| phenethyl | OH | OH | —(CH₂)₂—O— | 5-F |
| phenethyl | OH | OH | —(CH₂)₂—O— | 6-F |
| phenethyl | OH | OH | —(CH₂)₂—O— | 7-F |

TABLE 5-continued

| R¹ | R² | R³ | -A- | R⁵ |
|---|---|---|---|---|
| phenethyl | OH | OH | —(CH₂)₂—O— | 8-F |
| phenethyl | OH | OH | —(CH₂)₂—O— | 5-Cl |
| phenethyl | OH | OH | —(CH₂)₂—O— | 6-Cl |
| phenethyl | OH | OH | —(CH₂)₂—O— | 7-Cl |
| phenethyl | OH | OH | —(CH₂)₂—O— | 8-Cl |
| phenethyl | OH | OH | —(CH₂)₂—O— | 5-Me |
| phenethyl | OH | OH | —(CH₂)₂—O— | 6-Me |
| phenethyl | OH | OH | —(CH₂)₂—O— | 7-Me |
| phenethyl | OH | OH | —(CH₂)₂—O— | 8-Me |
| phenethyl | OH | OH | —(CH₂)₂—O— | 5-OMe |
| phenethyl | OH | OH | —(CH₂)₂—O— | 6-OMe |
| phenethyl | OH | OH | —(CH₂)₂—O— | 7-OMe |
| phenethyl | OH | OH | —(CH₂)₂—O— | 8-OMe |
| Me | H | OH | —(CH₂)₂—S— | (non-substituted) |
| Me | H | OH | —(CH₂)₂—S— | 5-F |
| Me | H | OH | —(CH₂)₂—S— | 6-F |
| Me | H | OH | —(CH₂)₂—S— | 7-F |
| Me | H | OH | —(CH₂)₂—S— | 8-F |
| Me | H | OH | —(CH₂)₂—S— | 5-Cl |
| Me | H | OH | —(CH₂)₂—S— | 6-Cl |
| Me | H | OH | —(CH₂)₂—S— | 7-Cl |
| Me | H | OH | —(CH₂)₂—S— | 8-Cl |
| Me | H | OH | —(CH₂)₂—S— | 5-Me |
| Me | H | OH | —(CH₂)₂—S— | 6-Me |
| Me | H | OH | —(CH₂)₂—S— | 7-Me |
| Me | H | OH | —(CH₂)₂—S— | 8-Me |
| Me | H | OH | —(CH₂)₂—S— | 5-OMe |
| Me | H | OH | —(CH₂)₂—S— | 6-OMe |
| Me | H | OH | —(CH₂)₂—S— | 7-OMe |
| Me | H | OH | —(CH₂)₂—S— | 8-OMe |
| phenethyl | H | OH | —(CH₂)₂—S— | (non-substituted) |
| phenethyl | H | OH | —(CH₂)₂—S— | 5-F |
| phenethyl | H | OH | —(CH₂)₂—S— | 6-F |
| phenethyl | H | OH | —(CH₂)₂—S— | 7-F |
| phenethyl | H | OH | —(CH₂)₂—S— | 8-F |
| phenethyl | H | OH | —(CH₂)₂—S— | 5-Cl |
| phenethyl | H | OH | —(CH₂)₂—S— | 6-Cl |
| phenethyl | H | OH | —(CH₂)₂—S— | 7-Cl |
| phenethyl | H | OH | —(CH₂)₂—S— | 8-Cl |
| phenethyl | H | OH | —(CH₂)₂—S— | 5-Me |
| phenethyl | H | OH | —(CH₂)₂—S— | 6-Me |
| phenethyl | H | OH | —(CH₂)₂—S— | 7-Me |
| phenethyl | H | OH | —(CH₂)₂—S— | 8-Me |
| phenethyl | H | OH | —(CH₂)₂—S— | 5-OMe |
| phenethyl | H | OH | —(CH₂)₂—S— | 6-OMe |
| phenethyl | H | OH | —(CH₂)₂—S— | 7-OMe |
| phenethyl | H | OH | —(CH₂)₂—S— | 8-OMe |
| Me | OH | OH | —(CH₂)₂—S— | (non-substituted) |
| Me | OH | OH | —(CH₂)₂—S— | 5-F |
| Me | OH | OH | —(CH₂)₂—S— | 6-F |
| Me | OH | OH | —(CH₂)₂—S— | 7-F |
| Me | OH | OH | —(CH₂)₂—S— | 8-F |
| Me | OH | OH | —(CH₂)₂—S— | 5-Cl |
| Me | OH | OH | —(CH₂)₂—S— | 6-Cl |
| Me | OH | OH | —(CH₂)₂—S— | 7-Cl |
| Me | OH | OH | —(CH₂)₂—S— | 8-Cl |
| Me | OH | OH | —(CH₂)₂—S— | 5-Me |
| Me | OH | OH | —(CH₂)₂—S— | 6-Me |
| Me | OH | OH | —(CH₂)₂—S— | 7-Me |
| Me | OH | OH | —(CH₂)₂—S— | 8-Me |
| Me | OH | OH | —(CH₂)₂—S— | 5-OMe |
| Me | OH | OH | —(CH₂)₂—S— | 6-OMe |
| Me | OH | OH | —(CH₂)₂—S— | 7-OMe |
| Me | OH | OH | —(CH₂)₂—S— | 8-OMe |
| phenethyl | OH | OH | —(CH₂)₂—S— | (non-substituted) |
| phenethyl | OH | OH | —(CH₂)₂—S— | 5-F |
| phenethyl | OH | OH | —(CH₂)₂—S— | 6-F |
| phenethyl | OH | OH | —(CH₂)₂—S— | 7-F |
| phenethyl | OH | OH | —(CH₂)₂—S— | 8-F |
| phenethyl | OH | OH | —(CH₂)₂—S— | 5-Cl |
| phenethyl | OH | OH | —(CH₂)₂—S— | 6-Cl |
| phenethyl | OH | OH | —(CH₂)₂—S— | 7-Cl |
| phenethyl | OH | OH | —(CH₂)₂—S— | 8-Cl |
| phenethyl | OH | OH | —(CH₂)₂—S— | 5-Me |
| phenethyl | OH | OH | —(CH₂)₂—S— | 6-Me |
| phenethyl | OH | OH | —(CH₂)₂—S— | 7-Me |
| phenethyl | OH | OH | —(CH₂)₂—S— | 8-Me |
| phenethyl | OH | OH | —(CH₂)₂—S— | 5-OMe |
| phenethyl | OH | OH | —(CH₂)₂—S— | 6-OMe |
| phenethyl | OH | OH | —(CH₂)₂—S— | 7-OMe |
| phenethyl | OH | OH | —(CH₂)₂—S— | 8-OMe |
| Me | H | OH | —(CH₂)₂—S(=O)— | (non-substituted) |
| Me | H | OH | —(CH₂)₂—S(=O)— | 5-F |
| Me | H | OH | —(CH₂)₂—S(=O)— | 6-F |
| Me | H | OH | —(CH₂)₂—S(=O)— | 7-F |
| Me | H | OH | —(CH₂)₂—S(=O)— | 8-F |
| Me | H | OH | —(CH₂)₂—S(=O)— | 5-Cl |
| Me | H | OH | —(CH₂)₂—S(=O)— | 6-Cl |
| Me | H | OH | —(CH₂)₂—S(=O)— | 7-Cl |
| Me | H | OH | —(CH₂)₂—S(=O)— | 8-Cl |
| Me | H | OH | —(CH₂)₂—S(=O)— | 5-Me |
| Me | H | OH | —(CH₂)₂—S(=O)— | 6-Me |
| Me | H | OH | —(CH₂)₂—S(=O)— | 7-Me |
| Me | H | OH | —(CH₂)₂—S(=O)— | 8-Me |
| Me | H | OH | —(CH₂)₂—S(=O)— | 5-OMe |
| Me | H | OH | —(CH₂)₂—S(=O)— | 6-OMe |
| Me | H | OH | —(CH₂)₂—S(=O)— | 7-OMe |
| Me | H | OH | —(CH₂)₂—S(=O)— | 8-OMe |
| phenethyl | H | OH | —(CH₂)₂—S(=O)— | (non-substituted) |
| phenethyl | H | OH | —(CH₂)₂—S(=O)— | 5-F |
| phenethyl | H | OH | —(CH₂)₂—S(=O)— | 6-F |
| phenethyl | H | OH | —(CH₂)₂—S(=O)— | 7-F |
| phenethyl | H | OH | —(CH₂)₂—S(=O)— | 8-F |
| phenethyl | H | OH | —(CH₂)₂—S(=O)— | 5-Cl |
| phenethyl | H | OH | —(CH₂)₂—S(=O)— | 6-Cl |
| phenethyl | H | OH | —(CH₂)₂—S(=O)— | 7-Cl |
| phenethyl | H | OH | —(CH₂)₂—S(=O)— | 8-Cl |
| phenethyl | H | OH | —(CH₂)₂—S(=O)— | 5-Me |
| phenethyl | H | OH | —(CH₂)₂—S(=O)— | 6-Me |
| phenethyl | H | OH | —(CH₂)₂—S(=O)— | 7-Me |
| phenethyl | H | OH | —(CH₂)₂—S(=O)— | 8-Me |
| phenethyl | H | OH | —(CH₂)₂—S(=O)— | 5-OMe |
| phenethyl | H | OH | —(CH₂)₂—S(=O)— | 6-OMe |
| phenethyl | H | OH | —(CH₂)₂—S(=O)— | 7-OMe |
| phenethyl | H | OH | —(CH₂)₂—S(=O)— | 8-OMe |
| Me | OH | OH | —(CH₂)₂—S(=O)— | (non-substituted) |
| Me | OH | OH | —(CH₂)₂—S(=O)— | 5-F |
| Me | OH | OH | —(CH₂)₂—S(=O)— | 6-F |
| Me | OH | OH | —(CH₂)₂—S(=O)— | 7-F |
| Me | OH | OH | —(CH₂)₂—S(=O)— | 8-F |
| Me | OH | OH | —(CH₂)₂—S(=O)— | 5-Cl |
| Me | OH | OH | —(CH₂)₂—S(=O)— | 6-Cl |
| Me | OH | OH | —(CH₂)₂—S(=O)— | 7-Cl |
| Me | OH | OH | —(CH₂)₂—S(=O)— | 8-Cl |
| Me | OH | OH | —(CH₂)₂—S(=O)— | 5-Me |
| Me | OH | OH | —(CH₂)₂—S(=O)— | 6-Me |

TABLE 5-continued

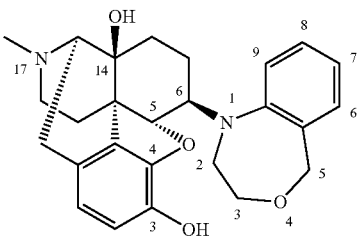

| R¹ | R² | R³ | -A- | R⁵ |
|---|---|---|---|---|
| Me | OH | OH | —(CH₂)₂—S(=O)— | 7-Me |
| Me | OH | OH | —(CH₂)₂—S(=O)— | 8-Me |
| Me | OH | OH | —(CH₂)₂—S(=O)— | 5-OMe |
| Me | OH | OH | —(CH₂)₂—S(=O)— | 6-OMe |
| Me | OH | OH | —(CH₂)₂—S(=O)— | 7-OMe |
| Me | OH | OH | —(CH₂)₂—S(=O)— | 8-OMe |
| phenethyl | OH | OH | —(CH₂)₂—S(=O)— | (non-substituted) |
| phenethyl | OH | OH | —(CH₂)₂—S(=O)— | 5-F |
| phenethyl | OH | OH | —(CH₂)₂—S(=O)— | 6-F |
| phenethyl | OH | OH | —(CH₂)₂—S(=O)— | 7-F |
| phenethyl | OH | OH | —(CH₂)₂—S(=O)— | 8-F |
| phenethyl | OH | OH | —(CH₂)₂—S(=O)— | 5-Cl |
| phenethyl | OH | OH | —(CH₂)₂—S(=O)— | 6-Cl |
| phenethyl | OH | OH | —(CH₂)₂—S(=O)— | 7-Cl |
| phenethyl | OH | OH | —(CH₂)₂—S(=O)— | 8-Cl |
| phenethyl | OH | OH | —(CH₂)₂—S(=O)— | 5-Me |
| phenethyl | OH | OH | —(CH₂)₂—S(=O)— | 6-Me |
| phenethyl | OH | OH | —(CH₂)₂—S(=O)— | 7-Me |
| phenethyl | OH | OH | —(CH₂)₂—S(=O)— | 8-Me |
| phenethyl | OH | OH | —(CH₂)₂—S(=O)— | 5-OMe |
| phenethyl | OH | OH | —(CH₂)₂—S(=O)— | 6-OMe |
| phenethyl | OH | OH | —(CH₂)₂—S(=O)— | 7-OMe |
| phenethyl | OH | OH | —(CH₂)₂—S(=O)— | 8-OMe |
| Me | H | OH | —(CH₂)₂—NH— | (non-substituted) |
| Me | H | OH | —(CH₂)₂—NH— | 5-F |
| Me | H | OH | —(CH₂)₂—NH— | 6-F |
| Me | H | OH | —(CH₂)₂—NH— | 7-F |
| Me | H | OH | —(CH₂)₂—NH— | 8-F |
| Me | H | OH | —(CH₂)₂—NH— | 5-Cl |
| Me | H | OH | —(CH₂)₂—NH— | 6-Cl |
| Me | H | OH | —(CH₂)₂—NH— | 7-Cl |
| Me | H | OH | —(CH₂)₂—NH— | 8-Cl |
| Me | H | OH | —(CH₂)₂—NH— | 5-Me |
| Me | H | OH | —(CH₂)₂—NH— | 6-Me |
| Me | H | OH | —(CH₂)₂—NH— | 7-Me |
| Me | H | OH | —(CH₂)₂—NH— | 8-Me |
| Me | H | OH | —(CH₂)₂—NH— | 5-OMe |
| Me | H | OH | —(CH₂)₂—NH— | 6-OMe |
| Me | H | OH | —(CH₂)₂—NH— | 7-OMe |
| Me | H | OH | —(CH₂)₂—NH— | 8-OMe |
| phenethyl | H | OH | —(CH₂)₂—NH— | (non-substituted) |
| phenethyl | H | OH | —(CH₂)₂—NH— | 5-F |
| phenethyl | H | OH | —(CH₂)₂—NH— | 6-F |
| phenethyl | H | OH | —(CH₂)₂—NH— | 7-F |
| phenethyl | H | OH | —(CH₂)₂—NH— | 8-F |
| phenethyl | H | OH | —(CH₂)₂—NH— | 5-Cl |
| phenethyl | H | OH | —(CH₂)₂—NH— | 6-Cl |
| phenethyl | H | OH | —(CH₂)₂—NH— | 7-Cl |
| phenethyl | H | OH | —(CH₂)₂—NH— | 8-Cl |
| phenethyl | H | OH | —(CH₂)₂—NH— | 5-Me |
| phenethyl | H | OH | —(CH₂)₂—NH— | 6-Me |
| phenethyl | H | OH | —(CH₂)₂—NH— | 7-Me |
| phenethyl | H | OH | —(CH₂)₂—NH— | 8-Me |
| phenethyl | H | OH | —(CH₂)₂—NH— | 5-OMe |
| phenethyl | H | OH | —(CH₂)₂—NH— | 6-OMe |
| phenethyl | H | OH | —(CH₂)₂—NH— | 7-OMe |
| phenethyl | H | OH | —(CH₂)₂—NH— | 8-OMe |
| Me | OH | OH | —(CH₂)₂—NH— | (non-substituted) |
| Me | OH | OH | —(CH₂)₂—NH— | 5-F |
| Me | OH | OH | —(CH₂)₂—NH— | 6-F |
| Me | OH | OH | —(CH₂)₂—NH— | 7-F |
| Me | OH | OH | —(CH₂)₂—NH— | 8-F |
| Me | OH | OH | —(CH₂)₂—NH— | 5-Cl |

TABLE 5-continued

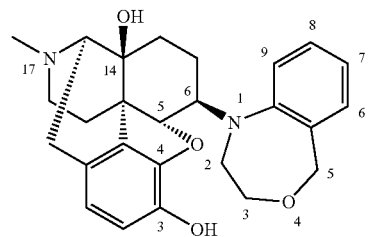

| R¹ | R² | R³ | -A- | R⁵ |
|---|---|---|---|---|
| Me | OH | OH | —(CH₂)₂—NH— | 6-Cl |
| Me | OH | OH | —(CH₂)₂—NH— | 7-Cl |
| Me | OH | OH | —(CH₂)₂—NH— | 8-Cl |
| Me | OH | OH | —(CH₂)₂—NH— | 5-Me |
| Me | OH | OH | —(CH₂)₂—NH— | 6-Me |
| Me | OH | OH | —(CH₂)₂—NH— | 7-Me |
| Me | OH | OH | —(CH₂)₂—NH— | 8-Me |
| Me | OH | OH | —(CH₂)₂—NH— | 5-OMe |
| Me | OH | OH | —(CH₂)₂—NH— | 6-OMe |
| Me | OH | OH | —(CH₂)₂—NH— | 7-OMe |
| Me | OH | OH | —(CH₂)₂—NH— | 8-OMe |
| phenethyl | OH | OH | —(CH₂)₂—NH— | (non-substituted) |
| phenethyl | OH | OH | —(CH₂)₂—NH— | 5-F |
| phenethyl | OH | OH | —(CH₂)₂—NH— | 6-F |
| phenethyl | OH | OH | —(CH₂)₂—NH— | 7-F |
| phenethyl | OH | OH | —(CH₂)₂—NH— | 8-F |
| phenethyl | OH | OH | —(CH₂)₂—NH— | 5-Cl |
| phenethyl | OH | OH | —(CH₂)₂—NH— | 6-Cl |
| phenethyl | OH | OH | —(CH₂)₂—NH— | 7-Cl |
| phenethyl | OH | OH | —(CH₂)₂—NH— | 8-Cl |
| phenethyl | OH | OH | —(CH₂)₂—NH— | 5-Me |
| phenethyl | OH | OH | —(CH₂)₂—NH— | 6-Me |
| phenethyl | OH | OH | —(CH₂)₂—NH— | 7-Me |
| phenethyl | OH | OH | —(CH₂)₂—NH— | 8-Me |
| phenethyl | OH | OH | —(CH₂)₂—NH— | 5-OMe |
| phenethyl | OH | OH | —(CH₂)₂—NH— | 6-OMe |
| phenethyl | OH | OH | —(CH₂)₂—NH— | 7-OMe |
| phenethyl | OH | OH | —(CH₂)₂—NH— | 8-OMe |
| Me | H | OH | —(CH₂)₂—NMe— | (non-substituted) |
| Me | H | OH | —(CH₂)₂—NMe— | 5-F |
| Me | H | OH | —(CH₂)₂—NMe— | 6-F |
| Me | H | OH | —(CH₂)₂—NMe— | 7-F |
| Me | H | OH | —(CH₂)₂—NMe— | 8-F |
| Me | H | OH | —(CH₂)₂—NMe— | 5-Cl |
| Me | H | OH | —(CH₂)₂—NMe— | 6-Cl |
| Me | H | OH | —(CH₂)₂—NMe— | 7-Cl |
| Me | H | OH | —(CH₂)₂—NMe— | 8-Cl |
| Me | H | OH | —(CH₂)₂—NMe— | 5-Me |
| Me | H | OH | —(CH₂)₂—NMe— | 6-Me |
| Me | H | OH | —(CH₂)₂—NMe— | 7-Me |
| Me | H | OH | —(CH₂)₂—NMe— | 8-Me |
| Me | H | OH | —(CH₂)₂—NMe— | 5-OMe |
| Me | H | OH | —(CH₂)₂—NMe— | 6-OMe |
| Me | H | OH | —(CH₂)₂—NMe— | 7-OMe |
| Me | H | OH | —(CH₂)₂—NMe— | 8-OMe |
| phenethyl | H | OH | —(CH₂)₂—NMe— | (non-substituted) |
| phenethyl | H | OH | —(CH₂)₂—NMe— | 5-F |
| phenethyl | H | OH | —(CH₂)₂—NMe— | 6-F |
| phenethyl | H | OH | —(CH₂)₂—NMe— | 7-F |
| phenethyl | H | OH | —(CH₂)₂—NMe— | 8-F |
| phenethyl | H | OH | —(CH₂)₂—NMe— | 5-Cl |
| phenethyl | H | OH | —(CH₂)₂—NMe— | 6-Cl |
| phenethyl | H | OH | —(CH₂)₂—NMe— | 7-Cl |
| phenethyl | H | OH | —(CH₂)₂—NMe— | 8-Cl |
| phenethyl | H | OH | —(CH₂)₂—NMe— | 5-Me |
| phenethyl | H | OH | —(CH₂)₂—NMe— | 6-Me |
| phenethyl | H | OH | —(CH₂)₂—NMe— | 7-Me |
| phenethyl | H | OH | —(CH₂)₂—NMe— | 8-Me |
| phenethyl | H | OH | —(CH₂)₂—NMe— | 5-OMe |
| phenethyl | H | OH | —(CH₂)₂—NMe— | 6-OMe |
| phenethyl | H | OH | —(CH₂)₂—NMe— | 7-OMe |
| phenethyl | H | OH | —(CH₂)₂—NMe— | 8-OMe |
| Me | OH | OH | —(CH₂)₂—NMe— | (non-substituted) |

TABLE 5-continued

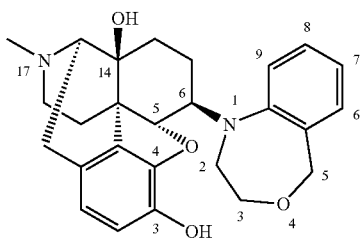

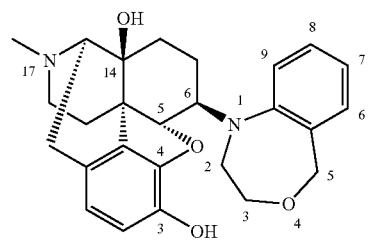

| R¹ | R² | R³ | -A- | R⁵ |
|---|---|---|---|---|
| Me | OH | OH | —(CH₂)₂—NMe— | 5-F |
| Me | OH | OH | —(CH₂)₂—NMe— | 6-F |
| Me | OH | OH | —(CH₂)₂—NMe— | 7-F |
| Me | OH | OH | —(CH₂)₂—NMe— | 8-F |
| Me | OH | OH | —(CH₂)₂—NMe— | 5-Cl |
| Me | OH | OH | —(CH₂)₂—NMe— | 6-Cl |
| Me | OH | OH | —(CH₂)₂—NMe— | 7-Cl |
| Me | OH | OH | —(CH₂)₂—NMe— | 8-Cl |
| Me | OH | OH | —(CH₂)₂—NMe— | 5-Me |
| Me | OH | OH | —(CH₂)₂—NMe— | 6-Me |
| Me | OH | OH | —(CH₂)₂—NMe— | 7-Me |
| Me | OH | OH | —(CH₂)₂—NMe— | 8-Me |
| Me | OH | OH | —(CH₂)₂—NMe— | 5-OMe |
| Me | OH | OH | —(CH₂)₂—NMe— | 6-OMe |
| Me | OH | OH | —(CH₂)₂—NMe— | 7-OMe |
| Me | OH | OH | —(CH₂)₂—NMe— | 8-OMe |
| phenethyl | OH | OH | —(CH₂)₂—NMe— | (non-substituted) |
| phenethyl | OH | OH | —(CH₂)₂—NMe— | 5-F |
| phenethyl | OH | OH | —(CH₂)₂—NMe— | 6-F |
| phenethyl | OH | OH | —(CH₂)₂—NMe— | 7-F |
| phenethyl | OH | OH | —(CH₂)₂—NMe— | 8-F |
| phenethyl | OH | OH | —(CH₂)₂—NMe— | 5-Cl |
| phenethyl | OH | OH | —(CH₂)₂—NMe— | 6-Cl |
| phenethyl | OH | OH | —(CH₂)₂—NMe— | 7-Cl |
| phenethyl | OH | OH | —(CH₂)₂—NMe— | 8-Cl |
| phenethyl | OH | OH | —(CH₂)₂—NMe— | 5-Me |
| phenethyl | OH | OH | —(CH₂)₂—NMe— | 6-Me |
| phenethyl | OH | OH | —(CH₂)₂—NMe— | 7-Me |
| phenethyl | OH | OH | —(CH₂)₂—NMe— | 8-Me |
| phenethyl | OH | OH | —(CH₂)₂—NMe— | 5-OMe |
| phenethyl | OH | OH | —(CH₂)₂—NMe— | 6-OMe |
| phenethyl | OH | OH | —(CH₂)₂—NMe— | 7-OMe |
| phenethyl | OH | OH | —(CH₂)₂—NMe— | 8-OMe |
| Me | H | OH | —CH₂—CONH— | (non-substituted) |
| Me | H | OH | —CH₂—CONH— | 5-F |
| Me | H | OH | —CH₂—CONH— | 6-F |
| Me | H | OH | —CH₂—CONH— | 7-F |
| Me | H | OH | —CH₂—CONH— | 8-F |
| Me | H | OH | —CH₂—CONH— | 5-Cl |
| Me | H | OH | —CH₂—CONH— | 6-Cl |
| Me | H | OH | —CH₂—CONH— | 7-Cl |
| Me | H | OH | —CH₂—CONH— | 8-Cl |
| Me | H | OH | —CH₂—CONH— | 5-Me |
| Me | H | OH | —CH₂—CONH— | 6-Me |
| Me | H | OH | —CH₂—CONH— | 7-Me |
| Me | H | OH | —CH₂—CONH— | 8-Me |
| Me | H | OH | —CH₂—CONH— | 5-OMe |
| Me | H | OH | —CH₂—CONH— | 6-OMe |
| Me | H | OH | —CH₂—CONH— | 7-OMe |
| Me | H | OH | —CH₂—CONH— | 8-OMe |
| phenethyl | H | OH | —CH₂—CONH— | (non-substituted) |
| phenethyl | H | OH | —CH₂—CONH— | 5-F |
| phenethyl | H | OH | —CH₂—CONH— | 6-F |
| phenethyl | H | OH | —CH₂—CONH— | 7-F |
| phenethyl | H | OH | —CH₂—CONH— | 8-F |
| phenethyl | H | OH | —CH₂—CONH— | 5-Cl |
| phenethyl | H | OH | —CH₂—CONH— | 6-Cl |
| phenethyl | H | OH | —CH₂—CONH— | 7-Cl |
| phenethyl | H | OH | —CH₂—CONH— | 8-Cl |
| phenethyl | H | OH | —CH₂—CONH— | 5-Me |
| phenethyl | H | OH | —CH₂—CONH— | 6-Me |
| phenethyl | H | OH | —CH₂—CONH— | 7-Me |
| phenethyl | H | OH | —CH₂—CONH— | 8-Me |
| phenethyl | H | OH | —CH₂—CONH— | 5-OMe |
| phenethyl | H | OH | —CH₂—CONH— | 6-OMe |
| phenethyl | H | OH | —CH₂—CONH— | 7-OMe |
| phenethyl | H | OH | —CH₂—CONH— | 8-OMe |
| Me | OH | OH | —CH₂—CONH— | (non-substituted) |
| Me | OH | OH | —CH₂—CONH— | 5-F |
| Me | OH | OH | —CH₂—CONH— | 6-F |
| Me | OH | OH | —CH₂—CONH— | 7-F |
| Me | OH | OH | —CH₂—CONH— | 8-F |
| Me | OH | OH | —CH₂—CONH— | 5-Cl |
| Me | OH | OH | —CH₂—CONH— | 6-Cl |
| Me | OH | OH | —CH₂—CONH— | 7-Cl |
| Me | OH | OH | —CH₂—CONH— | 8-Cl |
| Me | OH | OH | —CH₂—CONH— | 5-Me |
| Me | OH | OH | —CH₂—CONH— | 6-Me |
| Me | OH | OH | —CH₂—CONH— | 7-Me |
| Me | OH | OH | —CH₂—CONH— | 8-Me |
| Me | OH | OH | —CH₂—CONH— | 5-OMe |
| Me | OH | OH | —CH₂—CONH— | 6-OMe |
| Me | OH | OH | —CH₂—CONH— | 7-OMe |
| Me | OH | OH | —CH₂—CONH— | 8-OMe |
| phenethyl | OH | OH | —CH₂—CONH— | (non-substituted) |
| phenethyl | OH | OH | —CH₂—CONH— | 5-F |
| phenethyl | OH | OH | —CH₂—CONH— | 6-F |
| phenethyl | OH | OH | —CH₂—CONH— | 7-F |
| phenethyl | OH | OH | —CH₂—CONH— | 8-F |
| phenethyl | OH | OH | —CH₂—CONH— | 5-Cl |
| phenethyl | OH | OH | —CH₂—CONH— | 6-Cl |
| phenethyl | OH | OH | —CH₂—CONH— | 7-Cl |
| phenethyl | OH | OH | —CH₂—CONH— | 8-Cl |
| phenethyl | OH | OH | —CH₂—CONH— | 5-Me |
| phenethyl | OH | OH | —CH₂—CONH— | 6-Me |
| phenethyl | OH | OH | —CH₂—CONH— | 7-Me |
| phenethyl | OH | OH | —CH₂—CONH— | 8-Me |
| phenethyl | OH | OH | —CH₂—CONH— | 5-OMe |
| phenethyl | OH | OH | —CH₂—CONH— | 6-OMe |
| phenethyl | OH | OH | —CH₂—CONH— | 7-OMe |
| phenethyl | OH | OH | —CH₂—CONH— | 8-OMe |
| Me | H | OH | —CH₂—CONMe— | (non-substituted) |
| Me | H | OH | —CH₂—CONMe— | 5-F |
| Me | H | OH | —CH₂—CONMe— | 6-F |
| Me | H | OH | —CH₂—CONMe— | 7-F |
| Me | H | OH | —CH₂—CONMe— | 8-F |
| Me | H | OH | —CH₂—CONMe— | 5-Cl |
| Me | H | OH | —CH₂—CONMe— | 6-Cl |
| Me | H | OH | —CH₂—CONMe— | 7-Cl |
| Me | H | OH | —CH₂—CONMe— | 8-Cl |
| Me | H | OH | —CH₂—CONMe— | 5-Me |
| Me | H | OH | —CH₂—CONMe— | 6-Me |
| Me | H | OH | —CH₂—CONMe— | 7-Me |
| Me | H | OH | —CH₂—CONMe— | 8-Me |
| Me | H | OH | —CH₂—CONMe— | 5-OMe |
| Me | H | OH | —CH₂—CONMe— | 6-OMe |
| Me | H | OH | —CH₂—CONMe— | 7-OMe |
| Me | H | OH | —CH₂—CONMe— | 8-OMe |
| phenethyl | H | OH | —CH₂—CONMe— | (non-substituted) |
| phenethyl | H | OH | —CH₂—CONMe— | 5-F |
| phenethyl | H | OH | —CH₂—CONMe— | 6-F |
| phenethyl | H | OH | —CH₂—CONMe— | 7-F |
| phenethyl | H | OH | —CH₂—CONMe— | 8-F |
| phenethyl | H | OH | —CH₂—CQNMe— | 5-Cl |
| phenethyl | H | OH | —CH₂—CONMe— | 6-Cl |
| phenethyl | H | OH | —CH₂—CONMe— | 7-Cl |

TABLE 5-continued

| R¹ | R² | R³ | -A- | R⁵ |
|---|---|---|---|---|
| phenethyl | H | OH | —CH₂—CONMe— | 8-Cl |
| phenethyl | H | OH | —CH₂—CONMe— | 5-Me |
| phenethyl | H | OH | —CH₂—CONMe— | 6-Me |
| phenethyl | H | OH | —CH₂—CONMe— | 7-Me |
| phenethyl | H | OH | —CH₂—CONMe— | 8-Me |
| phenethyl | H | OH | —CH₂—CONMe— | 5-OMe |
| phenethyl | H | OH | —CH₂—CONMe— | 6-OMe |
| phenethyl | H | OH | —CH₂—CONMe— | 7-OMe |
| phenethyl | H | OH | —CH₂—CONMe— | 8-OMe |
| Me | OH | OH | —CH₂—CONMe— | (non-substituted) |
| Me | OH | OH | —CH₂—CONMe— | 5-F |
| Me | OH | OH | —CH₂—CONMe— | 6-F |
| Me | OH | OH | —CH₂—CONMe— | 7-F |
| Me | OH | OH | —CH₂—CONMe— | 8-F |
| Me | OH | OH | —CH₂—CONMe— | 5-Cl |
| Me | OH | OH | —CH₂—CONMe— | 6-Cl |
| Me | OH | OH | —CH₂—CONMe— | 7-Cl |
| Me | OH | OH | —CH₂—CONMe— | 8-Cl |
| Me | OH | OH | —CH₂—CONMe— | 5-Me |
| Me | OH | OH | —CH₂—CONMe— | 6-Me |
| Me | OH | OH | —CH₂—CONMe— | 7-Me |
| Me | OH | OH | —CH₂—CONMe— | 8-Me |
| Me | OH | OH | —CH₂—CONMe— | 5-OMe |
| Me | OH | OH | —CH₂—CONMe— | 6-OMe |
| Me | OH | OH | —CH₂—CONMe— | 7-OMe |
| Me | OH | OH | —CH₂—CONMe— | 8-OMe |
| phenethyl | OH | OH | —CH₂—CONMe— | (non-substituted) |
| phenethyl | OH | OH | —CH₂—CONMe— | 5-F |
| phenethyl | OH | OH | —CH₂—CONMe— | 6-F |
| phenethyl | OH | OH | —CH₂—CONMe— | 7-F |
| phenethyl | OH | OH | —CH₂—CONMe— | 8-F |
| phenethyl | OH | OH | —CH₂—CONMe— | 5-Cl |
| phenethyl | OH | OH | —CH₂—CONMe— | 6-Cl |
| phenethyl | OH | OH | —CH₂—CONMe— | 7-Cl |
| phenethyl | OH | OH | —CH₂—CONMe— | 8-Cl |
| phenethyl | OH | OH | —CH₂—CONMe— | 5-Me |
| phenethyl | OH | OH | —CH₂—CONMe— | 6-Me |
| phenethyl | OH | OH | —CH₂—CONMe— | 7-Me |
| phenethyl | OH | OH | —CH₂—CONMe— | 8-Me |
| phenethyl | OH | OH | —CH₂—CONMe— | 5-OMe |
| phenethyl | OH | OH | —CH₂—CONMe— | 6-OMe |
| phenethyl | OH | OH | —CH₂—CONMe— | 7-OMe |
| phenethyl | OH | OH | —CH₂—CONMe— | 8-OMe |
| Me | H | OH | —(CH₂)₂—O—CH₂— | (non-substituted) |
| Me | H | OH | —(CH₂)₂—O—CH₂— | 6-F |
| Me | H | OH | —(CH₂)₂—O—CH₂— | 7-F |
| Me | H | OH | —(CH₂)₂—O—CH₂— | 8-F |
| Me | H | OH | —(CH₂)₂—O—CH₂— | 9-F |
| Me | H | OH | —(CH₂)₂—O—CH₂— | 6-Cl |
| Me | H | OH | —(CH₂)₂—O—CH₂— | 7-Cl |
| Me | H | OH | —(CH₂)₂—O—CH₂— | 8-Cl |
| Me | H | OH | —(CH₂)₂—O—CH₂— | 9-Cl |
| Me | H | OH | —(CH₂)₂—O—CH₂— | 6-Me |
| Me | H | OH | —(CH₂)₂—O—CH₂— | 7-Me |
| Me | H | OH | —(CH₂)₂—O—CH₂— | 8-Me |
| Me | H | OH | —(CH₂)₂—O—CH₂— | 9-Me |
| Me | H | OH | —(CH₂)₂—O—CH₂— | 6-OMe |
| Me | H | OH | —(CH₂)₂—O—CH₂— | 7-OMe |
| Me | H | OH | —(CH₂)₂—O—CH₂— | 8-OMe |
| Me | H | OH | —(CH₂)₂—O—CH₂— | 9-OMe |
| phenethyl | H | OH | —(CH₂)₂—O—CH₂— | (non-substituted) |
| phenethyl | H | OH | —(CH₂)₂—O—CH₂— | 6-F |
| phenethyl | H | OH | —(CH₂)₂—O—CH₂— | 7-F |
| phenethyl | H | OH | —(CH₂)₂—O—CH₂— | 8-F |
| phenethyl | H | OH | —(CH₂)₂—O—CH₂— | 9-F |
| phenethyl | H | OH | —(CH₂)₂—O—CH₂— | 6-Cl |
| phenethyl | H | OH | —(CH₂)₂—O—CH₂— | 7-Cl |
| phenethyl | H | OH | —(CH₂)₂—O—CH₂— | 8-Cl |
| phenethyl | H | OH | —(CH₂)₂—O—CH₂— | 9-Cl |
| phenethyl | H | OH | —(CH₂)₂—O—CH₂— | 6-Me |
| phenethyl | H | OH | —(CH₂)₂—O—CH₂— | 7-Me |
| phenethyl | H | OH | —(CH₂)₂—O—CH₂— | 8-Me |
| phenethyl | H | OH | —(CH₂)₂—O—CH₂— | 9-Me |
| phenethyl | H | OH | —(CH₂)₂—O—CH₂— | 6-OMe |
| phenethyl | H | OH | —(CH₂)₂—O—CH₂— | 7-OMe |
| phenethyl | H | OH | —(CH₂)₂—O—CH₂— | 8-OMe |
| phenethyl | H | OH | —(CH₂)₂—O—CH₂— | 9-OMe |
| Me | OH | OH | —(CH₂)₂—O—CH₂— | (non-substituted) |
| Me | OH | OH | —(CH₂)₂—O—CH₂— | 6-F |
| Me | OH | OH | —(CH₂)₂—O—CH₂— | 7-F |
| Me | OH | OH | —(CH₂)₂—O—CH₂— | 8-F |
| Me | OH | OH | —(CH₂)₂—O—CH₂— | 9-F |
| Me | OH | OH | —(CH₂)₂—O—CH₂— | 6-Cl |
| Me | OH | OH | —(CH₂)₂—O—CH₂— | 7-Cl |
| Me | OH | OH | —(CH₂)₂—O—CH₂— | 8-Cl |
| Me | OH | OH | —(CH₂)₂—O—CH₂— | 9-Cl |
| Me | OH | OH | —(CH₂)₂—O—CH₂— | 6-Me |
| Me | OH | OH | —(CH₂)₂—O—CH₂— | 7-Me |
| Me | OH | OH | —(CH₂)₂—O—CH₂— | 8-Me |
| Me | OH | OH | —(CH₂)₂—O—CH₂— | 9-Me |
| Me | OH | OH | —(CH₂)₂—O—CH₂— | 6-OMe |
| Me | OH | OH | —(CH₂)₂—O—CH₂— | 7-OMe |
| Me | OH | OH | —(CH₂)₂—O—CH₂— | 8-OMe |
| Me | OH | OH | —(CH₂)₂—O—CH₂— | 9-OMe |
| phenethyl | OH | OH | —(CH₂)₂—O—CH₂— | (non-substituted) |
| phenethyl | OH | OH | —(CH₂)₂—O—CH₂— | 6-F |
| phenethyl | OH | OH | —(CH₂)₂—O—CH₂— | 7-F |
| phenethyl | OH | OH | —(CH₂)₂—O—CH₂— | 8-F |
| phenethyl | OH | OH | —(CH₂)₂—O—CH₂— | 9-F |
| phenethyl | OH | OH | —(CH₂)₂—O—CH₂— | 6-Cl |
| phenethyl | OH | OH | —(CH₂)₂—O—CH₂— | 7-Cl |
| phenethyl | OH | OH | —(CH₂)₂—O—CH₂— | 8-Cl |
| phenethyl | OH | OH | —(CH₂)₂—O—CH₂— | 9-Cl |
| phenethyl | OH | OH | —(CH₂)₂—O—CH₂— | 6-Me |
| phenethyl | OH | OH | —(CH₂)₂—O—CH₂— | 7-Me |
| phenethyl | OH | OH | —(CH₂)₂—O—CH₂— | 8-Me |
| phenethyl | OH | OH | —(CH₂)₂—O—CH₂— | 9-Me |
| phenethyl | OH | OH | —(CH₂)₂—O—CH₂— | 6-OMe |
| phenethyl | OH | OH | —(CH₂)₂—O—CH₂— | 7-OMe |
| phenethyl | OH | OH | —(CH₂)₂—O—CH₂— | 8-OMe |
| phenethyl | OH | OH | —(CH₂)₂—O—CH₂— | 9-OMe |

The morphinan derivatives represented by the above-described Formula (I), having a nitrogen-containing hetrocyclic group used as the effective ingredient of the therapeutic or prophylactic agent for urinary frequency or urinary incontinence may be produced by the methods hereinbelow described.

Among the compounds represented by Formula (I) (wherein $R^1$, $R^2$, $R^3$, $R^4$, $R^9$, $R^{10}$, $R^{11}$, X, Y, Z and k represent the same meanings as described above), the cyclic aminocompounds (Ia) wherein both Y and Z are valence bonds may be synthesized by the reductive amination reaction from the 6-oxo compound represented by Formula (IV)

(wherein $R^1$, $R^2$, $R^3$, $R^9$, $R^1$ and $R^{11}$ represent the same meanings as described above) through iminium salt (Va) (wherein $R^1$, $R^2$, $R^3$, $R^4$, $R^9$, $R^{10}$, $R^{11}$, X and k represent the same meanings as described above) or enamine (Vb) (wherein $R^1$, $R^2$, $R^3$, $R^4$, $R^9$, $R^{10}$, $R^{11}$, X, Y, Z and k represent the same meanings as described above), as shown by Scheme 1 below.

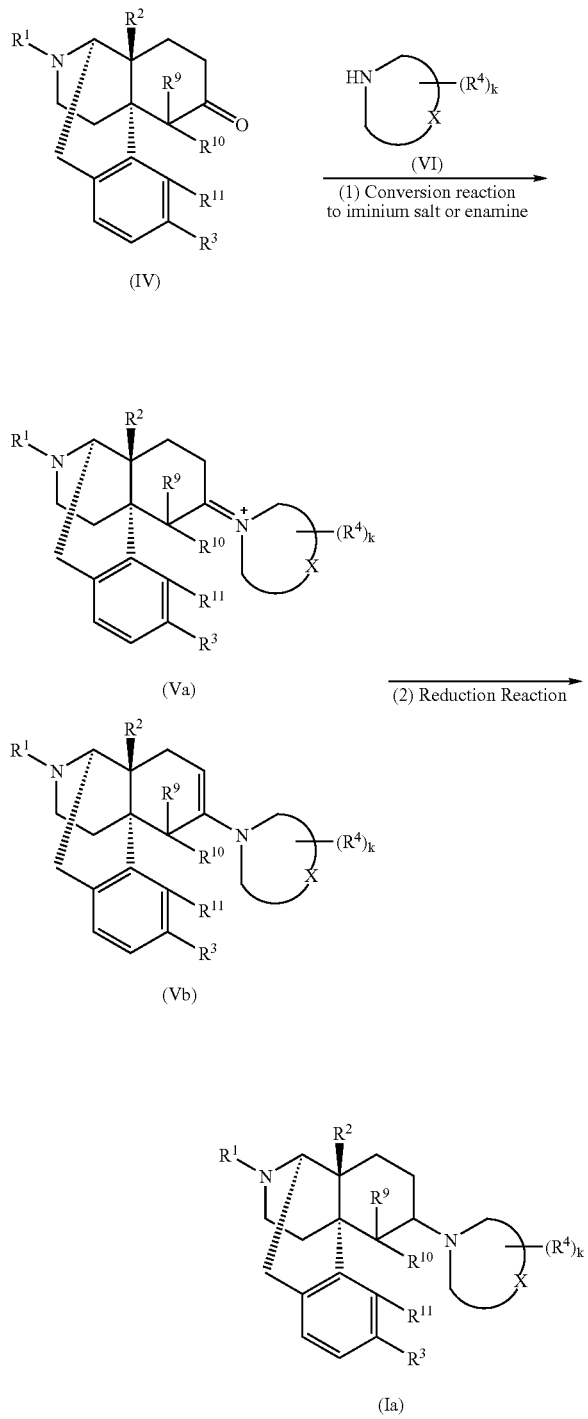

This reaction comprises two steps, that is, (1) conversion reaction to the iminium salt or enamine using an acid catalyst, and (2) reduction by a metal hydride reducing agent or hydrogenation reaction in the presence of acid and metal catalysts. The 6-oxo compound represented by Formula (IV) used as a starting material of this reaction is described in, for example, J. Org. Chem. 4, 220 (1939), J. Org. Chem. 15, 1103 (1950) and so on, and may be produced by the method described in this reference.

The step (1), that is, the conversion reaction to the iminium salt or enamine is the reaction to obtain an iminium salt (Va) or an enamine (Vb) from the oxo compound (IV) and an amine (VI) (wherein $R^4$, X and k represent the same meanings as described above). This reaction may be carried out by the method described in, for example, J. Org. Chem. 45, 3366 (1980), WO93/15081 and the like, that is, by the method in which the oxo compound (IV) and the amine (VI) are heated to reflux in an appropriate reaction solvent and the generated water is removed by azeotropic distillation together with the reaction solvent or by using a Dean-Stark water trap so as to proceed the reaction. Adding an appropriate dehydrating agent to the reaction system is also a preferred method for generating the iminium salt (Va) or the enamine (Vb). The dehydrating agent used here is not restricted, and inorganic dehydrating agents such as molecular sieve, anhydrous calcium sulfate, anhydrous copper sulfate, anhydrous sodium sulfate, anhydrous magnesium sulfate and anhydrous calcium chloride; and organic dehydrating agents such as ortho esters, acid anhydrides, dicyclohexylcarbodiimide, sulfur trioxide-pyridine complex, phosphorus oxychloride and thionyl chloride may be used. Among these, organic dehydrating agents such as ortho esters, dicyclohexylcarbodiimide, sulfur trioxide-pyridine complex are preferred, and ortho esters are especially preferred.

The amount of the amine (VI) used in this step is not restricted, and is usually 0.5 to 50 equivalents, preferably 1 to 30 equivalents, more preferably 1 to 10 equivalents.

As the acid to be made to coexist, any acid which usually forms a salt with amines may be used. Examples of the acid include inorganic acids such as hydrochloric acid, hydrobromic acid, sulfuric acid and phosphoric acid; sulfonic acids such as methanesulfonic acid and p-toluenesulfonic acid; and carboxylic acids such as benzoic acid, acetic acid and oxalic acid. Among these, hydrochloric acid, sulfuric acid, methanesulfonic acid, p-toluenesulfonic acid and benzoic acid are preferred, and p-toluenesulfonic acid and benzoic acid are especially preferred. The amount of the acid to be made to coexist is not restricted, and the reaction may be carried out in an amount of 0.5 to 50 equivalents. Satisfactory results are usually obtained by using 1 to 30 equivalents, preferably 1 to 10 equivalents of the acid.

In case of using an ortho ester as the dehydrating agent, examples of the ortho ester with which the reaction may be carried out include ortho formic acid esters such as trimethyl ortho formate, triethyl ortho formate, tri-n-propyl ortho formate, triisopropyl ortho formate, diethylphenyl ortho formate and tri-n-butyl ortho formate; ortho acetic acid esters such as trimethyl ortho acetate, triethyl ortho acetate, tri-n-propyl ortho acetate and triisopropyl ortho acetate; ortho propionic acid esters such as trimethyl ortho propionate, triethyl ortho propionate, tri-n-propyl ortho propionate and triisopropyl ortho propionate; ortho butyric acid esters such as trimethyl ortho butyrate, triethyl ortho butyrate, tri-n-propyl ortho butyrate and triisopropyl ortho butyrate; and ortho benzoic acid esters such as trimethyl ortho benzoate, triethyl ortho benzoate, tri-n-propyl ortho benzoate and triisopropyl ortho benzoate. Usually, ortho formic acid esters such as trimethyl ortho formate, triethyl ortho formate, tri-n-propyl ortho formate and triisopropyl ortho formate; and ortho acetic acid esters such as trimethyl ortho acetate, triethyl ortho acetate, tri-n-propyl ortho acetate and triisopropyl ortho acetate are used, and among these, trimethyl ortho formate, triethyl ortho formate, trimethyl ortho acetate, triethyl ortho acetate are preferred. Although the ortho ester may be used as the reaction solvent, usually 0.5 to 10 equivalents, preferably 1 to 5 equivalents of the ortho ester is used. The ortho ester may be made to coexist at the beginning of the reaction, or may be added sequentially and dividedly with the progress of the reaction.

As the reaction solvent, although not restricted, ether solvents such as tetrahydrofuran (THF), ether, dimethoxyethane (DME) and dioxane; aromatic hydrocarbon solvents such as benzene, toluene, xylene, and mesitylene; and polar solvents such as dimethylformamide (DMF) and dimethylsufoxide (DMSO) may be used. These solvents may be used individually or two or more of the solvents may be used in combination. Among these solvents, THF, toluene, xylene and DMF, as well as mixture of these solvents, are preferred.

The concentration of the oxo compound (IV) in the reaction mixture is not restricted, and satisfactory results are usually obtained at a concentration of 1 mmol/L to 1 mol/L. The reaction temperature may usually be 0 to 250° C., preferably 0 to 200° C., and satisfactory results are obtained at 20 to 150° C. The reaction time is appropriately selected depending on the conditions such as reaction temperature, satisfactory results are usually obtained when the reaction time is 3 to 100 hours.

In the reduction reaction in step (2), although, usually, the iminium salt (Va) or the enamine (Vb) is reduced by a metal hydride reducing agent or hydrogenation is carried out in the presence of an acid and metal catalysts without isolating the iminium salt (Va) or enamine (Vb), the desired cyclic amine compound (Ia) may be obtained even when the iminium salt (Va) or enamine (Vb) is isolated.

As the reaction solvent, although the solvent used for the conversion to the iminium salt or the enamine may be used as it is, preferred results are obtained by using an alcoholic solvent such as methanol or ethanol, especially by adding methanol. Alternatively, the reaction solvent used for the conversion to the iminium salt or the enamine may be evaporated under reduced pressure, and the reaction may be carried out using the alcoholic solvent alone such as methanol or ethanol.

As for the metal hydride reducing agent, the reaction may be carried out using a metal hydride reducing agent which is comparatively stable in the presence of an acid, such as sodium borohydride, sodium cyanoborohydride, zinc borohydride, sodium triacetoxy borohydride, tetramethylammonium triacetoxy borohydride or borane-pyridine complex. Among these, sodium cyanoborohydride, sodium triacetoxy borohydride or borane-pyridine complex is preferably used. The metal hydride reducing agent may be used in an amount of 0.5 to 50 equivalents, usually 1 to 20 equivalents, preferably 1 to 10 equivalents. As for reaction temperature, satisfactory results are obtained usually at −40° C. to 150° C., preferably −30° C. to 80° C. The reaction time is appropriately selected depending on the conditions such as reaction temperature, and satisfactory results are usually obtained when the reaction time is about 30 minutes to 10 hours. The concentration of the substrate (Va) or (Vb) in the reaction mixture is not restricted, and usually 1 mmol/L to 1 mol/L is preferred.

In case of conducting hydrogenation in the presence the acid and metal catalysts, as the reaction solvent, although the solvent used for the conversion to the iminium salt or the enamine may be used as it is, preferred results are also obtained when an alcoholic solvent such as methanol or ethanol, or an ether solvent such as THF or ether is added. Alternatively, the reaction solvent used for the conversion to the iminium salt or the enamine may be evaporated under reduced pressure, and the reaction may be carried out using the alcoholic solvent such as methanol or ethanol or the ether solvent such as THF or ether alone. As the acid to be made to coexist, any acid which forms a salt with an amine may usually be used. Examples of such an acid include inorganic acids such as hydrochloric acid, hydrobromic acid, sulfuric acid and phosphoric acid; sulfonic acids such as methanesulfonic acid and p-toluenesulfonic acid; and carboxylic acids such as benzoic acid, acetic acid and oxalic acid. Among these, hydrochloric acid, sulfuric acid, methanesulfonic acid, p-toluenesulfonic acid and benzoic acid are preferred, and p-toluenesulfonic acid and benzoic acid are especially preferred. The amount of the acid to be made to coexist is not restricted, and the reaction can be carried out at an amount of 0.5 to 50 equivalents. Satisfactory results may be obtained usually at an amount of 1 to 30 equivalents, preferably 1 to 10 equivalents.

As the metal catalyst, although any of the catalysts which are used for usual hydrogenation reaction, such as platinum oxide, palladium hydroxide and palladium-carbon may be used, platinum oxide or palladium-carbon is preferably employed. The reaction may be carried out at a reaction temperature of −30° C. to 80° C., preferably 10° C. to 50° C., under a hydrogen pressure of 1 atm to 100 atm, preferably 1 atm to 30 atm, and preferred results are usually obtained at room temperature under normal pressure. The reaction time is appropriately selected depending on the conditions, and satisfactory results are usually obtained when the reaction time is about 0.5 to 30 hours. The concentration of the substrate (Va) or (Vb) in the reaction mixture is not restricted, and usually 1 mmol/L to 1 mol/L is preferred.

Although α-isomer and β-isomer of the cyclic amino compound (Ia) are thought to be generated, they may be purified by usual column chromatography, recrystallization or slurry washing method, etc.

Among the compounds represented by Formula (I) (wherein $R^1$, $R^2$, $R^3$, $R^4$, $R^9$, $R^{10}$, $R^{11}$, X, Y, Z and k represent the same meanings as described above), the cyclic amide compounds (Ib) (wherein $R^1$, $R^2$, $R^3$, $R^4$, $R^9$, $R^{10}$, $R^{11}$ and k represent the same meanings as described above) wherein Y is —C(=O)— and Z is valence bond may be produced by the usual alkylation or amidation reaction of amino group so as to attain intramolecular cyclization, from the compound represented by Formula (VIIa) (wherein $R^1$, $R^2$, $R^3$, $R^4$, $R^9$, $R^{10}$, $R^{11}$ and k represent the same meanings as described above, T is chlorine, bromine, iodine or OTs or OMs) or the compound represented by Formula (VIIb) [wherein $R^1$, $R^2$, $R^3$, $R^4$, $R^9$, $R^{10}$, $R^{11}$ and k represent the same meanings as described above, T' is chlorine or $OR^{12}$ (wherein $R^{12}$ is hydrogen, $C_1$-$C_5$ alkoxy, $C_7$-$C_{13}$ aralkyloxy or $C_1$-$C_5$ alkanoyloxy)], as shown by Scheme 2 below. The compounds represented by Formula (VIIa) or (VIIb) used as the starting materials of the reaction shown in Scheme 2 may be obtained by the method described in WO93/15081 and so on.

Scheme 2

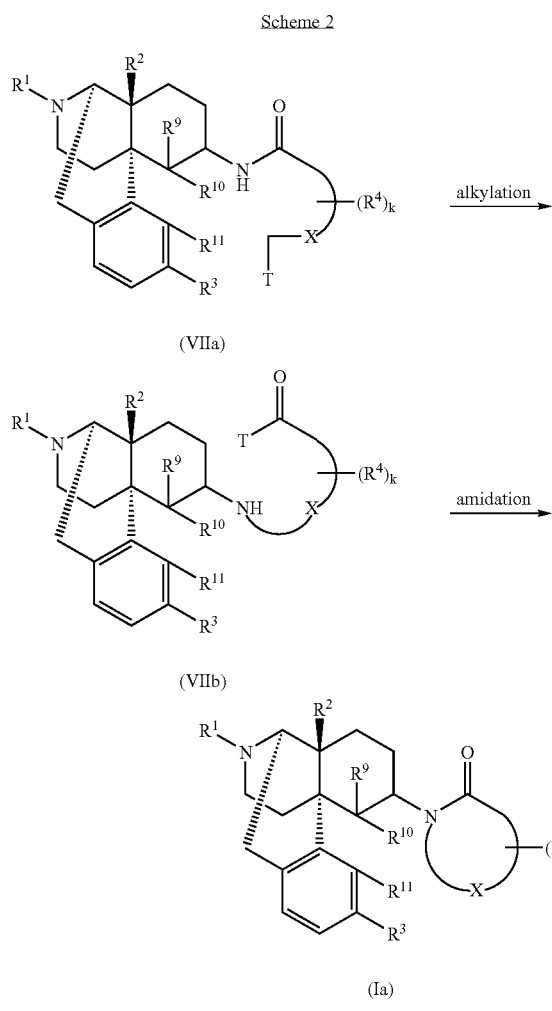

The alkylation or amidation may be carried out generally by a method in which a base is made to coexist in a solvent.

As the base, inorganic bases such as potassium carbonate, cesium carbonate, sodium hydroxide and potassium hydroxide; metal hydrides such as sodium hydride and potassium hydride; metal alkoxides such as sodium ethoxide and potassium t-butoxide; and organic bases such as triethylamine, diisopropylethylamine, pyridine and 4-dimethylaminopyridine may be used. The base is used in an amount of 1 to equivalents, preferably 1 to 10 equivalents with respect to the substrate. In case of amidation reaction, satisfactory results may be obtained without using a base in some cases.

As the solvent, aprotic polar solvents such as DMF, dimethylacetoamide and DMSO; ether solvents such as diethyl ether, THF, DME and dioxane; hydrocarbon solvents such as benzene and toluene; and halogen-containing solvents such as dichloromethane, chloroform and 1,2-dichloroethane may be used. Among these, DMF, THF and toluene are preferred.

As for the reaction temperature, satisfactory results may be usually obtained at −20° C. to 200° C., preferably 0° C. to 150° C. The reaction time is appropriately selected depending on the conditions such as reaction temperature, and satisfactory results are usually obtained when the reaction time is about 30 minutes to 100 hours. The concentration of the substrate (VIIa) or (VIIb) in the reaction mixture is not restricted, and usually 1 mmol/L to 1 mol/L is preferred.

Among the compounds represented by Formula (I) (wherein $R^1$, $R^2$, $R^3$, $R^4$, $R^9$, $R^{10}$, $R^{11}$, X, Y, Z and k represent the same meanings as described above), the cyclic imide derivatives represented by Formula (Ic) (wherein $R^1$, $R^2$, $R^3$, $R^4$, $R^9$, $R^{10}$ and $R^{11}$ represent the same meanings as described above) may be produced by reacting the primary amino compound represented by Formula (VIII) (wherein $R^1$, $R^2$, $R^3$, $R^9$, $R^{10}$ and $R^{11}$ represent the same meanings as described above) with the acid anhydride represented by Formula (IX) (wherein $R^4$ represents the same meaning as described above), as shown in Scheme 3 below. As required, the reaction may be carried out while making an acid or a base coexist in the reaction system.

Scheme 3

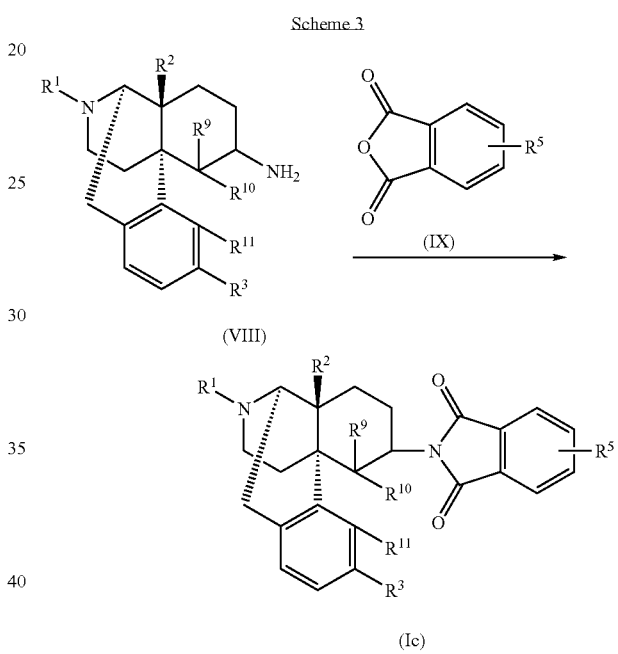

Acid anhydride (IX) may be used in an amount of 0.5 to 50 equivalents with respect to primary amino compound (VIII), preferably 1 to 20 equivalents, more preferably 1 to 10 equivalents. As the solvent, aprotic polar solvents such as DMF, dimethylacetoamide and DMSO; ether solvents such as diethyl ether, THF, DME and dioxane; hydrocarbon solvents such as benzene, toluene and xylene; and halogen-containing solvents such as dichloromethane, chloroform and 1,2-dichloroethane; alcoholic solvents such as methanol, ethanol, propanol and butanol; and acidic solvents such as acetic acid and propionic acid may be used. Among these, DMF, toluene and acetic acid are preferred.

Examples of the base which may be made to coexist as required include inorganic bases such as sodium carbonate, potassium carbonate, cesium carbonate and sodium acetate; and organic bases such as triethylamine, diisopropylethylamine, pyridine and 4-dimethylaminopyridine. Among these, triethylamine, pyridine, potassium carbonate and sodium carbonate are preferred. The base is used in an amount of 1 to 30 equivalents, preferably 1 to 10 equivalents with respect to the substrate. On the other hand, as the acid, inorganic acids such as hydrochloric acid, sulfuric acid and phosphoric acid; carboxylic acids such as acetic acid, propionic acid and benzoic acid; and sulfonic acids such as methanesulfonic acid, benzenesulfonic acid and p-toluenesulfonic acid may be used. Among these, carboxylic acids such as acetic acid, propionic acid and benzoic acid are preferred, and acetic acid is particularly preferred. The acid is used in an amount of 1 to 30 equivalents, preferably 1 to 10 equivalents with respect to the substrate.

As for the reaction temperature, satisfactory results may be usually obtained at −20° C. to 200° C., preferably 0° C. to 150° C. The reaction time is appropriately selected depending on the conditions such as reaction temperature, and satisfactory results are usually obtained when the reaction time is about 30 minutes to 30 hours. The concentration of the substrate (VIII) in the reaction mixture is not restricted, and usually 1 mmol/L to 1 mol/L is preferred.

The primary amino compound represented by Formula (VIII) used as a starting material of Scheme 3 may be synthesized by the method described in J. Med. Chem. 20, 1100 (1977), J. Org. Chem. 45, 3366 (1980) and so on. That is, the primary amino compound (IX) may be obtained with a high yield by the method comprising the three steps of (1) reacting the oxo compound (IV) with a primary or secondary amine having a deprotectable substituent to form an iminium salt or enamine; (2) reduction by a metal hydride reducing agent or hydrogenation in the presence of acid and metal catalysts; and (3) removal of the deprotectable substituent.

As the deprotectable substituent, any of the usual protective groups of amino group, described in, for example, PROTECTIVE GROUPS IN ORGANIC SYNTHESIS (JHON WILEY & SONS, INC. 1991) may be used. Preferred examples thereof include allyl, benzyl, 4-methoxybenzyl, 3,4-dimethoxybenzyl, 2-nitrobenzyl, 4-nitrobenzyl, 4-cyanobenzyl, dibenzosuberyl, diphenylmethyl, di(4-methoxyphenyl)methyl, triphenylmethyl, (4-methoxyphenyl), diphenylmethyl, fluorenyl, 9-phenylfluorenyl and ferrocenyl methyl. Among these, allyl, benzyl, 4-methoxybenzyl, 3,4-dimethoxybenzyl, 2-nitrobenzyl and 4-nitrobenzyl are preferred, and benzyl is especially preferred.

Good results are obtained in the step (1), that is, the reaction for conversion to the iminium salt or enamine, by reacting the oxo compound (IV) and the amine in the presence of an acid catalyst and a dehydrating agent as in the above-described Scheme 1. In this reaction, as the dehydrating agent, an ortho ester may preferably be employed.

The step (2), that is, the reduction by the metal hydride reducing agent or the hydrogenation reaction in the presence of the acid and metal catalysts may be carried out in the same manner as in the above-described Scheme 1.

The step (3), that is, the removal of the deprotectable substituent may be carried out by, for example, conducting hydrogenolysis in the presence of a metal catalyst using hydrogen gas as hydrogen source, when benzyl is employed as the deprotectable substituent. In this case, as the metal catalyst, any of the catalysts used for usual hydrogenolysis may be employed. Examples thereof include platinum catalysts such as platinum oxide and platinum hydroxide; palladium catalysts such as palladium hydroxide and palladium-carbon; and nickel catalysts such as Raney nickel. Among these, palladium catalysts, particularly, palladium-carbon is preferred.

As the reaction solvent, any of the solvents which is inert under the conditions of hydrogenation may be used. Examples thereof include alcoholic solvents such as methanol, ethanol and propanol; ether solvents such as THF, ether, DME and dioxane; and aromatic hydrocarbon solvents such as benzene, toluene and xylene. Among these, alcoholic solvents, particularly, methanol and ethanol are preferred.

The reaction may be carried out in the co-presence of an acid. In this case, as the acid catalyst, inorganic acids such as hydrochloric acid, hydrobromic acid, sulfuric acid and phosphoric acid; sulfonic acids such as methanesulfonic acid, benzenesulfonic acid, p-toluenesulfonic acid, camphorsulfonic acid; and carboxylic acids such as benzoic acid, acetic acid, oxalic acid and phthalic acid may be employed. Among these, inorganic acids such as hydrochloric acid and sulfuric acid; carboxylic acids such as acetic acid, benzoic acid and phthalic acid are preferred, and hydrochloric acid, acetic acid, benzoic acid and phthalic acid are particularly preferred. The reaction may be carried out at a reaction temperature of 0 to 150° C., preferably 10 to 100° C., under a hydrogen pressure of 1 to 100 atm, preferably 1 to 30 atm. Satisfactory results may usually be obtained at 20° C. to 80° C., at 1 to 10 atm. The reaction time is appropriately selected depending on the reaction conditions, and satisfactory results are usually obtained when the reaction time is 0.5 to 100 hours.

As the hydrogen source, a formic acid or its derivative such as ammonium formate may be used in place of hydrogen gas. Although the reaction may be carried out by using the formic acid or its derivative in an amount of 0.5 to 100 equivalents, the formic acid or its derivative may usually be used in an amount of 1 to 50 equivalents, preferably 1 to 10 equivalents. In this case, the conditions such as the metal catalyst, reaction solvent and reaction temperature are similar to those employed in the hydrogenolysis using hydrogen gas as the hydrogen source.

The cyclic imide derivative represented by Formula (Ic) (wherein $R^1$, $R^2$, $R^3$, $R^4$, $R^9$, $R^{10}$ and $R^{11}$ represent the same meanings as described above) may also be produced by Mitsunobu reaction described in Tetrahedron. 50, 9757 (1994). Among the compounds represented by Formula (I) (wherein $R^1$, $R^2$, $R^3$, $R^4$, $R^9$, $R^{10}$, $R^{11}$, X, Y, Z and k represent the same meanings as described above), the compounds wherein Y is —C(=O)—, that is, the compounds represented by Formula (XIa) or (XIb) (wherein $R^1$, $R^2$, $R^3$, $R^9$, $R^{10}$, $R^{11}$, X and Z represent the same meanings as described above, $R^{13}$ is $C_1$-$C_5$ alkyl or $C_7$-$C_{13}$ aralkyl) may be produced by alkylating or acylating the compounds represented by Formula (X) (wherein $R^1$, $R^2$, $R^3$, $R^9$, $R^{10}$, $R^{11}$, X and Z represent the same meanings as described above) in a solvent in the co-presence of a base, as shown in Scheme 4 below. The compounds of Formula (X) used as a starting material of Scheme 4 may be obtained by the method shown in Scheme 2.

Scheme 4

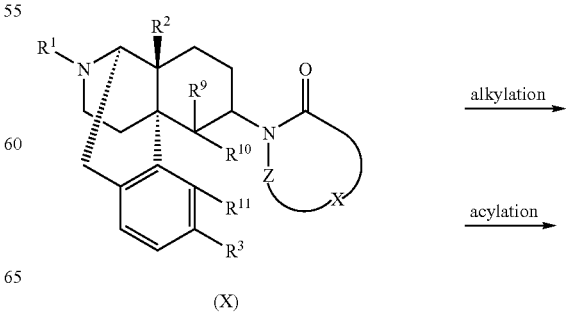

(X)

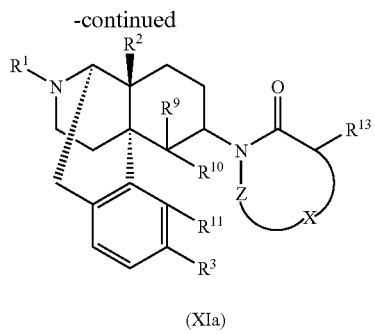

(XIa)

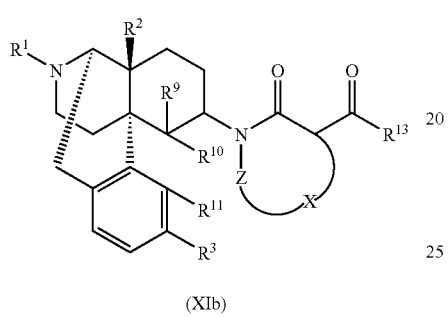

(XIb)

An alkylation agent or acylation agent may preferably be used in an amount of 1 to 20 equivalents, and satisfactory results are obtained by using the alkylation agent or acylation agent in an amount of 1 to 10 equivalents.

As the base, organic lithium reagents such as methyl lithium, butyl lithium and LDA; metal hydrides such as sodium hydride and potassium hydride; and metal alkoxide such as sodium ethoxide, potassium t-butoxide may be used, and LDA and butyl lithium are preferred. The base may be used in an amount of 1 to 30 equivalents, preferably 1 to 10 equivalents with respect to the substrate.

As the solvent, aprotic polar solvents such as DMF, dimethylacetoamide and DMSO; ether solvents such as diethyl ether, THF, DME and dioxane; and hydrocarbon solvents such as pentane, hexane, benzene and toluene may be used. Among these, THF and DME are preferred.

As for the reaction temperature, satisfactory results may be usually obtained at −100° C. to 200° C., preferably −80° C. to 150° C. The reaction time is appropriately selected depending on the conditions such as reaction temperature, and satisfactory results are usually obtained when the reaction time is about 30 minutes to 30 hours. The concentration of the substrate (X) in the reaction mixture is not restricted, and usually 1 mmol/L to 1 mol/L is preferred.

When synthesizing the compounds represented by Formula (I) wherein $R^3$ is hydroxy, that is, the compounds represented by Formula (XIII) (wherein $R^1$, $R^2$, $R^4$, $R^9$, $R^{10}$, $R^{11}$, X, Y, Z and k represent the same meanings as described above), the compounds may be synthesized through the compounds of Formula (XII) (wherein $R^1$, $R^2$, $R^4$, $R^9$, $R^{10}$, $R^{11}$, X, Y, Z and k represent the same meanings as described above), wherein $R^3$ is methoxy, in order to protect the phenol moiety. In this case, the deprotection may be carried out by the usual demethylation reaction of phenolic methyl ether, as shown in Scheme 5, more particularly, by (1) a method in which boron tribromide is used, or (2) a method in which an alkylthiol is used under basic condition.

Scheme 5

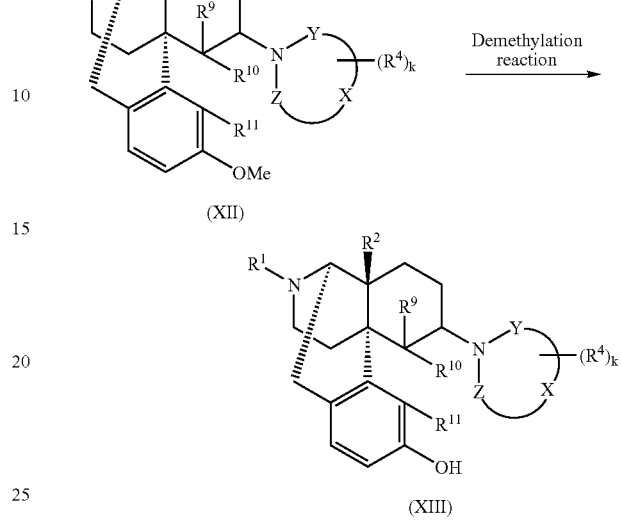

In the method (1), the amount of the boron tribromide is preferably 1 to 20 equivalents, and satisfactory results are obtained by using boron tribromide in an amount of 1 to 7 equivalents. As the reaction solvent, halogen-containing solvents such as dichloromethane, chloroform and 1,2-dichloroethane are preferred, and dichloromethane is preferred. The reaction temperature is preferably −70° C. to 50° C., and satisfactory results are obtained when the reaction temperature is −50° C. to 40° C. The reaction time is preferably 10 minutes to 10 hours, and satisfactory results are obtained when the reaction time is 30 minutes to 5 hours. The concentration of the compound (XII) in the reaction system is not restricted, and usually 1 mmol/L to 1 mol/L is preferred.

In the method (2), as the reagent, an alkylthiol such as ethanethiol, propanethiol or butanethiol is preferred, and propanethiol is especially preferred. The amount of the alkyltiol is preferably 1 to 20 equivalents, and satisfactory results are obtained by using alkylthiol in an amount of 1 to 7 equivalents. As the base, potassium t-butoxide, sodium hydride and potassium hydride are preferred, and potassium t-butoxide is especially preferred. The amount of the base is preferably 1 to 20 equivalents, and satisfactory results are obtained by using the base in an amount of 1 to 7 equivalents. As the reaction solvent, aprotic solvents such as DMF and dimethylacetoamide; and ether solvents such as THF and DME are preferred, and DMF which is an aprotic solvent is particularly preferred. The reaction temperature is preferably 50° C. to 200° C., and satisfactory results are obtained when the reaction temperature is 80° C. to 150° C. The reaction time is preferably 1 hour to 15 hours, and satisfactory results are obtained when the reaction time is 2 to 8 hours. The concentration of the compound (XII) in the reaction system is not restricted, and usually 1 mmol/L to 1 mol/L is preferred.

The compounds may be used as pharmaceuticals or pharmaceutical compositions. More particularly, they may be used as pharmaceuticals useful for therapy or prophylaxis of urinary frequency, urinary urgency or urinary incontinence. Particularly, the compounds may be used for the therapy or prophylaxis of urinary dysfunction such as urinary frequency and urinary incontinence caused by the diseases such as neurogenic bladder, nocturia, overactive bladder, unstable bladder, pollakisuria nervosa, psychogenic frequency, idiopathic frequency, enuresis, cystospasm, chronic cystitis, interstitial cystitis, chronic prostatitis, benign prostatic enlargement and prostate carcinoma. The term "neurogenic bladder" means that the function of urinary storage or voiding of the lower urinary tract is an abnormal state because of some damage of the nerve innervating the lower urinary tract comprising bladder, urethra and external urinary sphincter. Examples of the diseases which damage the nerve include cerebrovascular disease, brain tumor, brain injury, encephalitis, brain tumor, normal pressure hydrocephalus, dementia, Parkinson's disease, depression, striato-nigral degeneration, progressive supranuclear palsy, olivo-ponto-cerebellar atrophy, Shy-Drager syndrome, spinal cord injury, vascular disease of spinal cord, spinal cord tumor, myelitis, cervical cord compression disorder, syringomyelia, multiple sclerosis, spina bifida, myelomeningocele, spinal canal stenosis, Tethered cord syndrome, myelopathy, diabetes and pelvic cavity surgery. However, use of the therapeutic or prophylactic agent for urinary frequency or urinary incontinence is not restricted to these diseases.

The morphinan derivatives having a nitrogen-containing heterocyclic group represented by Formula (I) may be not only used as the pharmaceuticals useful for therapy or prophylaxis of urinary frequency, urinary urgency or urinary incontinence as mentioned above, but also may be used for the methods for therapy or prophylaxis of urinary frequency, urinary urgency or urinary incontinence, or may be used for applications of urinary frequency, urinary urgency or urinary incontinence. Further, they may be not only used as pharmaceuticals useful for therapy or prophylaxis of urinary frequency, urinary urgency or urinary incontinence of mammals such as mouse, rat, hamster, rabbit, cat, dog, bovine, sheep and monkey, but also may be used for the methods for therapy or prophylaxis of urinary frequency, urinary urgency or urinary incontinence, or may be used for applications of urinary frequency, urinary urgency or urinary incontinence.

The effects of the morphinan derivatives having a nitrogen-containing heterocyclic group represented by Formula (I) may be confirmed by the method described in Brain. Res., vol. 297, 191 (1984), or J. Pharmcol. Exp. Ther., vol. 240, 998 (1987), but the testing method is not restricted thereto.

When using the therapeutic or prophylactic agent for urinary frequency or urinary incontinence as a pharmaceutical, the pharmaceutical may be the free base or a salt thereof alone, or the pharmaceutical may optionally be admixed with one or more additives such as vehicles, stabilizers, preservatives, buffering agents, solubilizers, emulsifiers, diluents and isotonic agents. The administration form include formulations for oral administration such as tablets, capsules, granules, powders and syrups; formulations for parenteral administration such as injection solutions, suppositories and liquids; and formulations for topical administration such as ointments, creams and patches. The therapeutic or prophylactic agent for urinary frequency or urinary incontinence may prefeerably contains the above-described effective ingredient in an amount of 0.01 to 90% by weight, more preferably 0.1 to 70% by weight. Although the administration dose may be appropriately selected depending on the symptom, age, body weight, and administration method and the like, the dose of the effective component per adult per day may be 0.1 μg to 10 g, preferably 1 μg to 1 g, more preferably 10 μg to 100 mg, and may be administered in one time or dividedly in several times.

The compounds of Formula (I), or salts thereof may be used in combination with one or more other therapeutic or prophylactic agents for urinary frequency or urinary incontinence or with one or more therapeutic or prophylactic agents for diseases which cause a urinary dysfunction (e.g., benign prostatic hyperplasia, prostate carcinoma, diabetes, cerebrovascular disease, dementia including Alzheimer's disease, depression, Parkinson's disease and multiple sclerosis).

Examples of the other therapeutic or prophylactic agents for urinary dysfunction include anticholinergic agents such as Propantheline, Oxybutynin, Propiverine, Tolterodine, Temiverine, Trospium, Darifenacin, Solifenacin and KRP-197; smooth muscle relaxants such as Flavoxate; potassium channel openers such as NS-8, ZD-0947, KW-7158, ABT-598 and WAY-151616; calcium channel antagonists such as Nifedipine and Flunarizine; skeletal muscle relaxants such as Baclofen, Diazepam and Lanperisone; antidepressants such as Imipramine, Desipramine, Fluoxetine, Fluvoxamine, Milnacipran, Paroxetine and Duloxetine; vasopressin agonists such as Desmopressin; tachykinin antagonists such as TAK-637, SR-48968 and Talnetant; β agonists such as Clenbuterol and KUC-7483; vanilloid agonists such as capsaicin and resiniferatoxin; PGE antagonists such as ONO-8711 and ONO-8992; COX inhibitors such as Flurbiprofen; α1 agonists such as R-450; α1 antagonists such as Doxazosin, Indramin, Terazosin, Urapidil, Alfuzosin, Prazosin, Naftopidil, Tamsulosin, Selodosin, Fiduxosin and KMD-3213.

Examples of the diseases which cause urinary dysfunction include benign prostatic hyperplasia, prostate carcinoma, diabetes, cerebrovascular disease, dementia including Alzheimer's disease, depression, Parkinson's disease and multiple sclerosis. Examples of the therapeutic or prophylactic agent for benign prostatic hyperplasia include 5α-reductase inhibitors such as Finasteride, Dutasteride, Izonsteride, CS-891 and MK-434; androgen receptor antagonists such as Flutamide, Bicalutamide and Nilutamide; antiandrogen drugs such as Allylestrenol, Chlormadinone, Gestonorone, Cyproterone, Osaterone and Nomegestrol; endothelin antagonists such as SB-217242 and TA-0201; botanical drugs such as Eviprostat and Cernilton; and the above-described α1 antagonists.

Examples of the therapeutic or prophylactic agent for prostate carcinoma include LH-RH agonists such as Leuprorelin, Goserelin, Buserelin, Nafarelin and Triptorelin; LH-RH antagonists such as Cetrorelix, Ganirelix and Abarelix; the above-mentioned 5α-reductase inhibitors, the above-mentioned androgen receptor antagonists; and above-mentioned antiandrogen drugs.

Examples of the therapeutic or prophylactic agent for diabetes include anti-insulin resistance drugs such as Pioglitazone, Troglitazone and Rosiglitazone; insulin secretion enhancers such as Tolbutamide, Chlorpropamide, Tolazamide, Acetohezamide, Glyclopyramide, Glibenclamide, gliclazide, Glimepiride, Repaglinide and Nateglinide; biguanides such as Metformin and Buformin; α-glucosidase inhibitors such as insulin, Acarbose, Voglibose, Miglitol and Emiglitate; β3 adrenaline receptor agonists such as AJ-9677, SR-58611-A, SB-226552 and AZ40140; and other drugs such as Erogoset, Pramlintide, Leptin and BAY-27-9955.

Examples of the therapeutic or prophylactic agent for cerebrovascular disease include Aniracetam, Ibudilast, Tiapride, Cardiochrome, citicoline, γ-aminobutyric acid, ifenprodil, Nicergorine, vinpocetine, Nizofenone, bencyclane and cinepazide.

An example of the therapeutic or prophylactic agent for dementia including Alzheimer's disease is Donepezil.

Examples of the therapeutic or prophylactic agent for depression includes the above-mentioned antidepressants.

Examples of the therapeutic or prophylactic agent for Parkinson's disease include Amantadine, Trihexyphenidyl, Bromocriptine, Levodopa, Carbidopa and Apomorphine.

Examples of the therapeutic or prophylactic agent for multiple sclerosis include steroid drugs and interferon-β-1b.

EXAMPLES

Reference Example 1-1

Synthesis of 6β-dibenzylamino-17-cyclopropylmethyl-4,5α-epoxy-morphinan-3,14-diol

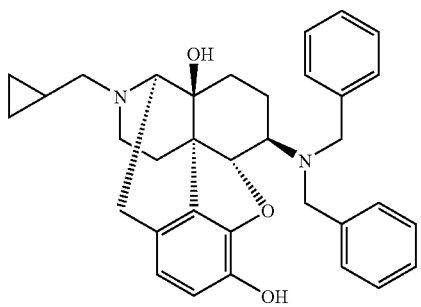

In a mixed solvent of 1700 mL of THF and 1700 mL of toluene, 249.8 g (0.731 mol) of naltrexone was dissolved, and 432.7 g (2.193 mol, 3.0 equivalents) of dibenzylamine was added. While stirring the mixture, the pressure in the reaction vessel was reduced and the atmosphere was replaced with argon. Then 357.7 g (2.929 mol, 4.0 equivalents) of benzoic acid was weighed in a beaker, and was slowly added to the solution to precipitate white solids. Using an oil bath, the reaction apparatus was started to be warmed, and the precipitated crystals were dissolved to form a solution with the elevation of inner temperature. Reflux started at an inner temperature of 81.5° C., which was regarded as the start of the reaction. The reaction was carried out at an inner temperature of 81.5° C. to 87.4° C. Thirty minutes after starting the reaction, 53.9 g (0.363 mol, 0.50 equivalents) of triethyl orthoformate was added, and at 2 hours and 30 minutes and at 4 hours and 30 minutes after the start, triethyl orthoformate was added in amounts of 54.0 g (0.364 mol, 0.50 equivalents) and 54.1 g (0.365 mol, 0.50 equivalents), respectively. Six hours and 30 minutes after the start of the reaction, the oil bath was removed from the reaction apparatus, thereby terminating the reaction for conversion to iminium.

During cooling the reaction vessel in ice bath, in which the reaction for conversion to iminium was carried out, 54.0 g (0.859 mol, 1.17 equivalents) of sodium cyanoborohydride was weighed in a separate 1 L three-necked flask, and 532.3 g of methanol was added to dissolve it. The thus prepared solution was dropped on the reaction solution of the conversion reaction to iminium for 10 minutes at an inner temperature of 2.5 to 10° C. Thirty minutes after completion of the dropping, the reaction was terminated and the mixture was subjected to post treatment.

In a 5 L Erlenmeyer flask, 446.0 g (3.22 mol) of potassium carbonate and 3399.6 g of distilled water were weighed to prepare an aqueous potassium carbonate solution. This solution was dropped on the reaction mixture for 12 minutes at an inner temperature of 5.0 to 18.0° C. After completion of the dropping, the mixture was stirred for 10 minutes to dissolve the gels and the reaction solution became clear. The reaction solution was then transferred to a 10 L separating bath. To the reaction solution, 599.8 g of THF and 615.5 g of ethyl acetate were added and the resulting mixture was stirred for 15 minutes. After stopping the stirring, the mixture was left to stand for 20 minutes to attain separation into layers, and 5175.5 g of the extraction aqueous layer was removed. To the organic layer in the separating bath, 1026.3 g of distilled water was added and the mixture was stirred for 15 minutes, followed by leaving the mixture to stand overnight. On the next day, the mixture was separated into layers, and the 1280.5 g of aqueous layer after washing with distilled water was removed, thereby obtaining 4186.2 g of organic layer after washing with distilled water. Thereafter, the organic layer was concentrated to obtain 2263.6 g of a concentration residue. To this residue, 1340.1 g of ethyl acetate was added to replace the solvent with ethyl acetate, and azeotropic distillation with water was carried out. Thereafter, the above-described operations were repeated 5 times, to obtain 2189.7 g of the final concentration residue. Then 1221.7 g of methanol was added and the mixture was concentrated, thereby replacing the solvent with methanol. Thereafter, these operations were repeated twice to obtain 2103.9 g of the final concentration residue. To this residue, 528.3 g of methanol was added, and the mixture was stirred while placing the vessel in an ice bath, thereby washing the slurry. The inner temperature at the beginning of the stirring was 22.0° C., and the washing with stirring was carried out for 30 minutes. At the termination of the washing, the inner temperature was 8° C. The slurry after washing with stirring was filtered through Millipore filter in an 1 L funnel. Inside the flask and the crystals were washed with 402.6 g of methanol. The crystals were transferred to a separable flask and dried under reduced pressure to obtain 329.2 g (yield: 86%) of the captioned compound as white crystals.

Reference Example 1-2

Synthesis of 6β-naltrexamine

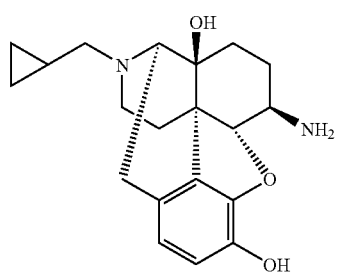

In a 5 L reaction vessel, 325.0 g (0.622 mol) of 6β-dibenzylamino-17-cyclopropylmethyl-4,5α-epoxy-morphinan-3, 14-diol obtained in Reference Example 1-1 and 65.0 g (20 wt %) of 10% Pd/C (50% wet) were weighed, and a reaction apparatus was assembled. Then 2561.3 g (3.25 L, 10 mL/g-substrate) was added and the stirring was started, followed by replacing the atmosphere with argon three times. In a beaker, 91.0 g (1.740 mol, 2.8 equivalents) of formic acid (88% sol.) was weighed, and dropped for 5 minutes at an inner temperature of 22.1 to 25.8° C. using a dropping funnel. At this time, elevation of the inner temperature and generation of gas were observed, After completion of the dropping, heating was started, and the time at which the inner temperature reached 51.1° C. was regarded as the start of the reaction. Two hours after the start of the reaction, analysis by HPLC was performed. Although the reaction had been completed at two hours after the start, in order to continue the reaction until the amount of the remaining formic acid reached not more than 0.03 equivalents, stirring and heating were carried out at 51.1 to 61.0° C. Twenty two hours after the start of the reaction, the reaction mixture was sampled and analyzed by HPLC and $^1$H-NMR. By HPLC, impurities and decomposition products which prominently increased were not observed. It was confirmed that the amount of the formic acid contained in the reaction mixture was 0.090 equivalents. Since termination of the decomposition step of formic acid was defined such that the amount of the remaining formic acid was not more than 0.03 equivalents, the reaction was continued at the same reaction temperature and the stirring rate. Twenty eight hours after the start of the reaction, the amount of the remaining formic acid was measured by $^1$H-NMR, which was 0.094 equivalents. Since this amount was about the same as that measured at 22 hours, the reaction was continued after raising the inner temperature to 60.9 to 61.4° C. Twelve hours after raising the reaction temperature (40 hours after the start of the reaction), the amount of the remaining formic acid was measured by $^1$H-NMR, which was 0.037 equivalents. Although the criterion of judgment of termination of the reaction was not more than 0.03 equivalents, the reaction was terminated, and the mixture was subjected to work up process.

After cooling the reaction mixture to an inner temperature of 20.7° C. by placing the vessel in an ice bath, Pd/C was removed by filtration through Millipore filter in a 1 L funnel. As the filter, 0.5 μm PTFE membrane filter was used. By washing the Pd/C obtained by the filtration with 227.5 g of methanol, 3035.8 g of filtrate was obtained. The obtained filtrate was transferred to a 10 L flask for evaporator, the vessel was washed with 61.1 g of methanol. After the transfer, the mixture was concentrated, and the concentration was once stopped when 1624.9 g of concentration residue was obtained. Then 1408.1 g of ethyl acetate was added thereto, and concentration was further carried out, thereby replacing the solvent with ethyl acetate from methanol. During the concentration, white powder precipitated, and the solution changed into a slurry. The concentration was stopped when 1455.4 g of residue in replacing solvent was obtained, and the replacement of solvent was carried out additionally twice in the same way. After the replacement of the solvent, the powder was collected by filtration and the obtained white powder was washed with 178.6 g of ethyl acetate. The powder was transferred to a 1 L separable flask, and the flask was immersed in a water bath at 50° C., followed by drying the powder for 3 hours under reduced pressure to obtain 185.5 g (yield: 87.2%) of the captioned compound.

Example 1-1

Synthesis of 4,5α-epoxy-6β-tetrahydroquinolino-3-methoxy-17-methyl-morphinan (Compound 201)

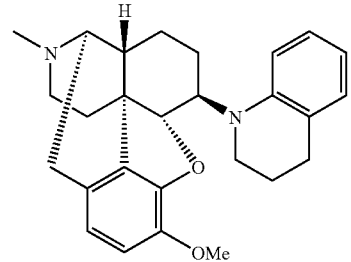

201

In a mixed solvent of 20 ml of xylene and 10 ml of dimethylformamide, 304 mg (1.02 mmol) of dihydrocodeinone and 0.12 ml (1.65 mmol) of methanesulfonic acid were dissolved, and 0.2 ml (1.59 mmol) of 1,2,3,4-tetrahydroquinoline was added thereto. The mixture was heated to reflux for 12 hours while azeotropically removing water in an oil bath at 175° C. After allowing the reaction solution to cool to room temperature, 50 ml of aqueous saturated sodium hydrogen carbonate and 3 ml of aqueous ammonia were added to the reaction mixture, and the resulting mixture was extracted with chloroform (50 ml×3 times). Organic layers were combined, washed with saturated saline, dried over anhydrous magnesium sulfate and concentrated to obtain 309 mg of a crude product. The obtained crude product was dissolved in 20 ml of methanol, and 1.014 g (16.1 mmol) of sodium cyanoborohydride was added. Then 0.17 ml (2.62 mmol) of methanesulfonic acid was added, and the mixture was stirred at room temperature for 24 hours. To the reaction mixture, 50 ml of aqueous saturated sodium hydrogen carbonate solution and 3 ml of aqueous ammonia were added, and the resulting mixture was extracted with chloroform (50 ml×3 times). Organic layers were combined, washed with saturated saline, dried over anhydrous magnesium sulfate and concentrated to obtain a crude product. The obtained crude product was purified by silica gel column chromatography [ChromatorexNH 40 g: cyclohexane-ethyl acetate (30:1)] to obtain 103 mg (yield: 33%) of the captioned compound.

$^1$H-NMR (ppm) (300 MHz, CDCl$_3$) 6.93-6.88 (2H, m), 6.77 (1H, d, J=8.2 Hz), 6.67 (1H, d, J=8.2 Hz), 6.52-6.45 (2H, m), 4.69 (1H, d, J=8.2 Hz), 3.83 (3H, s), 3.66-3.56 (1H, m), 3.49-3.20 (2H, m), 3.11-3.09 (1H, m), 3.03 (1H, d, J=18.2 Hz), 2.77-2.73 (2H, m), 2.56-2.50 (1H, m), 2.42 (3H, s), 2.40-2.34 (1H, m), 2.23-2.14 (2H, m), 2.05-1.82 (3H, m), 1.77-1.73 (1H, m), 1.68-1.63 (3H, m), 1.15-1.00 (1H, m) IR (cm$^{-1}$) (KBr) 2926, 1600, 1570, 1499, 1438, 1373, 1341, 1277, 1256, 1190, 1148, 1104, 1079, 1050, 1016, 1000, 940, 910, 893, 855, 795, 743

Example 1-2

Synthesis of 4,5α-epoxy-6β-tetrahydroquinolino-17-methyl-morphinan-3-ol•tartaric acid salt (Compound 1)

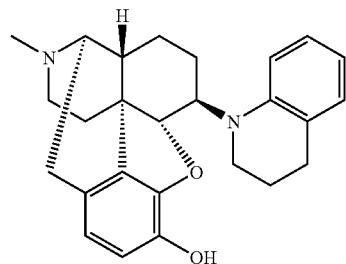

In DMF (5 mL), 103 mg (0.25 mmol) of 4,5α-epoxy-6β-tetrahydroquinolino-3-methoxy-17-methyl-morphinan obtained in Example 1-1 was dissolved, and 0.12 ml (1.32 mmol) of n-propanethiol and 142.6 mg (1.27 mmol) of potassium t-butoxide were added thereto, followed by allowing reaction at 120° C. for 4 hours. The reaction solution was allowed to cool to room temperature, and 20 ml of aqueous saturated sodium hydrogen carbonate solution and 3 ml of aqueous ammonia were added, followed by extraction of the resulting mixture with chloroform (50 ml×3 times). Organic layers were combined, washed with saturated saline, dried over anhydrous magnesium sulfate and concentrated to obtain a crude product. The obtained crude product was purified by silica gel column chromatography (ChromatorexNH 5 g: ethyl acetate) to obtain 75 mg (yield: 75%) of free form of the captioned compound. This product was converted to tartaric acid salt to obtain the captioned compound 1.

$^1$H-NMR (ppm) (300 MHz, CDCl$_3$) 6.93-6.87 (2H, m), 6.70 (1H, d, J=8.2 Hz), 6.58 (1H, d, J=8.2 Hz), 6.51-6.46 (1H, m), 6.37 (1H, d, J=8.5 Hz), 4.62 (1H, d, J=8.5 Hz), 3.19-3.11 (3H, m), 3.08-3.02 (1H, m), 2.96 (1H, d, J=18.5 Hz), 2.74-2.70 (2H, m), 2.52-2.44 (1H, m), 2.35 (3H, s), 2.31-2.29 (1H, m), 2.20-1.48 (9H, m), 1.11-1.00 (1H, m) (free form) IR (cm$^{-1}$) (KBr) 3001, 2932, 2855, 1600, 1498, 1458, 1371, 1344, 1293, 1260, 1214, 1191, 1149, 1128, 1107, 1075, 1025, 1000 Elementary Analysis Formula: C$_{26}$H$_{30}$N$_2$O$_2$.1.50C$_4$H$_6$O$_6$.0.8H$_2$O Calcd.: C, 59.86; H, 6.37; N, 4.36. Found: C, 59.77; H, 6.52; N, 4.38.

Example 2-1

Synthesis of 4,5α-epoxy-6β-(3,4-dihydro-2H-benzo[1,4]thiazino)-3-methoxy-17-methyl-morphinan (Compound 202)

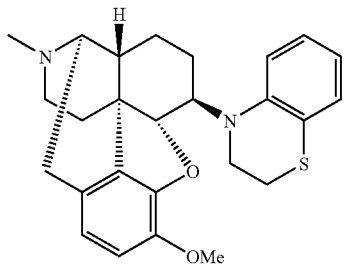

In a manner similar to the method described in Example 1-1, using 3,4-dihydro-2H-benzo[1,4]thiazine in place of 1,2,3,4-tetrahydroquinoline, 239 mg (yield: 63%) of the captioned compound was obtained.

$^1$H-NMR (ppm) (300 MHz, CDCl$_3$) 6.98 (1H, dd, J=1.8, 7.9 Hz), 6.86 (1H, ddd, J=1.8, 7.3, 8.5 Hz), 6.78 (1H, d, J=8.2 Hz), 6.69-6.65 (2H, m), 6.61-6.55 (1H, ddd, J=1.2, 7.6, 8.5 Hz), 4.61 (1H, d, J=8.2 Hz), 3.85 (3H, s), 3.60-3.51 (3H, m), 3.14-2.96 (4H, m), 2.55-2.50 (1H, m), 2.41 (3H, s), 2.38-2.32 (1H, m), 2.23-2.12 (2H, m), 1.91-1.47 (5H, m), 1.12-1.00 (1H, m) IR (cm$^{-1}$) (KBr) 2924, 1735, 1606, 1584, 1483, 1438, 1373, 1338, 1275, 1257, 1176, 1148, 1112, 1079, 1047, 1006, 937, 907, 891, 854, 793, 744

Example 2-2

Synthesis of 4,5α-epoxy-6β-(3,4-dihydro-2H-benzo[1,4]thiazino)-17-methyl-morphinan-3-ol•methanesulfonic acid salt (Compound 2)

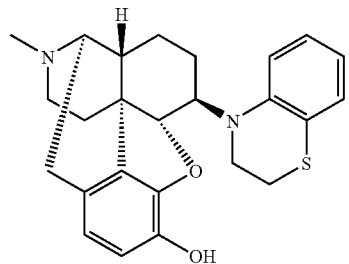

In a manner similar to the method described in Example 1-2, using 239 mg of 4,5α-epoxy-6β-(3,4-dihydro-2H-benzo[1,4]thiazino)-3-methoxy-17-methyl-morphinan obtained in Example 2-1, 198 mg (yield: 86%) of free form of the captioned compound 2 was obtained. This product was converted to methanesulfonic acid salt to obtained the captioned compound 2.

$^1$H-NMR (ppm) (300 MHz, CDCl$_3$) 7.00 (1H, dd, J=1.8, 7.6 Hz), 6.92-6.87 (1H, m), 6.76 (1H, d, J=8.2 Hz), 6.64 (1H, d, J=8.2 Hz), 6.60-6.54 (2H, m), 4.58 (1H, d, J=8.2 Hz), 3.63-3.51 (3H, m), 3.16-2.98 (4H, m), 2.57-2.52 (1H, m), 2.38 (3H, s), 2.34-2.32 (1H, m), 2.22-2.14 (2H, m), 1.91-1.44 (5H, m), 1.16-1.02 (1H, m) (free form) IR (cm$^{-1}$) (KBr) 2925, 1609, 1584, 1484, 1440, 1373, 1337, 1280, 1253, 1175, 1146, 1112, 1069, 1045, 1025, 965, 925, 892, 855 Elementary Analysis Formula: C$_{25}$H$_{28}$N$_2$O$_2$S.1.08MeSO$_3$H.0.9H$_2$O Calcd.: C, 57.95; H, 6.36; N, 5.18; O, 18.17; S, 12.34. Found: C, 57.77; H, 6.52; N, 5.18; O, 18.10; S, 12.43.

Example 3

Synthesis of 4-(4,5α-epoxy-3-hydroxy-17-methyl-morphinan-6β-yl)-3,4-dihydro-2H-benzo[1,4]thiazine-1-oxide (diastereomer mixture)•methanesulfonic acid salt (Compound 3)

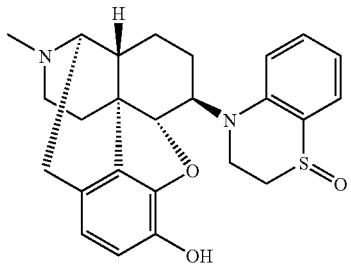

In 5 mL of acetic acid, 164 mg (0.39 mmol) of 4,5α-epoxy-6β-(3,4-dihydro-2H-benzo[1,4]thiazino)-17-methyl-morphinan-3-ol obtained in Example 2-2 was dissolved, and 63 mg (0.40 mmol) of sodium perborate tetrahydrate was added, followed by stirring the mixture at room temperature for 1 hour. To this reaction solution, 1 μL of concentrated hydrochloric acid was added and the mixture was stirred for 30 minutes. Thereafter, aqueous saturated sodium hydrogen carbonate solution was added, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 114 mg (yield: 67%) of free form of the captioned compound 3. This product was converted to methanesulfonic acid salt to obtain the captioned compound 3.

$^1$H-NMR (ppm) (300 MHz, CDCl$_3$) 7.54 (0.5H, t, J=7.6 Hz), 7.53 (0.5H, t, J=7.6 Hz), 7.2-7.25 (1H, m), 6.78 (0.5H, d, J=8.2 Hz), 6.77 (0.5H, d, J=8.2 Hz), 6.60-6.75 (3H, m), 4.74 (0.5H, d, J=8.2 Hz), 4.67 (0.5H, d, J=8.2 Hz), 3.90-4.05 (1H, m), 3.75-4.85 (1H, m), 3.50-3.60 (1H, m), 3.10-3.20 (2H, m), 3.04 (1H, d, J=18.5 Hz), 2.50-2.75 (2H, m), 2.41 (3H, s), 2.3-2.4 (1H, m), 2.10-2.25 (2H, m), 1.6-1.9 (5H, m), 1.1-1.2 (1H, m) (free form) Mass (ESI): 437(M$^+$+1)

Example 4-1

Synthesis of 4,5α-epoxy-6β-(3,4-dihydro-2H-benzo[1,4]oxazino)-3-methoxy-17-methyl-morphinan (Compound 204)

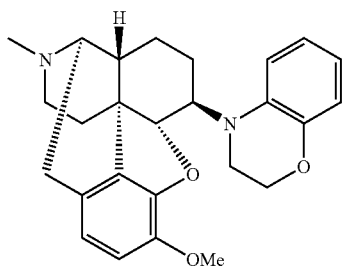

204

In a manner similar to the method described in Example 1-1, using 3,4-dihydro-2H-benzo[1,4]oxazine in place of 1,2,3,4-tetrahydroquinoline, 134 mg (yield: 29%) of the captioned compound was obtained.

$^1$H-NMR (ppm) (300 MHz, CDCl$_3$) 6.79-6.67 (4H, m), 6.58-6.52 (2H, m), 4.63 (1H, d, J=8.2 Hz), 4.32-4.14 (2H, m), 3.84 (3H, s), 3.60-3.51 (1H, m), 3.46-3.33 (2H, m), 3.12-3.10 (1H, m), 3.04 (1H, d, J=18.2 Hz), 2.55-2.43 (1H, m), 2.42 (3H, s), 2.38-2.34 (1H, m), 2.23-2.14 (2H, m), 1.91-1.45 (5H, m), 1.15-1.03 (1H, m) IR (cm$^{-1}$) (KBr) 2926, 2796, 1736, 1634, 1604, 1577, 1500, 1441, 1373, 1341, 1310, 1278, 1246, 1207, 1176, 1149, 1130, 1080, 1051, 1006, 974, 940, 913, 856, 823, 797, 741

Example 4-2

Synthesis of 4,5α-epoxy-6β-(3,4-dihydro-2H-benzo[1,4]oxazino)-17-methyl-morphinan-3-ol•methanesulfonic acid salt (Compound 4)

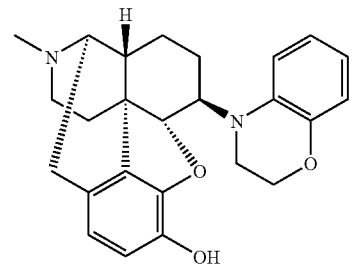

4

In 6 mL of methylene chloride, 127 mg (0.30 mmol) of 4,5α-epoxy-6β-(3,4-dihydro-2H-benzo[1,4]oxazino)-3-methoxy-17-methyl-morphinan obtained in Example 4-1 was dissolved, and the mixture was cooled to 0° C. To the mixture, 2.0 mL (2.0 mmol) of 1N boron tribromide solution in methylene chloride was added in the dark, and the mixture was warmed to room temperature, followed by stirring the mixture for 30 minutes. To this reaction solution, 2 mL of aqueous ammonia was added and the mixture was stirred for 1 hour. To the reaction mixture, aqueous saturated sodium hydrogen carbonate solution was then added, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 61 mg (yield: 49%) of free form of the captioned compound 4. This product was converted to methanesulfonic acid salt to obtain the captioned compound 4.

$^1$H-NMR (ppm) (300 MHz, CDCl$_3$) 6.80-6.73 (3H, m), 6.66 (1H, d, J=8.2 Hz), 6.58 (1H, dt, J=1.5, 7.6 Hz), 6.51-6.48 (1H, m), 4.62 (1H, d, J=8.2 Hz), 4.31-4.11 (2H, m), 3.65-3.57 (1H, m), 3.45-3.31 (2H, m), 3.18-3.14 (1H, m), 3.02 (1H, d, J=18.5 Hz), 2.61-2.56 (1H, m), 2.42 (3H, s), 2.39-2.36 (1H, m), 2.25-2.17 (2H, m), 1.94-1.84 (1H, m), 1.74-1.47 (4H, m), 1.16-1.04 (1H, m) (free form) IR (cm$^{-1}$) (KBr) 2927, 1736, 1604, 1501, 1448, 1375, 1341, 1310, 1278, 1242, 1208, 1179, 1148, 1128, 1059, 975, 925, 860, 823, 796, 735

Example 5-1

Synthesis of 4,5α-epoxy-6β-indolino-17-phenethyl-3-methoxy-morphinan-14-ol (Compound 205)

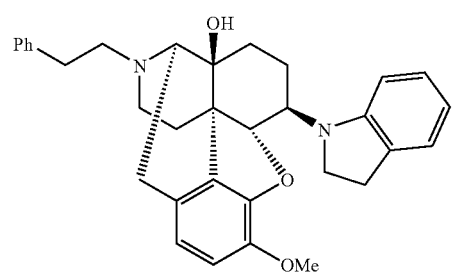

205

In a manner similar to the method described in Example 1-1, using indoline in place of 1,2,3,4-tetrahydroquinoline, and using 4,5α-epoxy-3-methoxy-6-oxo-17-phenethyl-morphinan-14-ol in place of dihydrocodeinone, 103 mg (yield: 96%) of the captioned compound was obtained.

¹H-NMR (ppm) (300 MHz, CDCl₃) 7.34-7.18 (5H, m), 7.02-6.91 (2H, m), 6.76 (1H, d, J=8.2 Hz), 6.64 (1H, d, J=8.2 Hz), 6.57-6.52 (1H, m), 6.29 (1H, d, J=8.0 Hz), 4.79 (1H, d, J=8.0 Hz), 3.84 (3H, s), 3.65-3.46 (2H, m), 3.40-3.31 (1H, m), 3.10 (1H, d, J=18.1 Hz), 3.02-2.96 (2H, m), 2.86-2.61 (6H, m), 2.19-2.15 (3H, m), 1.59-1.42 (5H, m) IR (cm⁻¹) (KBr) 3387, 3024, 2926, 2832, 1759, 1605, 1496, 1438, 1397, 1368, 1327, 1279, 1257, 1187, 1154, 1128, 1049, 1024, 982, 937, 908, 852, 745, 700

Example 5-2

Synthesis of 4,5α-epoxy-6β-indolino-17-phenethyl-morphinan-3,14-diol•methanesulfonic acid salt (Compound 5)

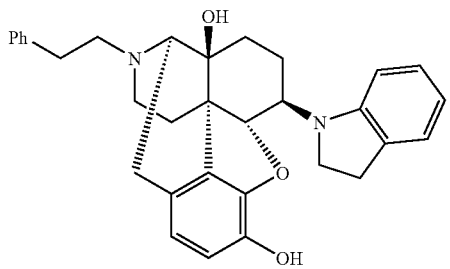

In a manner similar to the method described in Example 4-2, using 103 mg of 4,5α-epoxy-6β-indolino-17-phenethyl-3-methoxy-morphinan-14-ol obtained in Example 5-1, 90 mg (yield: 90%) of free form of the captioned compound 5 was obtained. This product was converted to methanesulfonic acid salt to obtain the captioned compound 5.

¹H-NMR (ppm) (300 MHz, CDCl₃) 7.34-7.18 (5H, m), 7.05-6.96 (2H, m), 6.77 (1H, d, J=8.2 Hz), 6.64-6.55 (2H, m), 6.25 (1H, d, J=7.7 Hz), 4.81 (1H, d, J=8.2 Hz), 3.64-3.36 (3H, m), 3.09 (1H, d, J=18.7 Hz), 3.05-2.99 (2H, m), 2.85-2.54 (7H, m), 2.24-2.04 (3H, m), 1.65-1.44 (4H, m) (free form) IR (cm⁻¹) (KBr) 3376, 3025, 2926, 2831, 1736, 1605, 1489, 1455, 1398, 1325, 1242, 1187, 1152, 1125, 1036, 993, 941, 917, 854, 746, 700, 634, 583 Elementary Analysis Formula: $C_{32}H_{34}N_2O_3 \cdot 1.94MeSO_3H \cdot 0.40H_2O$ Calcd.: C, 59.23; H, 6.23; N, 4.07; S, 9.26. Found: C, 59.14; H, 6.32; N, 4.05; S, 9.26. Mass (FAB): 495(M⁺+1)

Example 6-1

Synthesis of 4,5α-epoxy-3-methoxy-17-methyl-6β-tetrahydroquinolino-morphinan-14-ol (Compound 206)

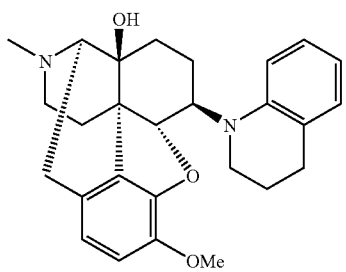

In a manner similar to the method described in Example 1-1, using oxycodone in place of dihydrocodeinone, 325 mg (yield: 75%) of the captioned compound was obtained.

¹H-NMR (ppm) (300 MHz, CDCl₃) 6.98-6.89 (2H, m), 6.78 (1H, d, J=8.2 Hz), 6.66 (1H, d, J=8.2 Hz), 6.54-6.48 (2H, m), 4.78 (1H, d, J=8.2 Hz), 3.84 (3H, s), 3.66 (1H, ddd, J=12.6, 8.0, 4.1 Hz), 3.40-3.28 (2H, m), 3.16 (1H, d, J=18.0 Hz), 2.82-2.73 (3H, m), 2.60 (1H, dd, J=18.0, 6.0 Hz), 2.44-2.39 (1H, m), 2.38 (3H, s), 2.33-2.10 (4H, m), 2.00-1.84 (3H, m), 1.66-1.60 (1H, m), 1.53-1.44 (1H, m) IR (cm⁻¹) (KBr) 3395, 3065, 3017, 2932, 2839, 1671, 1636, 1600, 1572, 1503, 1441, 1394, 1369, 1344, 1280, 1252, 1229, 1189, 1162, 1144, 1113, 1049, 1013, 976, 941, 910, 883, 851, 825, 802, 780, 762, 742, 689

Example 6-2

Synthesis of 4,5α-epoxy-17-methyl-6β-tetrahydroquinolino-morphinan-3,14-diol•tartaric acid salt (Compound 6)

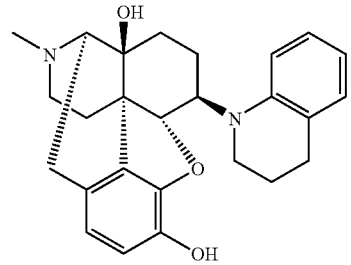

In a manner similar to the method described in Example 4-2, using 4,5α-epoxy-3-methoxy-17-methyl-6β-tetrahydroquinolino-morphinan-14-ol obtained in Example 6-1, 220 mg (yield: 70%) of free form of the captioned compound 6 was obtained. This product was converted to tartaric acid salt to obtain the captioned compound 6.

¹H-NMR (ppm) (300 MHz, CDCl₃) 6.99-6.91 (2H, m), 6.79 (1H, d, J=8.2 Hz), 6.65 (1H, d, J=8.2 Hz), 6.59-6.45 (2H, m), 4.78 (1H, d, J=8.0 Hz), 3.73 (1H, ddd, J=12.6, 8.0, 4.1 Hz), 3.38-3.27 (2H, m), 3.15 (1H, d, J=18.0 Hz), 2.80-2.76 (3H, m), 2.60 (1H, dd, J=18.0, 5.2 Hz), 2.44-2.40 (1H, m), 2.38 (3H, s), 2.29-2.11 (2H, m), 2.05-1.90 (2H, m), 2.16 (3H, s), 1.67-1.62 (1H, m), 1.52-1.41 (1H, m) (free form) IR (cm⁻¹) (KBr) 3200, 2929, 1736, 1638, 1601, 1572, 1499, 1458, 1372, 1341, 1307, 1241, 1189, 1161, 1125, 1110, 1061, 1034, 1016, 994, 979, 941 Elementary Analysis Formula: $C_{26}H_{30}N_2O_3 \cdot 1.0C_4H_6O_6 \cdot 1.0H_2O$ Calcd.: C, 61.42; H, 6.53; N, 4.78. Found: C, 61.41; H, 6.62; N, 4.74. Mass (EI): 418(M⁺)

Example 7-1

Synthesis of 4-(4,5α-epoxy-14-hydroxy-3-methoxy-17-methylmorphinan-6β-yl)-3,4-dihydro-1H-quinoxalino-2-one (Compound 207)

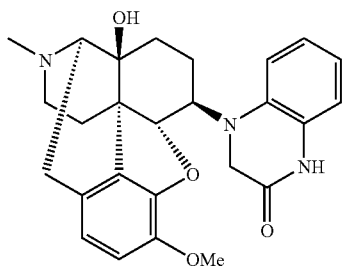

207

In a manner similar to the method described in Example 1-1, using 3,4-dihydro-2-oxo-1H-quinoxaline in place of 1,2,3,4-tetrahydroquinoline, and using oxycodone in place of dihydrocodeinone, 866 mg (yield: 31%) of the captioned compound was obtained.

$^1$H-NMR (ppm) (300 MHz, CDCl$_3$) 6.93-6.87 (1H, m), 6.78-6.67 (5H, m), 4.81 (1H, d, J=8.0 Hz), 3.91 (2H, s), 3.82 (3H, s), 3.54-3.46 (1H, m), 3.16 (1H, d, J=18.4 Hz), 2.79 (1H, d, J=5.2 Hz), 2.61 (1H, dd, J=18.4, 5.2 Hz), 2.38 (3H, s), 2.36-2.10 (5H, m), 1.68-1.42 (3H, m) IR (cm$^{-1}$) (KBr) 3214, 2934, 1686, 1607, 1505, 1437, 1389, 1338, 1279, 1205, 1188, 1165, 1115, 1053, 1038, 1020, 981, 935, 909, 882, 851, 746, 687, 666

Example 7-2

Synthesis of 4-(4,5α-epoxy-3,14-dihydroxy-17-methyl-morphinan-6β-yl)-3,4-dihydro-1H-quinoxalino-2-one•tartaric acid salt (Compound 7)

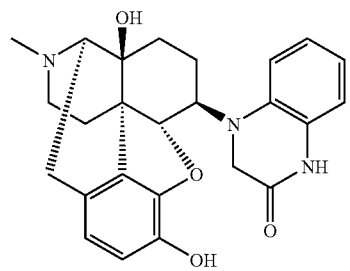

7

In a manner similar to the method described in Example 1-2, using 4-(4,5α-epoxy-14-hydroxy-3-methoxy-17-methyl-morphinan-6β-yl)-3,4-dihydro-1H-quinoxalino-2-one obtained in Example 7-1, 158 mg (yield: 19%) of free form of the captioned compound 7 was obtained. This product was converted to tartaric acid salt to obtain the captioned compound 7.

$^1$H-NMR (ppm) (300 MHz, CDCl$_3$) 6.93-6.80 (3H, m), 6.75-6.70 (2H, m), 6.66 (1H, d, J=8.2 Hz), 4.81 (1H, d, J=8.0 Hz), 3.91 (1H, d, J=12.2 Hz), 3.65 (1H, d, J=12.2 Hz), 3.18-3.07 (2H, m), 2.72 (1H, d, J=5.2 Hz), 2.51 (1H, dd, J=18.4, 5.2 Hz), 2.34 (3H, s), 2.36-2.10 (3H, m), 1.68-1.38 (5H, m) (free form) Elementary Analysis Formula: C$_{25}$H$_{27}$N$_3$O$_4$.1.02C$_4$H$_6$O$_6$.0.6H$_2$O Calcd.: C, 58.47; H, 5.79; N, 7.03. Found: C, 58.47; H, 5.63; N, 7.13. Mass (EI): 433(M$^+$)

Example 8-1

Synthesis of 4-(4,5α-epoxy-14-hydroxy-3-methoxy-17-methyl-morphinan-6β-yl)-1-methyl-3,4-dihydro-1H-quinoxalino-2-one (Compound 208)

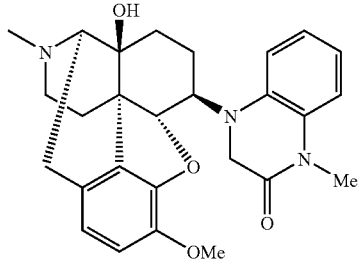

208

In a manner similar to the method described in Example 1-1, using 3,4-dihydro-1-methyl-2-oxo-1H-quinoxaline in place of 1,2,3,4-tetrahydroquinoline, and using oxycodone in place of dihydrocodeinone, 398 mg (yield: 31%) of the captioned compound was obtained.

Mass (ESI): 462(M$^+$+1)

Example 8-2

Synthesis of 4-(4,5α-epoxy-3,14-dihydroxy-17-methyl-morphinan-6β-yl)-1-methyl-3,4-dihydro-1H-quinoxalino-2-one•tartaric acid salt (Compound 8)

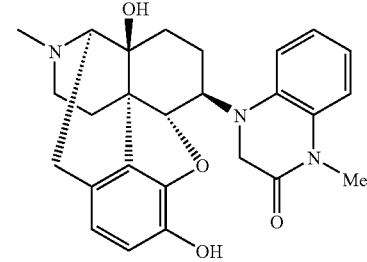

8

In a manner similar to the method described in Example 1-2, using 4-[4,5α-epoxy-14-hydroxy-3-methoxy-17-methyl-morphinan-6β-yl]-1-methyl-3,4-dihydro-1H-quinoxalino-2-one obtained in Example 8-1, 116 mg (yield: 53%) of free form of the captioned compound 8 was obtained. This product was converted to tartaric acid salt to obtain the captioned compound 8.

$^1$H-NMR (ppm) (300 MHz, CDCl$_3$) 7.01-6.93 (3H, m), 6.90-6.82 (1H, m), 6.72 (1H, d, J=8.1 Hz), 6.58 (1H, d, J=8.1 Hz), 5.26 (1H, s), 4.38 (1H, d, J=8.1 Hz), 3.88 (1H, d, J=15.9 Hz), 3.62 (1H, d, J=15.9 Hz), 3.36 (3H, s), 3.14-3.00 (2H, m), 2.73 (1H, d, J=5.4 Hz), 2.53 (1H, dd, J=18.9, 5.7 Hz), 2.40-2.28 (1H, m), 2.32 (3H, s), 2.20-2.02 (2H, m), 1.74-1.56 (2H, m), 1.46-1.30 (2H, m) (free form) Mass (ESI): 448(M$^+$+1)

Example 9-1

Synthesis of 4,5α-epoxy-6β-(3,4-dihydro-1-methyl-1H-quinoxalino)-3-methoxy-17-methyl-morphinan-14-ol (Compound 209)

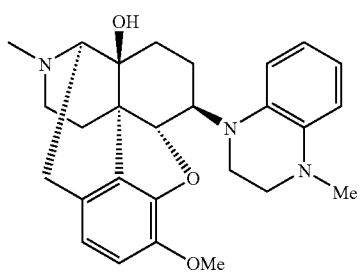

209

In 10 ml of THF, 144 mg (0.31 mmol) of 4,5α-epoxy-6β-(3,4-dihydro-1-methyl-2-oxo-1H-quinoxalino)-3-methoxy-17-methyl-morphinan-14-ol obtained in Example 8-1 was dissolved, and 0.78 mL (1.56 mmol) of 2N borane-dimethyl sulfide solution in THF was added, followed by stirring the mixture at room temperature for 5 hours. Thereafter, the temperature was elevated to 50° C. and the mixture was stirred for 2 hours. After allowing the reaction solution to cool to room temperature, aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 76 mg (yield: 54%) of the captioned compound.

Mass (ESI): 448($M^+$+1)

Example 9-2

Synthesis of 4,5α-epoxy-6β-(3,4-dihydro-1-methyl-1H-quinoxalino)-17-methyl-morphinan-3,14-diol•tartaric acid salt (Compound 9)

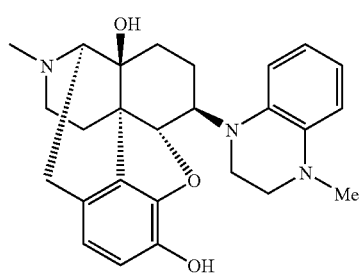

9

In 5 ml of DMF, 42 mg (0.14 mmol) of 4,5α-epoxy-6β-(3,4-dihydro-1-methyl-1H-quinoxalino)-3-methoxy-17-methyl-morphinan-14-ol obtained in Example 9-2 was dissolved, and 0.06 ml (0.70 mmol) of n-propanethiol and 76 mg (0.67 mmol) of potassium t-butoxide were added thereto, followed by allowing reaction at 120° C. for 4 hours. The reaction solution was allowed to cool to room temperature, and 20 ml of aqueous saturated sodium hydrogen carbonate solution and 3 ml of aqueous ammonia were added, followed by extraction of the resulting mixture with chloroform (50 ml×3 times). Organic layers were combined, washed with saturated saline, dried over anhydrous magnesium sulfate and concentrated to obtain a crude product. The obtained crude product was purified by silica gel column chromatography to obtain 25 mg (yield: 34%) of free form of the captioned compound 9. This product was converted to tartaric acid salt to obtain the captioned compound 9.

$^1$H-NMR (ppm) (300 MHz, CDCl$_3$) 6.74 (1H, d, J=8.1 Hz), 6.64-6.47 (4H, m), 6.44-6.36 (1H, m), 4.73 (1H, d, J=7.6 Hz), 3.70-3.56 (1H, m), 3.48-3.38 (2H, m), 3.31-3.20 (1H, m), 3.20-3.11 (1H, m), 3.09 (1H, d, J=18.6 Hz), 2.82 (3H,s), 2.75 (1H, d, J=3.0 Hz), 2.56 (1H, dd, J=18.3, 5.4 Hz), 2.42-2.30 (1H, m), 2.33 (3H, s), 2.22-2.04 (3H, m), 1.66-1.34 (4H, m) (free form) Mass (ESI): 434($M^+$+1)

Example 10-1

Synthesis of 4,5α-epoxy-6β-(1,2,3,5-tetrahydro-benzo[e][1,4]oxazepino)-3-methoxy-17-methyl-morphinan (Compound 210)

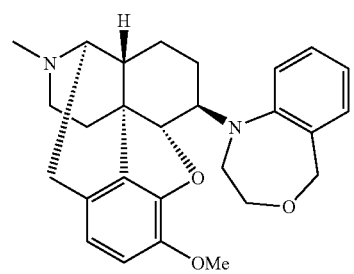

210

In a manner similar to the method described in Example 1-1, using 1,2,3,5-tetrahydro-benzo[e][1,4]oxazepine in place of 1,2,3,4-tetrahydroquinoline, 34 mg (yield: 24%) of the captioned compound was obtained.

Example 10-2

Synthesis of 4,5α-epoxy-6β-(1,2,3,5-tetrahydro-benzo[e][1,4]oxazepino)-17-methyl-morphinan-3-ol•methanesulfonic acid salt (Compound 10)

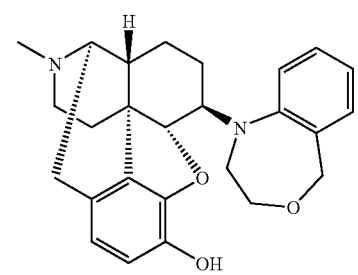

10

In a manner similar to the method described in Example 1-2, using 4,5α-epoxy-6β-(1,2,3,5-tetrahydro-benzo[e][1,4]oxazepino)-3-methoxy-17-methyl-morphinan obtained in Example 10-1, 33 mg (yield: 99%) of free form of the captioned compound 10 was obtained. This product was converted to methanesulfonic acid salt to obtain the captioned compound 10.

¹H-NMR (ppm) (300 MHz, CDCl₃) 1.10-1.19 (1H, m), 1.51-1.62 (1H, m), 1.65-1.68 (2H, m), 1.83-1.96 (3H, m), 2.14-2.22 (2H, m), 2.31-2.34 (1H, m), 2.36 (3H, s), 2.38 (1H, dd, J=4.7, 18.2 Hz), 3.08-3.12 (2H, m), 3.29-3.34 (2H, m), 3.75-3.89 (2H, m), 4.49 (1H, d, J=8.2 Hz), 4.57 (1H, d, J=13.2 Hz), 4.65 (1H, d, J=13.2 Hz), 6.59 (1H, d, J=8.2 Hz), 6.67 (1H, d, J=8.2 Hz), 6.78-6.87 (2H, m), 7.10-7.14 (2H, m) (free form) Mass (ESI): 419(M⁺+1)

Example 11

Synthesis of N-(17-cyclopropylmethyl-4,5α-epoxy-3,14-dihydroxy-morphinan-6β-yl)-phthalimide•hydrochloric acid salt (Compound 11)

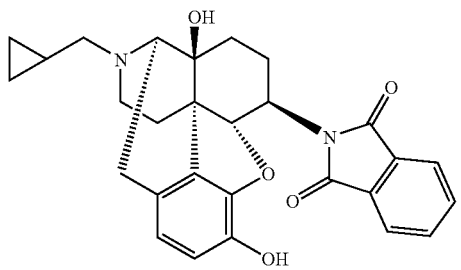

In 7 mL of DMF, 150 mg (0.44 mmol) of 6β-naltrexamine was dissolved, and 71 mg (0.48 mmol) of phthalic anhydride and 0.92 mL (0.66 mmol) of triethylamine were added thereto, followed by stirring the mixture at 140° C. for 4 hours. The reaction solution was allowed to cool to room temperature, and aqueous saturated sodium hydrogen carbonate solution was added, followed by extraction of the resulting mixture with ethyl acetate. Organic layers were combined, washed with water and saturated saline, dried over anhydrous magnesium sulfate and concentrated to obtain a crude product. The obtained crude product was purified by silica gel column chromatography to obtain 120 mg (11 f: yield: 58%) of free form of the captioned compound 11. This product was converted to hydrochloric acid salt to obtain the captioned compound 11.

¹H-NMR (ppm) (300 MHz, CDCl₃) 7.8-7.9 (2H, m), 7.7-7.8 (2H, m), 6.76 (1H, d, J=7.9 Hz), 6.63 (1H, d, J=8.2 Hz), 5.18 (1H, d, J=8.5 Hz), 4.0-4.1 (1H, m), 3.11 (1H, d, J=5.6 Hz), 3.05 (1H, d, J=18.8 Hz), 2.6-2.9 (3H, m), 2.3-2.4 (3H, m), 2.15 (1H, dt, J=12.0, 3.5 Hz), 1.4-1.7 (4H, m), 0.8-0.9 (1H, m), 0.5-0.6 (2H, m), 0.1-0.2 (2H, m) (free form) IR (cm⁻¹) (KBr) 3320, 1769, 1708, 1626, 1504, 1466, 1428, 1379, 1323, 1271, 1240, 1190, 1173, 1075 Elementary Analysis Formula: C₂₈H₂₈N₂O₅.1.0HCl.1.0H₂O Calcd.: C, 63.81; H, 5.93; N, 5.32; Cl, 6.73. Found: C, 63.72; H, 6.03; N, 5.40; Cl, 6.49. Mass (EI): 472(M⁺)

Example 12

Synthesis of N-(17-cyclopropylmethyl-4,5α-epoxy-3,14-dihydroxy-morphinan-6β-yl)-4-methylphthalimide•hydrochloric acid salt (Compound 12)

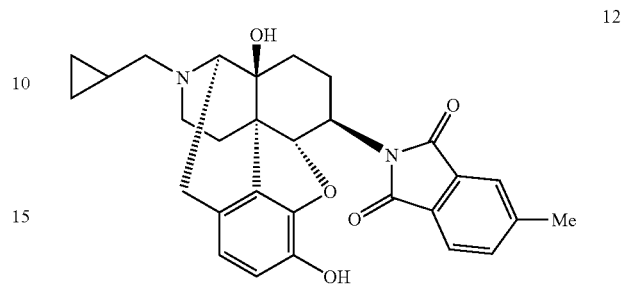

In a manner similar to the method described in Example 11, using 4-methylphthalic anhydride in place of phthalic anhydride, 219 mg (yield: 77%) of free form of the captioned compound 12 was obtained. This product was converted to hydrochloric acid salt to obtain the captioned compound 12.

¹H-NMR (ppm) (300 MHz, CDCl₃) 7.67 (1H, d, J=7.7 Hz), 7.61 (1H, s), 7.46 (1H, d, J=7.7 Hz), 6.76 (1H, d, J=7.9 Hz), 6.62 (1H, d, J=7.9 Hz), 5.17 (1H, d, J=8.2 Hz), 4.0-4.1 (1H, m), 3.10 (1H, d, J=5.8 Hz), 3.04 (1H, d, J=18.4 Hz), 2.60-2.85 (3H, m), 2.49 (3H, s), 2.35-2.4 (3H, m), 2.13 (1H, dt, J=12.0, 3.5 Hz), 1.4-1.7 (4H, m), 0.8-0.9 (1H, m), 0.5-0.6 (2H, m), 0.1-0.2 (2H, m)(free form) IR (cm⁻¹) (KBr) 3401, 1769, 1707, 1618, 1504, 1464, 1429, 1376, 1324, 1240, 1188, 1100, 1074, 1032 Elementary Analysis Formula: C₂₉H₃₀N₂O₅.1.0HCl.0.9H₂O Calcd.: C, 64.59; H, 6.13; N, 5.19; Cl, 6.57. Found: C, 64.88; H, 6.21; N, 5.28; Cl, 6.25. Mass (EI): 486(M⁺)

Example 13

Synthesis of N-(17-allyl-4,5α-epoxy-3,14-dihydroxy-morphinan-6β-yl)-phthalimide•tartaric acid salt (Compound 13)

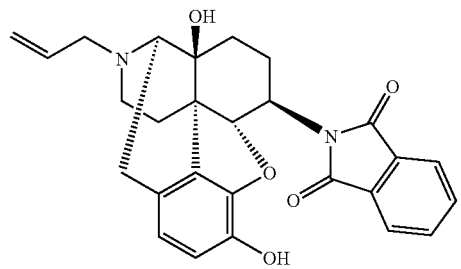

In a manner similar to the method described in Example 11, using 6β-naloxamine in place of 6β-naltrexamine, 24 mg (yield: 34%) of free form of the captioned compound 13 was obtained. This product was converted to tartaric acid salt to obtain the captioned compound 13.

¹H-NMR (ppm) (300 MHz, CDCl₃) 7.75-7.8 (2H, m), 7.6-7.7 (2H, m), 6.72 (1H, d, J=8.2 Hz), 6.59 (1H, d, J=8.2 Hz), 5.7-5.8 (1H, m), 5.1-5.2 (3H, m), 4.0-4.05 (1H, m), 3.0-3.1 (3H, m), 2.45-2.9 (5H, m), 2.0-2.3 (2H, m), 1.6-1.7 (1H, m), 1.4-1.5 (2H, m) (free form)

Mass (ESI): 459 (M⁺+1)

Example 14

Synthesis of N-(4,5α-epoxy-3,14-dihydroxy-morphinan-6β-yl)-phthalimide•tartaric acid salt (Compound 14)

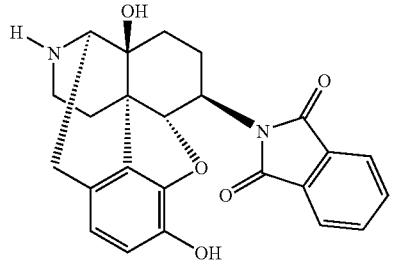

In a mixed solvent of 8 mL of acetonitrile, 4 mL of 1,2-dichloroethane and 2 mL of water, 300 mg (0.65 mmol) of N-(17-allyl-4,5α-epoxy-3,14-dihydroxy-morphinan-6β-yl)-phthalimide produced by the method described in Example 13 was dissolved, and 120 mg (0.13 mmol) of $(Ph_3P)_3RhCl$ was added, followed by heating the mixture to reflux at 100° C. for 18 hours. The reaction solution was allowed to cool to room temperature, and aqueous saturated sodium hydrogen carbonate solution was added, followed by extraction of the resulting mixture with chloroform. Organic layers were combined, washed with saturated saline, dried over anhydrous magnesium sulfate and concentrated to obtain a crude product. The obtained crude product was purified by silica gel column chromatography to obtain 120 mg (yield: 44%) of free form of the captioned compound 14. This product was converted to tartaric acid salt to obtain the captioned compound 14.

$^1$H-NMR (ppm) (300 MHz, CDCl$_3$) 7.8-7.9 (2H, m), 7.7-7.8 (2H, m), 6.73 (1H, d, J=8.2 Hz), 6.60 (1H, d, J=8.2 Hz), 5.06 (1H, d, J=8.2 Hz), 4.0-4.1 (1H, m), 2.9-3.1 (3H, m), 2.2-2.7 (6H, m), 1.4-1.65 (4H, m)(free form) Mass (ESI): 419(M$^+$+1)

Example 15

Synthesis of N-(17-cyclopropylmethyl-4,5α-epoxy-3,14-dihydroxy-morphinan-6β-yl)-4-chlorophthalimide•tartaric acid salt (Compound 15)

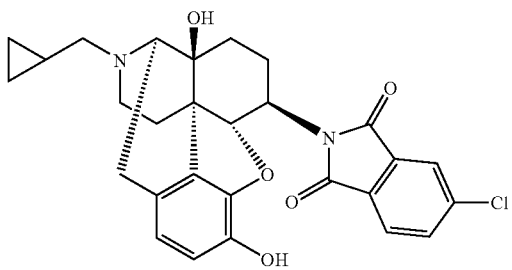

In a manner similar to the method described in Example 11, using 4-chlorophthalic anhydride in place of phthalic anhydride, 91 mg (yield: 77%) of free form of the captioned compound 15 was obtained. This product was converted to tartaric acid salt to obtain the captioned compound 15.

$^1$H-NMR (ppm) (300 MHz, CDCl$_3$) 7.75-7.8 (2H, m), 7.65-7.7 (1H, m), 6.76 (1H, d, J=8.2 Hz), 6.62 (1H, d, J=8.2 Hz), 5.14 (1H, d, J=8.2 Hz), 4.0-4.1 (1H, m), 3.11 (1H, d, J=5.6 Hz), 3.05 (1H, d, J=18.8 Hz), 2.6-2.8 (3H, m), 2.3-2.4 (3H, m), 2.14 (1H, dt, J=12.0, 3.5 Hz), 1.4-1.7 (4H, m), 0.8-0.9 (1H, m), 0.5-0.6 (2H, m), 0.1-0.2 (2H, m) (free form) Mass (ESI): 507(M$^+$+1)

Example 16

Synthesis of N-(17-cyclopropylmethyl-4,5α-epoxy-3,14-dihydroxy-morphinan-6β-yl)-4-fluorophthalimide•tartaric acid salt (Compound 16)

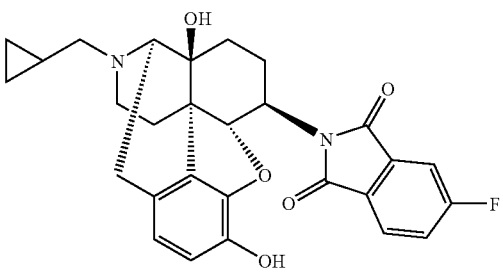

In a manner similar to the method described in Example 11, using 4-fluorophthalic anhydride in place of phthalic anhydride, 80 mg (yield: 70%) of free form of the captioned compound 16 was obtained. This product was converted to tartaric acid salt to obtain the captioned compound 16.

$^1$H-NMR (ppm) (300 MHz, CDCl$_3$) 7.75-7.85 (1H, m), 7.47 (1H, m), 7.3-7.4 (1H, m), 6.72 (1H, d, J=7.9 Hz), 6.58 (1H, d, J=8.2 Hz), 5.10 (1H, d, J=8.2 Hz), 3.95-4.05 (1H, m), 3.07 (1H, d, J=5.9 Hz), 3.02 (1H, d, J=18.8 Hz), 2.55-2.8 (3H, m), 2.35-2.4 (3H, m), 2.10 (1H, dt, J=12.0, 3.5 Hz), 1.4-1.7 (4H, m), 0.8-0.9 (1H, m), 0.5-0.6 (2H, m), 0.1-0.2 (2H, m)(free form) Mass (ESI): 491(M$^+$+1)

Example 17

Synthesis of N-(17-cyclopropylmethyl-4,5α-epoxy-3,14-dihydroxy-morphinan-6β-yl)-3-fluorophthalimide•tartaric acid salt (Compound 17)

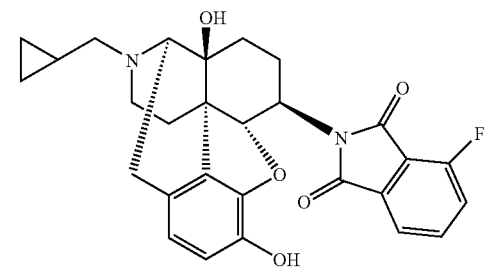

In a manner similar to the method described in Example 11, using 3-fluorophthalic anhydride in place of phthalic anhydride, 123 mg (yield: 57%) of free form of the captioned compound 17 was obtained. This product was converted to tartaric acid salt to obtain the captioned compound 17.

$^1$H-NMR (ppm) (300 MHz, CDCl$_3$) 7.65-7.75 (2H, m), 7.35-7.4 (1H, m), 6.76 (1H, d, J=7.9 Hz), 6.62 (1H, d, J=8.2 Hz), 5.15 (1H, d, J=8.2 Hz), 4.0-4.1 (1H, m), 3.11 (1H, d, J=5.8 Hz), 3.05 (1H, d, J=18.5 Hz), 2.60-2.85 (3H, m), 2.35-2.4 (3H, m), 2.13 (1H, dt, J=12.0, 3.5 Hz), 1.4-1.7 (4H, m), 0.8-0.9 (1H, m), 0.5-0.6 (2H, m), 0.1-0.2 (2H, m) (free form) Mass (ESI): 491 (M$^+$+1)

Example 18

Synthesis of N-(17-cyclopropylmethyl-4,5α-epoxy-3,14-dihydroxy-morphinan-6β-yl)-3-methylphthalimide•tartaric acid salt (Compound 18)

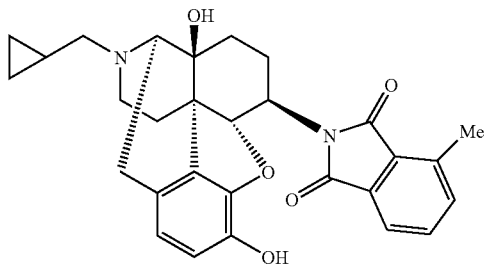

In a manner similar to the method described in Example 11, using 3-methylphthalic anhydride in place of phthalic anhydride, 108 mg (yield: 51%) of free form of the captioned compound 18 was obtained. This product was converted to tartaric acid salt to obtain the captioned compound 18.

$^1$H-NMR (ppm) (300 MHz, CDCl$_3$) 7.67 (1H, d, J=7.3 Hz), 7.56 (1H, t, J=7.3 Hz), 7.45 (1H, d, J=7.3 Hz), 6.75 (1H, d, J=8.2 Hz), 6.62 (1H, d, J=7.9 Hz), 5.18 (1H, d, J=8.2 Hz), 4.0-4.1 (1H, m), 3.11 (1H, d, J=5.6 Hz), 3.05 (1H, d, J=18.5 Hz), 2.60-2.85 (3H, m), 2.69 (3H, s), 2.35-2.4 (3H, m), 2.14 (1H, dt, J=12.0, 3.5 Hz), 1.4-1.7 (4H, m), 0.8-0.9 (1H, m), 0.5-0.6 (2H, m), 0.1-0.2 (2H, m) (free form) Mass (ESI): 487(M$^+$+1)

Example 19

Synthesis of N-(17-cyclopropylmethyl-4,5α-epoxy-3,14-dihydroxy-morphinan-6β-yl)-naphthalenedicarboximide•hydrochloric acid salt (Compound 19)

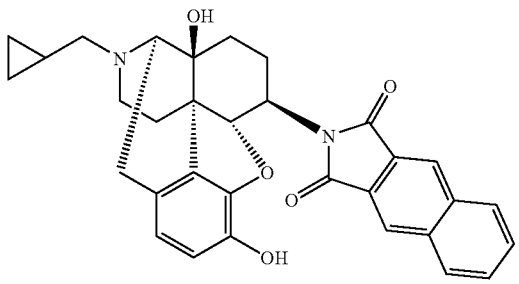

In a manner similar to the method described in Example 11, using naphthalenedicarboxylic anhydride in place of phthalic anhydride, 263 mg (yield: 86%) of free form of the captioned compound 19 was obtained. This product was converted to hydrochloric acid salt to obtain the captioned compound 19.

$^1$H-NMR (ppm) (300 MHz, CDCl$_3$) 8.17 (2H, s), 7.95-8.00 (2H, m), 7.68-7.72 (2H, m), 6.78 (1H, d, J=8.0 Hz), 6.63 (1H, d, J=8.3 Hz), 5.28 (1H, d, J=8.2 Hz), 4.1-4.2 (1H, m), 3.12 (1H, d, J=5.8 Hz), 3.06 (1H, d, J=18.4 Hz), 2.60-2.85 (3H, m), 2.35-2.4 (3H, m), 2.15 (1H, dt, J=12.0, 3.5 Hz), 1.4-1.7 (4H, m), 0.8-0.9 (1H, m), 0.5-0.6 (2H, m), 0.1-0.2 (2H, m) (free form) IR (cm$^{-1}$) (KBr) 3320, 1762, 1699, 1638, 1504, 1448, 1426, 1371, 1240, 1151, 1113, 1056, 1031, 1011 Elementary Analysis Formula: C$_{32}$H$_{30}$N$_2$O$_5$.1.0HCl.0.6H$_2$O Calcd.: C, 67.45; H, 5.70; N, 4.92; Cl, 6.22. Found: C, 67.25; H, 5.92; N, 5.05; Cl, 6.42. Mass (EI): 522(M$^+$)

Example 20

Synthesis of N-(3-acetoxy-17-cyclopropylmethyl-4,5α-epoxy-14-hydroxy-morphinan-6β-yl)-succinimide (Compound 220)

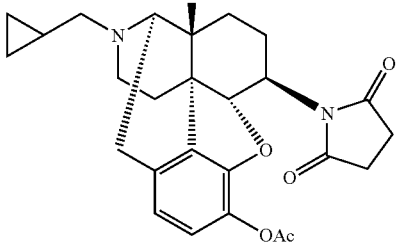

In 10 mL of chloroform, 300 mg (0.88 mmol) of 6β-naltrexamine was dissolved, and 92 mg (0.92 mmol) of succinic anhydride was added, followed by stirring the mixture at room temperature for 2 hours. Thereafter, 305 mg (2.82 mmol) of acetic anhydride and 286 mg (2.82 mmol) of triethylamine were added to the reaction solution, and the resulting mixture was heated to reflux for 15 hours. The reaction solution was allowed to cool to room temperature, and aqueous saturated sodium hydrogen carbonate solution was added, followed by extraction of the resulting mixture with chloroform. Organic layers were combined, washed with saturated saline, dried over anhydrous magnesium sulfate and concentrated to obtain a crude product. The obtained crude product was purified by silica gel column chromatography to obtain 258 mg (yield: 63%) of the captioned compound.

Mass (EI): 466(M$^+$)

Example 20-2

Synthesis of N-(17-cyclopropylmethyl-4,5α-epoxy-3,14-dihydroxy-morphinan-6β-yl)-succinimide•tartaric acid salt (Compound 20)

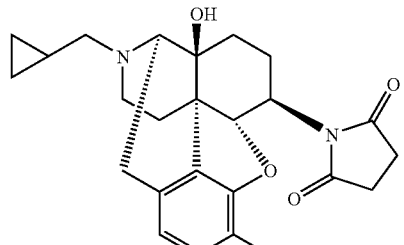

In 10 mL of methanol, 221 mg (0.47 mmol) of N-(3-acetoxy-17-cyclopropylmethyl-4,5α-epoxy-14-hydroxy-morphinan-6β-yl)-succinic imide obtained in Example 20-1 was dissolved, and 1 mL of 28% aqueous ammonia was added at 0° C., followed by stirring the mixture for 1 hour. Thereafter, chloroform was added to the reaction mixture to carry out extraction. Organic layers were combined, washed with saturated saline, dried over anhydrous magnesium sulfate and concentrated to obtain a crude product. The obtained crude product was purified by silica gel column chromatography to obtain 190 mg (yield: 95%) of free form of the captioned compound 20. This product was converted to tartaric acid salt to obtain the captioned compound 20.

$^1$H-NMR (ppm) (300 MHz, CDCl$_3$) 6.72 (1H, d, J=8.2 Hz), 6.59 (1H, d, J=8.2 Hz), 5.16 (1H, d, J=8.2 Hz), 3.9-4.0 (1H, m), 3.07 (1H, d, J=5.8 Hz), 3.02 (1H, d, J=18.7 Hz), 2.55-2.85 (6H, m), 2.25-2.40 (4H, m), 2.11 (1H, dt, J=12.0, 3.5 Hz), 1.6-1.7 (1H, m), 1.3-1.5 (3H, m), 0.8-0.9 (1H, m), 0.5-0.6 (2H, m), 0.1-0.2 (2H, m) (free form) IR (cm$^{-1}$) (KBr) 3322, 1772, 1697, 1603, 1502, 1459, 1385, 1328, 1198, 1175, 1128, 1066, 1036, 1005 Elementary Analysis Formula: $C_{24}H_{28}N_2O_5 \cdot 0.5C_4H_6O_6 \cdot 1.6H_2O$ Calcd.: C, 59.10; H, 6.52; N, 5.30. Found: C, 59.03; H, 6.54; N, 5.29. Mass (EI): 424(M$^+$)

Example 21-1

Synthesis of N-(3-acetoxy-17-cyclopropylmethyl-4,5α-epoxy-14-hydroxy-morphinan-6β-yl)-maleimide (Compound 121)

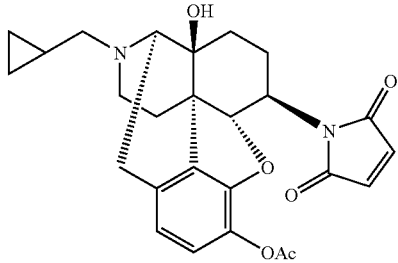

121

In a manner similar to the method described in Example 20-1, using maleic anhydride in place of succinic anhydride, 200 mg (yield: 75%) of the captioned compound was obtained.

Mass (EI): 464(M$^+$)

Example 21-2

Synthesis of N-(3-acetoxy-17-cyclopropylmethyl-4,5α-epoxy-14-hydroxy-morphinan-6β-yl)-2-benzylidene-succinimide (Compound 221)

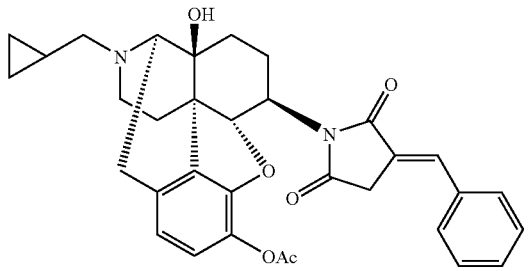

221

In 5 mL of THF, 200 mg (0.43 mmol) of N-(3-acetoxy-17-cyclopropylmethyl-4,5α-epoxy-14-hydroxy-morphinan-6β-yl)-maleimide obtained in Example 21-1 was dissolved, and 85 mg (0.62 mmol) of nitromethylbenzene and 66 mg (0.43 mmol) of DBU were added, followed by stirring the mixture at room temperature for 1 hour. To the reaction mixture, aqueous saturated sodium hydrogen carbonate solution was added, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 196 mg (yield: 82%) of the captioned compound.

Mass (EI): 554(M$^+$)

Example 21-3

Synthesis of N-(17-cyclopropylmethyl-4,5α-epoxy-3,14-dihydroxy-morphinan-6β-yl)-2-benzylidene-succinimide•tartaric acid salt (Compound 21)

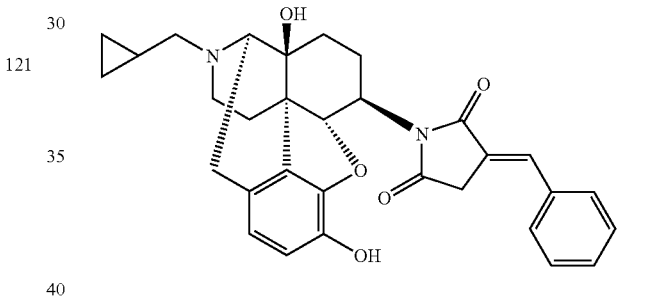

21

In 10 mL of methanol, 195 mg (0.35 mmol) of N-(3-acetoxy-17-cyclopropylmethyl-4,5α-epoxy-14-hydroxy-morphinan-6β-yl)-2-benzylidene-succinimide obtained in Example 21-2 was dissolved, and 1 mL of 28% aqueous ammonia was added at 0° C., followed by stirring the mixture for 1 hour. Thereafter, chloroform was added to the reaction mixture to carry out extraction. Organic layers were combined, washed with saturated saline, dried over anhydrous magnesium sulfate and concentrated to obtain a crude product. The obtained crude product was purified by silica gel column chromatography to obtain 170 mg (yield: 95%) of free form of the captioned compound 21. This product was converted to tartaric acid salt to obtain the captioned compound 21.

$^1$H-NMR (ppm) (300 MHz, CDCl$_3$) 7.40-7.45 (6H, m), 6.75 (1H, d, J=8.0 Hz), 6.60 (1H, d, J=8.2 Hz), 5.26 (1H, d, J=8.2 Hz), 4.0-4.1 (1H, m), 3.57 (2H, s), 3.08 (1H, d, J=5.5 Hz), 3.03 (1H, d, J=18.7 Hz), 2.55-2.80 (3H, m), 2.2-2.4 (3H, m), 2.10 (1H, dt, J=12.0, 3.5 Hz), 1.6-1.7 (1H, m), 1.3-1.5 (3H, m), 0.8-0.9 (1H, m), 0.5-0.6 (2H, m), 0.1-0.2 (2H, m) (free form) IR (cm$^{-1}$) (KBr) 3319, 1762, 1700, 1654, 1503, 1450, 1378, 1308, 1265, 1218, 1194, 1174, 1134, 1068 Mass (EI): 512(M$^+$)

Example 22-1

Synthesis of N-(3-acetoxy-17-cyclopropylmethyl-4,5α-epoxy-14-hydroxy-morphinan-6β-yl)-2-ethylidene-succinimide (Compound 222)

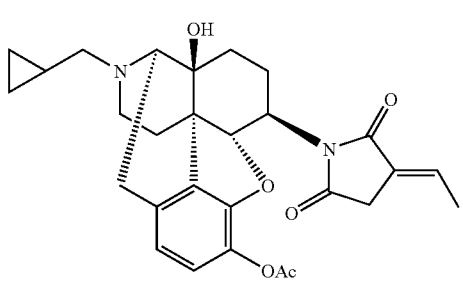

In a manner similar to the method described in Example 21-2, using nitroethane in place of nitromethylbenzene, 192 mg (yield: 45%) of the captioned compound was obtained.
Mass (EI): 492(M+)

Example 22-2

Synthesis of N-(17-cyclopropylmethyl-4,5α-epoxy-3,14-dihydroxy-morphinan-6β-yl)-2-ethylidene-succinimide•tartaric acid salt (Compound 22)

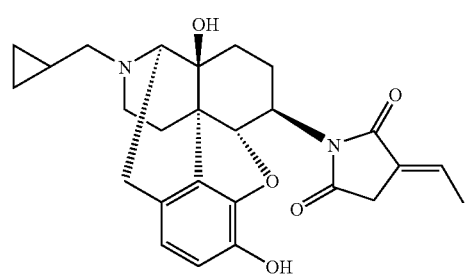

In a manner similar to the method described in Example 21-3, using 160 mg of N-(3-acetoxy-17-cyclopropylmethyl-4,5α-epoxy-14-hydroxy-morphinan-6β-yl)-2-ethylidene-succinimide obtained in Example 22-1, 146 mg (yield: 95%) of free form of the captioned compound 22 was obtained. This product was converted to tartaric acid salt to obtain the captioned compound 22.

$^1$H-NMR (ppm) (300 MHz, CDCl$_3$) 6.80-6.85 (1H, m), 6.74 (1H, d, J=8.1 Hz), 6.60 (1H, d, J=8.1 Hz), 5.18 (1H, d, J=8.2 Hz), 3.98-4.03 (1H, m), 3.24 (2H, s), 3.08 (1H, d, J=5.5 Hz), 3.03 (1H, d, J=18.3 Hz), 2.55-2.80 (3H, m), 2.25-2.40 (3H, m), 2.12 (1H, dt, J=12.0, 3.5 Hz), 1.87 (3H, d, J=7.0 Hz), 1.6-1.7 (1H, m), 1.3-1.5 (3H, m), 0.8-0.9 (1H, m), 0.5-0.6 (2H, m), 0.1-0.2 (2H, m) (free form) IR (cm$^{-1}$) (KBr) 3315, 1762, 1702, 1676, 1609, 1503, 1378, 1309, 1265, 1206, 1152, 1128, 1067, 1033 Mass (EI): 450(M+)

Example 23-1

Synthesis of N-(3-acetoxy-17-cyclopropylmethyl-4,5α-epoxy-14-hydroxy-morphinan-6β-yl)-2-cyclohexylmethylidene-succinimide (Compound 223)

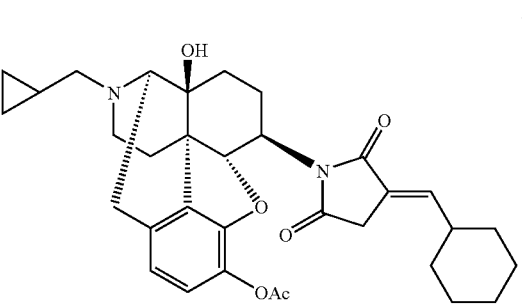

In a manner similar to the method described in Example 21-2, using nitromethylcyclohexane in place of nitromethylbenzene, 120 mg (yield: 50%) of the captioned compound was obtained.
Mass (EI): 560(M+)

Example 23-2

Synthesis of N-(17-cyclopropylmethyl-4,5α-epoxy-3,14-dihydroxy-morphinan-6β-yl)-2-cyclohexylmethylidene-succinimide•tartaric acid salt (Compound 23)

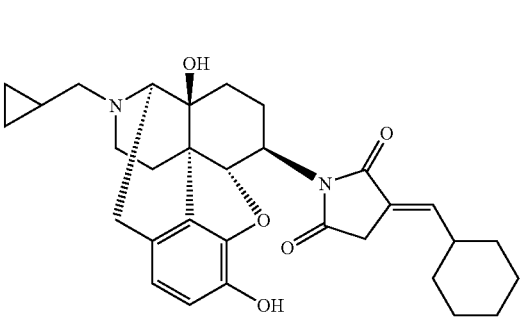

In a manner similar to the method described in Example 21-3, using 120 mg of N-(3-acetoxy-17-cyclopropylmethyl-4,5α-epoxy-14-hydroxy-morphinan-6β-yl)-2-cyclohexylmethylidene-succinimide obtained in Example 23-1, 107 mg (yield: 96%) of free form of the captioned compound 23 was obtained. This product was converted to tartaric acid salt to obtain the captioned compound 23.

$^1$H-NMR (ppm) (300 MHz, CDCl$_3$) 6.71 (1H, d, J=8.2 Hz), 6.60-6.65 (1H, m), 6.58 (1H, d, J=8.2 Hz), 5.16 (1H, d, J=8.2 Hz), 3.95-4.05 (1H, m), 3.23 (2H, d, J=1.9 Hz), 3.07 (1H, d, J=5.8 Hz), 3.02 (1H, d, J=18.7 Hz), 2.55-2.80 (3H, m), 2.25-2.40 (3H, m), 2.05-2.20 (2H, m), 1.6-1.8 (6H, m), 1.1-1.5 (8H, m), 0.8-0.9 (1H, m), 0.5-0.6 (2H, m), 0.1-0.2 (2H, m) (free form) IR (cm$^{-1}$) (KBr) 3319, 2927, 1763, 1701, 1671, 1617, 1507, 1377, 1309, 1266, 1197, 1132, 1067, 1032 Mass (EI): 518(M+)

Example 24-1

Synthesis of N-(3-acetoxy-17-cyclopropylmethyl-4,5α-epoxy-14-hydroxy-morphinan-6β-yl)-2-butylidene-succinimide (Compound 224)

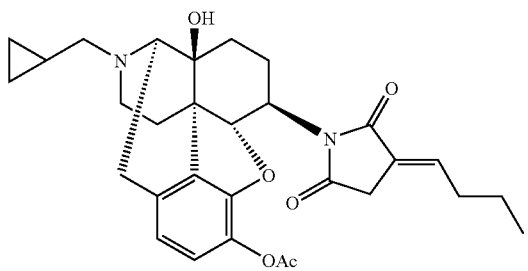

In a manner similar to the method described in Example 21-2, using nitrobutane in place of nitromethylbenzene, 535 mg (yield: 96%) of the captioned compound was obtained.

Mass (EI): 520(M+)

Example 24-2

Synthesis of N-(17-cyclopropylmethyl-4,5α-epoxy-3,14-dihydroxy-morphinan-6β-yl)-2-butylidene-succinimide•tartaric acid salt (Compound 24)

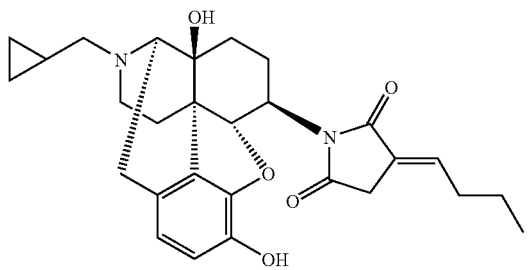

In a manner similar to the method described in Example 21-3, using 535 mg of N-(3-acetoxy-17-cyclopropylmethyl-4,5α-epoxy-14-hydroxy-morphinan-6β-yl)-2-butylidene-succinimide obtained in Example 24-1, 286 mg (yield: 58%) of free form of the captioned compound 24 was obtained. This product was converted to tartaric acid salt to obtain the captioned compound 24.

$^1$H-NMR (ppm) (300 MHz, CDCl$_3$) 6.77-6.85 (1H, m), 6.73 (1H, d, J=8.0 Hz), 6.59 (1H, d, J=8.2 Hz), 5.16 (1H, d, J=8.2 Hz), 3.95-4.05 (1H, m), 3.22 (2H, s), 3.08 (1H, d, J=5.8 Hz), 3.03 (1H, d, J=18.7 Hz), 2.55-2.80 (3H, m), 2.25-2.40 (3H, m), 2.05-2.20 (3H, m), 1.3-1.7 (6H, m), 0.96 (3H, t, J=7.4 Hz), 0.8-0.9 (1H, m), 0.5-0.6 (2H, m), 0.1-0.2 (2H, m) (free form) Mass (EI): 478(M+)

Example 25

Synthesis of 2-(17-cyclopropylmethyl-4,5α-epoxy-3,14-dihydroxy-morphinan-6β-yl)-3-hydroxy-2,3-dihydro-isoindol-1-one (diastereomer mixture)•tartaric acid salt (Compound 25)

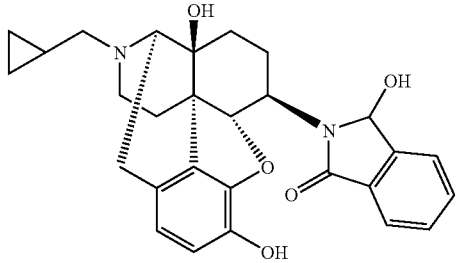

In a mixed solvent of 5 mL of methanol and 5 mL of chloroform, 156 mg (0.33 mmol) of N-(17-cyclopropylmethyl-4,5α-epoxy-3,14-dihydroxy-morphinan-6β-yl)-phthalimide produced by the method described in Example 11 was dissolved, and 61 mg (1.61 mmol) of sodium borohydride was added thereto at 0° C., followed by stirring the mixture for 2 hours. Thereafter, aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 130 mg (yield: 83%) of free form of the captioned compound 25. This product was converted to tartaric acid salt to obtain the captioned compound 25.

$^1$H-NMR (ppm) (300 MHz, CDCl$_3$) 7.35-7.65 (4H, m), 6.68 (0.5H, d, J=8.2 Hz), 6.63 (0.5H, d, J=8.2 Hz), 6.56 (0.5H, d, J=8.2 Hz), 6.51 (0.5H, d, J=8.2 Hz), 6.07 (1.5H, s), 5.81 (1.5H, s), 5.39 (0.5H, d, J=8.2 Hz), 5.22 (0.5H, d, J=8.0 Hz), 4.70 (1H, dd, J=6.0, 3.3 Hz), 4.0-4.1 (0.5H, m), 3.6-3.7 (0.5H, m), 2.95-3.05 (2H, m), 2.4-2.7 (3H, m), 2.2-2.4 (2H, m), 2.0-2.1 (2H, m), 1.6-1.7 (1H, m), 1.2-1.6 (3H, m), 0.8-0.9 (1H, m), 0.5-0.6 (2H, m), 0.1-0.2 (2H, m) (free form)
Mass (EI): 474(M+)

Example 26-1 (27-1)

Synthesis of 2-(3-benzyloxy-17-cyclopropylmethyl-4,5α-epoxy-14-hydroxy-morphinan-6β-yl)-3-hydroxy-2,3-dihydro-isoindol-1-one (diastereomer mixture) (Compound 126)

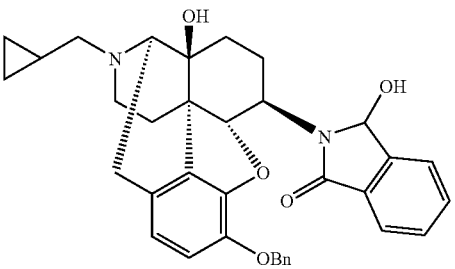

In 20 mL of DMF, 2.00 g (4.23 mmol) of N-(17-cyclopropylmethyl-4,5α-epoxy-3,14-dihydroxy-morphinan-6β-yl)-phthalimide produced by the method described in Example 11 was dissolved, and 1.76 g (12.7 mmol) of potassium carbonate and 0.5 mL (4.70 mmol) of benzyl bromide were added, followed by stirring the mixture at room temperature for 18 hours. Thereafter, 40 mL of water was added to the reaction mixture, and the resulting mixture was extracted with ethyl acetate. Organic layers were combined, washed with water and saturated saline, dried over anhydrous magnesium sulfate and concentrated to obtain a crude product. The obtained crude product was then dissolved in a mixed solution of 30 mL of methanol and 10 mL of chloroform, and 161 mg (4.26 mmol) of sodium borohydride was added at 0° C., followed by stirring the mixture for 2 hours. Organic layers were combined, washed with saturated saline, dried over anhydrous magnesium sulfate and concentrated to obtain a crude product. The obtained crude product was purified by silica gel column chromatography to obtain 1.90 g (2 steps yield: 80%) of the captioned compound.

Mass (EI): 564(M+)

Examples 26-2 and 27-2

Synthesis of 2-(3-benzyloxy-17-cyclopropylmethyl-4,5α-epoxy-14-hydroxy-morphinan-6β-yl)-2,3-dihydro-3-methoxycarbonylmethyl-isoindol-1-one (Compounds 226 and 227)

226 and 227

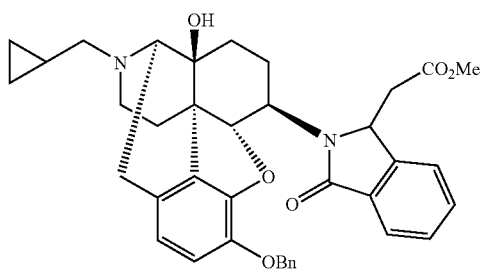

In 10 mL of toluene, 200 mg (0.35 mmol) of 2-(3-benzyloxy-17-cyclopropylmethyl-4,5α-epoxy-14-hydroxy-morphinan-6β-yl)-3-hydroxy-2,3-dihydro-isoindol-1-one obtained in Example 26-1 was dissolved, and 147 mg (0.43 mmol) of (carbomethoxymethylene)triphenylphosphorane was added thereto, followed by heating the mixture to reflux for 15 hours. Thereafter, aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain the captioned compound as 33 mg of low polarity component and 38 mg of high polarity component (yields: 15% and 17%, respectively).

Low polarity component: Mass (EI): 620(M+)
High polarity component: Mass (EI): 620(M+)

Example 26-3, 27-3

Synthesis of 2-(17-cyclopropylmethyl-4,5α-epoxy-3,14-dihydroxy-morphinan-6β-yl)-2,3-dihydro-3-methoxycarbonylmethyl-isoindol-1-one•tartaric acid salt (Compounds 26 and 27)

26 and 27

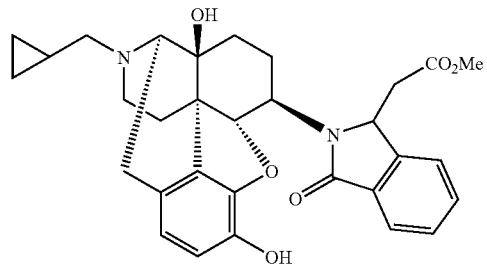

In 4 mL of methanol, 33 mg (0.05 mmol) of the low polarity component of 2-(3-benzyloxy-17-cyclopropylmethyl-4,5α-epoxy-14-hydroxy-morphinan-6β-yl)-2,3-dihydro-3-methoxycarbonylmethyl-isoindol-1-one obtained in Example 26-2 was dissolved, and 19 mg of Pd/C was added thereto, followed by stirring the mixture under hydrogen atmosphere at room temperature for 20 hours. The reaction mixture was then filtered through Celite, and the obtained filtrate was concentrated to obtain a crude product. The obtained crude product was purified by silica gel column chromatography to obtain 15 mg (yield: 54%) of free form of the captioned compound 26. This product was converted to tartaric acid salt to obtain the captioned compound 26.

$^1$H-NMR (ppm) (300 MHz, CDCl$_3$) 7.84 (1H, d, J=6.8 Hz), 7.53 (1H, d, J=7.4 Hz), 7.46 (1H, t, J=6.8 Hz), 7.36 (1H, d, J=7.4 Hz), 6.75 (1H, d, J=8.2 Hz), 6.60 (1H, d, J=8.0 Hz), 5.43 (1H, d, J=8.0 Hz), 4.70 (1H, dd, J=6.0, 3.3 Hz), 3.57 (3H, s), 3.2-3.3 (1H, m), 3.05-3.15 (2H, m), 3.03 (1H, d, J=18.8 Hz), 2.8-2.9 (2H, m), 2.63 (2H, dt, J=18.6, 5.5 Hz), 2.3-2.4 (3H, m), 2.11 (1H, dt, J=12.0, 3.5 Hz), 1.6-1.7 (1H, m), 1.4-1.5 (3H, m), 0.8-0.9 (1H, m), 0.5-0.6 (2H, m), 0.1-0.2 (2H, m) (free form) Mass (EI): 530(M+)

On the other hand, 38 mg (0.06 mmol) of the high polarity component of 2-(3-benzyloxy-17-cyclopropylmethyl-4,5α-epoxy-14-hydroxy-morphinan-6β-yl)-2,3-dihydro-3-methoxycarbonylmethyl-isoindol-1-one obtained in Example 27-2 was dissolved in 4 mL of methanol, and 20 mg of Pd/C was added thereto, followed by stirring the mixture under hydrogen atmosphere at room temperature for 20 hours. The reaction mixture was then filtered through Celite, and the obtained filtrate was concentrated to obtain a crude product. The obtained crude product was purified by silica gel column chromatography to obtain 17 mg (yield: 53%) of free form of the captioned compound 27. This product was converted to tartaric acid salt to obtain the captioned compound 27.

$^1$H-NMR (ppm) (300 MHz, CDCl$_3$) 7.83 (1H, d, J=6.6 Hz), 7.4-7.5 (2H, m), 7.35 (1H, d, J=7.4 Hz), 6.78 (1H, d, J=8.2 Hz), 6.60 (1H, d, J=8.0 Hz), 5.12 (1H, d, J=8.0 Hz), 5.05 (1H, dd, J=7.3, 5.5 Hz), 3.61 (3H, s), 3.4-3.5 (1H, m), 3.09 (1H, d, J=5.5 Hz), 3.04 (1H, d, J=18.7 Hz), 2.8-2.9 (2H, m), 2.5-2.7 (3H, m), 2.2-2.4 (3H, m), 2.11 (1H, dt, J=12.0, 3.5 Hz), 1.6-1.7 (1H, m), 1.4-1.5 (3H, m), 0.8-0.9 (1H, m), 0.5-0.6 (2H, m), 0.1-0.2 (2H, m) (free form) Mass (EI): 530(M+)

Example 28

Synthesis of 2-(17-cyclopropylmethyl-4,5α-epoxy-3,14-dihydroxy-morphinan-6β-yl)-2,3-dihydro-isoisoindol-1-one•tartaric acid salt (Compound 28)

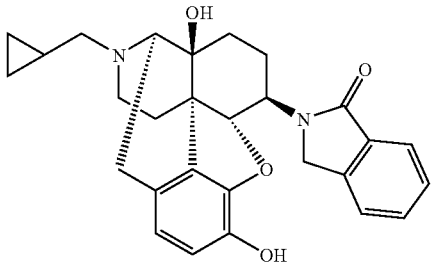

In a mixed solvent of 7 mL of methylene chloride and 25 mL of chloroform, 150 mg (0.32 mmol) of 2-(17-cyclopropylmethyl-4,5α-epoxy-3,14-dihydroxy-morphinan-6β-yl)-3-hydroxy-2,3-dihydro-isoindol-1-one (diastereomer mixture) produced by the method described in Example 25 was dissolved, and 0.22 mL (1.73 mmol) of boron trifluoride ether complex and 0.28 mL (1.73 mmol) of triethylsilane were added at 0° C., followed by stirring the mixture for 22 hours. Thereafter, aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 55 mg (yield: 38%) of free form of the captioned compound 28. This product was converted to tartaric acid salt to obtain the captioned compound 28.

$^1$H-NMR (ppm) (300 MHz, CDCl$_3$) 7.85 (d, J=8.2 Hz, 1H), 7.58-7.45 (m, 3H), 6.79 (d, J=8.2 Hz, 1H), 6.62 (d, J=8.2 Hz, 1H), 4.68 (d, J=8.2 Hz, 1H), 4.52 (d, J=16.8 Hz, 1H), 4.44 (d, J=16.8 Hz, 1H), 4.27 (ddd, J=12.6, 8.2, 4.4 Hz, 1H), 3.11 (d, J=5.5 Hz, 1H), 3.06 (d, J=18.4 Hz, 1H), 2.70-2.59 (m, 2H), 2.39 (d, J=6.6 Hz, 2H), 2.31-2.12 (m, 3H), 1.72-1.49 (m, 4H), 0.93-0.79 (m, 1H), 0.58-0.50 (m, 2H), 0.17-0.11 (m, 2H) (free form) IR (cm$^{-1}$) (KBr) 3075, 3004, 2925, 2818, 1658, 1622, 1498, 1455, 1377, 1330, 1307, 1279, 1228, 1188, 1153, 1117, 1069, 1051, 1034, 981, 943, 919, 884, 859, 740 Mass (EI): 458(M$^+$)

Example 29

Synthesis of 1-(4,5α-epoxy-3,14-dihydroxy-17-methyl-morphinan-6β-yl)-pyrrolidin-(2S)-carboxyl diethylamide•tartaric acid salt (Compound 29)

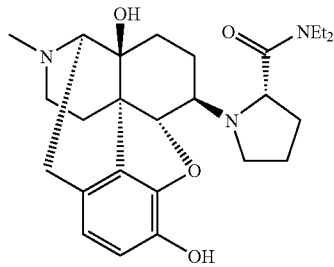

In 15 mL of toluene, 300 mg (1.00 mmol) of oxymorphone and 244 mg (2.00 mmol) of benzoic acid were dissolved, and 200 mg (1.17 mmol) of (S)-proline diethylamide was added, followed by heating the mixture to reflux for 12 hours while azeotropically removing water in an oil bath at 145° C. After allowing the reaction solution to cool to room temperature, 188 mg (3.00 mmol) of 10 mL of sodium cyanoborohydride solution in methanol was added, and the resulting mixture was stirred at room temperature for 3 hours. Aqueous saturated sodium hydrogen carbonate solution was added to the reaction mixture, and the resulting mixture was extracted with ethyl acetate. Organic layers were combined, washed with saturated saline, dried over anhydrous magnesium sulfate and concentrated to obtain a crude product. The obtained crude product was purified by silica gel column chromatography to obtain 202 mg (yield: 44%) of free form of the captioned compound 29. This product was converted to tartaric acid salt to obtain the captioned compound 29.

$^1$H-NMR (ppm) (300 MHz, CDCl$_3$) 6.69 (1H, d, J=8.2 Hz), 6.52 (1H, d, J=8.2 Hz), 4.52 (1H, d, J=8.0 Hz), 3.15-3.60 (6H, m), 3.09 (1H, d, J=18.4 Hz), 2.6-2.7 (2H, m), 2.51 (1H, dd, J=18.2, 5.9 Hz), 2.3-2.4 (2H, m), 2.34 (3H, s), 2.1-2.2 (2H, m), 1.7-2.0 (5H, m), 1.4-1.55 (3H, m), 1.1-1.3 (1H, m), 1.07 (3H, t, J=7.0 Hz), 1.01 (3H, t, J=7.0 Hz) (free form) Mass (ESI): 456(M$^+$+1)

Example 30-1

Synthesis of 1-(4,5α-epoxy-14-hydroxy-3-methoxy-17-methyl-morphinan-6β-yl)-pyrrolidin-(2R)-carboxyl diethylamide (Compound 230)

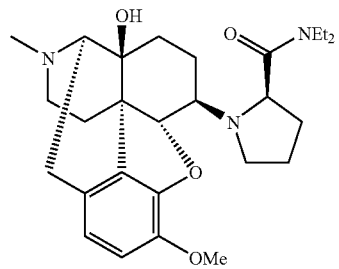

In a manner similar to the method described in Example 1-1, using oxycodone in place of dihydrocodeinone, and using (R)-proline diethylamide in place of 1,2,3,4-tetrahydroquinoline, 62 mg (yield: 26%) of the captioned compound was obtained.

Mass (ESI): 470(M$^+$+1)

Example 30-2

Synthesis of 1-(4,5α-epoxy-3,14-dihydroxy-17-methyl-morphinan-6β-yl)-pyrrolidin-(2R)-carboxyl diethylamide•tartaric acid salt (Compound 30)

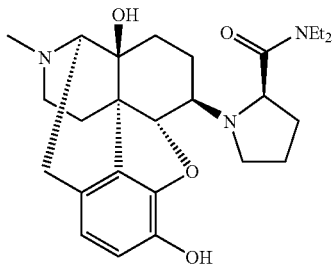

In a manner similar to the method described in Example 1-2, using 1-(4,5α-epoxy-14-hydroxy-3-methoxy-17-methyl-morphinan-6β-yl)-pyrrolidin-(2R)-carboxyl diethylamide obtained in Example 30-1, 42 mg (yield: 71%) of free form of the captioned compound 30 was obtained. This product was converted to tartaric acid salt to obtain the captioned compound 30.

¹H-NMR (ppm) (300 MHz, CDCl₃) 6.70 (1H, d, J=8.2 Hz), 6.53 (1H, d, J=7.9 Hz), 4.66 (1H, d, J=7.9 Hz), 4.12 (1H, t, J=8.2 Hz), 3.7-3.8 (1H, m), 3.4-3.7 (2H, m), 3.10 (1H, d, J=18.4 Hz), 3.0-3.1 (2H, m), 2.6-2.8 (3H, m), 2.53 (1H, dd, J=18.4, 5.5 Hz), 2.4 (1H, m), 2.36 (3H, s), 2.1-2.2 (2H, m), 1.7-2.0 (5H, m), 1.45-1.65 (3H, m), 1.3-1.4 (1H, m), 1.10 (3H, t, J=7.0 Hz), 0.98 (3H, t, J=7.0 Hz) (free form) Mass (ESI): 456(M⁺+1)

Examples 31 and 32

Synthesis of 1-(4,5α-epoxy-3-hydroxy-17-methyl-morphinan-6α-yl)-pyrrolidin-(2S)-carboxyl diethylamide•tartaric acid salt (Compound 31), and 1-(4,5α-epoxy-3-hydroxy-17-methyl-morphinan-6β-yl)-pyrrolidin-(2S)-carboxyl diethylamide tartaic acid salt (Compound 32)

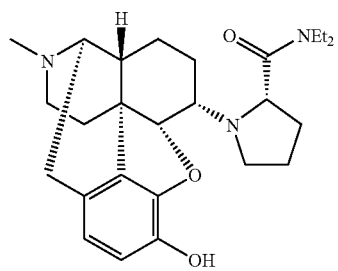

31

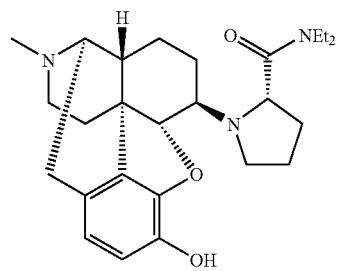

32

In 20 mL of toluene, 188 mg (0.45 mmol) of 3-benzyloxycarbonyloxy-4,5α-epoxy-17-methyl-6-oxo-morphinan and 88 mg (0.72 mmol) of benzoic acid were dissolved, and 115 mg (0.68 mmol) of (S)-proline diethylamide was added, followed by heating the mixture to reflux for 12 hours while azeotropically removing water in an oil bath at 145° C. After allowing the reaction solution to cool to room temperature, 10 mL of a solution containing 99 mg (1.58 mmol) of sodium cyanoborohydride in methanol was added, and the resulting mixture was stirred at room temperature for 3 hours. Aqueous saturated sodium hydrogen carbonate solution was added to the reaction mixture, and the resulting mixture was extracted with ethyl acetate. Organic layers were combined, washed with saturated saline, dried over anhydrous magnesium sulfate and concentrated to obtain 1-(3-benzyloxycarbonyloxy-4,5α-epoxy-17-methyl-morphinan-6-yl)-pyrrolidin-(2S)-carboxyl diethylamide (diastereomer mixture) as a crude product.

This crude product was dissolved in 10 mL of ethyl acetate, and 15 mg of Pd/C was added, followed by stirring the mixture under hydrogen atmosphere at room temperature for 20 hours. The reaction mixture was filtered through Celite, and the obtained filtrate was concentrated to obtain a crude product. The obtained crude product was purified by silica gel column chromatography to obtain 13 mg (2 steps yield: 6.6%) of free form of the captioned compound 31, and 9 mg (2 steps yield: 4.6%) of free form of the captioned compound 32. This product was converted to tartaric acid salt to obtain the captioned compounds 31 and 32.

Compound 31

¹H-NMR (ppm) (300 MHz, CDCl₃) 6.74 (1H, d, J=7.9 Hz), 6.53 (1H, d, J=8.2 Hz), 4.58 (1H, dd, J=13.0, 1.6 Hz), 3.7-3.8 (1H, m), 3.2-3.6 (5H, m), 3.0-3.1 (1H, m), 2.94 (1H, d, J=18.5 Hz), 2.7-2.8 (2H, m), 2.4-2.5 (1H, m), 2.38 (3H, s), 2.1-2.3 (4H, m), 1.7-1.9 (4H, m), 1.5-1.7 (2H, m), 1.2-1.3 (1H, m), 1.20 (3H, t, J=7.0 Hz), 1.09 (3H, t, J=7.0 Hz), 0.8-1.0 (2H, m) (free form) Mass (ESI): 440(M⁺+1)

Compound 32

¹H-NMR (ppm) (300 MHz, CDCl₃) 6.69 (1H, d, J=7.9 Hz), 6.53 (1H, d, J=8.2 Hz), 4.45 (1H, d, J=8.2 Hz), 3.55-3.65 (1H, m), 3.2-3.5 (5H, m), 3.05-3.10 (1H, m), 2.97 (1H, d, J=18.5 Hz), 2.5-2.6 (2H, m), 2.1-2.5 (5H, m), 2.41 (3H, s), 1.9-2.1 (2H, m), 1.7-1.9 (2H, m), 1.5-1.7 (2H, m), 1.2-1.3 (2H, m), 1.09 (3H, t, J=7.0 Hz), 1.02 (3H, t, J=7.0 Hz), 0.8-0.9 (1H, m) (free form) Mass (ESI): 440(M⁺+1)

Example 33-1

Synthesis of 1-(4,5α-epoxy-14-hydroxy-17-methyl-3-methoxy-morphinan-6β-yl)-piperidin-3-carboxyl diethylamide (diastereomer mixture) (Compound 233)

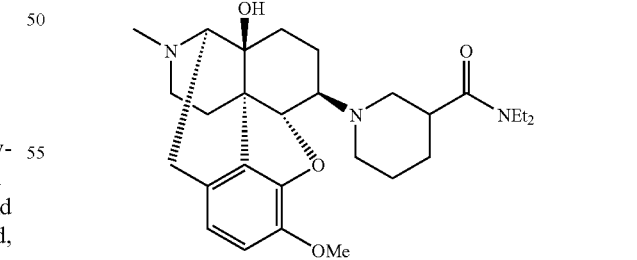

233

In a manner similar to the method described in Example 1-1, using oxycodone in place of dihydrocodeinone, and using pipecolin diethylamide in place of 1,2,3,4-tetrahydroquinoline, 96 mg (yield: 12%) of the captioned compound was obtained.

Mass (ESI): 484(M⁺+1)

Example 33-2

Synthesis of 1-(4,5α-epoxy-3,14-dihydroxy-17-methyl-3-morphinan-6β-yl)-piperidin-3-carboxyl diethylamide (diastereomer mixture)•tartaric acid salt (Compound 33)

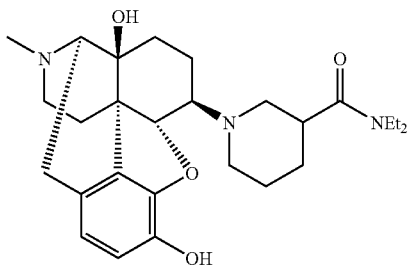

In a manner similar to the method described in Example 1-2, using 1-(4,5α-epoxy-14-hydroxy-17-methyl-3-methoxy-morphinan-6β-yl)-piperidin-3-carboxyl diethylamide (diastereomer mixture) obtained in Example 33-1, 66 mg (yield: 74%) of free form of the captioned compound 33 was obtained. This product was converted to tartaric acid salt to obtain the captioned compound 33.

$^1$H-NMR (ppm) (300 MHz, CDCl$_3$) 6.70 (1H, d, J=7.9 Hz), 6.56 (1H, d, J=7.9 Hz), 4.70 (0.5H, d, J=7.9 Hz), 4.63 (0.5H, d, J=7.9 Hz), 3.2-3.4 (4H, m), 3.09 (1H, d, J=18.5 Hz), 2.8-3.0 (3H, m), 2.60-2.75 (2H, m), 2.3-2.5 (4H, m), 2.35 (3H, s), 2.1-2.2 (2H, m), 1.7-2.0 (3H, m), 1.2-1.7 (6H, m), 1.18 (1.5H, t, J=7.0 Hz), 1.17 (1.5H, t, J=7.0 Hz), 1.10 (1.5H, t, J=7.0 Hz), 1.08 (1.5H, t, J=7.0 Hz) (free form) Mass (ESI): 470(M$^+$+1)

Example 34

Synthesis of 1-(17-cyclopropylmethyl-4,5α-epoxy-3,14-dihydroxy-morphinan-6α-yl)-pyrrolidin-2-one•hydrochloric acid salt (Compound 34)

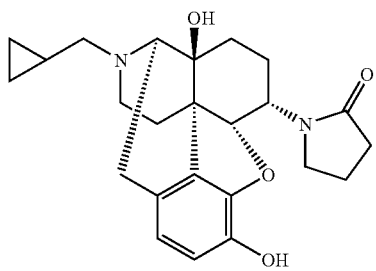

In 100 mL of methanol, 0.445 g (1.96 mmol) of platinum oxide was dissolved, and the mixture was stirred under hydrogen atmosphere at room temperature for 2 hours. Thereafter, to this reaction solution, 150 mL of a solution containing 10.0 g (26.5 mmol) of naltrexone hydrochloric acid salt and 17.8 g (105.9 mmol) of ethyl 4-aminobutyrate hydrochloric acid salt in methanol was added, and the resulting mixture was stirred at room temperature for 15 hours. The reaction mixture was filtered through Celite, and the obtained filtrate was concentrated. To the obtained residue, aqueous saturated sodium hydrogen carbonate solution was added, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 5.46 g (yield: 45%) of 17-cyclopropylmethyl-4,5α-epoxy-6α-[4-(ethoxycarbonyl)butylamino]-morphinan-3,14-diol.

In 30 mL of toluene, 4.46 g (9.77 mmol) of this purified product was dissolved, and the mixture was heated to reflux for 72 hours. The reaction solution was allowed to cool to room temperature, and concentrated to obtain a crude product. The obtained crude product was purified by silica gel column chromatography to obtain 1.78 g (yield: 44%) of free form of the captioned compound 34. This product was converted to hydrochloric acid salt to obtain the captioned compound 34.

$^1$H-NMR (ppm) (300 MHz, CDCl$_3$) 6.73 (d, J=8.0 Hz, 1H), 6.54 (d, J=8.0 Hz, 1H), 4.82 (d, J=3.8 Hz, 1H), 4.67 (dt, J=13.5, 3.8 Hz, 1H), 3.68 (td, J=9.3, 5.8 Hz, 1H), 3.35 (td, J=9.3, 5.5 Hz, 1H), 3.10 (d, J=6.9 Hz, 1H), 3.03 (d, J=18.4 Hz, 1H), 2.66-1.70 (m, 1H), 1.57-1.24 (m, 4H), 0.90-0.75 (m, 1H), 0.56-0.50 (m, 2H), 0.16-0.09 (m, 2H) (free form) IR (cm$^{-1}$) (KBr) 2959, 2823, 1655, 1499, 1463, 1310, 1160, 1116, 1070, 1040, 978, 951, 859, 802, 759 Mass (EI): 410(M$^+$)

Example 35

Synthesis of 1-(17-cyclopropylmethyl-4,5α-epoxy-3,14-dihydroxy-morphinan-6α-yl)-3-benzyl-pyrrolidin-2-one (diastereomer mixture)•tartaric acid salt (Compound 35)

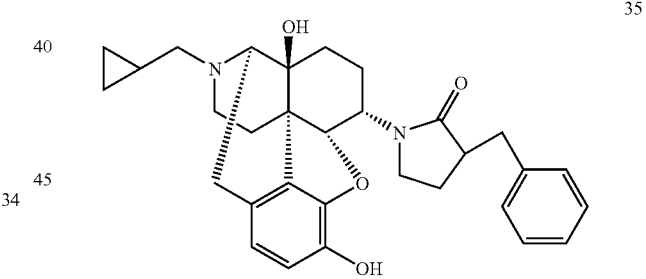

In 10 mL of THF, 269 mg (0.65 mmol) of 1-(17-cyclopropylmethyl-4,5α-epoxy-3,14-dihydroxy-morphinan-6α-yl)-pyrrolidin-2-one produced by the method described in Example 34 was dissolved, and 6.0 mL (2.16 mmol) of 0.36 N LDA/THF solution was added at 0° C., followed by stirring the mixture for 30 minutes. Thereafter, 0.23 mL (1.96 mmol) of benzyl bromide was added, and the mixture was stirred for 100 minutes. Aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 49 mg (yield: 15%) of free form of the captioned compound 35. This product was converted to tartaric acid salt to obtain the captioned compound 35.

¹H-NMR (ppm) (300 MHz, CDCl₃) 7.33-7.18 (m, 5H), 6.72 (d, J=8.0 Hz, 1H), 6.53 (d, J=8.0 Hz, 1H), 4.79 (d, J=4.1 Hz, 1H), 4.67 (dt, J=13.2, 4.1 Hz, 1H), 3.50-3.38 (m, 1H), 3.28 (q, J=9.2 Hz, 1H), 3.21-3.10 (m, 2H), 3.03 (d, J=18.7 Hz, 1H), 2.75-2.55 (m, 4H), 2.42-2.18 (m, 4H), 2.05-1.93 (m, 1H), 1.87-1.68 (m, 2H), 1.58-1.22 (m, 4H), 0.93-0.77 (m, 1H), 0.58-0.50 (m, 2H), 0.15-0.09 (m, 2H) (free form) IR (cm⁻¹) (KBr) 2936, 2858, 1648, 1619, 1498, 1459, 1438, 1321, 1276, 1173, 1119, 1071, 1031, 918, 801, 748, 702 Mass (EI): 500(M⁺)

Example 36-1

Synthesis of 1-(3-benzyloxy-17-cyclopropylmethyl-4,5α-epoxy-14-hydroxy-morphinan-6α-yl)-pyrrolidin-2-one (Compound 136)

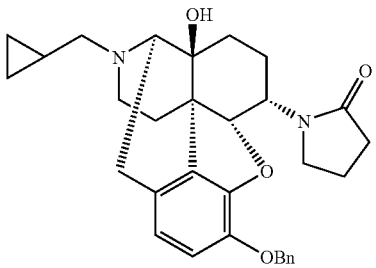

136

In 5 mL of DMF, 219 mg (0.53 mmol) of 1-(17-cyclopropylmethyl-4,5α-epoxy-3,14-dihydroxy-morphinan-6α-yl)-pyrrolidin-2-one produced by the method described in Example 34 was dissolved, and 738 mg (5.34 mmol) of potassium carbonate and 0.19 mL (1.60 mmol) of benzyl bromide were added thereto, followed by stirring the mixture at room temperature for 96 hours. Aqueous saturated sodium hydrogen carbonate solution was added to the reaction mixture, and the resulting mixture was extracted with diethyl ether. Organic layers were combined, washed with saturated saline, dried over anhydrous magnesium sulfate and concentrated to obtain a crude product. The obtained crude product was purified by silica gel column chromatography to obtain 265 mg (yield: 99%) of the captioned compound.

¹H-NMR (ppm) (300 MHz, CDCl₃) 7.43-7.29 (m, 5H), 6.77 (d, J=8.2 Hz, 1H), 6.54 (d, J=8.2 Hz, 1H), 5.18 (d, J=11.8 Hz, 1H), 5.09 (d, J=11.8 Hz, 1H), 4.79 (d, J=3.8 Hz, 1H), 4.70 (dt, J=13.4, 3.8 Hz, 1H), 3.76 (td, J=8.2, 5.8 Hz, 1H), 3.28 (td, J=8.5, 5.8 Hz, 1H), 3.10 (d, J=6.9 Hz, 1H), 3.03 (d, J=18.4 Hz, 1H), 2.67-1.20 (m, 15H), 0.87-0.81 (m, 1H), 0.56-0.49 (m, 2H), 0.13-0.08 (m, 2H). IR (cm⁻¹) (KBr) 2955, 2927, 2868, 1681, 1634, 1607, 1502, 1453, 1423, 1378, 1308, 1287, 1263, 1202, 1174, 1123, 1050, 941, 909, 854, 788, 764 Mass (EI): 500(M⁺)

Example 36-2

Synthesis of 1-(3-benzyloxy-17-cyclopropylmethyl-4,5α-epoxy-14-hydroxy-morphinan-6α-yl)-3-ethyl-pyrrolidin-2-one (diastereomer mixture) (Compound 236)

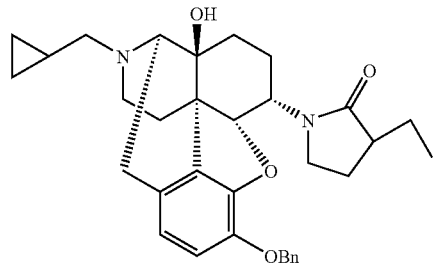

236

In 5 mL of THF, 248 mg (0.50 mmol) of 1-(3-benzyloxy-17-cyclopropylmethyl-4,5α-epoxy-14-hydroxy-morphinan-6α-yl)-pyrrolidin-2-one obtained in Example 36-1 was dissolved, and 4.1 mL (1.48 mmol) of 0.36N LDA/THF solution was added at 0° C., followed by stirring the mixture for 1 hour. Thereafter, 0.08 mL (0.99 mmol) of iodoethane was added thereto and the resulting mixture was stirred for 3 hours. Aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 176 mg (yield: 67%) of the captioned compound.
Mass (EI): 528(M⁺)

Example 36-3

Synthesis of 1-(17-cyclopropylmethyl-4,5α-epoxy-3,14-dihydroxy-morphinan-6α-yl)-3-ethyl-pyrrolidin-2-one (diastereomer mixture)•tartaric acid salt (Compound 36)

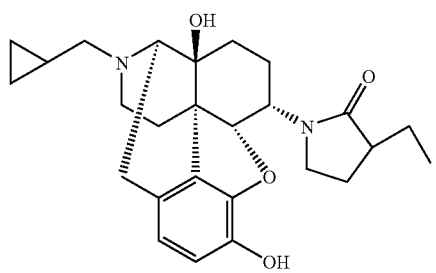

36

In 10 mL of methanol, 171 mg (0.32 mmol) of 1-(3-benzyloxy-17-cyclopropylmethyl-4,5α-epoxy-14-hydroxy-morphinan-6α-yl)-3-ethyl-pyrrolidin-2-one (diastereomer mixture) obtained in Example 36-2 and 108 mg (0.65 mmol) of o-phthalic acid were dissolved, and 150 mg of Pd/C was added thereto, followed by stirring the mixture under hydrogen atmosphere at room temperature for 19 hours. The reaction mixture was filtered through Celite, and the obtained filtrate was concentrated. To the obtained residue, aqueous saturated sodium hydrogen carbonate solution was added, and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 68 mg (yield: 48%) of free form of the captioned compound 36. This product was converted to tartaric acid salt to obtain the captioned compound 36.

$^1$H-NMR (ppm) (300 MHz, CDCl$_3$) 6.73 (d, J=8.2 Hz, 1H), 6.53 (d, J=8.2 Hz, 1H), 4.85 (d, J=3.8 Hz, 1H), 4.65 (dt, J=13.2, 3.8 Hz, 1H), 3.56 (q, J=8.0 Hz, 1H), 3.30 (td, J=5.9, 3.3 Hz, 1H), 3.10 (d, J=6.6 Hz, 1H), 3.03 (d, J=18.4 Hz, 1H), 2.65-2.50 (m, 2H), 2.49-2.10 (m, 5H), 1.95-1.70 (m, 3H), 1.65-1.25 (m, 6H), 0.95 (t, J=7.1 Hz, 3H), 0.91-0.81 (m, 1H), 0.56-0.49 (m, 2H), 0.14-0.09 (m, 2H) (free form) Mass (EI): 438(M$^+$)

Examples 37-1 and 38-1

Synthesis of 1-(3-benzyloxy-17-cyclopropylmethyl-4,5α-epoxy-14-hydroxy-morphinan-6α-yl)-3-butyl-pyrrolidin-2-one (diastereomer mixture) (Compounds 237 and 238)

237 and 238

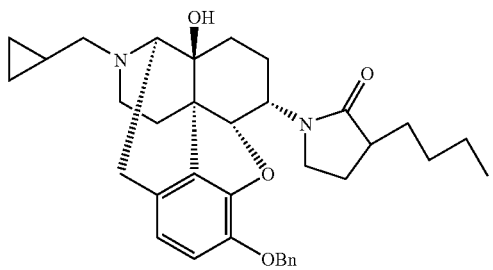

In a manner similar to the method described in Example 36-2, using 1-(3-benzyloxy-17-cyclopropylmethyl-4,5α-epoxy-14-hydroxy-morphinan-6α-yl)-pyrrolidin-2-one obtained in Example 36-1, and using iodobutane in place of iodoethane, 203 mg (yield: 62%) of the captioned compound was obtained as a diastereomer mixture.

Mass (EI): 556(M$^+$)

Examples 37-2 and 38-2

Synthesis of 1-(17-cyclopropylmethyl-4,5α-epoxy-3,14-dihydroxy-morphinan-6α-yl)-3-butyl-pyrrolidin-2-one·tartaric acid salt (Compounds 37 and 38)

37 and 38

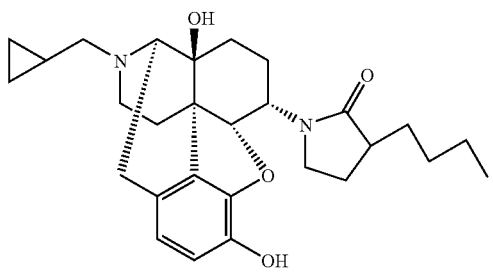

In a manner similar to the method described in Example 36-3, using 1-(3-benzyloxy-17-cyclopropylmethyl-4,5α-epoxy-14-hydroxy-morphinan-6α-yl)-3-butyl-pyrrolidin-2-one obtained in Example 37-1, 85 mg (yield: 47%) of free form (high polarity component) of the captioned compound 37 and 22 mg (yield: 12%) of free form (low polarity component) of the captioned compound 38 were obtained. These products were converted to tartaric acid salts to obtain the captioned compounds 37 and 38.

Compound 37

$^1$H-NMR (ppm) (300 MHz, CDCl$_3$) 6.73 (d, J=8.2 Hz, 1H), 6.53 (d, J=8.2 Hz, 1H), 4.84 (d, J=4.1 Hz, 1H), 4.63 (dt, J=12.9, 4.1 Hz, 1H), 3.55 (dt, J=9.1, 7.7 Hz, 1H), 3.30 (td, J=9.0, 3.0 Hz, 1H), 3.09 (d, J=6.9 Hz, 1H), 3.03 (d, J=18.4 Hz, 1H), 2.67-2.13 (m, 8H), 1.94-1.74 (m, 2H), 1.65-1.24 (m, 10H), 0.96-0.78 (m, 4H), 0.57-0.49 (m, 2H), 0.15-0.08 (m, 2H) (free form) IR (cm$^{-1}$) (KBr) 2928, 1656, 1499, 1459, 1377, 1324, 1262, 1164, 1118, 1070, 942, 859, 796, 752 Mass (EI): 466(M$^+$) Elementary Analysis Formula: C$_{28}$H$_{38}$N$_2$O$_4$·1.00C$_4$H$_6$O$_6$·1.35H$_2$O Calcd.: C, 60.00; H, 7.05; N, 4.35. Found: C, 59.96; H, 7.34; N, 4.37.

Compound 38

$^1$H-NMR (ppm) (300 MHz, CDCl$_3$) 6.72 (d, J=8.2 Hz, 1H), 6.54 (d, J=8.2 Hz, 1H), 4.78 (d, J=4.1 Hz, 1H), 4.66 (dt, J=13.5, 4.1 Hz, 1H), 3.58 (td, J=9.1, 3.0 Hz, 1H), 3.23 (dt, J=9.3, 8.0 Hz, 1H), 3.11 (d, J=6.6 Hz, 1H), 3.04 (d, J=18.7 Hz, 1H), 2.68-2.54 (m, 2H), 2.42-2.06 (m, 5H), 1.98-1.24 (m, 13H), 0.96-0.78 (m, 4H), 0.57-0.49 (m, 2H), 0.15-0.08 (m, 2H) (free form) IR (cm$^{-1}$) (KBr) 2929, 1656, 1501, 1459, 1377, 1324, 1262, 1164, 1119, 1071, 942, 859, 795, 750 Mass (EI): 466(M$^+$) Elementary Analysis Formula: C$_{28}$H$_{38}$N$_2$O$_4$·1.15C$_4$H$_6$O$_6$·2.80H$_2$O Calcd.: C, 57.01; H, 7.01; N, 4.15. Found: C, 56.78; H, 7.38; N, 4.06.

Examples 39-1 and 40-1

Synthesis of 1-(3-benzyloxy-17-cyclopropylmethyl-4,5α-epoxy-14-hydroxy-morphinan-6α-yl)-3-(4-methyl-benzyl)-pyrrolidin-2-one (Compounds 239 and 240)

239 and 240

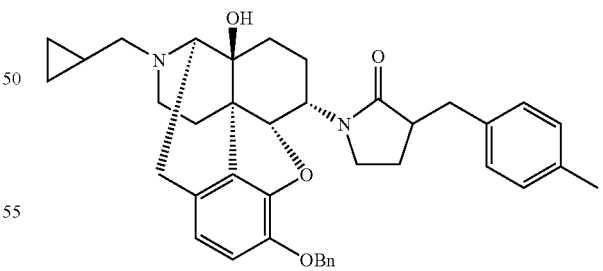

In a manner similar to the method described in Example 36-2, using 289 mg of 1-(3-benzyloxy-17-cyclopropylmethyl-4,5α-epoxy-14-hydroxy-morphinan-6α-yl)-pyrrolidin-2-one obtained in Example 36-1, and using α-bromoxylene in place of iodoethane, 224 mg (yield: 64%) of the captioned compound was obtained as a diastereomer mixture.

Mass (EI): 604(M$^+$)

Examples 39-2 and 40-2

Synthesis of 1-(17-cyclopropylmethyl-4,5α-epoxy-3,14-dihydroxy-morphinan-6α-yl)-3-(4-methyl-benzyl)-pyrrolidin-2-one•tartaric acid salt (Compounds 39 and 40)

39 and 40

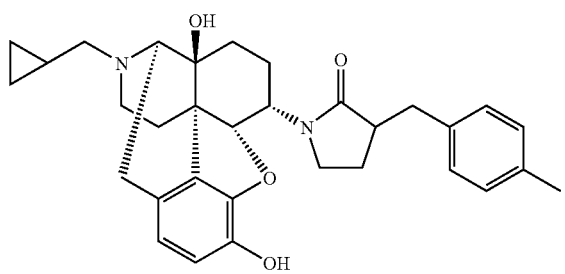

In a manner similar to the method described in Example 36-3, using 224 mg of 1-(3-benzyloxy-17-cyclopropylmethyl-4,5α-epoxy-14-hydroxy-morphinan-6α-yl)-3-(4-methyl-benzyl)-pyrrolidin-2-one obtained in Example 39-1, 124 mg (yield: 65%) of free form (high polarity component) of the captioned compound 39 and 31 mg (yield: 16%) of free form (low polarity component) of the captioned compound 40 were obtained. These products were converted to tartaric acid salts to obtain the captioned compounds 39 and 40.

Compound 39

$^1$H-NMR (ppm) (300 MHz, CDCl$_3$) 7.08 (s, 4H), 6.70 (d, J=8.2 Hz, 1H), 6.52 (d, J=8.2 Hz, 1H), 4.84 (d, J=4.1 Hz, 1H), 4.64 (dt, J=13.2, 4.1 Hz, 1H), 3.44 (dt, J=9.1, 8.2 Hz, 1H), 3.16 (dd, J=13.5, 3.8 Hz, 1H), 3.12-2.98 (m, 3H), 2.77 (qd, J=8.6, 3.8 Hz, 1H), 2.68-2.53 (m, 3H), 2.41-2.16 (m, 4H), 2.30 (s, 3H), 2.10-1.96 (m, 1H), 1.86-1.18 (m, 6H), 0.90-0.78 (m, 1H), 0.57-0.50 (m, 2H), 0.16-0.10 (m, 2H) (free form) IR (cm$^{-1}$) (KBr) 2925, 1657, 1500, 1459, 1439, 1313, 1263, 1162, 1116, 1069, 939, 858, 795, 751 Mass (EI): 514(M$^+$) Elementary Analysis Formula: C$_{32}$H$_{38}$N$_2$O$_4$.1.10C$_4$H$_6$O$_6$.1.55H$_2$O Calcd.: C, 61.58; H, 6.39; N, 3.96. Found: C, 61.78; H, 6.79; N, 3.96.

Compound 40

$^1$H-NMR (ppm) (300 MHz, CDCl$_3$) 7.14 (d, J=8.2 Hz, 2H), 7.10 (d, J=8.2 Hz, 2H), 6.71 (d, J=8.2 Hz, 1H), 6.53 (d, J=8.2 Hz, 1H), 4.80 (d, J=3.8 Hz, 1H), 4.66 (dt, J=13.2, 3.8 Hz, 1H), 3.44 (td, J=8.5, 3.5 Hz, 1H), 3.28-2.99 (m, 4H), 2.74-2.54 (m, 4H), 2.43-2.16 (m, 4H), 2.32 (s, 3H), 2.05-1.20 (m, 7H), 0.90-0.79 (m, 1H), 0.58-0.50 (m, 2H), 0.16-0.10 (m, 2H) (free form) IR (cm$^{-1}$) (KBr) 2927, 1656, 1502, 1459, 1439, 1376, 1323, 1271, 1163, 1118, 1070, 941, 858, 797, 754 Mass (EI): 514(M$^+$) Elementary Analysis Formula: C$_{32}$H$_{38}$N$_2$O$_4$.2.30C$_4$H$_6$O$_6$.0.30H$_2$O Calcd.: C, 57.23; H, 6.33; N, 3.45. Found: C, 57.19; H, 6.10; N, 3.24.

Examples 41-1 and 42-1

Synthesis of 1-(3-benzyloxy-17-cyclopropylmethyl-4,5α-epoxy-14-hydroxy-morphinan-6α-yl)-3-(4-fluoro-benzyl)-pyrrolidin-2-one (Compounds 241 and 242)

241 and 242

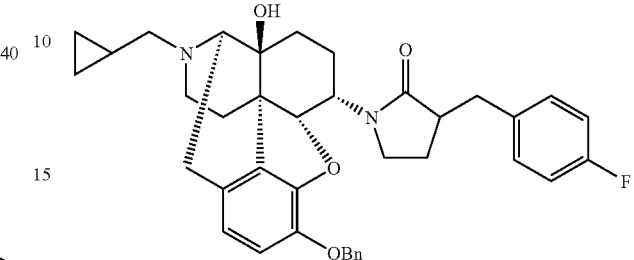

In a manner similar to the method described in Example 36-2, using 281 mg of 1-(3-benzyloxy-17-cyclopropylmethyl-4,5α-epoxy-14-hydroxy-morphinan-6α-yl)-pyrrolidin-2-one obtained in Example 36-1, and using 4-fluorobenzyl bromide in place of iodoethane, 205 mg (yield: 67%) of the captioned compound was obtained as a diastereomer mixture.

Mass (EI): 608(M$^+$)

Examples 41-2 and 42-2

Synthesis of 1-(17-cyclopropylmethyl-4,5α-epoxy-3,14-dihydroxy-morphinan-6α-yl)-3-(4-fluoro-benzyl)-pyrrolidin-2-one•tartaric acid salt (Compounds 41 and 42)

41 and 42

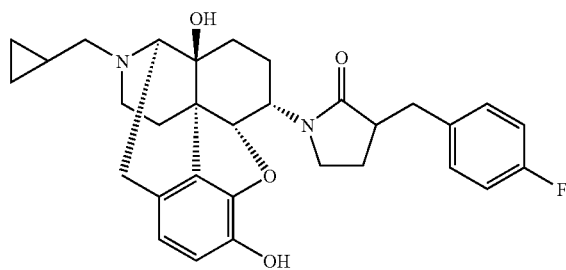

In a manner similar to the method described in Example 36-3, using 195 mg of 1-(3-benzyloxy-17-cyclopropylmethyl-4,5α-epoxy-14-hydroxy-morphinan-6α-yl)-3-(4-fluoro-benzyl)-pyrrolidin-2-one obtained in Example 41-1, 105 mg (yield: 63%) of free form (high polarity component) of the captioned compound 41 and 33 mg (yield: 20%) of free form (low polarity component) of the captioned compound 42 were obtained. These products were converted to tartaric acid salts to obtain the captioned compounds 41 and 42.

Compound 41

$^1$H-NMR (ppm) (300 MHz, CDCl$_3$) 7.15 (dd, J=8.8, 5.4 Hz, 2H), 6.95 (t, J=8.8 Hz, 2H), 6.70 (d, J=8.2 Hz, 1H), 6.53 (d, J=8.2 Hz, 1H), 4.84 (d, J=4.1 Hz, 1H), 4.64 (dt, J=12.9, 4.1 Hz, 1H), 3.45 (dt, J=9.3, 8.0 Hz, 1H), 3.18-2.98 (m, 4H), 2.80-2.53 (m, 4H), 2.42-2.16 (m, 4H), 2.10-1.96 (m, 1H), 1.86-1.14 (m, 6H), 0.89-0.78 (m, 1H), 0.58-0.49 (m, 2H), 0.15-0.08 (m, 2H) (free form) IR (cm$^{-1}$) (KBr) 2929, 1657, 1509, 1459, 1439, 1313, 1271, 1221, 1159, 1117, 1069, 940, 859, 796, 757 Mass (EI): 518(M+) Elementary Analysis Formula: $C_{31}H_{35}FN_2O_4 \cdot 1.10C_4H_6O_6 \cdot 2.20H_2O$ Calcd.: C, 58.68; H, 6.05; N, 4.00; F, 2.62. Found: C, 58.73; H, 6.41; N, 3.87; F, 2.63.

Compound 42

1H-NMR (ppm) (300 MHz, CDCl3) 7.20 (dd, J=8.5, 5.2 Hz, 2H), 6.98 (t, J=8.5 Hz, 2H), 6.71 (d, J=8.2 Hz, 1H), 6.54 (d, J=8.2 Hz, 1H), 4.77 (d, J=4.1 Hz, 1H), 4.67 (dt, J=13.5, 4.1 Hz, 1H), 3.46 (td, J=9.3, 3.6 Hz, 1H), 3.29-2.99 (m, 4H), 2.74-2.55 (m, 4H), 2.42-2.22 (m, 4H), 2.05-1.22 (m, 7H), 0.91-0.80 (m, 1H), 0.58-0.49 (m, 2H), 0.16-0.09 (m, 2H) (free form) IR (cm−1) (KBr) 2932, 1657, 1509, 1459, 1439, 1323, 1272, 1222, 1158, 1119, 1071, 941, 859, 795, 757 Mass (EI): 518(M+) Elementary Analysis Formula: $C_{31}H_{35}FN_2O_4 \cdot 2.50C_4H_6O_6 \cdot 2.20H_2O$ Calcd.: C, 52.81; H, 5.52; N, 3.09; F, 1.99. Found: C, 52.75; H, 5.87; N, 3.00; F, 2.04.

Examples 43-1 and 44-1

Synthesis of 1-(3-benzyloxy-17-cyclopropylmethyl-4,5α-epoxy-14-hydroxy-morphinan-6α-yl)-3-(4-trifluoromethoxy-benzyl)-pyrrolidin-2-one (Compounds 243 and 244)

243 and 244

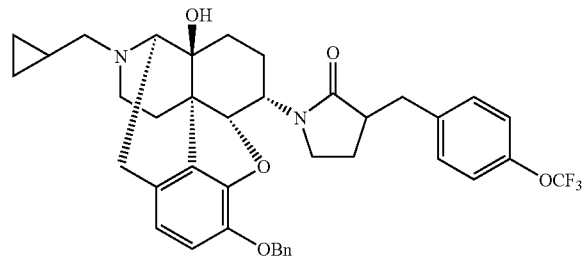

In a manner similar to the method described in Example 36-2, using 281 mg of 1-(3-benzyloxy-17-cyclopropylmethyl-4,5α-epoxy-14-hydroxy-morphinan-6α-yl)-pyrrolidin-2-one obtained in Example 36-1, and using 4-trifluoromethoxybenzyl bromide in place of iodoethane, 383 mg (yield: 100%) of the captioned compound was obtained as a diastereomer mixture.
Mass (EI): 674(M+)

Examples 43-2 and 44-2

Synthesis of 1-(I 7-cyclopropylmethyl-4,5α-epoxy-3,14-dihydroxy-morphinan-6α-yl)-3-(4-trifluoromethoxy-benzyl)-pyrrolidin-2-one•tartaric acid salt (Compounds 43 and 44)

43 and 44

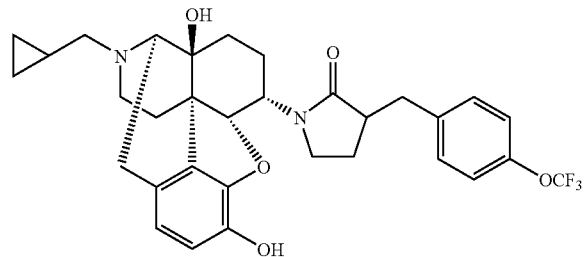

In a manner similar to the method described in Example 36-3, using 376 mg of 1-(3-benzyloxy-17-cyclopropylmethyl-4,5α-epoxy-14-hydroxy-morphinan-6α-yl)-3-(4-trifluoromethoxy-benzyl)-pyrrolidin-2-one obtained in Example 43-1, 172 mg (yield: 53%) of free form (high polarity component) of the captioned compound 43 and 52 mg (yield: 16%) of free form (low polarity component) of the captioned compound 44 were obtained. These products were converted to tartaric acid salts to obtain the captioned compounds 43 and 44.

Compound 43

1H-NMR (ppm) (300 MHz, CDCl3) 7.22 (d, J=8.8 Hz, 2H), 7.11 (d, J=8.8 Hz, 2H), 6.72 (d, J=8.2 Hz, 1H), 6.53 (d, J=8.2 Hz, 1H), 4.83 (d, J=4.1 Hz, 1H), 4.63 (dt, J=12.4, 4.1 Hz, 1H), 3.46 (dt, J=9.9, 7.7 Hz, 1H), 3.21-2.98 (m, 4H), 2.82-2.54 (m, 4H), 2.42-2.16 (m, 4H), 2.10-1.96 (m, 1H), 1.87-1.18 (m, 6H), 0.90-0.78 (m, 1H), 0.58-0.49 (m, 2H), 0.16-0.09 (m, 2H) (free form) IR (cm−1) (KBr) 2933, 1656, 1613, 1508, 1460, 1439, 1381, 1261, 1224, 1159, 1117, 1070, 939, 859, 795, 764 Mass (EI): 584(M+) Elementary Analysis Formula: $C_{32}H_{35}F_3N_2O_5 \cdot 1.00C_4H_6O_6 \cdot 2.80H_2O$ Calcd.: C, 55.22; H, 5.76; N, 3.65; F, 7.07. Found: C, 55.07; H, 5.98; N, 3.57; F, 7.26.

Compound 44

1H-NMR (ppm) (300 MHz, CDCl3) 7.26 (d, J=8.5 Hz, 2H), 7.14 (d, J=8.5 Hz, 2H), 6.72 (d, J=8.2 Hz, 1H), 6.54 (d, J=8.2 Hz, 1H), 4.76 (d, J=4.1 Hz, 1H), 4.68 (dt, J=13.2, 4.1 Hz, 1H), 3.50 (td, J=9.6, 3.3 Hz, 1H), 3.34-2.98 (m, 4H), 2.76-2.54 (m, 4H), 2.42-2.18 (m, 4H), 2.08-1.94 (m, 1H), 1.88-1.60 (m, 2H), 1.58-1.20 (m, 4H), 0.92-0.78 (m, 1H), 0.58-0.50 (m, 2H), 0.16-0.10 (m, 2H) (free form) IR (cm−1) (KBr) 2932, 1656, 1508, 1460, 1440, 1377, 1261, 1223, 1162, 1117, 1070, 940, 860, 795, 763 Mass (EI): 584(M+) Elementary Analysis Formula: $C_{32}H_{35}F_3N_2O_5 \cdot 1.20C_4H_6O_6 \cdot 3.30H_2O$ Calcd.: C, 53.97; H, 5.64; N, 3.36; F, 6.60. Found: C, 53.63; H, 5.97; N, 3.40; F, 6.92.

Example 45

Synthesis of 1-(17-cyclopropylmethyl-4,5α-epoxy-3,14-hydroxy-morphinan-6α-yl)-3-benzylidene-pyrrolidin-2-one•tartaric acid salt (Compounds 45)

45

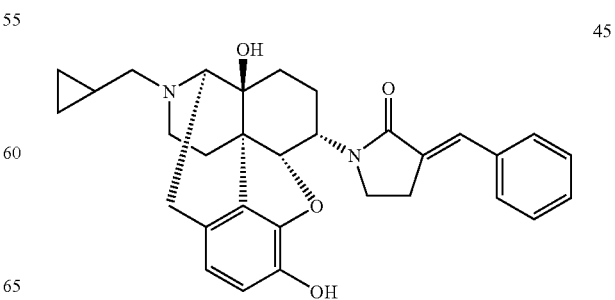

In 10 mL of THF, 482 mg (0.96 mmol) of 1-(3-benzyloxy-17-cyclopropylmethyl-4,5α-epoxy-14-hydroxy-morphinan-6α-yl)-pyrrolidin-2-one obtained in Example 36-1 was dissolved, and 6.9 mL (2.89 mmol) of 0.42 N LDA/THF solution was added thereto at −78° C., followed by stirring the mixture for 1 hour. Thereafter, 0.22 mL (1.92 mmol) of benzoyl chloride was added and the mixture was stirred for 2 hours. Aqueous saturated sodium hydrogen carbonate solution was then added to the reaction mixture, and the resulting mixture was extracted with chloroform. Organic layers were combined, washed with saturated saline, dried over anhydrous magnesium sulfate and concentrated to obtain 1-(3-benzyloxy-17-cyclopropylmethyl-4,5α-epoxy-14-hydroxy-morphinan-6α-yl)-3-benzoyl-pyrrolidin-2-one as a crude product.

The thus obtained crude product was dissolved in 15 mL of methanol, and 158 mg (4.18 mmol) of sodium borohydride was added thereto, followed by stirring the mixture at room temperature for 2 hours. Aqueous saturated sodium hydrogen carbonate solution was then added to the reaction mixture, and the resulting mixture was extracted with chloroform. Organic layers were combined, washed with saturated saline, dried over anhydrous magnesium sulfate and concentrated to obtain 1-(3-benzyloxy-17-cyclopropylmethyl-4,5α-epoxy-14-hydroxy-morphinan-6α-yl)-3-(hydroxy-phenyl-methyl)-pyrrolidin-2-one as a crude product.

The thus obtained crude product and 282 mg (1.70 mmol) of o-phthalic acid were dissolved in 40 mL of methanol, and 200 mg of Pd/C was added, followed by stirring the mixture under hydrogen atmosphere at room temperature for 18 hours. The reaction solution was filtered through Celite and the filtrate was concentrated. To the obtained residue, aqueous saturated sodium hydrogen carbonate solution was added and the resulting mixture was extracted with chloroform. Organic layers were combined, washed with saturated saline, dried over anhydrous magnesium sulfate and concentrated to obtain 1-(17-cyclopropylmethyl-4,5α-epoxy-3,14-dihydroxy-morphinan-6α-yl)-3-(hydroxy-phenyl-methyl)-pyrrolidin-2-one as a crude product.

The thus obtained crude product was dissolved in 60 mL of toluene, and 323 mg (1.39 mmol) of camphor sulfonic acid was added, followed by heating the mixture to reflux for 23 hours. After allowing the reaction solution to cool to room temperature, the reaction solution was concentrated. To the obtained residue, aqueous saturated sodium hydrogen carbonate solution was added and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 153 mg (4 steps yield: 32%) of free form of the captioned compound 45. This product was converted to tartaric acid salt to obtain the captioned compound 45.

$^1$H-NMR (ppm) (300 MHz, CDCl$_3$) 7.50-7.26 (m, 6H), 6.74 (d, J=8.2 Hz, 1H), 6.55 (d, J=8.2 Hz, 1H), 4.94 (d, J=4.1 Hz, 1H), 4.83 (dt, J=13.2, 4.1 Hz, 1H), 3.82-3.72 (m, 1H), 3.51-3.40 (m, 1H), 3.13 (d, J=6.9 Hz, 1H), 3.05 (d, J=19.0 Hz, 1H), 3.03-2.85 (m, 2H), 2.70-2.55 (m, 2H), 2.42-2.17 (m, 4H), 1.91-1.77 (m, 1H), 1.60-1.35 (m, 4H), 0.93-0.76 (m, 1H), 0.58-0.47 (m, 2H), 0.19-0.08 (m, 2H) (free form) IR (cm$^{-1}$) (KBr) 2927, 2824, 1665, 1636, 1493, 1444, 1370, 1309, 1284, 1157, 1117, 1068, 1034, 942, 858, 798, 748, 690 Mass (EI): 498(M$^+$) Elementary Analysis Formula: C$_{31}$H$_{34}$N$_2$O$_4$.1.00C$_4$H$_6$O$_6$.2.60H$_2$O Calcd.: C, 60.32; H, 6.41; N, 3.89. Found: C, 60.44; H, 6.55; N, 4.03.

Example 46

Synthesis of 1-(17-cyclopropylmethyl-4,5α-epoxy-3,14-dihydroxy-morphinan-6β-yl)-pyrrolidin-2-one•hydrochloric acid salt (Compounds 46)

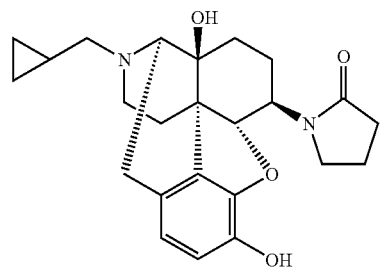

46

In 250 mL of methylene chloride, 6.70 g (19.6 mmol) of 6β-naltrexamine was dissolved, and 5.19 g (48.9 mmol) of sodium carbonate and 4.59 mL (41.1 mmol) of 4-chlorobutyric acid chloride were added thereto, followed by stirring the mixture at room temperature for 18 hours. The reaction solution was concentrated and aqueous saturated sodium hydrogen carbonate solution was added to the obtained residue, followed by extracting the resulting mixture with chloroform. Organic layers were combined, washed with saturated saline, dried over anhydrous magnesium sulfate and concentrated to obtain a crude product. The obtained crude product was purified by silica gel column chromatography to obtain 4.74 g (yield: 54%) of 6β-(4-chlorobutaneamide)-17-cyclopropylmethyl-4,5α-epoxy-morphinan-3,14-diol.

In 10 mL of DMF, 1.59 g (3.56 mmol) of this purified product was dissolved, and 799 mg (7.12 mmol) of potassium t-butoxide was added thereto, followed by stirring the mixture at room temperature for 18 hours. To this reaction solution, aqueous saturated sodium hydrogen carbonate solution was added and the resulting mixture was extracted with chloroform. Organic layers were combined, washed with saturated saline, dried over anhydrous magnesium sulfate and concentrated to obtain a crude product. The obtained crude product was purified by silica gel column chromatography to obtain 577 mg (yield: 40%) of free form of the captioned compound 46. This product was converted to hydrochloric acid salt to obtain the captioned compound 46.

$^1$H-NMR (ppm) (300 MHz, CDCl$_3$) 6.75 (d, J=8.2 Hz, 1H), 6.58 (d, J=8.2 Hz, 1H), 4.55 (d, J=8.2 Hz, 1H), 4.00 (ddd, J=13.1, 8.2, 4.7 Hz, 1H), 3.59-3.40 (m, 2H), 3.07 (d, J=5.8 Hz, 1H), 3.03 (d, J=18.4 Hz, 1H), 2.66-2.02 (m, 1H), 1.65-1.36 (m, 4H), 0.90-0.78 (m, 1H), 0.57-0.49 (m, 2H), 0.16-0.08 (m, 2H) (free form) IR (cm$^{-1}$) (KBr) 2925, 2849, 1685, 1663, 1499, 1450, 1425, 1375, 1329, 1291, 1239, 1189, 1155, 1128, 1038, 978, 927, 860, 74 Mass (EI): 410(M$^+$)

Example 47-1

Synthesis of 1-(3-benzyloxy-17-cyclopropylmethyl-4,5α-epoxy-14-hydroxy-morphinan-6β-yl)-pyrrolidin-2-one (Compound 247)

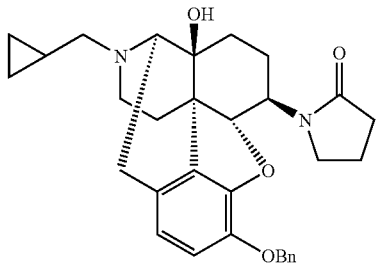

247

In 7 mL of DMF, 284 mg (0.69 mmol) of 1-(17-cyclopropylmethyl-4,5α-epoxy-3,14-dihydroxy-morphinan-6β-yl)-pyrrolidin-2-one produced by the method described in Example 46 was dissolved, and 958 mg (6.93 mmol) of potassium carbonate and 0.25 mL (2.08 mmol) of benzyl bromide were added thereto, followed by stirring the mixture at room temperature for 17 hours. To this reaction solution, aqueous saturated sodium hydrogen carbonate solution was added and the resulting mixture was extracted with diethyl ether. Organic layers were combined, washed with saturated saline, dried over anhydrous magnesium sulfate and concentrated to obtain a crude product. The obtained crude product was purified by silica gel column chromatography to obtain 281 mg (yield: 81%) of the captioned compound.

$^1$H-NMR (ppm) (300 MHz, CDCl$_3$) 7.46-7.24 (m, 5H), 6.72 (d, J=8.1 Hz, 1H), 6.55 (d, J=8.1 Hz, 1H), 5.21 (d, J=12.1 Hz, 1H), 5.09 (d, J=12.1 Hz, 1H), 4.64 (d, J=8.2 Hz, 1H), 4.01 (ddd, J=12.9, 8.2, 4.7 Hz, 1H), 3.61-3.41 (m, 2H), 3.06 (d, J=5.5 Hz, 1H), 3.02 (d, J=18.7 Hz, 1H), 2.70-2.55 (m, 2H), 2.47-1.99 (m, 9H), 1.66-1.39 (m, 4H), 0.86-0.78 (m, 1H), 0.55-0.49 (m, 2H), 0.14-0.09 (m, 2H) IR (cm$^{-1}$) (KBr) 2927, 2829, 1677, 1606, 1496, 1435, 1389, 1333, 1187, 1155, 1129, 1097, 1040, 1018, 979, 920, 883, 859, 749, 697 Mass (EI): 500(M$^+$)

Examples 47-2 and 48-2

Synthesis of 1-(17-cyclopropylmethyl-4,5α-epoxy-3,14-dihydroxy-morphinan-6β-yl)-3-benzyl-pyrrolidin-2-one•tartaric acid salt (Compounds 47 and 48)

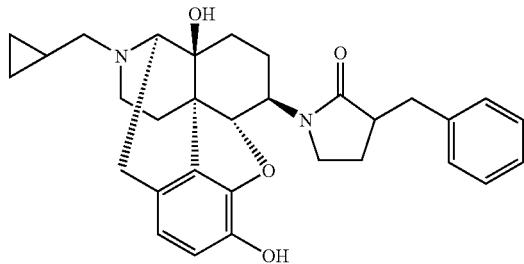

47 and 48

In 5 mL of THF, 145 mg (0.35 mmol) of 1-(3-benzyloxy-17-cyclopropylmethyl-4,5α-epoxy-14-hydroxy-morphinan-6β-yl)-pyrrolidin-2-one obtained in Example 47-1 was dissolved, and 2.84 mL (1.02 mmol) of 0.36 N LDA/THF solution was added at −78° C., followed by stirring the mixture for 1 hour. Thereafter, 0.10 mL (0.87 mmol) of benzyl bromide was added thereto and the resulting mixture was stirred for 3 hours. To this reaction solution, aqueous saturated sodium hydrogen carbonate solution was added and the resulting mixture was extracted with chloroform. Organic layers were combined, washed with saturated saline, dried over anhydrous magnesium sulfate and concentrated to obtain 1-(3-benzyloxy-17-cyclopropylmethyl-4,5α-epoxy-14-hydroxy-morphinan-6β-yl)-3-benzyl-pyrrolidin-2-one as a crude product.

This crude product and 66 mg (0.40 mmol) of o-phthalic acid were dissolved in 10 mL of methanol, and 100 mg of Pd/C was added thereto, followed by stirring the mixture under hydrogen atmosphere at room temperature for 4.5 hours. The reaction solution was filtered through Celite and the filtrate was concentrated. To the obtained residue, aqueous saturated sodium hydrogen carbonate solution was added and the resulting mixture was extracted with chloroform. Organic layers were combined, washed with saturated saline, dried over anhydrous magnesium sulfate and concentrated to obtain 32 mg (2 steps yield: 18%) of free form (high polarity component) of the captioned compound 47 and 10 mg (2 steps yield: 5.4%) of free form (low polarity component) of the captioned compound 48. These products were converted to tartaric acid salt to obtain the captioned compounds 47 and 48.

Compound 47

$^1$H-NMR (ppm) (300 MHz, CDCl$_3$) 7.29-7.16 (m, 5H), 6.76 (d, J=8.2 Hz, 1H), 6.58 (d, J=8.2 Hz, 1H), 4.51 (d, J=8.2 Hz, 1H), 3.98 (ddd, J=12.9, 8.2, 4.4 Hz, 1H), 3.38-3.30 (m, 1H), 3.17-2.99 (m, 4H), 2.87-2.55 (m, 4H), 2.36 (d, J=6.6 Hz, 2H), 2.25-1.91 (m, 4H), 1.82-1.41 (m, 4H), 1.30-1.24 (m, 1H), 0.85-0.80 (m, 1H), 0.53-0.49 (m, 2H), 0.14-0.06 (m, 2H) (free form) IR (cm$^{-1}$) (KBr) 2928, 1663, 1498, 1456, 1376, 1325, 1292, 1236, 1185, 1153, 1127, 1037, 987, 918, 858, 802, 746, 700 Mass (EI): 500(M$^+$)

Compound 48

$^1$H-NMR (ppm) (300 MHz, CDCl$_3$) 7.33-7.17 (m, 5H), 6.77 (d, J=8.0 Hz, 1H), 6.59 (d, J=8.0 Hz, 1H), 4.50 (d, J=8.2 Hz, 1H), 3.98 (ddd, J=12.9, 8.2, 4.7 Hz, 1H), 3.36-3.25 (m, 3H), 3.07-3.00 (m, 2H), 2.80-2.55 (m, 4H), 2.37 (d, J=6.6 Hz, 2H), 2.26-1.38 (m, 9H), 0.90-0.75 (m, 1H), 0.57-0.48 (m, 2H), 0.15-0.09 (m, 2H)(free form) IR (cm$^{-1}$) (KBr) 2926, 1655, 1498, 1458, 1377, 1330, 1240, 1187, 1155, 1128, 1037, 986, 921, 859, 750, 702 Mass (EI): 500(M$^+$)

Example 49

Synthesis of 1-(17-cyclopropylmethyl-4,5α-epoxy-3,14-dihydroxy-morphinan-6β-yl)-3-butyl-pyrrolidin-2-one (diastereomer mixture)•tartaric acid salt (Compound 49)

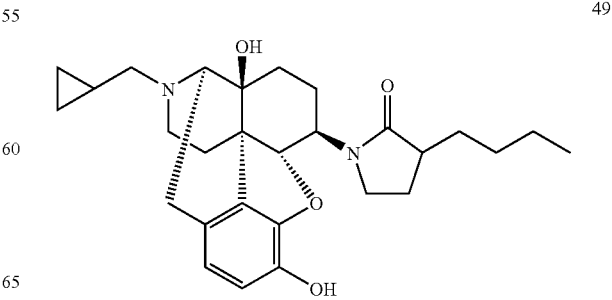

49

In a manner similar to the method described in Examples 47-2 and 48-2, using iodobutane in place of benzyl bromide, 16 mg (2 steps yield: 7.3%) of free form of the captioned compound 49 was obtained. This product was converted to tartaric acid salt to obtain the captioned compound 49.

$^1$H-NMR (ppm) (300 MHz, CDCl$_3$) 6.75 (d, J=8.2 Hz, 1H), 6.57 (d, J=8.2 Hz, 1H), 4.56 (d, J=8.2 Hz, 1H), 3.97 (ddd, J=13.2, 8.2, 4.7 Hz, 1H), 3.48-3.24 (m, 2H), 3.07 (d, J=6.9 Hz, 1H), 3.03 (d, J=18.7 Hz, 1H), 2.68-2.41 (m, 3H), 2.37 (d, J=6.6 Hz, 2H), 2.35-2.03 (m, 4H), 1.86-1.23 (m, 11H), 0.94-0.78 (m, 4H), 0.56-0.46 (m, 2H), 0.16-0.08 (m, 2H) (free form) IR (cm$^{-1}$) (KBr) 2927, 2855, 1656, 1499, 1458, 1377, 1330, 1237, 1187, 1152, 1127, 1038, 986, 921, 859, 800, 747, 703 Mass (EI): 466(M$^+$)

Example 50

Synthesis of 1-(17-cyclopropylmethyl-4,5α-epoxy-3,14-dihydroxy-morphinan-6β-yl)-3-benzylidene-pyrrolidin-2-one•tartaric acid salt (Compound 50)

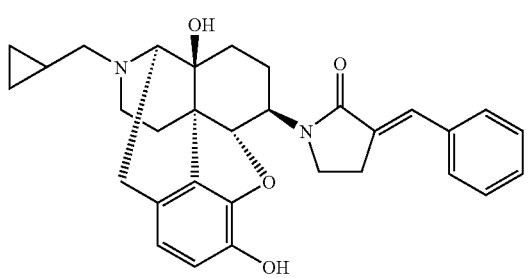

In a manner similar to the method described in Example 45, using 1-(3-benzyloxy-17-cyclopropylmethyl-4,5α-epoxy-14-hydroxy-morphinan-6β-yl)-pyrrolidin-2-one obtained in Example 47-1 in place of 1-(3-benzyloxy-17-cyclopropylmethyl-4,5α-epoxy-14-hydroxy-morphinan-6α-yl)-pyrrolidin-2-one, 41 mg (4 steps yield: 10%) of free form of the captioned compound 50 was obtained. This product was converted to tartaric acid salt to obtain the captioned compound 50.

$^1$H-NMR (ppm) (300 MHz, CDCl$_3$) 7.49-7.28 (m, 6H), 6.76 (d, J=8.2 Hz, 1H), 6.59 (d, J=8.2 Hz, 1H), 4.65 (d, J=8.2 Hz, 1H), 4.16 (ddd, J=13.2, 8.2, 4.7 Hz, 1H), 3.70-3.52 (m, 2H), 3.12-2.98 (m, 4H), 2.66-2.58 (m, 2H), 2.38 (d, J=6.3 Hz, 2H), 2.30-2.08 (m, 3H), 1.71-1.44 (m, 4H), 0.91-0.77 (m, 1H), 0.58-0.49 (m, 2H), 0.16-0.09 (m, 2H) (free form) IR (cm$^{-1}$) (KBr) 2935, 2822, 1671, 1642, 1496, 1461, 1376, 1323, 1295, 1156, 1116, 1035, 989, 923, 860, 760, 694 Mass (EI): 498(M$^+$)

Example 51

Synthesis of 1-(17-cyclopropylmethyl-4,5α-epoxy-3,14-dihydroxy-morphinan-6β-yl)-3-butylidene-pyrrolidin-2-one•tartaric acid salt (Compound 51)

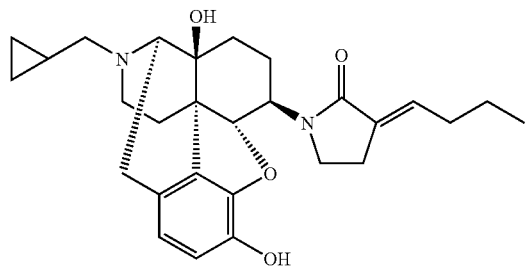

In a manner similar to the method described in Example 45, using 1-(3-benzyloxy-17-cyclopropylmethyl-4,5α-epoxy-14-hydroxy-morphinan-6β-yl)-pyrrolidin-2-one obtained in Example 47-1 in place of 1-(3-benzyloxy-17-cyclopropylmethyl-4,5α-epoxy-14-hydroxy-morphinan-6α-yl)-pyrrolidin-2-one, and using butyryl chloride in place of benzoyl chloride, 29 mg (4 steps yield: 11%) of free form of the captioned compound 51 was obtained. This product was converted to tartaric acid salt to obtain the captioned compound 51.

$^1$H-NMR (ppm) (300 MHz, CDCl$_3$) 6.75 (d, J=8.2 Hz, 1H), 6.57 (d, J=8.2 Hz, 1H), 6.49-6.40 (m, 1H), 4.61 (d, J=8.2 Hz, 1H), 4.09 (ddd, J=13.7, 8.2, 4.7 Hz, 1H), 3.61-3.30 (m, 2H), 3.10-2.95 (m, 2H), 2.76-2.55 (m, 3H), 2.38 (d, J=6.3 Hz, 2H), 2.30-2.04 (m, 4H), 1.75-1.37 (m, 8H), 1.00-0.77 (m, 4H), 0.59-0.50 (m, 2H), 0.18-0.09 (m, 2H) (free form) IR (cm$^{-1}$) (KBr) 2926, 1656, 1499, 1450, 1376, 1331, 1289, 1238, 1187, 1152, 1127, 1036, 989, 921, 859, 747 Mass (E): 464 (M$^+$)

Example 52

Synthesis of 1-[17-cyclopropylmethyl-4,5α-epoxy-3,14-dihydroxy-morphinan-6β-yl]-3-phenethylidene-pyrrolidin-2-one•tartaric acid salt (Compound 52)

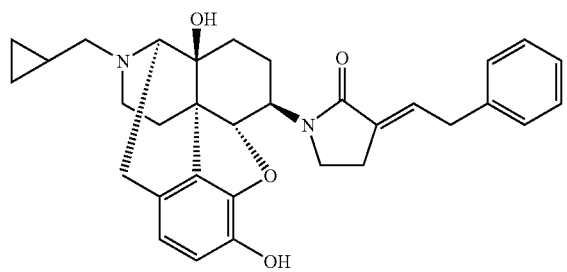

In a manner similar to the method described in Example 45, using 1-(3-benzyloxy-17-cyclopropylmethyl-4,5α-epoxy-14-hydroxy-morphinan-6β-yl)-pyrrolidin-2-one obtained in Example 47-1 in place of 1-(3-benzyloxy-17-cyclopropylmethyl-4,5α-epoxy-14-hydroxy-morphinan-6α-yl)-pyrrolidin-2-one, and using phenylacetyl chloride in place of benzoyl chloride, 19 mg (4 steps yield: 6.2%) of free form of the captioned compound 52 was obtained. This product was converted to tartaric acid salt to obtain the captioned compound 52.

$^1$H-NMR (ppm) (300 MHz, CDCl$_3$) 7.38-7.16 (m, 5H), 6.75 (d, J=8.0 Hz, 1H), 6.70-6.60 (m, 1H), 6.58 (d, J=8.0 Hz, 1H), 4.61 (d, J=8.0 Hz, 1H), 4.10 (ddd, J=13.5, 8.0, 4.7 Hz, 1H), 3.65-3.44 (m, 3H), 3.31-2.96 (m, 2H), 2.83-2.74 (m, 1H), 2.68-2.43 (m, 2H), 2.37 (d, J=6.3 Hz, 2H), 2.30-2.02 (m, 4H), 1.68-1.38 (m, 5H), 0.90-0.76 (m, 1H), 0.58-0.45 (m, 2H), 0.18-0.08 (m, 2H) (free form) IR (cm$^{-1}$) (KBr) 2925, 1656, 1493, 1451, 1376, 1331, 1292, 1236, 1152, 1128, 1036, 990, 921, 859, 746, 700 Mass (EI): 512(M$^+$)

Examples 53 and 54

Synthesis of 1-(17-cyclopropylmethyl-4,5α-epoxy-3,14-dihydroxy-morphinan-6β-yl)-3-(4-chloro-phenoxy)-pyrrolidin-2-one•tartaric acid salt (Compounds 53 and 54)

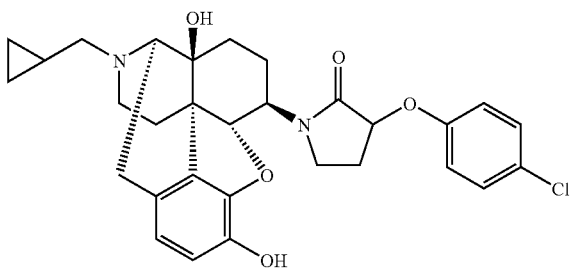

53 and 54

In 30 mL of methylene chloride, 1.06 g (3.09 mmol) of 6β-naltrexamine was dissolved, and 820 mg (7.73 mmol) of sodium carbonate and 1.73 g (6.49 mmol) of 4-chloro-2-(4-chlorophenoxy)butyryl chloride were added thereto, followed by stirring the mixture at room temperature for 24 hours. To this reaction solution, aqueous saturated sodium hydrogen carbonate solution was added and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 116 mg (yield: 6.5%) of 6β-(4-chloro-2-(4-chlorophenoxy)butaneamide)-17-cyclopropylmethyl-4,5α-epoxy-morphinan-3,14-diol.

In 10 mL of DMF, 96 mg (0.18 mmol) of this purified product was dissolved, and 100 mg (0.89 mmol) of potassium t-butoxide was added thereto, followed by stirring the mixture at room temperature for 70 hours. To this reaction solution, aqueous saturated sodium hydrogen carbonate solution was added and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 25 mg (yield: 27%) of free form (high polarity component) of the captioned compound 53 and 19 mg (yield: 20%) of free form (low polarity component) of the captioned compound 54. These products were converted to tartaric acid salt to obtain the captioned compounds 53 and 54.

Compound 53

$^1$H-NMR (ppm) (300 MHz, CDCl$_3$) 7.22 (d, J=8.8 Hz, 2H), 6.98 (d, J=8.8 Hz, 2H), 6.75 (d, J=8.2 Hz, 1H), 6.59 (d, J=8.2 Hz, 1H), 4.90 (dd, J=7.9, 6.3 Hz, 1H), 4.59 (d, J=8.2 Hz, 1H), 3.99 (ddd, J=12.9, 8.2, 4.4 Hz, 1H), 3.63-3.46 (m, 2H), 3.08 (d, J=5.8 Hz, 1H), 3.04 (d, J=18.4 Hz, 1H), 2.68-2.52 (m, 3H), 2.38 (d, J=6.6 Hz, 2H), 2.30-2.06 (m, 4H), 1.71-1.62 (m, 1H), 1.55-1.42 (m, 3H), 0.90-0.77 (m, 1H), 0.57-0.48 (m, 2H), 0.17-0.08 (m, 2H) (free form) IR (cm$^{-1}$) (KBr) 2926, 1686, 1490, 1451, 1331, 1299, 1240, 1187, 1152, 1128, 1091, 1037, 989, 922, 859, 825, 748 Mass (EI): 536(M$^+$)

Compound 54

$^1$H-NMR (ppm) (300 MHz, CDCl$_3$) 7.24 (d, J=9.1 Hz, 2H), 7.00 (d, J=9.1 Hz, 2H), 6.76 (d, J=8.2 Hz, 1H), 6.59 (d, J=8.2 Hz, 1H), 4.85 (t, J=7.6 Hz, 1H), 4.60 (d, J=8.2 Hz, 1H), 4.00 (ddd, J=13.7, 8.2, 4.1 Hz, 1H), 3.63 (td, J=9.3, 3.3 Hz, 1H), 3.43 (dt, J=9.3, 7.1 Hz, 1H), 3.08 (d, J=5.5 Hz, 1H), 3.04 (d, J=18.3 Hz, 1H), 2.69-2.52 (m, 3H), 2.38 (d, J=6.6 Hz, 2H), 2.30-2.06 (m, 4H), 1.76-1.40 (m, 4H), 0.90-0.78 (m, 1H), 0.58-0.50 (m, 2H), 0.18-0.10 (m, 2H) (free form) IR (cm$^{-1}$) (KBr) 2927, 1687, 1490, 1452, 1332, 1298, 1241, 1151, 1128, 1092, 1037, 989, 921, 859, 826, 749 Mass (EI): 536(M$^+$)

Example 55

Synthesis of N-[17-(cyclopropylmethyl)-4,5α-epoxy-3,14-dihydroxymorphinan-6β-yl]-4,5-dichlorophthaimide•tartaric acid salt (Compound 55)

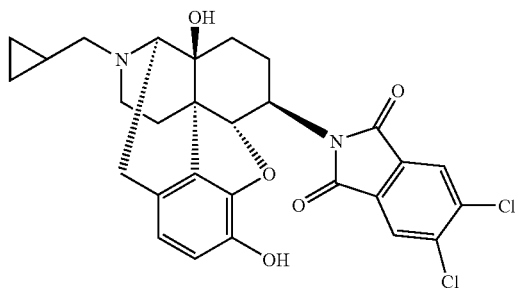

55

In a manner similar to the method described in Example 11, using 4,5-dichlorophthalic anhydride in place of phthalic anhydride, 130 mg (yield: 83%) of free form of the captioned compound 55 was obtained. This product was converted to tartaric acid salt to obtain the captioned compound 55.

$^1$H-NMR (ppm) (300 MHz, CDCl$_3$) 7.92 (2H, s), 6.76 (1H, d, J=7.8 Hz), 6.63 (1H, d, J=7.8 Hz), 5.11 (1H, d, J=8.7 Hz), 4.05-4.08 (1H, m), 3.11 (2H, t, J=5.7 Hz), 3.03 (1H, s), 2.59-2.71 (3H, m), 2.29-2.39 (3H, m), 2.09-2.17 (2H, m), 1.69-1.73 (2H, m), 1.44-1.48 (2H, m), 0.86-0.88 (1H, m), 0.53-0.55 (2H, m), 0.13-0.14 (2H, m) (free form) Mass (ESI): 541 (M$^+$+1)

Example 56

Synthesis of N-(17-allyl-4,5α-epoxy-3,14-dihydroxymorphinan-6β-yl)-4-methylphthalimide•tartaric acid salt (Compound 56)

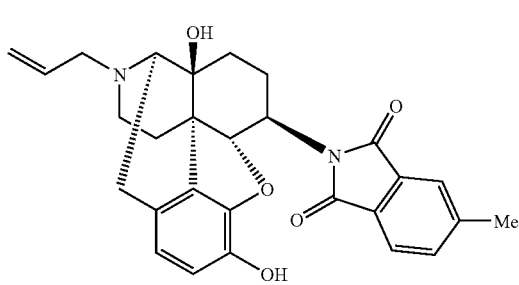

In a manner similar to the method described in Example 11, using 6β-naloxamine in place of 6β-naltrexamine, and using 4-methylphthalic anhydride in place of phthalic anhydride, 46 mg (yield: 32%) of free form of the captioned compound 56 was obtained. This product was converted to tartaric acid salt to obtain the captioned compound 56.

$^1$H-NMR (ppm) (300 MHz, CDCl$_3$) 7.69 (1H, d, J=7.6 Hz), 7.63 (1H, s), 7.48 (1H, d, J=7.8 Hz), 6.78 (1H, d, J=8.1 Hz), 6.64 (1H, d, J=8.1 Hz), 5.76-5.86 (1H, m), 5.16-5.24 (3H, m), 4.05 (1H, ddd, J=13.2, 8.5, 4.4 Hz), 3.15 (2H, d, J=6.4 Hz), 3.10 (1H, d, J=18.3 Hz), 2.51 (3H, s), 2.54-2.96 (4H, m), 2.32 (1H, dt, J=12.4, 4.9 Hz), 2.15 (1H, dt, J=12.1, 3.7 Hz), 1.67-1.70 (1H, m), 1.43-1.53 (3H, m) (free form) Mass (ESI): 473(M$^+$+1)

Example 57

Synthesis of N-(17-allyl-4,5α-epoxy-3,14-dihydroxymorphinan-6β-yl)-4-chlorophthalimide•tartaric acid salt (Compound 57)

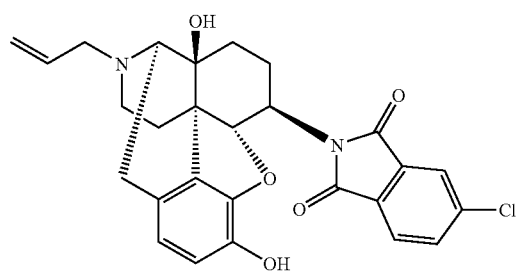

In a manner similar to the method described in Example 11, using 6β-naloxamine in place of 6β-naltrexamine, and using 4-chlorophthalic anhydride in place of phthalic anhydride, 66 mg (yield: 44%) of free form of the captioned compound 57 was obtained. This product was converted to tartaric acid salt to obtain the captioned compound 57.

$^1$H-NMR (ppm) (300 MHz, CDCl$_3$) 7.81 (1H, s), 7.78 (1H, d, J=7.8 Hz), 7.68 (1H, d, J=7.8 Hz) 6.78 (1H, d, J=8.4 Hz), 6.65 (1H, d, J=8.4 Hz), 5.75-5.86 (1H, m), 5.13-5.25 (3H, m), 4.06 (1H, ddd, J=13.1, 8.3, 4.5 Hz), 3.15 (2H, d, J=6.6 Hz), 3.11 (1H, d, J=19.8 Hz), 2.95 (1H, d, J=5.4 Hz), 2.54-2.80 (3H, m), 2.32 (1H, dt, J=11.7, 3.6 Hz), 2.14 (1H, dt, J=11.7, 3.6 Hz), 1.68-1.72 (1H, m), 1.26-1.53 (3H, m) (free form) Mass (ESI): 493(M$^+$+1)

Example 58

Synthesis of N-(17-allyl-4,5α-epoxy-3,14-dihydroxymorphinan-6β-yl)-4-fluorophthalimide•tartaric acid salt (Compound 58)

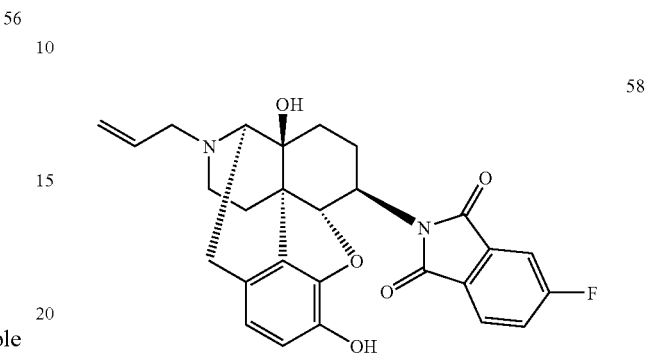

In a manner similar to the method described in Example 11, using 6β-naloxamine in place of 6β-naltrexamine, and using 4-fluorophthalic anhydride in place of phthalic anhydride, 43 mg (yield: 30%) of free form of the captioned compound 58 was obtained. This product was converted to tartaric acid salt to obtain the captioned compound 58.

$^1$H-NMR (ppm) (300 MHz, CDCl$_3$) 7.84 (1H, dd, J=8.0, 4.4 Hz), 7.51 (1H, dd, J=6.8, 2.2, Hz), 7.37 (1H, dt, J=8.4, 2.4 Hz), 6.76 (1H, d, J=8.3 Hz), 6.64 (1H, d, J=8.3 Hz), 5.75-5.85 (1H, m), 5.13-5.23 (3H, m), 4.05 (1H, ddd, J=13.2, 8.5, 4.4 Hz), 3.14 (2H, d, J=6.4 Hz), 3.11 (1H, d, J=18.3 Hz), 2.94 (1H, d, J=5.6 Hz), 2.53-2.82 (3H, m), 2.23 (1H, dt, J=12.0, 4.9 Hz), 2.21 (1H, dt, J=12.0, 4.9 Hz), 1.67-1.71 (1H, m), 1.43-1.51 (3H, m) (free form) Mass (ESI): 477(M$^+$+1)

Example 59

Synthesis of N-(17-allyl-4,5α-epoxy-3,14-dihydroxymorphinan-6β-yl)-4,5-dichlorophthalimide•tartaric acid salt (Compound 59)

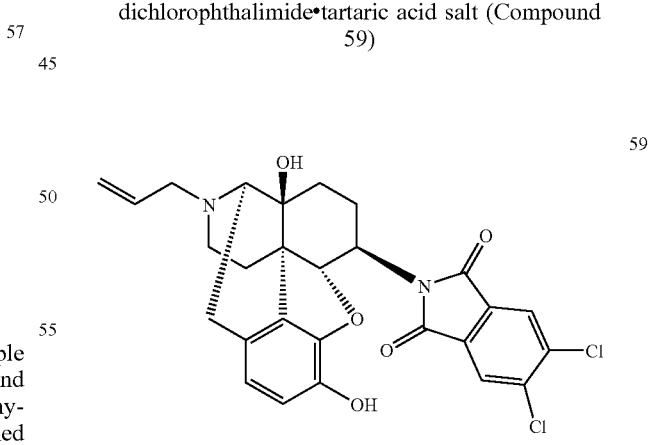

In a manner similar to the method described in Example 11, using 6β-naloxamine in place of 6β-naltrexamine, and using 4,5-dichlorophthalic anhydride in place of phthalic anhydride, 120 mg (yield: 75%) of free form of the captioned compound 59 was obtained. This product was converted to tartaric acid salt to obtain the captioned compound 59.

$^1$H-NMR (ppm) (300 MHz, CDCl$_3$) 7.91 (2H, s,) 6.77 (1H, d, J=8.7 Hz), 6.65 (1H, d, J=8.7 Hz), 5.74-5.86 (1H, m), 5.16-5.25 (2H, m), 5.12 (1H, d, J=8.4 Hz), 4.05 (1H, ddd, J=13.1, 8.3, 4.5 Hz), 3.15 (2H, d, J=6.6 Hz), 3.11 (1H, d, J=19.8 Hz), 2.95 (1H, d, J=5.4 Hz), 2.54-2.78 (3H, m), 2.31 (1H, dt, J=11.7, 3.6 Hz), 2.13 (1H, dt, J=11.7, 3.6 Hz), 1.68-1.72 (1H, m), 1.43-1.53 (3H, m) (free form) Mass (ESI): 527 (M$^+$+1)

Examples 60 and 61

Synthesis of N-(17-allyl-4,5α-epoxy-3,14-dihydroxymorphinan-6β-yl)-3-methylphthalimide•tartaric acid salt (Compound 60) and N-(17-allyl-4,5α-epoxy-3,14-dihydroxymorphinan-6α-yl)-3-methylphthalimide•tartaric acid salt (Compound 61)

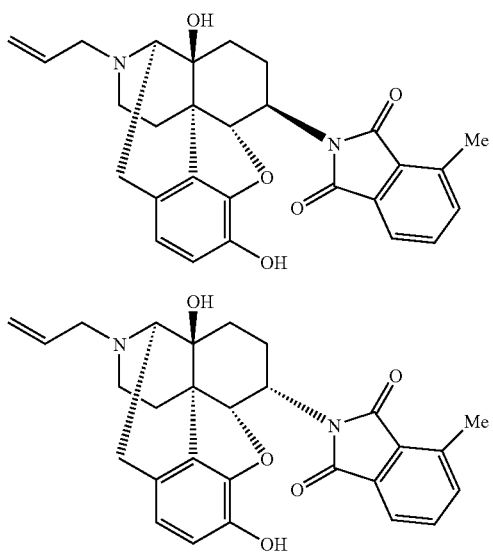

In a manner similar to the method described in Example 11, using 6-naloxamine (diastereomer mixture) in place of 6β-naltrexamine, and using 3-methylphthalic anhydride in place of phthalic anhydride, and performing heating to reflux for 20 hours, 38 mg (yield: 26%) of free form of the captioned compound 60 and 16 mg (yield: 11%) of free form of the captioned compound 61 were obtained. These products were converted to tartaric acid salt to obtain the captioned compounds 60 and 61.

Compound 60
$^1$H-NMR (ppm) (300 MHz, CDCl$_3$) 7.67 (1H, d, J=7.3 Hz), 7.56 (1H, t, J=7.4 Hz), 7.45 (1H, d, J=7.5 Hz), 6.76 (1H, d, J=8.1 Hz), 6.64 (1H, d, J=8.1 Hz), 5.75-5.85 (1H, m), 5.16-5.23 (3H, m), 4.05 (1H, ddd, J=13.2, 8.5, 4.4 Hz), 3.14 (2H, d, J=6.3 Hz), 3.11 (1H, d, J=18.6 Hz), 2.69 (3H,s), 2.54-2.96 (4H, m), 2.31 (1H, dt, J=12.4, 4.9 Hz), 2.15 (1H, dt, J=12.0, 3.6 Hz), 1.67-1.70 (1H, m), 1.43-1.51 (3H, m) (free form) Mass (ESI): 473(M$^+$+1)

Compound 61
$^1$H-NMR (ppm) (300 MHz, CDCl$_3$) 7.68 (d, 1H, J=7.4 Hz), 7.56 (t, 1H, J=7.4 Hz), 7.45 (d, 1H, J=7.4 Hz), 6.83 (d, 1H, J=8.4 Hz), 6.61 (d, 1H, J=8.4 Hz), 5.79-5.88 (m, 1H), 5.17-5.25 (m, 2H), 4.82 (dt, 1H, J=4.1 Hz, J=14.0 Hz), 4.65 (d, 1H, J=4.1 Hz), 3.12 (d, 2H, J=6.3 Hz), 3.11 (d, 1H, J=15.6 Hz), 2.98 (d, 1H, J=6.6 Hz), 2.57-2.71 (m, 1H), 2.69 (s, 3H), 2.20-2.30 (m, 3H), 1.77-1.89 (m, 2H), 1.49-1.66 (m, 3H) (free form) Mass (ESI): 473(M$^+$+1)

Example 62

Synthesis of N-(17-allyl-4,5α-epoxy-3,14-dihydroxymorphinan-6β-yl)-3-fluorophthalimide•tartaric acid salt (Compound 62)

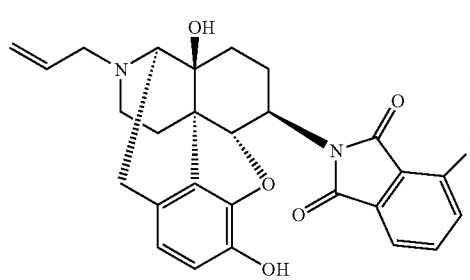

In a manner similar to the method described in Example 11, using 6β-naloxamine in place of 6β-naltrexamine, and using 3-fluorophthalic anhydride in place of phthalic anhydride, 42 mg (yield: 29%) of free form of the captioned compound 62 was obtained. This product was converted to tartaric acid salt to obtain the captioned compound 62.

$^1$H-NMR (ppm) (300 MHz, CDCl$_3$) 7.74 (1H, dt, J=7.7, 4.0 Hz), 7.68 (1H, d, J=6.8 Hz), 7.38 (1H, t, J=8.3 Hz), 6.77 (1H, d, J=8.1 Hz), 6.65 (1H, d, J=8.1 Hz), 5.76-5.86 (1H, m), 5.15-5.24 (3H, m), 4.06 (1H, ddd, J=13.2, 8.5, 4.4 Hz), 3.14 (2H, d, J=6.3 Hz), 3.10 (1H, d, J=18.5 Hz), 2.94 (1H, d, J=5.6 Hz), 2.78-2.85 (1H, m), 2.63 (1H, dd, J=18.4, 5.7 Hz), 2.56 (1H, dd, J=11.6, 4.5 Hz), 2.31 (1H, dt, J=12.5, 5.0 Hz), 2.15 (1H, dt, J=12.0, 4.0 Hz), 1.68-1.72 (1H, m), 1.45-1.52 (3H, m) (free form) Mass (ESI): 477 (M$^+$+1)

Example 63

Synthesis of N-(17-allyl-4,5α-epoxy-3,14-dihydroxymorphinan-6α-yl)-3-fluorophthalimide•tartaric acid salt (Compound 63)

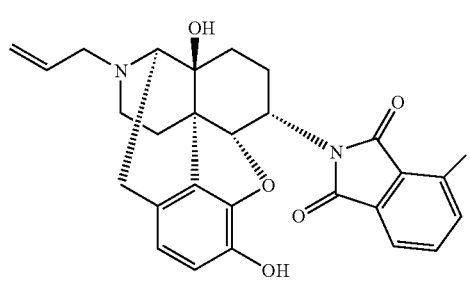

In a manner similar to the method described in Example 11, using 6α-naloxamine in place of 6β-naltrexamine, and using 3-fluorophthalic anhydride in place of phthalic anhydride, and performing heating to reflux for 20 hours, 70 mg (yield: 32%) of free form of the captioned compound 63 was obtained. This product was converted to tartaric acid salt to obtain the captioned compound 63.

¹H-NMR (ppm) (300 MHz, CDCl₃) 7.82-7.92 (m, 2H), 7.54 (t; 1H, J=7.4 Hz), 6.98 (d, 1H, J=8.2 Hz), 6.77 (d, 1H, J=8.2 Hz), 5.95-6.04 (m, 1H), 5.33-5.42 (m, 2H), 4.99 (dt, 1H, J=4.1, 14.0 Hz), 4.81 (d, 1H, J=4.1 Hz), 3.28 (d, 2H, J=6.3 Hz), 3.19 (d, 1H, J=15.6 Hz), 2.98 (d, 1H, J=6.9 Hz), 2.83 (1H, dd, J=7.1, 18.5 Hz), 2.73-2.76 (m, 1H), 2.36-2.46 (m, 3H), 1.39-2.00 (m, 4H) (free form) Mass (ESI): 477 (M⁺+1)

Example 64

Synthesis of N-(17-allyl-4,5α-epoxy-3,14-dihydroxymorphinan-6α-yl)-phthalimide•tartaric acid salt (Compound 64)

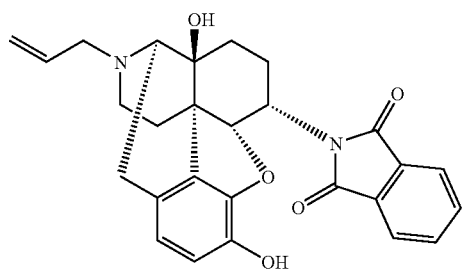

In a manner similar to the method described in Example 11, using 6α-naloxamine in place of 6β-naltrexamine, and performing heating to reflux for 20 hours, 24 mg (yield: 26%) of free form of the captioned compound 64 was obtained. This product was converted to tartaric acid salt to obtain the captioned compound 64.

¹H-NMR (ppm) (300 MHz, CDCl₃) 7.81-7.85 (m, 2H), 7.69-7.73 (m, 2H), 6.82 (d, 1H, J=8.2 Hz), 6.59 (d, 1H, J=8.2 Hz), 5.75-5.90 (m, 1H), 5.16-5.24 (m, 2H), 4.83 (dt, 1H, J=4.0, 14.2 Hz), 4.65 (d, 1H, J=4.0 Hz), 3.12 (d, 2H, J=6.3 Hz), 3.11 (d, 1H, J=15.2 Hz), 2.97 (d, 1H, J=6.9 Hz), 2.52-2.71 (m, 2H), 2.17-2.34 (m, 3H), 1.50-1.89 (m, 4H) (free form) Mass (ESI): 459(M⁺+1)

Example 65

Synthesis of N-(17-allyl-4,5α-epoxy-3,14-dihydroxymorphinan-6α-yl)-4-fluorophthalimide•tartaric acid salt (Compound 65)

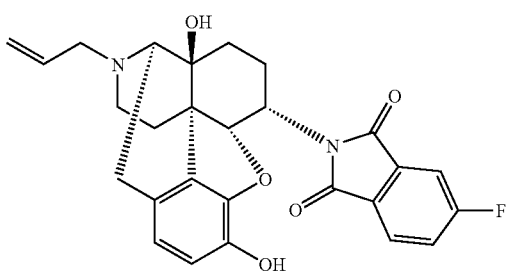

In a manner similar to the method described in Example 11, using 6α-naloxamine in place of 6β-naltrexamine, using 4-fluorophthalic anhydride in place of phthalic anhydride, and performing heating to reflux for 20 hours, 70 mg (yield: 32%) of free form of the captioned compound 65 was obtained. This product was converted to tartaric acid salt to obtain the captioned compound 65.

¹H-NMR (ppm) (300 MHz, CDCl₃) 7.84 (dd, 1H, J=4.4, 8.2 Hz), 7.51 (dd, 1H, J=2.2, 4.4 Hz), 7.37 (dt, 1H, J=2.2, 8.2 Hz), 6.81 (d, 1H, J=8.3 Hz), 6.61 (d, 1H, J=8.3 Hz), 5.86-5.77 (m, 1H), 5.24-5.17 (m, 2H), 4.85-4.79 (m, 2H), 4.64-4.63 (m, 1H), 3.09-3.13 (m, 1H), 2.97 (d, 1H, J=6.6 Hz), 2.67 (dd, 1H, J=6.8, 18.4, Hz), 2.57 (m, 1H), 2.20-2.30 (m, 3H), 1.79-1.87 (m, 1H), 1.51-1.65 (m, 4H) (free form) Mass (ESI): 477(M⁺+1)

Example 66

Synthesis of N-(17-cyclopropylmethyl-4,5α-epoxy-3,14-dihydroxymorphinan-6α-yl)-phthalimide•tartaric acid salt (Compound 66)

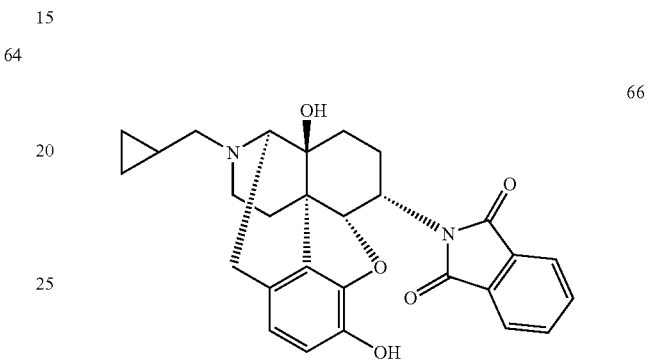

In a manner similar to the method described in Example 11, using 6α-naltrexamine in place of 6β-naltrexamine, and performing heating to reflux for 20 hours, 46 mg (yield: 22%) of free form of the captioned compound 66 was obtained. This product was converted to tartaric acid salt to obtain the captioned compound 66.

¹H-NMR (ppm) (300 MHz, CDCl₃) 7.81-7.87 (m, 2H), 7.68-7.74 (m, 2H), 6.81 (d, 1H, J=7.9 Hz), 6.59 (d, 1H, J=7.9 Hz), 5.08 (bs, 1H), 4.83 (dt, 1H, J=3.9, 14.1 Hz), 4.65 (d, 1H J=3.9 Hz), 3.15 (d, 1H, J=6.8 Hz), 3.07 (d, 1H, J=18.4 Hz), 2.69 (d, 1H, J=6.6 Hz), 2.63 (d, 1H, J=6.9 Hz), 2.43-2.19 (m, 5H), 1.79-1.91 (m, 1H), 1.49-1.69 (m, 3H), 0.83-0.92 (m, 1H), 0.54-0.59 (m, 2H), 0.12-0.17 (m, 2H) (free form) Mass (ESI): 473(M⁺+1)

Example 67

Synthesis of N-(17-cyclopropylmethyl-4,5α-epoxy-3,14-dihydroxymorphinan-6α-yl)-3-fluorophthalimide•tartaric acid salt (Compound 67)

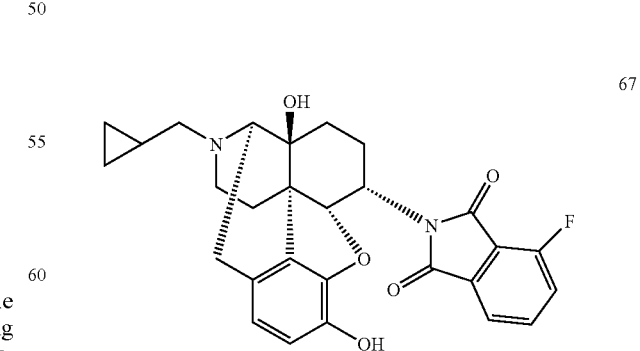

In a manner similar to the method described in Example 11, using 6α-naltrexamine in place of 6β-naltrexamine, using 3-fluorophthalic anhydride in place of phthalic anhydride, and performing heating to reflux for 20 hours, 5 mg (yield: 4%) of free form of the captioned compound 67 was obtained. This product was converted to tartaric acid salt to obtain the captioned compound 67.

$^1$H-NMR (ppm) (300 MHz, CDCl$_3$) 7.74-7.67 (m, 2H), 7.39 (t, 1H, J=7.9 Hz), 6.82 (d, 1H, J=7.8 Hz), 6.60 (d, 1H, J=7.8 Hz), 4.82 (dt, 1H, J=3.9, 14.1 Hz), 4.65 (d, 1H, J=4.2 Hz), 3.16 (d, 1H, J=6.6 Hz), 3.08 (d, 1H, J=18.3 Hz), 2.70 (d, 1H, J=7.2 Hz), 2.64 (d, 1H, J=7.2 Hz), 2.21-2.42 (m, 5H), 1.91-1.53 (m, 4H), 0.86-0.88 (m, 1H), 0.54-0.59 (m, 2H), 0.14-0.18 (m, 2H) (free form) Mass (ESI): 491 (M$^+$+1)

Example 68

Synthesis of N-(17-cyclopropylmethyl-4,5α-epoxy-3,14-dihydroxymorphinan-6α-yl)-4-fluorophthalimide•tartaric acid salt (Compound 68)

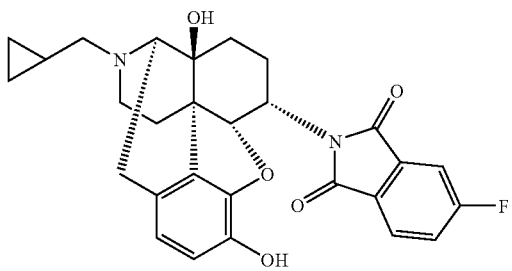

In a manner similar to the method described in Example 11, using 6α-naltrexamine in place of 6β-naltrexamine, using 4-fluorophthalic anhydride in place of phthalic anhydride, and performing heating to reflux for 20 hours, 102 mg (yield: 34%) of free form of the captioned compound 68 was obtained. This product was converted to tartaric acid salt to obtain the captioned compound 68.

$^1$H-NMR (ppm) (300 MHz, CDCl$_3$) 0.14 (dd, 2H, J=9.6, 5.2 Hz), 0.55 (m, 2H), 0.87 (m, 1H), 1.59 (m, 4H), 1.84 (dt, 1H, J=14.4, 10.0 Hz), 2.24 (tt, 2H, J=14.4, 9.6 Hz), 2.31 (d, 1H, J=7.2 Hz), 2.38 (ddd, 2H, J=26.0, 12.8, 6.4 Hz), 2.64 (d, 1H, J=6.8 Hz), 2.68 (d, 1H, J=7.2 Hz), 3.07 (d, 1H, J=18.8 Hz), 3.15 (d, 1H, J=6.8 Hz), 4.65 (d, 1H, J=4.0 Hz), 4.82 (brdt, 2H, J=14.4, 4.0 Hz), 6.60 (d, 1H, J=8.4 Hz), 6.81 (d, 1H, J=8.4 Hz), 7.38 (td, 1H, J=8.0, 2.4 Hz), 7.52 (dd, 1H, J=7.2, 2.4 Hz), 7.85 (dd, 1H, J=8.0, 4.0 Hz) (free form) Mass (ESI): 491 (M$^+$+1)

Example 69

Synthesis of N-(17-cyclopropylmethyl-4,5α-epoxy-3,14-dihydroxymorphinan-6β-yl)-hexahydrophthalimide•tartaric acid salt (Compound 69)

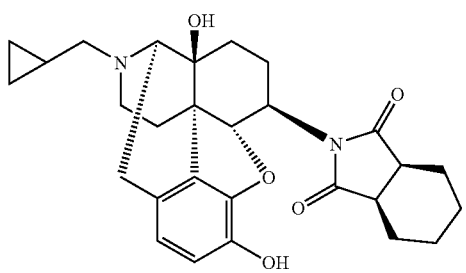

In a manner similar to the method described in Example 11, using hexahydrophthalic anhydride in place of phthalic anhydride, 34 mg (yield: 47%) of free form of the captioned compound 69 was obtained. This product was converted to tartaric acid salt to obtain the captioned compound 69.

$^1$H-NMR (ppm) (300 MHz, CDCl$_3$) 6.75 (d, 1H, J=8.2 Hz), 6.61 (d, 1H, J=8.2 Hz), 5.10 (d, 1H, J=8.2 Hz), 3.98 (ddd, 1H, J=4.5, 8.3, 13.1 Hz), 3.10 (d, 1H, J=5.1 Hz), 3.04 (d, 1H, J=18.4 Hz), 2.84-2.90 (m, 2H), 2.58-2.77 (m, 3H), 2.28-2.39 (m, 3H), 2.10-2.18 (m, 1H), 1.23-1.94 (m, 14H), 0.83-0.85 (m, 1H), 0.51-0.57 (m, 2H), 0.13-0.14 (m, 2H) (free form) Mass (ESI): 479(M$^+$+1)

Example 70

Synthesis of N-(17-cyclopropylmethyl-4,5α-epoxy-3,14-dihydroxymorphinan-6β-yl)-2,3-diphenylmaleimide•tartaric acid salt (Compound 70)

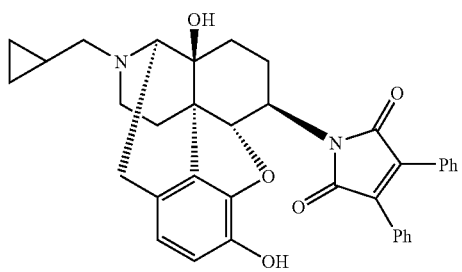

In a manner similar to the method described in Example 11, using 2,3-diphenylmaleic anhydride in place of phthalic anhydride, and using toluene as a solvent in place of DMF, 98 mg (yield: 58%) of free form of the captioned compound 70 was obtained. This product was converted to tartaric acid salt to obtain the captioned compound 70.

$^1$H-NMR (ppm) (300 MHz, CDCl$_3$) 7.49 (d, 4H, J=7.2 Hz), 7.33-7.39 (m, 6H), 6.74 (d, 1H, J=8.0 Hz), 6.61 (d, 1H, J=8.0 Hz), 5.20 (d, 1H, J=8.0 Hz), 4.08 (ddd, 1H, J=4.4, 8.2, 13.0 Hz), 3.13 (d, 1H, J=5.2 Hz), 3.06 (d, 1H, J=18.4 Hz), 2.61-2.94 (m, 3H), 2.31-2.40 (m, 3H), 2.14 (dt, 1H, J=3.2, 10.3 Hz), 1.71 (d, 1H, J=12.8 Hz), 1.47-1.53 (m, 3H), 0.82-0.89 (m, 1H), 0.53-0.55 (m, 2H), 0.13-0.14 (m, 2H) (free form) Mass (ESI): 574(M$^+$)

Example 71

Synthesis of N-(17-cyclopropylmethyl-4,5α-epoxy-3,14-dihydroxymorphinan-6β-yl)-2-phenyl-succinimide (diastereomer mixture)•tartaric acid salt (Compound 71)

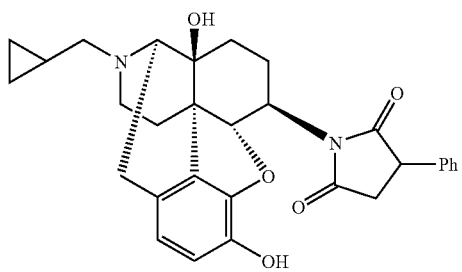

In a manner similar to the method described in Example 11, using 2-phenyl-succinic anhydride in place of phthalic anhydride, and using toluene as a solvent in place of DMF, 113 mg (yield: 78%) of free form (diastereomer mixture) of the captioned compound 71 was obtained. This product was converted to tartaric acid salt to obtain the captioned compound 71.

$^1$H-NMR (ppm) (300 MHz, CDCl$_3$) 7.23-7.37 (m, 5H), 6.73 (d, 1H, J=8.0 Hz), 6.60 (d, 1H, J=8.0 Hz), 5.17 (d, 1H, J=8.0 Hz), 4.08 (m, 2H), 3.10-3.27 (m, 2H), 3.03 (d, 1H, J=18.8 Hz), 2.58-2.87 (m, 4H), 2.31-2.38 (m, 3H), 2.12 (dt, 1H, J=3.2, 10.3 Hz), 1.68 (d, 1H, J=12.8 Hz), 1.37-1.50 (m, 3H), 0.82-0.89 (m, 1H), 0.53-0.55 (m, 2H), 0.13-0.14 (m, 2H) (free form) Mass (ESI): 500(M$^+$)

Example 72

Synthesis of N-(17-cyclopropylmethyl-4,5α-epoxy-3,14-dihydroxymorphinan-6α-yl)-3,4,5,6-tetrahydrophthalimide•methanesulfonic acid salt (Compound 72)

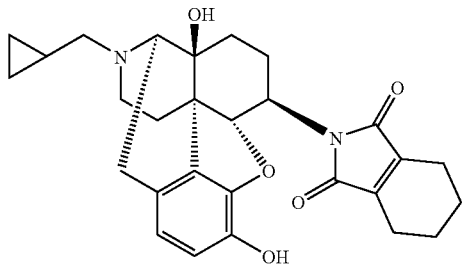

In a manner similar to the method described in Example 11, using 6α-naltrexamine in place of 6β-naltrexamine, using 3,4,5,6-tetrahydrophthalic anhydride in place of phthalic anhydride, using toluene as a solvent in place of DMF, and performing heating to reflux for 22 hours, 18 mg (yield: 13%) of free form of the captioned compound 72 was obtained. This product was converted to methanesulfonic acid salt to obtain the captioned compound 72.

$^1$H-NMR (ppm) (400 MHz, CDCl$_3$) 6.79 (1H, d, J=8.3 Hz), 6.57 (1H, d, J=8.3 Hz), 4.61 (1H, dt, J=14.2, 4.0 Hz), 4.55 (1H, m), 3.12 (1H, d, J=6.6 Hz), 3.05 (1H, d, J=18.5 Hz), 2.6-2.7 (2H, m), 2.2-2.4 (8H, m), 2.05-2.10 (1H, m), 1.7-1.8 (5H, m), 1.6 (1H, m), 1.40-1.55 (2H, m), 0.8-0.9 (1H, m), 0.5-0.6 (2H, m), 0.1-0.2 (2H, m) (free form) Mass (ESI): 476(M$^+$)

Example 73

Synthesis of N-(17-allyl-4,5α-epoxy-3,14-dihydroxymorphinan-6β-yl)-3,4,5,6-tetrahydrophthalimide•methanesulfonic acid salt (Compound 73)

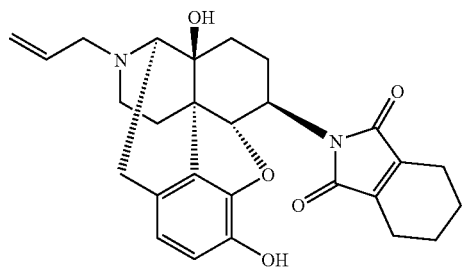

In a manner similar to the method described in Example 11, using 6β-naloxamine in place of 6β-naltrexamine, using 3,4,5,6-tetrahydrophthalic anhydride in place of phthalic anhydride, and using toluene as a solvent in place of DMF, 216 mg (yield: 71%) of free form of the captioned compound 73 was obtained. This product was converted to methanesulfonic acid salt to obtain the captioned compound 73.

$^1$H-NMR (ppm) (400 MHz, CDCl$_3$) 1.35-1.46 (3H, m), 1.64 (1H, m), 1.76 (4H, br), 2.26 (1H, dd, J=12.4, 4.8 Hz), 2.33 (5H, br), 2.54-2.65 (3H, m), 2.92 (1H, br), 3.07 (1H, d, J=18.4 Hz), 3.13 (3H, brd, J=6.0 Hz), 3.82 (1H, ddd, J=12.8, 8.4, 4.8 Hz), 5.04 (1H, d, J=8.4 Hz), 5.16 (2H, brd, J=20.4 Hz), 5.20 (1H, d, J=10.8 Hz), 5.80 (1H, ddt, J=16.8, 10.0, 6.8 Hz), 6.62 (1H, d, J=8.0 Hz), 6.75 (1H, d, J=8.0 Hz) (free form) Mass (ESI): 463(M$^+$+1)

Example 74

Synthesis of N-(17-allyl-4,5α-epoxy-3,14-dihydroxymorphinan-6α-yl)-3,4,5,6-tetrahydrophthalimide•methanesulfonic acid salt (Compound 74)

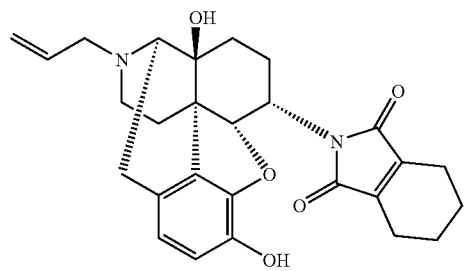

In a manner similar to the method described in Example 11, using 6α-naloxamine in place of 6β-naltrexamine, using 3,4,5,6-tetrahydrophthalic anhydride in place of phthalic anhydride, using toluene as a solvent in place of DMF, and performing heating to reflux for 20 hours, 30 mg (yield: 21%) of free form of the captioned compound 74 was obtained. This product was converted to methanesulfonic acid salt to obtain the captioned compound 74.

$^1$H-NMR (ppm) (400 MHz, CDCl$_3$) 6.81 (d, 1H, J=8.1 Hz), 6.60 (d, 1H, J=8.3 Hz), 5.83 (m, 1H), 5.22 (d, 1H, J=17.3 Hz), 5.19 (d, 1H, J=10.0 Hz), 4.60-4.64 (m, 1H), 4.56 (d, 1H, J=3.2 Hz), 3.09-3.13 (m, 3H), 2.97 (d, 1H, J=6.6 Hz), 2.65 (dd, 1H, J=6.6, 16.8 Hz), 2.58 (d, 1H, J=7.8 Hz), 2.25-2.34 (m, 5H), 2.06-2.13 (m, 1H), 1.77-1.82 (m, 4H), 1.64 (d, 1H, J=9.5 Hz), 1.43-1.54 (m, 2H) (free form) Mass (ESI): 463(M$^+$+1)

Example 75

Synthesis of N-(17-cyclopropylmethyl-4,5α-epoxy-3,14-dihydroxy-morphinan-6β-yl)-2,3-dimethyl-maleimide•tartaric acid salt (Compound 75)

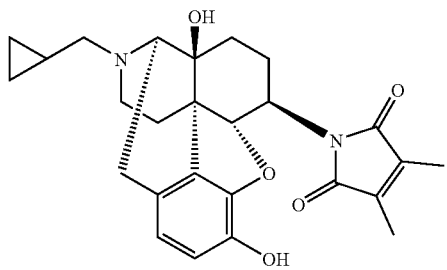

In 10 ml of acetic acid, 100 mg (0.29 mmol) of 6β-naltrexamine was dissolved, and 110 mg (0.88 mmol) of 2,3-dimethylmaleic anhydride was added thereto, followed by stirring the mixture at 125° C. for 20 hours. The reaction solution was allowed to cool to room temperature, and the reaction mixture was concentrated by an evaporator. To the reaction residue, aqueous saturated sodium hydrogen carbonate solution was added, and the resulting mixture was extracted with chloroform. Organic layers were combined, washed with water and saturated saline, dried over anhydrous magnesium sulfate and concentrated to obtain a crude product. The thus obtained crude product was purified by silica gel column chromatography to obtain 36 mg (yield: 27%) of free form of the captioned compound 75. This product was converted to tartaric acid salt to obtain the captioned compound 75.

$^1$H-NMR (ppm) (300 MHz, CDCl$_3$) 6.73 (brs, 1H), 6.60 (brs, 1H), 5.02 (brd, 1H, J=7.1 Hz), 3.81-3.87 (m, 1H), 3.47 (brd, 1H, J=5.4 Hz), 3.01-3.09 (brm, 2H), 2.64 (brs, 2H), 2.59 (brs, 1H), 2.37 (brd, 2H, J=6.4 Hz), 2.12 (brt, 1H, J=12.2 Hz), 1.96 (s, 6H), 1.65 (brd, 1H, J=13.2 Hz), 1.36-1.47 (brm, 3H), 0.84 (brs, 1H), 0.52-0.54 (brm, 2H), 0.13 (brs, 2H) (free form) Mass (ESI): 451(M$^+$+1)

Example 76

Synthesis of N-(17-cyclopropylmethyl-4,5α-epoxy-3,14-dihydroxy-morphinan-6α-yl)-2,3-dimethyl-maleimide•tartaric acid salt (Compound 76)

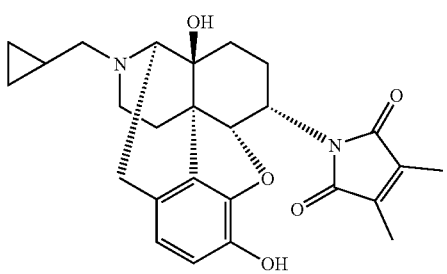

In a manner similar to the method described in Example 75, using 6α-naltrexamine in place of 6β-naltrexamine, 8 mg (yield: 7.5%) of free form of the captioned compound 76 was obtained. This product was converted to tartaric acid salt to obtain the captioned compound 76.

$^1$H-NMR (ppm) (300 MHz, CDCl$_3$) 6.78 (d, 1H, J=8.1 Hz), 6.56 (d, 1H, J=8.1 Hz), 4.61 (dt, 1H, J=3.9, 14.2 Hz), 4.54 (d, 1H, J=3.9 Hz), 3.12 (d, 1H, J=6.6 Hz), 3.04 (d, 1H, J=18.3 Hz), 2.60-2.78 (brm, 2H), 2.22-2.41 (m, 4H), 1.99-2.12 (m, 1H), 1.95 (s, 6H), 1.74-1.83 (m, 1H), 1.58-1.66 (brm, 1H), 1.50 (dd, 1H, J=9.3, 14.9 Hz), 1.37-1.44 (m, 1H), 0.81-0.90 (m, 1H), 0.53-0.57 (m, 2H), 0.11-0.15 (m, 2H) (free form) Mass (ESI): 451(M$^+$+1)

Example 77

Synthesis of N-(17-cyclopropylmethyl-4,5α-epoxy-3,14-dihydroxy-morphinan-6β-yl)-3,4,5,6-tetrahydrophthalimide•tartaric acid salt (Compound 77)

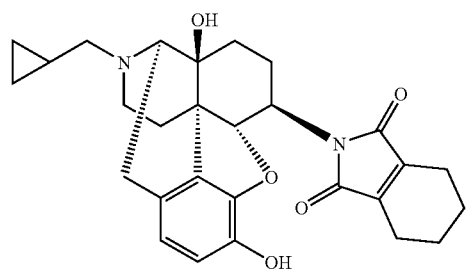

In 3.3 mL of chloroform, 113 mg (0.33 mmol) of 6β-naltrexamine was dissolved, and 58 mg (0.38 mmol) of 3,4,5,6-tetrahydrophthalic anhydride and 114 μL (0.82 mmol) of triethylamine were added thereto, followed by stirring the mixture at room temperature for 50 minutes. Thereafter, 234 μL (1.68 mmol) of triethylamine and 158 μL (1.68 mmol) of acetic anhydride were added, and the resulting mixture was heated to reflux for 1 hour. Thereafter, the reaction mixture was allowed to cool to room temperature, and concentrated by an evaporator. To the resulting mixture, 3 mL of methanol and 300 μL of 28% aqueous ammonia were added, and the mixture was stirred at room temperature for 4 hours. Water was then added to the reaction solution, and the resulting mixture was extracted with chloroform. Organic layers were combined, washed with water and saturated saline, dried over anhydrous magnesium sulfate and concentrated to obtain a crude product. The thus obtained crude product was purified by silica gel column chromatography to obtain 121 mg (yield: 77%) of free form of the captioned compound 77. This product was converted to methanesulfonic acid salt to obtain the captioned compound 77.

$^1$H-NMR (ppm) (300 MHz, CDCl$_3$) 0.12 (2H, m), 0.52 (2H, m), 0.84 (1H, m), 1.43 (3H, m), 1.65 (1H, m), 1.76 (4H, br), 2.12 (3H, td, J=12.0, 3.6 Hz), 2.26-2.38 (7H, m), 2.63 (3H,m), 3.03 (1H, d, J=18.4 Hz), 3.08 (1H, d, J=5.6 Hz), 3.83 (1H, ddd, J=13.2, 8.4, 3.6 Hz), 5.05 (1H, d, J=8.4 Hz), 6.60 (1H, d, J=8.4 Hz) (free form) Mass (ESI): 477(M$^+$+1)

Example 78

Synthesis of N-(17-cyclopropylmethyl-4,5α-epoxy-3,14-dihydroxy-morphinan-6β-yl)-cis-1,2,3,6-tetrahydrophthalimide•methanesulfonic acid salt (Compound 78)

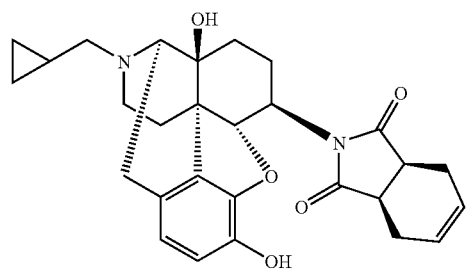

In a manner similar to the method described in Example 77, using cis-1,2,3,6-tetrahydrophthalic anhydride in place of 3,4,5,6-tetrahydrophthalic anhydride, 13 mg (yield: 11%) of free form of the captioned compound 78 was obtained. This product was converted to methanesulfonic acid salt to obtain the captioned compound 78.

$^1$H-NMR (ppm) (300 MHz, CDCl$_3$) 0.10 (2H, m), 0.51 (2H, m), 0.83 (1H, m), 1.12 (1H, t, J=7.2 Hz), 1.18 (1H, t, J=7.2 Hz), 1.25 (1H, m), 1.42 (2H, dd, J=13.2, 3.0 Hz), 1.62 (2H, brdt, J=13.2, 3.3 Hz), 2.07-2.24 (3H, m), 2.28 (1H, dd, J=12.3, 4.8 Hz), 2.35 (2H, d, J=6.3 Hz), 2.55-2.69 (4H, m), 3.05-3.09 (3H, m), 3.88 (1H, ddd, J=13.2, 8.1, 4.8 Hz), 5.06 (2H, brd, J=8.1 Hz), 5.91 (2H, t, J=3.0 Hz), 6.59 (1H, d, J=8.4 Hz), 6.73 (1H, d, J=8.4 Hz) (free form) Mass (ESI): 477(M$^+$+1)

Example 79

Synthesis of N-(17-cyclopropylmethyl-4,5α-epoxy-3,14-dihydroxy-morphinan-6β-yl)-1,2-cyclopropanedicarboimide•methanesulfonic acid salt (Compound 79)

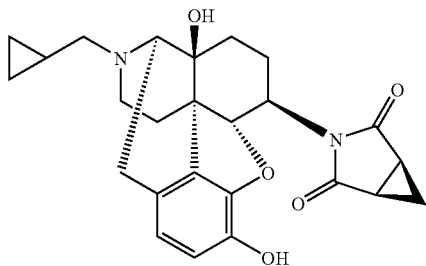

In a manner similar to the method described in Example 77, using 1,2-cyclopropanedicarboxylic anhydride in place of 3,4,5,6-tetrahydrophthalic anhydride, 5 mg (yield: 5%) of free form of the captioned compound 79 was obtained. This product was converted to methanesulfonic acid salt to obtain the captioned compound 79.

$^1$H-NMR (ppm) (300 MHz, CDCl$_3$) 0.18 (2H, m), 0.57 (2H, m), 0.89 (3H, m), 1.25-1.45 (8H, m), 1.53 (1H, ddd, J=12.9, 7.8, 4.5 Hz), 1.69 (1H, brd, J=13.5 Hz), 2.19 (1H, m), 2.32-2.45 (2H, m), 2.48 (2H, dd, J=7.8, 3.6 Hz), 2.61-2.70 (2H, m), 3.70 (1H, m), 4.99 (1H, d, J=8.1 Hz), 6.60 (1H, d, J=8.1 Hz), 6.75 (1H, d, J=8.1 Hz) (free form) Mass (ESI): 437(M$^+$+1)

Example 80

Synthesis of N-(17-cyclopropylmethyl-4,5α-epoxy-3,14-dihydroxy-morphinan-6β-yl)-2,3-pyridinedicarboimide•methanesulfonic acid salt (Compound 80)

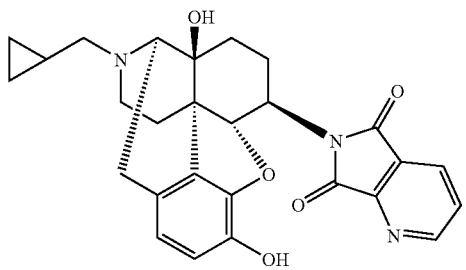

In 3.3 mL of chloroform, 113 mg (0.33 mmol) of 6β-naltrexamine was dissolved, and 57 mg (0.38 mmol) of 2,3-pyridinedicarboxylic anhydride and 136 µL (0.96 mmol) of triethylamine were added thereto, followed by stirring the mixture at room temperature for 2 hours. Thereafter, 227 µL (1.63 mmol) of triethylamine and 154 µL (1.63 mmol) of acetic anhydride were added, and the resulting mixture was heated to reflux for 3 hours. The mixture was allowed to cool to room temperature and aqueous saturated sodium hydrogen carbonate solution was added to the reaction mixture, followed by extracting the mixture with chloroform. Organic layers were combined, washed with water and saturated saline, dried over anhydrous magnesium sulfate and concentrated to obtain a crude product.

This reaction product was dissolved in 3 mL of acetone and 1.5 mL of 3N hydrochloric acid was added, followed by heating the mixture to reflux for 27 hours. Water was then added to the reaction solution, and the resulting mixture was extracted with chloroform. Organic layers were combined, washed with water and saturated saline, dried over anhydrous magnesium sulfate and concentrated to obtain a crude product. The thus obtained crude product was purified by silica gel column chromatography to obtain 13 mg (yield: 8%) of free form of the captioned compound 80. This product was converted to methanesulfonic acid salt to obtain the captioned compound 80.

$^1$H-NMR (ppm) (300 MHz, CDCl$_3$) 0.13 (2H, m), 0.54 (2H, m), 0.87 (1H, m), 1.49 (3H, m), 1.73 (2H, brd, J=13.2 Hz), 1.99 (1H, d, J=16.1 Hz), 2.38 (5H, m), 2.67 (2H, d, J=6.1 Hz), 3.07 (1H, d, J=9.8 Hz), 3.15 (1H, br), 4.15 (1H, ddd, J=12.7, 8.8, 4.8 Hz), 5.17 (1H, d, J=7.3 Hz), 6.62 (1H, d, J=8.3 Hz), 6.78 (1H, d, J=8.3 Hz), 7.63 (1H, dd, J=7.6, 5.1 Hz), 8.17 (1H, dd, J=7.6, 1.2 Hz), 8.98 (1H, dd, J=4.8, 1.2 Hz) (free form) Mass (ESI): 474(M$^+$+1)

Example 81

Synthesis of 2-(17-cyclopropylmethyl-4,5α-epoxy-3,14-dihydroxy-morphinan-6β-yl)-4-fluoro-2,3-dihydro-isoindol-1-one•methanesulfonic acid salt (Compound 81)

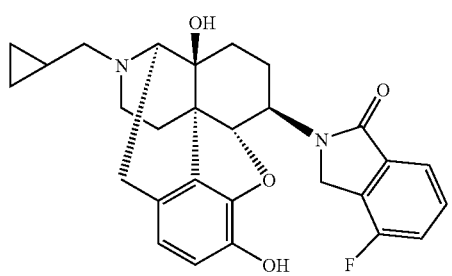

In a manner similar to the method described in Examples 25 and 28, using N-(17-cyclopropylmethyl-4,5α-epoxy-3,14-dihydroxy-morphinan-6β-yl)-3-fluoro-phthalimide obtained in Example 17 in place of N-(17-cyclopropylmethyl-4,5α-epoxy-3,14-dihydroxy-morphinan-6β-yl)-phthalimide, 11 mg (yield: 13%, 2 steps) of free form of the captioned compound 81 was obtained. This product was converted to methanesulfonic acid salt to obtain the captioned compound 81.

$^1$H-NMR (ppm) (300 MHz, CDCl$_3$) 0.14 (2H, m), 0.54 (2H, m), 0.85 (1H, m), 1.47-1.73 (4H, m), 2.13-2.29 (4H, m), 2.38 (2H, d, J=6.3 Hz), 2.59-2.67 (2H, m), 3.05 (1H, d, J=18.9 Hz), 3.10 (1H, d, J=5.4 Hz), 4.25 (1H, ddd, J=13.5, 8.1, 4.8 Hz), 4.53 (3H, m), 4.68 (1H, d, J=7.8 Hz), 6.62 (1H, d, J=8.1 Hz), 6.76 (1H, d, J=8.1 Hz), 7.22 (1H, t, J=8.7 Hz), 7.42-7.49 (1H, m), 7.64 (1H, d, J=7.8 Hz) (free form) Mass (ESI): 477(M$^+$+1)

Example 82

Synthesis of 2-(17-cyclopropylmethyl-4,5α-epoxy-3,14-dihydroxy-morphinan-6β-yl)-6-fluoro-2,3-dihydro-isoindol-1-one•methanesulfonic acid salt (Compound 82)

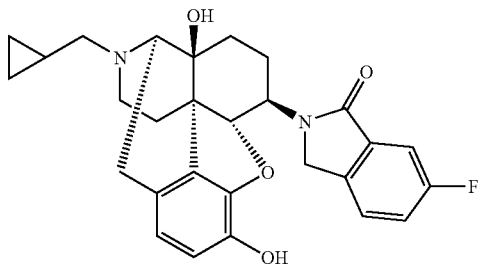

In a manner similar to the method described in Examples 25 and 28, using N-(17-cyclopropylmethyl-4,5α-epoxy-3,14-dihydroxy-morphinan-6β-yl)-4-fluoro-phthalimide obtained in Example 16 in place of N-(17-cyclopropylmethyl-4,5α-epoxy-3,14-dihydroxy-morphinan-6β-yl)-phthalimide, 19 mg (yield: 25%, 2 steps) of free form of the captioned compound 82 was obtained. This product was converted to methanesulfonic acid salt to obtain the captioned compound 82.

$^1$H-NMR (ppm) (300 MHz, CDCl$_3$) 0.13 (2H, m), 0.53 (2H, m), 0.85 (1H, m), 1.47-1.72 (4H, m), 2.15-2.27 (4H, m), 2.39 (2H, d, J=6.3 Hz), 2.59-2.67 (2H, m), 3.06 (1H, d, J=18.6 Hz), 3.12 (1H, d, J=5.4 Hz), 4.23 (1H, ddd, J=12.9, 8.4, 3.6 Hz), 4.46 (3H, m), 4.66 (1H, d, J=8.4 Hz), 6.60 (1H, d, J=8.1 Hz), 6.77 (1H, dd, J=8.1, 1.5 Hz), 7.11-7.82 (3H, m) (free form) Mass (ESI): 477(M$^+$+1)

Example 83

Synthesis of 2-(17-cyclopropylmethyl-4,5α-epoxy-3,14-dihydroxy-morphinan-6β-yl)-2,3,4,5,6,7-hexahydro-isoindol-1-one•tartaric acid salt (Compound 83)

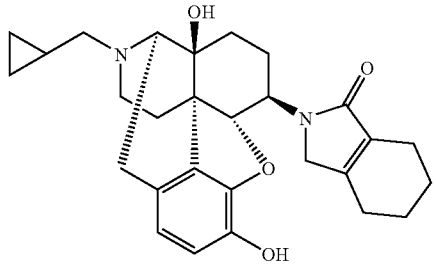

In a manner similar to the method described in Examples 25 and 28, using N-(17-cyclopropylmethyl-4,5α-epoxy-3,14-dihydroxy-morphinan-6β-yl)-3,4,5,6-tetrahydrophthalimide obtained in Example 77 in place of N-(17-cyclopropylmethyl-4,5α-epoxy-3,14-dihydroxy-morphinan-6β-yl)-phthalimide, 16 mg (yield: 43%, 2 steps) of free form of the captioned compound 83 was obtained. This product was converted to methanesulfonic acid salt to obtain the captioned compound 83.

$^1$H-NMR (ppm) (400 MHz, CDCl$_3$) 6.75 (d, 1H, J=8.3 Hz), 6.58 (d, 1H, J=8.3 Hz) 4.54 (d, 1H, J=8.1 Hz), 4.06 (ddd, J=4.5, 8.3, 13.1 Hz), 3.93 (d, 1H, J=18.8 Hz), 3.85 (d, 1H, J=18.8 Hz), 3.09 (bs, 1H), 3.03 (d, 1H, J=18.3 Hz), 2.65-2.59 (m, 2H), 2.06-2.39 (m, 9H), 1.47-1.74 (m, 8H), 0.83-0.85 (m, 1H), 0.52-0.54 (m, 2H), 0.13-0.14 (m, 2H) (free form) Mass (ESI): 463(M$^+$+1)

Example 84

Synthesis of 2-(17-allyl-4,5α-epoxy-3,14-dihydroxy-morphinan-6-yl)-2,3,4,5,6,7-hexahydro-isoindol-1-one•methanesulfonic acid salt (Compound 84)

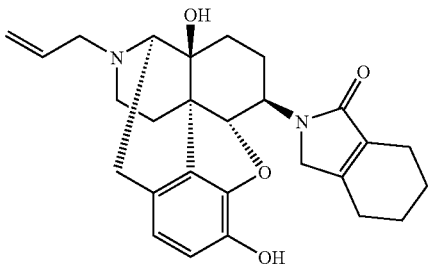

In a manner similar to the method described in Examples 25 and 28, using N-(17-allyl-4,5α-epoxy-3,14-dihydroxy-morphinan-6β-yl)-3,4,5,6-tetrahydrophthalimide obtained in Example 73 in place of N-(17-cyclopropylmethyl-4,5α-epoxy-3,14-dihydroxy-morphinan-6β-yl)-phthalimide, 77 mg (yield: 52%, 2 steps) of free form of the captioned compound 84 was obtained. This product was converted to methanesulfonic acid salt to obtain the captioned compound 84.

$^1$H-NMR (ppm) (400 MHz, CDCl$_3$) 1.41-1.80 (8H, m), 2.07-2.29 (7H, m), 2.51 (1H, br), 2.60 (1H, dd, J=18.0, 5.6 Hz), 2.90 (1H, d, J=5.6 Hz), 3.07 (1H, d, J=18.0 Hz), 3.12 (3H, brd, J=6.0 Hz), 3.88 (1H, d, J=18.8 Hz), 3.96 (1H, d, J=18.8 Hz), 4.15 (1H, ddd, J=12.8, 7.6, 4.4 Hz), 4.45 (1H, d, J=8.0 Hz), 5.15 (2H, brd, J=10.0 Hz), 5.21 (1H, d, J=16.8 Hz), 5.79 (1H, ddt, J=16.8, 10.0, 6.4 Hz), 6.59 (1H, d, J=8.0 Hz), 6.76 (1H, d, J=8.0 Hz) (free form) Mass (ESI): 449 (M$^+$+1)

Example 85

Synthesis of 2-(17-allyl-4,5α-epoxy-3,14-dihydroxy-morphinan-6α-yl)-2,3,4,5,6,7-hexahydro-isoindol-1-one•tartaric acid salt (Compound 85)

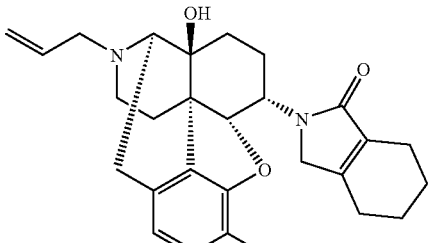

In a manner similar to the method described in Examples 25 and 28, using N-(17-allyl-4,5α-epoxy-3,14-dihydroxymorphinan-6α-yl)-3,4,5,6-tetrahydrophthalimide obtained in Example 74 in place of N-(17-cyclopropylmethyl-4,5α-epoxy-3,14-dihydroxy-morphinan-6β-yl)-phthalimide, 8 mg (yield: 40%, 2 steps) of free form of the captioned compound 85 was obtained. This product was converted to tartaric acid salt to obtain the captioned compound 85.

¹H-NMR (ppm) (400 MHz, CDCl₃) 6.74 (d, 1H, J=8.3 Hz), 6.57 (d, 1H, J=8.3 Hz), 5.80-5.84 (m, 1H), 5.18-5.25 (m, 2H), 4.86 (d, 1H, J=2.0 Hz), 4.78-4.82 (m, 1H), 3.70-3.77 (m, 2H), 3.09-3.15 (m, 3H), 2.96 (d, 1H, J=7.0 Hz), 2.57-2.67 (m, 2H), 2.25-2.30 (m, 5H), 1.73-1.87 (m, 5H), 1.48-1.57 (m, 2H), 1.25-1.29 (m, 3H) (free form) Mass (ESI): 449(M⁺+1)

Example 86

Synthesis of 2-(17-allyl-4,5α-epoxy-3,14-dihydroxy-morphinan-6β-yl)-2,3-dihydro-isoindol-1-one•tartaric acid salt (Compound 86)

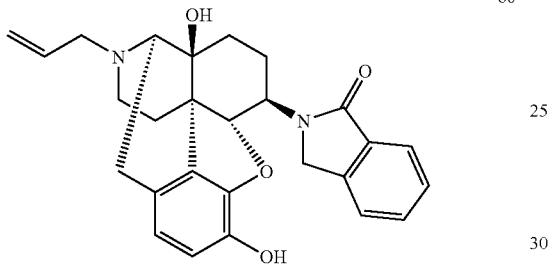

In a manner similar to the method described in Examples 25 and 28, using N-(17-allyl-4,5α-epoxy-3,14-dihydroxy-morphinan-6β-yl)-phthalimide obtained in Example 13 in place of N-(17-cyclopropylmethyl-4,5α-epoxy-3,14-dihydroxy-morphinan-6β-yl)-phthalimide, 10 mg (yield: 6.9%, 2 steps) of free form of the captioned compound 86 was obtained. This product was converted to tartaric acid salt to obtain the captioned compound 86.

¹H-NMR (ppm) (400 MHz, CDCl₃) 7.85 (1H, m), 7.5-7.6 (1H, m), 7.4-7.5 (2H, m), 6.79 (1H, d, J=8.2 Hz), 6.64 (1H, d, J=8.2 Hz), 5.75-5.85 (1H, m), 5.15-5.25 (2H, m), 4.66 (1H, d, J=8.0 Hz), 4.54 (1H, d, J=16.6 Hz), 4.46 (1H, d, J=16.6 Hz), 4.25-4.30 (1H, m), 3.15 (1H, d, J=6.6 Hz), 3.10 (1H, d, J=18.3 Hz), 2.94 (1H, d, J=5.6 Hz), 2.5-2.7 (2H, m), 2.2-2.3 (3H, m), 1.5-1.7 (5H, m) (free form) Mass (ESI): 445(M⁺+1)

Example 87

Synthesis of 2-(17-allyl-4,5α-epoxy-3,14-dihydroxy-morphinan-6α-yl)-2,3-dihydro-isoindol-1-one•tartaric acid salt (Compound 87)

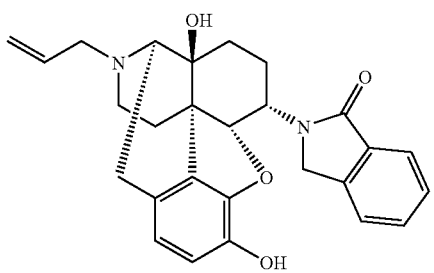

In a manner similar to the method described in Examples 25 and 28, using N-(17-allyl-4,5α-epoxy-3,14-dihydroxy-morphinan-6α-yl)-phthalimide obtained in Example 64 in place of N-(17-cyclopropylmethyl-4,5α-epoxy-3,14-dihydroxy-morphinan-6β-yl)-phthalimide, 7 mg (yield: 13%, 2 steps) of free form of the captioned compound 87 was obtained. This product was converted to tartaric acid salt to obtain the captioned compound 87.

¹H-NMR (ppm) (400 MHz, CDCl₃) 7.90 (d, 1H, J=7.1 Hz), 7.51 (t, 1H, J=7.1 Hz), 7.46 (t, 1H, J=7.1 Hz), 7.37 (d, 1H, J=7.1 Hz), 6.78 (d, 1H, J=8.1 Hz), 6.60 (d, 1H, J=8.1 Hz), 5.80-5.87 (m, 1H), 5.18-5.25 (m, 2H), 4.95-5.02 (m, 2H), 4.69 (d, 1H, J=17.3 Hz), 4.33 (d, 1H, J=17.3 Hz), 3.10-3.15 (m, 3H), 2.98 (d, 1H, J=6.6 Hz), 2.65 (dd, 1H, J=7.6, 18.4 Hz), 2.56 (d, 1H, J=6.6 Hz), 2.26-2.28 (m, 2H), 1.85-1.91 (m, 1H), 1.49-1.60 (m, 5H) (free form) Mass (ESI): 445(M⁺+1)

Examples 88 and 89

Synthesis of 2-(17-allyl-4,5α-epoxy-3,14-dihydroxy-morphinan-6β-yl)-7-fluoro-2,3-dihydro-isoindol-1-one•methanesulfonic acid salt (Compound 88) and 2-(17-allyl-4,5α-epoxy-3,14-dihydroxy-morphinan-6β-yl)-4-fluoro-2,3-dihydro-isoindol-1-one•methanesulfonic acid salt (Compound 89)

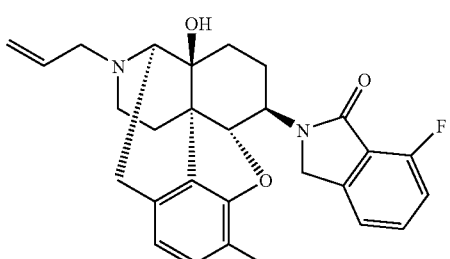

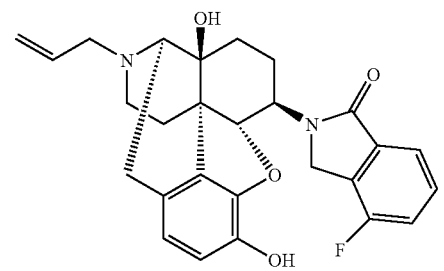

In a manner similar to the method described in Examples 25 and 28, using N-(17-allyl-4,5α-epoxy-3,14-dihydroxy-morphinan-6β-yl)-3-fluoro-phthalimide obtained in Example 62 in place of N-(17-cyclopropylmethyl-4,5α-epoxy-3,14-dihydroxy-morphinan-6β-yl)-phthalimide, 23 mg (yield: 8%, 2 steps) of free form of the captioned compound 88 and 52 mg (yield: 15%, 2 steps) of free from of the captioned compound 89 were obtained. These products were converted to methanesulfonic acid salt to obtain the captioned compound 88 and the captioned compound 89.

Compound 88

¹H-NMR (ppm) (400 MHz, CDCl₃) 1.45-1.68 (3H, m), 2.12-2.33 (4H, m), 2.55 (1H, m), 2.64 (1H, dd, J=18.6, 5.8 Hz), 2.94 (1H, d, J=5.8 Hz), 3.09 (1H, d, J=18.6 Hz), 3.14 (3H, brd, J=6.4 Hz), 4.25 (1H, ddd, J=13.2, 8.6, 4.6 Hz), 4.48 (1H, d, J=17.1 Hz), 4.52 (1H, d, J=17.1 Hz), 4.67 (1H, d, J=8.3 Hz), 5.13-5.26 (3H, m), 5.81 (1H, m), 6.63 (1H, d, J=8.3 Hz), 6.79 (1H, d, J=8.3 Hz), 7.20-7.68 (3H, m) (free form) Mass (ESI): 463(M$^+$+1)

Compound 89

$^1$H-NMR (ppm) (400 MHz, CDCl$_3$) 1.45-1.72 (3H, m), 2.20-2.32 (4H, m), 2.54 (1H, br), 2.64 (1H, dd, J=18.6, 5.8 Hz), 2.93 (1H, d, J=5.8 Hz), 3.10 (1H, d, J=18.6 Hz), 3.15 (3H, brd, J=6.4 Hz), 4.27 (1H, m), 4.44-4.68 (3H, m), 5.19 (3H, m), 5.81 (1H, m), 6.63 (1H, d, J=8.3 Hz), 6.78 (1H, d, J=8.3 Hz), 7.06-7.55 (3H, m) (free form) Mass (ESI): 463(M$^+$+1)

Example 90

Synthesis of 2-(17-allyl-4,5α-epoxy-3,14-dihydroxy-morphinan-6β-yl)-6-fluoro-2,3-dihydro-isoindol-1-one•methanesulfonic acid salt (Compound 90)

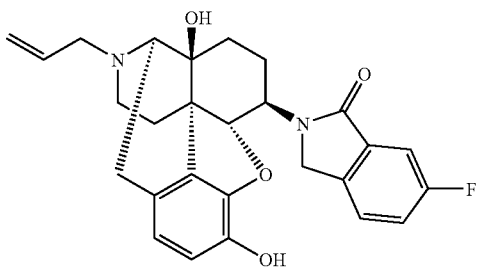

In a manner similar to the method described in Examples 25 and 28, using N-(17-allyl-4,5α-epoxy-3,14-dihydroxy-morphinan-6β-yl)-4-fluoro-phthalimide obtained in Example 58 in place of N-(17-cyclopropylmethyl-4,5α-epoxy-3,14-dihydroxy-morphinan-6β-yl)-phthalimide, 86 mg (yield: 48%, 2 steps) of free form of the captioned compound 90 was obtained. This product was converted to methanesulfonic acid salt to obtain the captioned compound 90.

$^1$H-NMR (ppm) (400 MHz, CDCl$_3$) 1.48 (1H, m), 1.56 (1H, m), 1.67 (1H, m), 2.08-2.29 (4H, m), 2.53 (1H, d, J=7.2 Hz), 2.63 (1H, dd, J=18.4, 5.6 Hz), 2.93 (1H, d, J=5.2 Hz), 3.10 (1H, d, J=18.4 Hz), 3.14 (3H, brd, J=6.8 Hz), 4.23 (1H, m), 4.40-4.51 (2H, m), 4.66 (1H, d, J=8.4 Hz), 5.15-5.24 (3H, m), 5.81 (1H, ddt, J=23.2, 16.8, 6.4 Hz), 6.62 (1H, d, J=8.4 Hz), 6.77 (1H, d, J=8.4 Hz) 7.03-7.75 (3H, m) (free form) Mass (ESI): 463(M$^+$+1)

Example 91

Synthesis of N-(14-acetoxy-17-cyclopropylmethyl-4,5α-epoxy-3-hydroxymorphinan-6β-yl)-phthalimide•tartaric acid salt (Compound 91)

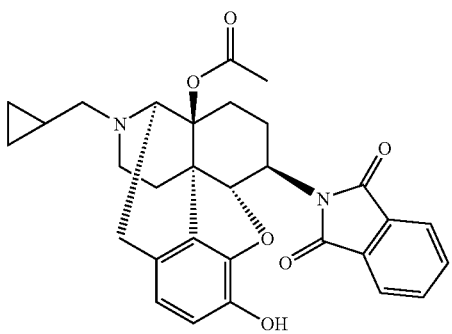

In 2.5 mL of pyridine, 100 mg (0.21 mmol) of N-(17-cyclopropylmethyl-4,5α-epoxy-3,14-dihydroxy-morphinan-6β-yl)-phthalimide obtained in Example 11 was dissolved, and 5.0 mL of acetic anhydride was added, followed by stirring the mixture at 80° C. for 24 hours. After concentrating the reaction solution, 5 mL of toluene was added and the mixture was then concentrated. This operation was repeated 5 times to obtain N-(3,14-diacetoxy-17-cyclopropylmethyl-4,5α-epoxy-morphinan-6β-yl)-phthalimide as a crude product.

This crude product was dissolved in 10 mL of ethanol, and 1 mL of 28% aqueous ammonia was added, followed by stirring the mixture at room temperature for 1 hour. Water was added to the reaction mixture, and the mixture was extracted with ethyl acetate. Organic layers were combined, washed with saturated saline, dried over anhydrous magnesium sulfate and concentrated to obtain a crude product. The thus obtained crude product was purified by silica gel column chromatography to obtain 50 mg (yield: 46%, 2 steps) of free form of the captioned compound 91. This product was converted to tartaric acid salt to obtain the captioned compound 91.

$^1$H-NMR (ppm) (400 MHz, CDCl$_3$) 7.8-7.9 (2H, m), 7.7-7.8 (2H, m), 6.77 (1H, d, J=8.0 Hz), 6.63 (1H, d, J=8.0 Hz), 5.15 (1H, d, J=8.1 Hz), 4.39 (1H, d, J=5.2 Hz), 4.0-4.1 (1H, m), 3.08 (1H, d, J=18.3 Hz), 2.65-2.70 (2H, m), 2.4-2.6 (3H, m), 2.25-2.35 (2H, m), 2.22 (3H, s), 2.14 (1H, dt, J=11.9, 3.9 Hz), 1.4-1.5 (3H, m), 0.7-0.8 (1H, m), 0.5 (2H, m), 0.05-0.10 (2H, m) (free form) Mass (ESI): 514(M$^+$)

Example 92

Synthesis of N-(14-acetoxy-17-allyl-4,5α-epoxy-3-hydroxymorphinan-6β-yl)-phthalimide•tartaric acid salt (Compound 92)

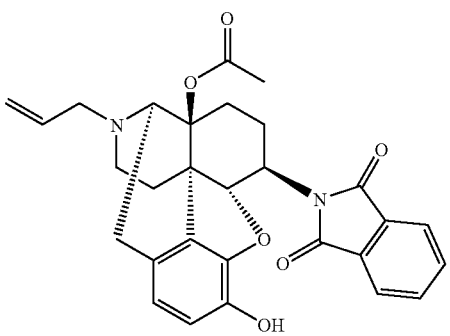

In a manner similar to the method described in Example 91, using N-(17-allyl-4,5α-epoxy-3,14-dihydroxy-morphinan-6β-yl)-phthalimide obtained in Example 13 in place of N-(17-cyclopropylmethyl-4,5α-epoxy-3,14-dihydroxy-morphinan-6β-yl)-phthalimide, 66 mg (yield: 30%, 2 steps) of free form of the captioned compound 92 was obtained. This product was converted to tartaric acid salt to obtain the captioned compound 92.

$^1$H-NMR (ppm) (400 MHz, CDCl$_3$) 7.8-7.9 (2H, m), 7.7-7.8 (2H, m), 6.78 (1H, d, J=8.1 Hz), 6.66 (1H, d, J=8.1 Hz), 5.7-5.8 (1H, m), 5.1-5.2 (2H, m), 5.15 (1H, d, J=8.0 Hz), 4.23 (1H, d, J=5.1 Hz), 4.05-4.15 (1H, m), 3.05-3.15 (2H, m), 2.4-2.7 (5H, m), 2.22 (3H, s), 2.1-2.2 (2H, m), 1.7 (1H, m), 1.4-1.5 (2H, m) (free form) Mass (ESI): 500(M$^+$)

Example 93

Synthesis of N-(14-acetoxy-17-cyclopropylmethyl-4,5α-epoxy-3-hydroxymorphinan-6β-yl)-2,3,4,5,6,7-hexahydro-isoindol-1-one•tartaric acid salt (Compound 93)

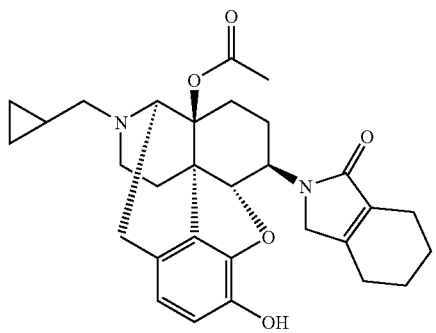

93

In a manner similar to the method described in Example 91, using 2-(17-cyclopropylmethyl-4,5α-epoxy-3,14-dihydroxy-morphinan-6β-yl)-2,3,4,5,6,7-hexahydro-isoindol-1-one obtained in Example 83 in place of N-(17-cyclopropylmethyl-4,5α-epoxy-3,14-dihydroxy-morphinan-6β-yl)-phthalimide, 38 mg (yield: 58%, 2 steps) of free form of the captioned compound 93 was obtained. This product was converted to tartaric acid salt to obtain the captioned compound 93.

$^1$H-NMR (ppm) (400 MHz, CDCl$_3$) 6.76 (d, 1H, J=8.2 Hz), 6.59 (d, 1H, J=8.2 Hz), 4.69 (d, 1H, J=8.1 Hz), 4.35 (m, 1H), 3.91 (s, 2H), 3.03-3.08 (m, 2H), 2.49-2.74 (m, 3H), 2.16-2.35 (m, 1H), 1.95-2.04 (m, 1H), 1.71-1.73 (m, 3H), 1.35-1.49 (m, 4H), 0.73-0.80 (m, 1H), 0.46-0.58 (m, 2H), 0.08-0.09 (m, 2H) (free form) Mass (ESI): 504(M$^+$)

Example 94

Synthesis of N-(4,5α-epoxy-3,14-dihydroxy-17-propyl-morphinan-6β-yl)-phthalimide•tartaric acid salt (Compound 94)

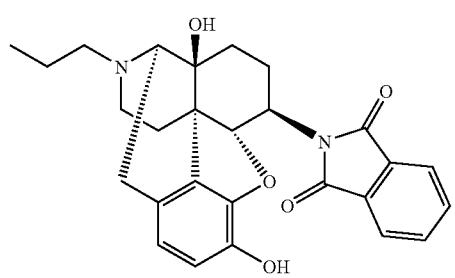

94

In 10 mL of dichloromethane, 50 mg (0.11 mmol) of N-(17-allyl-4,5α-epoxy-3,14-dihydroxy-morphinan-6β-yl)-phthalimide obtained in Example 13 was dissolved, and 10 mg of 10% Pd/C was added, followed by stirring the mixture under hydrogen atmosphere at room temperature for 8 hours. The reaction solution was filtered through Celite, and the filtrate was concentrated to obtain a crude product. The thus obtained crude product was purified by silica gel column chromatography to obtain 49 mg (yield: 100%) of free form of the captioned compound 94. This product was converted to tartaric acid salt to obtain the captioned compound 94.

$^1$H-NMR (ppm) (400 MHz, CDCl$_3$) 7.8-7.9 (2H, m), 7.7-7.8 (2H, m), 6.77 (1H, d, J=8.2 Hz), 6.63 (1H, d, J=8.2 Hz), 5.17 (1H, d, J=8.2 Hz), 4.0-4.1 (1H, m), 3.10 (1H, d, J=18.5 Hz), 2.7-2.9 (2H, m), 2.54 (1H, dd, J=12.0, 4.0 Hz), 2.3-2.5 (4H, m), 2.15 (1H, m), 1.4-1.7 (6H, m), 0.93 (3H, t, J=7.3 Hz) (free form) Mass (ESI): 461(M$^+$+1)

Example 95-1

Synthesis of N-(4,5α-epoxy-3-methoxy-17-methyl-morphinan-6β-yl)-phthalimide (Compound 295)

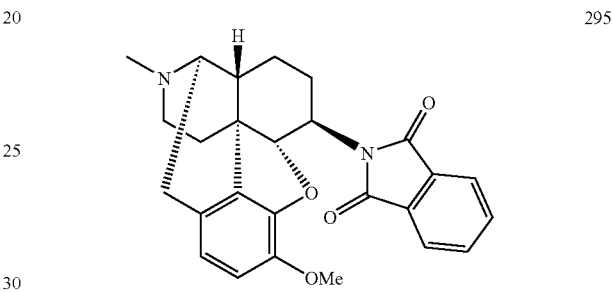

295

In 15 mL of DMF, 321 mg (0.70 mmol) of toluene-4-sulfonic acid-(4,5α-epoxy-3-methoxy-17-methyl-morphinan-6β-yl)-ester was dissolved, and 196 mg of potassium phthalimide was added thereto, followed by stirring the mixture at 80° C. for 15 hours and then at 140° C. for 20 hours. After allowing the reaction solution to cool to room temperature, water was added to the reaction mixture and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 116 mg (yield: 38%) of the captioned compound.

Mass (ESI): 431(M$^+$+1)

Example 95-2

Synthesis of N-(4,5α-epoxy-3-hydroxy-17-methyl-morphinan-6β-yl)-phthalimide•tartaric acid salt (Compound 95)

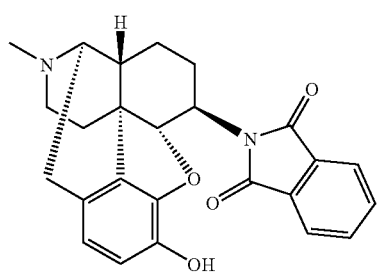

95

In 5 mL of methylene chloride, 44 mg (0.10 mmol) of N-(4,5α-epoxy-3-methoxy-17-methyl-morphinan-6β-yl)-phthalimide obtained in Example 95-1 was dissolved, and 0.32 mL of boron tribromide was added at −30° C., followed by stirring the mixture at 0° C. for 3 hours. To this reaction solution, 2 mL of aqueous ammonia was then added and the mixture was stirred for 1 hour. Thereafter, aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 16 mg (yield: 37%) of free form of the captioned compound 95. This product was converted to tartaric acid salt to obtain the captioned compound 95.

$^1$H-NMR (ppm) (300 MHz, CDCl$_3$) 7.97-8.03 (m, 2H), 7.86-7.92 (m, 2H), 6.78 (d, 1H, J=8.2 Hz), 6.63 (d, 1H, J=8.2 Hz), 5.07 (d, 1H, J=8.2 Hz), 4.12-4.20 (ddd, 1H, J=4.1, 8.2, 13.2 Hz), 3.33-3.75 (m, 1H), 3.18 (d, 1H, J=18.5 Hz), 2.77 (dd, 1H, J=3.2, 11.7 Hz), 2.52-2.53 (m, 5H), 2.31-2.45 (m, 2H), 2.16 (dt, 1H, J=4.7, 12.3 Hz), 1.71-1.87 (m, 3H), 1.21-1.34 (m, 1H) (free form) Mass (ESI): 417(M$^+$+1)

Example 96

Synthesis of N-(17-cyclopropylmethyl-4,5α-epoxy-3,14-dihydroxy-morphinan-6β-yl)-3-hydroxy-phthalimide•tartaric acid salt (Compound 96)

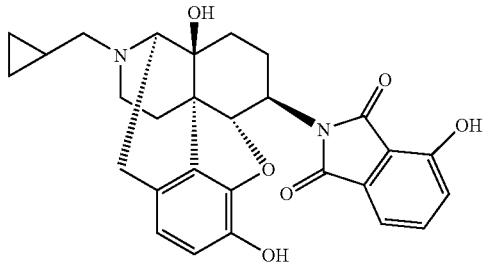

96

In a manner similar to the method described in Example 11, using 3-hydroxyphthalic anhydride in place of phthalic anhydride, 23 mg (yield: 16%) of free form of the captioned compound 96 was obtained. This product was converted to tartaric acid salt to obtain the captioned compound 96.

$^1$H-NMR (ppm) (300 MHz, CDCl$_3$) 9.03 (brs, 1H), 7.62 (t, 1H, J=7.9 Hz), 7.25 (dd, 2H, J=7.3, 16.4 Hz), 6.60 (dd, 2H, J=7.8, 14.4 Hz), 5.04 (d, 1H, J=8.2 Hz), 3.77-3.85 (m, 1H), 3.34 (brs, 1H), 2.98-3.07 (m, 2H), 2.31-2.64 (m, 4H), 1.96-2.02 (m, 1H), 1.57 (d, 1H, J=12.5 Hz), 1.41-1.43 (m, 2H), 1.25 (d, 1H, J=10.3 Hz), 0.79-0.93 (m, 1H), 0.48 (d, 2H, J=7.9 Hz), 0.14 (d, 2H, J=4.4 Hz) (free form) Mass (ESI): 489(M$^+$+1)

Example 97-1

Synthesis of N-(17-cyclopropylmethyl-4,5α-epoxy-3,14-dihydroxy-morphinan-6β-yl)-3-nitro-phthalimide (Compound 297)

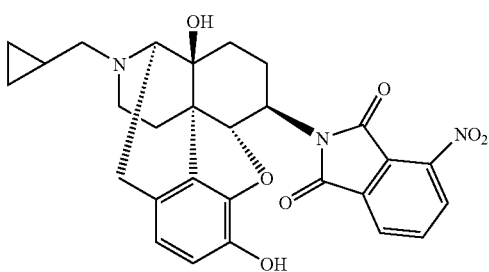

297

In a manner similar to the method described in Example 11, using 3-nitrophthalic anhydride in place of phthalic anhydride, 151 mg of the captioned compound was obtained as a crude product.

Mass (ESI): 518(M$^+$+1)

Example 97-2

Synthesis of N-(17-cyclopropylmethyl-4,5α-epoxy-3,14-dihydroxy-morphinan-6β-yl)-3-amino-phthalimide•methanesulfonic acid salt (Compound 97)

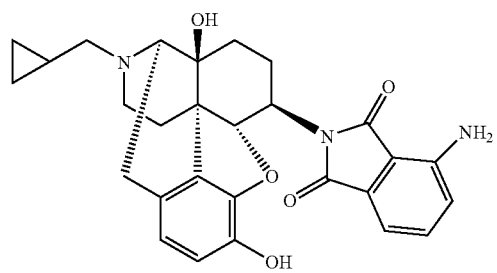

97

In 10 mL of methanol, 150 mg of N-(17-cyclopropylmethyl-4,5α-epoxy-3,14-dihydroxy-morphinan-6β-yl)-3-nitro-phthalimide obtained in Example 97-1 as a crude product was dissolved, and 20 mg of 10% Pd/C was added, followed by stirring the mixture under hydrogen atmosphere at room temperature for 7 hours. The reaction solution was filtered through Celite, and the filtrate was concentrated to obtain a crude product. The thus obtained crude product was purified by silica gel column chromatography to obtain 22 mg (yield: 10%, 2 steps) of free form of the captioned compound 97. This product was converted to methanesulfonic acid salt to obtain the captioned compound 97.

$^1$H-NMR (ppm) (400 MHz, CDCl$_3$) 7.92 (s, 2H), 6.76 (d, 1H, J=7.8 Hz), 6.63 (d, 1H, J=7.8 Hz), 5.11 (d, 1H, J=8.7 Hz), 4.05-4.08 (m, 1H), 3.11 (t, 2H, J=5.7 Hz), 3.03 (s, 1H), 2.59-2.71 (m, 3H), 2.29-2.39 (m, 3H), 2.09-2.17 (m, 2H), 1.69-1.73 (m, 2H), 1.44-1.48 (m, 2H), 0.86-0.88 (m, 1H), 0.53-0.55 (m, 2H), 0.13-0.14 (m, 2H) (free form) Mass (ESI): 488(M$^+$+1)

Example 98-1

Synthesis of N-(17-cyclopropylmethyl-4,5α-epoxy-3,14-dihydroxy-morphinan-6β-yl)-4-nitro-phthalimide (Compound 298)

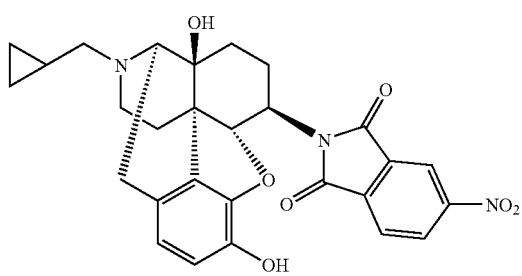

In a manner similar to the method described in Example 11, using 4-nitrophthalic anhydride in place of phthalic anhydride, the captioned compound was obtained as a crude product.

Mass (ESI): 518(M$^+$+1)

Example 98-2

Synthesis of N-(17-cyclopropylmethyl-4,5α-epoxy-3,14-dihydroxy-morphinan-6β-yl)-4-amino-phthalimide•tartaric acid salt (Compound 98)

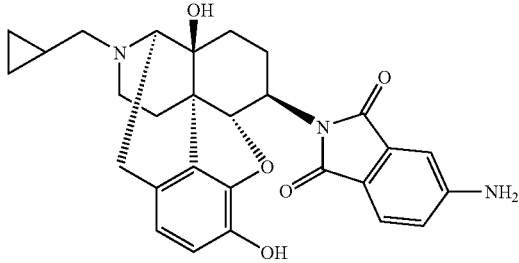

In a manner similar to the method described in Example 97-2, using N-(17-cyclopropylmethyl-4,5α-epoxy-3,14-dihydroxy-morphinan-6β-yl)-4-nitro-phthalimide obtained in Example 98-1 as a crude product in place of N-(17-cyclopropylmethyl-4,5α-epoxy-3,14-dihydroxy-morphinan-6β-yl)-3-nitro-phthalimide, 10 mg (yield: 15%, 2 steps) of free form of the captioned compound 98 was obtained. This product was converted to tartaric acid salt to obtain the captioned compound 98.

$^1$H-NMR (ppm) (300 MHz, CDCl$_3$) 7.56 (brs, 1H), 7.00 (brs, 1H), 6.72-6.80 (brm, 2H), 6.60 (brs, 1H), 5.12 (d, 1H, J=8.2 Hz), 4.40-4.58 (m, 2H), 4.00 (brs, 1H), 3.70 (brs, 1H), 2.86-3.07 (m, 3H), 2.63-2.95 (m, 2H), 2.34 (brs, 1H), 1.23-2.11 (m, 4H), 0.86 (brs, 1H), 0.50 (brs, 2H), 0.11 (brs, 2H) (free form) Mass (ESI): 488(M$^+$+1)

Example 99-1

Synthesis of N-(17-allyl-4,5α-epoxy-3,14-dihydroxy-morphinan-6β-yl)-4-nitro-phthalimide (Compound 299)

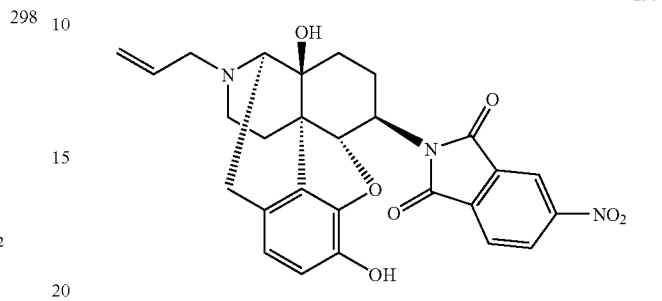

In a manner similar to the method described in Example 11, using 6β-naloxamine in place of 6β-naltrexamine, and using 4-nitrophthalic anhydride in place of phthalic anhydride, the captioned compound was obtained as a crude product.

Mass (ESI): 504(M$^+$+1)

Example 99-2

Synthesis of N-(17-allyl-4,5α-epoxy-3,14-dihydroxy-morphinan-6β-yl)-4-amino-phthalimide•tartaric acid salt (Compound 99)

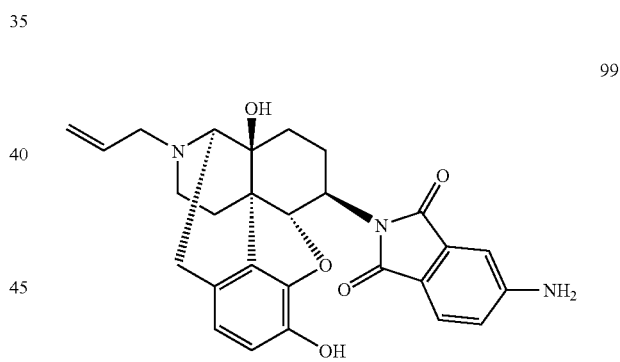

N-(17-allyl-4,5α-epoxy-3,14-dihydroxy-morphinan-6β-yl)-4-nitro-phthalimide obtained in Example 99-1 as a crude product was dissolved in ethanol, and Tin chloride dihydrate was added thereto, followed by stirring the mixture at 80° C. for 8 hours. Aqueous saturated sodium hydrogen carbonate solution was added to this reaction solution, and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 15 mg (yield: 8%, 2 steps) of free form of the captioned compound 99. This product was converted to tartaric acid salt to obtain the captioned compound 99.

$^1$H-NMR (ppm) (300 MHz, CDCl$_3$) 7.55 (d, 1H, J=7.6 Hz), 6.99 (s, 1H), 6.75-6.79 (m, 2H), 6.62 (d, 1H, J=8.2 Hz), 5.73-5.87 (m, 1H), 5.15-5.23 (brs, 3H), 4.50 (brs, 2H), 3.95-4.04 (m, 1H), 3.13 (d, 2H, J=6.2 Hz), 3.05 (s, 1H), 2.93

(d, 1H, J=5.3 Hz), 2.52-2.75 (m, 2H), 2.11-2.30 (m, 2H), 1.64-1.67 (m, 1H), 1.37-1.50 (m, 3H), 1.21-1.26 (m, 1H) (free form) Mass (ESI): 474

Example 100-1 ($M^+$+1)

Synthesis of N-(17-allyl-4,5α-epoxy-3,14-dihydroxy-morphinan-6β-yl)-3-nitro-phthalimide (Compound 300)

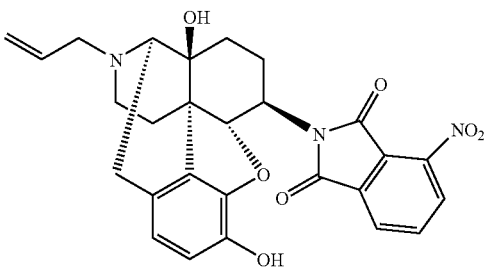

In a manner similar to the method described in Example 11, using 6β-naloxamine in place of 6β-naltrexamine, and using 3-nitrophthalic anhydride in place of phthalic anhydride, the captioned compound was obtained as a crude product.
Mass (ESI): 504($M^+$+1)

Example 100-2

Synthesis of N-(17-allyl-4,5α-epoxy-3,14-dihydroxy-morphinan-6β-yl)-3-amino-phthalimide•tartaric acid salt (Compound 100)

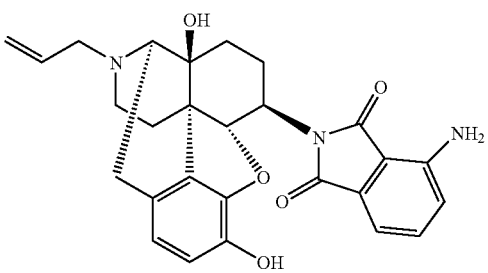

In a manner similar to the method described in Example 99-2, using N-(17-allyl-4,5α-epoxy-3,14-dihydroxy-morphinan-6β-yl)-3-nitro-phthalimide obtained in Example 100-1 as a crude product in place of N-(17-allyl-4,5α-epoxy-3,14-dihydroxy-morphinan-6β-yl)-4-nitro-phthalimide, 12 mg (yield: 25%, 2 steps) of free form of the captioned compound 100 was obtained. This product was converted to tartaric acid salt to obtain the captioned compound 100.
$^1$H-NMR (ppm) (300 MHz, CDCl$_3$) 7.33 (dd, 1H, J=7.3, 8.2 Hz), 7.09 (d, 1H, J=7.0 Hz), 6.76 (d, 2H, J=8.2 Hz), 6.64 (d, 1H, J=8.2 Hz), 5.74-5.87 (m, 1H), 5.32 (s, 1H), 5.20 (dd, 2H, J=1.5, 17.2 Hz), 5.13 (d, 1H, J=8.2 Hz), 3.95-4.03 (m, 1H), 3.13 (d, 2H, J=6.4 Hz), 3.06 (s, 1H), 2.93 (d, 1H, J=5.6 Hz), 2.52-2.79 (m, 2H), 2.10-2.35 (m, 2H), 1.63-1.69 (m, 1H), 1.41-1.53 (m, 3H), 1.23 (t, 1H, J=7.0 Hz) (free form) Mass (ESI): 474($M^+$+1)

Example 101

Synthesis of N-(4,5α-epoxy-3,14-dihydroxy-17-propyl-morphinan-6β-yl)-3-amino-phthalimide•tartaric acid salt (Compound 101)

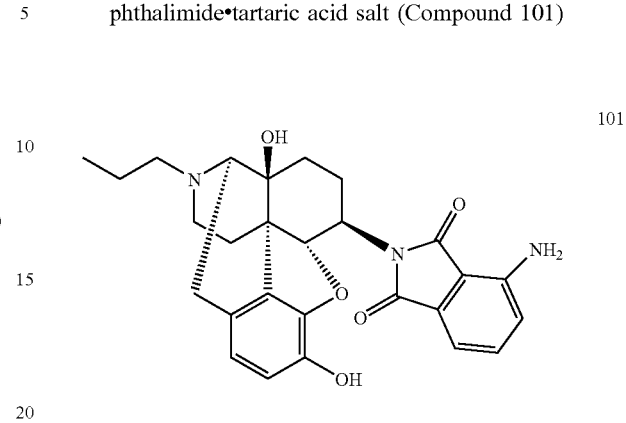

N-(17-allyl-4,5α-epoxy-3,14-dihydroxy-morphinan-6β-yl)-3-nitro-phthalimide obtained in Example 100-1 as a crude product was dissolved in methanol, and 10% Pd/C was added, followed by stirring the mixture under hydrogen atmosphere at room temperature for 12 hours. The reaction solution was filtered through Celite, and the filtrate was concentrated to obtain a crude product. The thus obtained crude product was purified by silica gel column chromatography to obtain 10 mg (yield: 53%, 2 steps) of free form of the captioned compound 101. This product was converted to tartaric acid salt to obtain the captioned compound 101.
$^1$H-NMR (ppm) (400 MHz, CDCl$_3$) 7.33 (t, 1H, J=7.8 Hz), 7.09 (d, 1H, J=7.2 Hz), 6.77 (d, 2H, J=8.1 Hz), 6.64 (d, 1H, J=7.8 Hz), 5.33 (bs, 2H), 5.14 (d, 1H, J=7.8 Hz), 4.00 (ddd, 1H, J=4.5, 8.3, 13.1 Hz), 3.10 (d, 1H, J=18.0 Hz), 2.90 (d, 1H, J=5.5 Hz), 2.15-2.79 (m, 8H), 1.26-1.70 (m, 8H) (free form) Mass (ESI): 476($M^+$+1)

Example 102-1

Synthesis of N-(17-cyclopropylmethyl-4,5α-epoxy-14-hydroxy-3-methoxymethoxy-morphinan-6β-yl)-3-hydroxy-phthalimide (Compound 302)

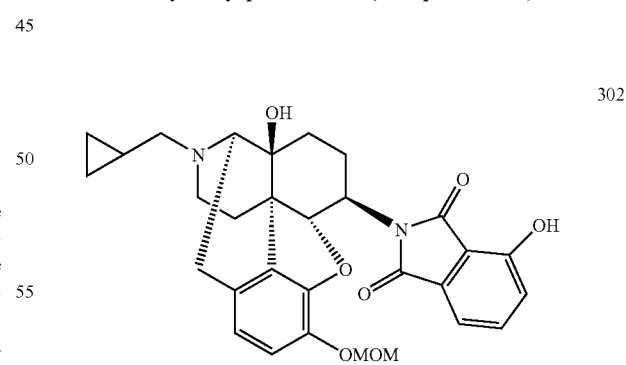

In a manner similar to the method described in Example 11, using 166 mg (0.44 mmol) of 6β-amino-17-cyclopropylmethyl-4,5α-epoxy-3-methoxymethoxy-morphinan-14-ol in place of 6β-naltrexamine, using 3-hydroxyphthalic anhydride in place of phthalic anhydride, using toluene as a solvent in place of DMF, and performing heating to reflux for 20 hours, 119 mg (yield: 52%) of the captioned compound 302 was obtained. Mass (ESI): 533($M^+$+1)

Example 102-2

Synthesis of N-(17-cyclopropylmethyl-4,5α-epoxy-3,14-dihydroxy-morphinan-6β-yl)-3-methoxy-phthalimide•tartaric acid salt (Compound 102)

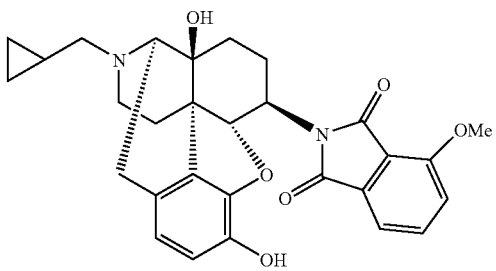

In 5 mL of DMF, 119 mg (0.22 mmol) of N-(17-cyclopropylmethyl-4,5α-epoxy-14-hydroxy-3-methoxymethoxy-morphinan-6-yl)-3-hydroxy-phthalimide obtained in Example 102-1 was dissolved, and 93 mg of potassium carbonate and 0.02 mL of methyl iodide were added thereto, followed by stirring the mixture at room temperature for 3.5 hours. Aqueous saturated sodium hydrogen carbonate solution was added to this reaction solution, and the resulting mixture was extracted with chloroform. Organic layers were combined, washed with saturated saline, dried over anhydrous magnesium sulfate and concentrated to obtain 112 mg of N-(17-cyclopropylmethyl-4,5α-epoxy-14-hydroxy-3-methoxymethoxy-morphinan-6β-yl)-3-methoxy-phthalimide as a crude product.

The thus obtained 112 mg of N-(17-cyclopropylmethyl-4,5α-epoxy-14-hydroxy-3-methoxymethoxy-morphinan-6β-yl)-3-methoxy-phthalimide was dissolved in 10 mL of methanol and 4 mL of chloroform, and 0.1 mL of concentrated hydrochloric acid was added thereto dropwise at 0° C., followed by stirring the mixture at room temperature for 9.5 hours. Aqueous saturated sodium hydrogen carbonate solution was added to this reaction solution, and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 115 mg (yield: 100%, 2 steps) of free form of the captioned compound 102. This product was converted to tartaric acid salt to obtain the captioned compound 102.

$^1$H-NMR (ppm) (300 MHz, CDCl$_3$) 7.64 (dd, 1H, J=7.3, 8.2 Hz), 7.42 (d, 1H, J=7.3 Hz), 7.18 (d, 1H, J=8.5 Hz), 6.74 (d, 1H, J=7.9 Hz), 6.60 (d, 1H, J=8.2 Hz), 5.18 (d, 1H, J=8.2 Hz), 3.98-4.07 (m, 4H), 2.58-3.10 (m, 5H), 2.26-2.38 (m, 3H), 2.12 (dt, 1H, J=3.5, 12.0 Hz), 1.64-1.70 (m, 1H), 1.42-1.53 (m, 3H), 0.78-0.91 (m, 1H), 0.49-0.55 (m, 2H), 0.10-0.14 (m, 2H) (free form) Mass (ESI): 503(M$^+$+1)

Example 103

Synthesis of 2-(17-cyclopropylmethyl-4,5α-epoxy-3,14-dihydroxy-morphinan-6β-yl)-1,2-dihydro-indazol-3-one•tartaric acid salt (Compound 103)

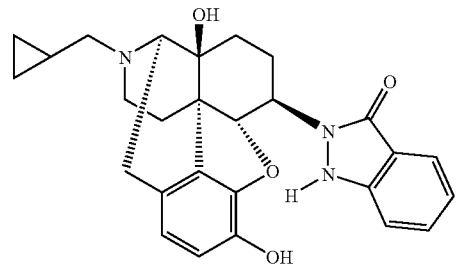

In 10 mL of THF, 100 mg (0.29 mmol) of 6β-naltrexamine was dissolved, and 132 mg of sodium carbonate and 108 mg of 2-nitrobenzoyl chloride were added thereto, followed by stirring the mixture at room temperature for 1 hour. After concentration of the solvent under reduced pressure, 5 mL of ethanol and 4 mL of aqueous 1N NaOH solution were added, and the resulting mixture was stirred at room temperature for 30 minutes. Thereafter, 96 mg of Zn powder was added, and the resulting mixture was heated to reflux for 3 hours. After allowing the reaction solution to cool to room temperature, aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 29 mg (yield: 22%) of free form of the captioned compound 103. This product was converted to tartaric acid salt to obtain the captioned compound 103.

$^1$H-NMR (ppm) (400 MHz, CDCl$_3$) 7.82 (d, 1H, J=8.0 Hz), 7.49 (t, 1H, J=8.0 Hz), 7.24 (d, 1H, J=8.0 Hz), 7.17 (t, 1H, J=8.0 Hz), 6.79 (d, 1H, J=8.0 Hz), 6.60 (d, 1H, J=8.0 Hz), 4.89 (d, 1H, J=7.7 Hz), 4.44 (ddd, 1H, J=4.5, 8.3, 13.1 Hz), 3.16 (d, 1H, J=5.5 Hz), 2.98-3.09 (m, 3H), 2.61-2.69 (m, 2H), 2.43-2.50 (m, 2H), 2.15-2.12 (m, 2H), 1.27-1.76 (m, 4H), 0.83-0.85 (m, 1H), 0.51-0.57 (m, 2H), 0.13-0.14 (m, 2H) (free form) Mass (ESI): 460(M$^+$+1)

Example 104

Synthesis of 3-(17-cyclopropylmethyl-4,5α-epoxy-3,14-dihydroxy-morphinan-6β-yl)-1H-quinazolin-2,4-dione•tartaric acid salt (Compound 104)

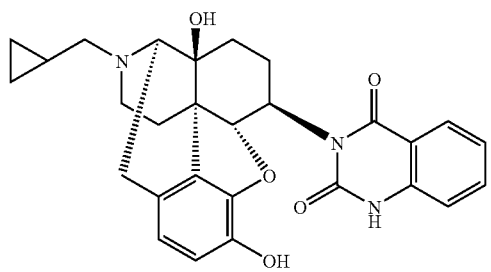

In 10 mL of THF, 100 mg (0.29 mmol) of 6β-naltrexamine was dissolved, and 132 mg of sodium carbonate and 108 mg of 2-nitrobenzoyl chloride were added thereto, followed by stirring the mixture at room temperature for 1 hour. After concentration of the solvent under reduced pressure, 5 mL of methanol and 4 mL of aqueous 1N NaOH solution were added, and the resulting mixture was stirred at room temperature for 30 minutes. Aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product.

The thus obtained residue was dissolved in 5 mL of methanol, and 20 mg of 10% Pd/C was added, followed by stirring the mixture under hydrogen atmosphere at room temperature for 3 hours. The reaction solution was filtered through Celite, and the filtrate was concentrated to obtain a crude product. The thus obtained crude product was purified by silica gel column chromatography to obtain 90 mg (yield: 67%) of 2-amino-N-(17-cyclopropylmethyl-4,5α-epoxy-3,14-dihydroxy-morphinan-6β-yl)-benzamide.

In dichloromethane, 80 mg of the thus obtained 2-amino-N-(17-cyclopropylmethyl-4,5α-epoxy-3,14-dihydroxy-morphinan-6β-yl)-benzamide was dissolved, and 42 mg of 1,1'-carbonyldiimidazole was added, followed by stirring the mixture at room temperature for 12 hours. After evaporating the solvent under reduced pressure, 4 mL of THF and 4 mL of aqueous 1N HCl solution were added, and the resulting mixture was stirred at room temperature for 30 minutes. Aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 27 mg (yield: 32%) of free form of the captioned compound 104. This product was converted to tartaric acid salt to obtain the captioned compound 104.

$^1$H-NMR (ppm) (400 MHz, CDCl$_3$) 7.55 (d, 1H, J=7.7 Hz), 7.45 (t, 1H, J=7.7 Hz), 6.91 (t, 1H, J=7.7 Hz), 6.84 (d, 1H, J=8.2 Hz), 6.75 (d, 1H, J=8.2 Hz), 6.70 (d, 1H, J=8.2 Hz), 5.62 (d, 1H, J=8.2 Hz), 4.92 (ddd, 1H, J=4.5, 8.3, 13.1 Hz), 2.99-3.18 (m, 3H), 2.21-2.75 (m, 5H), 1.45-1.98 (m, 6H), 0.83-0.85 (m, 1H), 0.55-0.58 (m, 2H), 0.16-0.18 (m, 2H) (free form) Mass (ESI): 488(M$^+$+1)

Example 105

Synthesis of 3-(17-cyclopropylmethyl-4,5α-epoxy-3,14-dihydroxy-morphinan-6β-yl)-2-thioxo-2,3-dihydro-1H-quinazolin-4-one•tartaric acid salt (Compound 105)

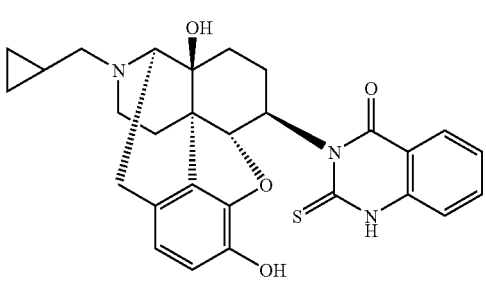

105

In a manner similar to the method described in Example 104, using 1,1'-thiocarbonyldiimidazole in place of 1,1'-carbonyldiimidazole, 10 mg (yield: 13%, 2 steps) of free form of the captioned compound 105 was obtained. This product was converted to tartaric acid salt to obtain the captioned compound 105.

$^1$H-NMR (ppm) (300 MHz, CDCl$_3$) 7.91 (d, 1H, J=7.4 Hz), 7.63 (t, 1H, J=7.4 Hz), 7.23 (t, 1H, J=7.4 Hz), 7.08 (d, 1H, J=8.2 Hz), 6.79 (d, 1H, J=8.0 Hz), 6.66 (d, 1H, J=8.2 Hz), 5.85 (ddd, 1H, J=4.5, 8.3, 13.1 Hz), 5.55 (d, 1H, J=8.2 Hz), 2.98-3.16 (m, 3H), 2.63-2.71 (m, 2H), 2.17-2.47 (m, 4H), 1.52-1.74 (m, 5H), 0.86-0.90 (m, 1H), 0.53-0.58 (m, 2H), 0.15-0.18 (m, 2H) (free form) Mass (ESI): 504(M$^+$+1)

Example 106

Synthesis of 2-(17-cyclopropylmethyl-4,5α-epoxy-3,14-dihydroxy-morphinan-6β-yl)-4H-isoquinolin-1,3-dione•tartaric acid salt (Compound 106)

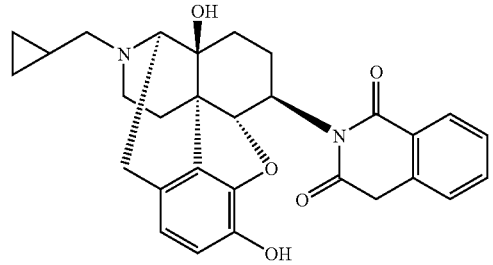

106

In a manner similar to the method described in Example 11, using homophthalic anhydride in place of phthalic anhydride, using pyridine in place of triethylamine, using toluene as a solvent in place of DMF, and performing heating to reflux for 10 hours, 12 mg (yield: 17%) of free form of the captioned compound 106 was obtained. This product was converted to tartaric acid salt to obtain the captioned compound 106.

$^1$H-NMR (ppm) (300 MHz, CDCl$_3$) 8.21 (d, 1H, J=7.4 Hz), 7.58 (t, 1H, J=7.4 Hz), 7.44 (t, 1H, J=7.4 Hz), 7.25 (d, 1H, J=7.4 Hz), 6.72 (d, 1H, J=8.2 Hz), 6.65 (d, 1H, J=8.2 Hz), 5.32 (d, 1H, J=8.2 Hz), 4.80 (ddd, 1H, J=4.5, 8.3, 13.1 Hz), 4.06 (s, 2H), 2.89-3.12 (m, 3H), 2.59-2.69 (m, 3H), 2.10-2.40 (m, 4H), 1.24-1.70 (m, 4H), 0.84-0.90 (m, 1H), 0.51-0.57 (m, 2H), 0.13-0.16 (m, 2H) (free form) Mass (ESI): 487(M$^+$+1)

Example 107

Synthesis of 2-(17-cyclopropylmethyl-4,5α-epoxy-3,14-dihydroxy-morphinan-6β-yl)-benzo[1,3,2]dithiazol-1,1,3,3-tetraoxide•methanesulfonic acid salt (Compound 107)

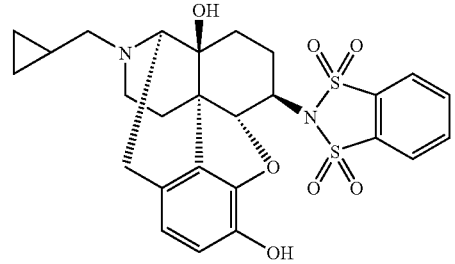

107

In 5 mL of dichloromethane, 117 mg (0.30 mmol) of 6β-amino-17-cyclopropylmethyl-4,5α-epoxy-3-methoxymethoxy-morphinan-14-ol was dissolved, and 0.04 mL (0.29 mmol) of triethylamine and 79 mg (0.31 mmol) of benzene-1,2-disulfonyl dichloride were added, followed by heating the mixture to reflux for 1 hour. After allowing the reaction solution to cool to room temperature, aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain 192 mg of 2-(17-cyclopropylmethyl-4,5α-epoxy-14-hydroxy-3-methoxymethoxy-morphinan-6β-yl)-benzo[1,3,2]dithiazol-1,1,3,3-tetroxide as a crude product.

The thus obtained 192 mg of crude product was dissolved in 3 mL of 1,4-dioxane, and 0.3 mL of concentrated hydrochloric acid and 1 mL of 2-propanol were added, followed by stirring the mixture at room temperature for 16 hours. Aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 76 mg (yield: 46%, 2 steps) of free form of the captioned compound 107. This product was converted to tartaric acid salt to obtain the captioned compound 107.

$^1$H-NMR (ppm) (300 MHz, CDCl$_3$) 8.03-8.00 (m, 2H), 7.94-7.90 (m, 2H), 6.79 (d, 1H, J=8.2 Hz), 6.65 (d, 1H, J=8.2 Hz), 5.25 (d, 1H, J=8.5 Hz), 3.95 (ddd, 1H, J=4.1, 8.5, 13.8 Hz), 3.10 (d, 1H, J=7.6 Hz), 3.06 (d, 1H, J=19.0 Hz), 2.86-2.56 (m, 3H), 2.38 (d, 2H, J=6.4 Hz), 2.33 (m, 1H), 2.15 (ddd, 1H, J=3.8, 12.0, 12.0), 2.01 (m, 1H), 1.78 (m, 1H), 1.57-1.43 (m, 3H), 0.85 (m, 1H), 0.57-0.51 (m, 2H), 0.16-0.11 (m, 2H) (free form) Mass (ESI): 545(M$^+$+1)

Example 108

Synthesis of N-(17-cyclopropylmethyl-4,5α-epoxy-3,14-dihydroxy-morphinan-6β-yl)-O-sulfonebenzimide•tartaric acid salt (Compound 108)

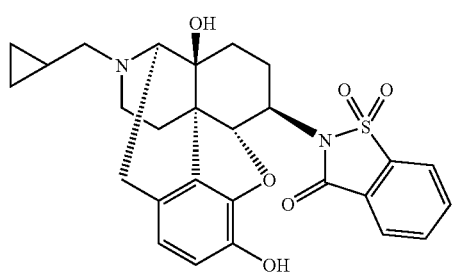

In 10 mL of chloroform, 203 mg (0.53 mmol) of 6β-amino-17-cyclopropylmethyl-4,5α-epoxy-3-methoxymethoxy-morphinan-14-ol was dissolved, and 0.15 mL of triethylamine and 136 mg of methyl-(2-chlorosulfonyl) benzoate were added at 0° C., followed by stirring the mixture at room temperature for 8 hours and then heating the mixture to reflux for 30 minutes. After allowing the reaction solution to cool to room temperature, aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 219 mg (yield: 71%) of 2-[(17-cyclopropylmethyl-4,5α-epoxy-14-hydroxy-3-methoxymethoxy-morphinan-6β-yl)-sulfamoyl]-benzoic acid methyl ester.

In 10 mL of DMF, 91 mg (0.16 mmol) of the thus obtained 2-[(17-cyclopropylmethyl-4,5α-epoxy-14-hydroxy-3-methoxymethoxy-morphinan-6β-yl)-sulfamoyl]-benzoic acid methyl ester was dissolved, and 352 mg of potassium carbonate was added thereto, followed by stirring the mixture at 80° C. for 3 hours. After allowing the reaction solution to cool to room temperature, the reaction solution was filtered through Celite, and the filtrate was concentrated to obtain N-(17-cyclopropylmethyl-4,5α-epoxy-14-hydroxy-3-methoxymethoxy-morphinan-6β-yl)-O-sulfonebenzimide as a crude product.

The thus obtained crude product was dissolved in 2 mL of 2-propanol and 2 mL of chloroform, and 0.2 mL of concentrated hydrochloric acid was added thereto, followed by stirring the mixture at room temperature for 13 hours. Aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 67 mg (yield: 85%, 2 steps) of free form of the captioned compound 108. This product was converted to tartaric acid salt to obtain the captioned compound 108.

$^1$H-NMR (ppm) (300 MHz, CDCl$_3$) 8.06-8.08 (m, 1H), 7.82-7.97 (m, 3H), 6.80 (d, 1H, J=8.1 Hz), 6.65 (d, 1H, J=8.1 Hz), 5.28 (d, 1H, J=8.3 Hz), 3.92 (ddd, 1H, J=3.9, 8.3, 13.1 Hz), 3.11 (d, 1H, J=5.6 Hz), 3.06 (d, 1H, J=18.3 Hz), 2.78-2.87 (m, 1H), 2.60-2.70 (m, 2H), 2.32-2.39 (m, 3H), 2.13-2.20 (m, 1H), 1.46-1.76 (m, 4H), 0.82-0.88 (m, 1H), 0.52-0.57 (m, 2H), 0.12-0.15 (m, 2H) (free form) Mass (ESI): 509(M$^+$+1)

Example 109

Synthesis of N-(17-allyl-4,5α-epoxy-3,14-dihydroxy-morphinan-6β-yl)-O-sulfonebenzimide•tartaric acid salt (Compound 109)

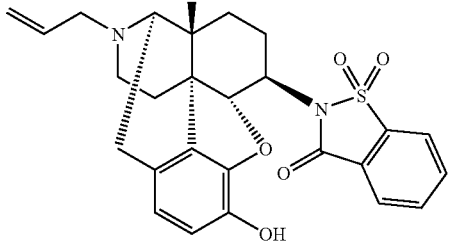

In a manner similar to the method described in Example 108, using 17-allyl-6β-amino-4,5α-epoxy-3-methoxymethoxy-morphinan-14-ol in place of 6β-amino-17-cyclopropylmethyl-4,5α-epoxy-3-methoxymethoxy-morphinan-14-ol, 8.7 mg of free form of the captioned compound 109 was obtained. This product was converted to tartaric acid salt to obtain the captioned compound 109.

$^1$H-NMR (ppm) (300 MHz, CDCl$_3$) 7.99-8.08 (m, 2H), 7.50-7.92 (m, 4H), 6.61-6.81 (m, 2H), 5.74-5.85 (m, 1H), 5.27 (d, 1H, J=8.3 Hz), 3.89-3.96 (m, 1H), 3.08-3.15 (m, 3H), 2.94-3.03 (m, 3H), 2.48-2.66 (m, 1H), 2.29-2.36 (m, 1H), 2.13-2.20 (m, 2H), 1.45-1.75 (m, 3H) (free form) Mass (ESI): 495(M$^+$+1)

Example 110

Synthesis of N-(17-cyclopropylmethyl-4,5α-epoxy-3,14-dihydroxy-morphinan-6β-yl)-2,3-dihydro-benzo[d]isothiazol-1,1-dioxide-tartaric acid salt (Compound 110)

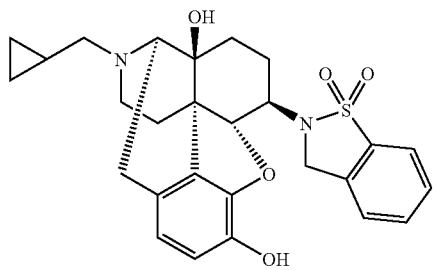

In 5 mL of THF, 37 mg (0.07 mmol) of N-(17-cyclopropylmethyl-4,5α-epoxy-14-hydroxy-3-methoxymethoxy-morphinan-6β-yl)-O-sulfonebenzimide obtained in Example 108 as an intermediate was dissolved, and 2.0 mL of 1.03M borane.THF complex was added, followed by heating the mixture to reflux for 3 days. After allowing the reaction solution to cool to room temperature, aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain N-(17-cyclopropylmethyl-4,5α-epoxy-14-hydroxy-3-methoxymethoxy-morphinan-6β-yl)-2,3-dihydro-benzo[d]isothiazol-1,1-dioxide as a crude product.

The thus obtained crude product was dissolved in 3 mL of 2-propanol and 1 mL of chloroform, and 0.3 mL of concentrated hydrochloric acid was added, followed by stirring the mixture at room temperature for 13 hours. Aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 22 mg (yield: 67%, 2 steps) of free form of the captioned compound 110. This product was converted to tartaric acid salt to obtain the captioned compound 110.

$^1$H-NMR (ppm) (300 MHz, CDCl$_3$) 7.79 (d, 1H, J=7.8 Hz), 7.61 (m, 1H), 7.53 (m, 1H), 7.44 (d, 1H, J=7.8 Hz), 6.77 (d, 1H, J=7.8 Hz), 6.62 (d, 1H, J=8.3 Hz), 4.65 (d, 1H, J=8.3 Hz), 4.59 (s, 2H), 3.64-3.70 (m, 1H), 3.10 (d, 1H, J=5.6 Hz), 3.04 (d, 1H, J=18.3 Hz), 2.60-2.67 (m, 2H), 2.38 (d, 2H, J=6.6 Hz), 2.21-2.33 (m, 2H), 2.13-2.19 (m, 1H), 1.78-1.83 (m, 1H), 1.68-1.72 (m, 1H), 1.50-1.59 (m, 2H), 0.81-0.86 (m, 1H), 0.51-0.56 (m, 2H), 0.10-0.14 (m, 2H) (free form) Mass (ESI): 495(M$^+$+1)

Example 111

Synthesis of 17-cyclopropylmethyl-4,5α-epoxy-6β-(pyrrolidin-1-yl)-morphinan-3,14-diol•tartaric acid salt (Compound 111)

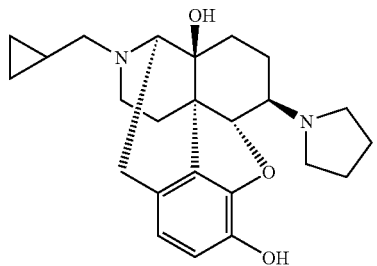

In 20 mL of benzene, 200 mg (0.43 mmol) of naltrexone.benzoic acid salt was dissolved, and 2 mL of pyrrolidine was added thereto, followed by heating the mixture to reflux in an oil bath at 100° C. for 16 hours while azeotropically removing water. After allowing the reaction solution to cool to room temperature, 10 mL of a solution containing 81 mg (1.29 mmol) of sodium cyanoborohydride in methanol was added thereto, and the resulting mixture was stirred at room temperature for 2 hours. Aqueous saturated sodium hydrogen carbonate solution was added to the reaction mixture, and the resulting mixture was extracted with chloroform. Organic layers were combined, washed with saturated saline, dried over anhydrous magnesium sulfate and concentrated to obtain a crude product. The thus obtained crude product was purified by silica gel column chromatography to obtain 142 mg (yield: 83%) of free form of the captioned compound 111. This product was converted to tartaric acid salt to obtain the captioned compound 111.

$^1$H-NMR (ppm) (300 MHz, CDCl$_3$) 6.73 (1H, d, J=8.1 Hz), 6.58 (1H, d, J=8.1 Hz), 4.66 (1H, d, J=6.9 Hz), 3.10 (1H, d, J=5.6 Hz), 3.04 (1H, d, J=18.3 Hz), 2.5-2.8 (6H, m), 2.38 (2H, d, J=6.6 Hz), 2.1-2.4 (5H, m), 1.90-2.05 (1H, m), 1.8 (2H, m), 1.7 (1H, m), 1.65 (1H, m), 1.5 (1H, m), 1.4 (1H, m), 0.8-0.9 (1H, m), 0.5-0.6 (2H, m), 0.1-0.2 (2H, m) (free form) Mass (ESI): 397(M$^+$+1)

Example 112

Inhibitory Effect Against Rhythmic Bladder Contractions in Rats

Female SD rats were anesthetized with an intraperitoneal administration of urethane (1.0 g/kg). A polyethylene tube was inserted from the urethra to the bladder and the tube was fixed by ligation. Then physiological saline was appropriately infused (infusion rate: about 0.2 ml/min., maximum: about 1.5 ml/animal) through the tube to cause rhythmic bladder contractions. The rhythmic bladder contractions were monitored by measuring the intravesical pressure through a polyethylene tube inserted into the bladder. After confirming that stable rhythmic bladder contractions occurred at least 10 times, a vehicle containing a prescribed dose of a test compound was intravenously administration at a dose of 1 ml/kg. In cases where the intravesical pressure, within 10 minutes after the administration of the test compound, decreased to 50% or less of the intravesical pressure immediately after the administration, the test compound was judged as having inhibitory effect against urinary bladder contractions, and the time period until the intravesical pressure returned to more than 50% was defined as inhibitory time of rhythmic bladder contractions. As the vehicle for administration, physiological saline was used for test compounds 4, 7, 8, 9, 10, 13, 29, 30, 31, 33, 34, 75, 76, 79, 80, 81, 82, 84, 89, 90, 91, 93, 94, 95, 110 and 111, aqueous 10% dimethylsulfoxide (DMSO) solution was used for test compounds 11, 12, 14, 15, 16, 17, 18, 20, 21, 23, 28, 46, 47, 50, 55, 56, 57, 58, 59, 60, 61, 62, 63, 64, 65, 66, 68, 69, 70, 71, 72, 73, 74, 77, 78, 83, 85, 86, 87, 88, 92, 96, 97, 98, 99, 100, 102, 103, 104, 105, 106, 107, 108 and 102, aqueous 20% dimethylsulfoxide (DMSO) solution was used for test compounds 1, 2, 67 and 101, and aqueous 5% xylitol solution was used for test compounds 5 and 35. The aqueous 10% DMSO solution, aqueous 20% DMSO solution and the aqueous 5% xylitol solution per se, which may influence on the inhibitory time of rhythmic bladder contractions, were also tested at a dose of 1 ml/kg. The results are shown in Table 6. With any of the compounds, prolongation of the inhibitory time of rhythmic bladder contractions was observed when compared with that obtained in the group to which the vehicle alone was administered.

TABLE 6

| Test Compound | Dose (mg/kg body Weight) | Vehicle | Number of Cases | Mean Inhibitory Time of Rhythmic Bladder Contractions (min) |
|---|---|---|---|---|
| Compound 1 | 0.1 | aqueous 20% DMSO solution | 4 | 11.7 |
| Compound 2 | 0.1 | aqueous 20% DMSO solution | 4 | 15.5 |
| Compound 4 | 0.1 | physiological saline | 4 | 15.6 |
| Compound 5 | 0.1 | aqueous 5% xylitol solution | 4 | 9.9 |
| Compound 7 | 1.0 | physiological saline | 5 | 3.8 |
| Compound 8 | 0.3 | physiological saline | 4 | 6.8 |
| Compound 9 | 0.1 | physiological saline | 6 | 9.1 |
| Compound 10 | 0.3 | physiological saline | 4 | 7.8 |
| Compound 11 | 0.005 | aqueous 10% DMSO solution | 5 | 15.5 |
| Compound 11f | 0.005 | aqueous 5% xylitol solution | 5 | 10.3 |
| Compound 12 | 0.03 | aqueous 10% DMSO solution | 5 | 16.5 |
| Compound 13 | 0.03 | physiological saline | 4 | 11.7 |
| Compound 14 | 1.0 | aqueous 10% DMSO solution | 5 | 7.9 |
| Compound 15 | 0.01 | aqueous 10% DMSO solution | 5 | 12.2 |
| Compound 16 | 0.005 | aqueous 10% DMSO solution | 5 | 14.8 |
| Compound 17 | 0.005 | aqueous 10% DMSO solution | 5 | 13.2 |
| Compound 18 | 0.01 | aqueous 10% DMSO solution | 4 | 13.7 |
| Compound 20 | 1.0 | aqueous 10% DMSO solution | 5 | 18.1 |
| Compound 21 | 1.0 | aqueous 10% DMSO solution | 4 | 19.0 |
| Compound 23 | 1.0 | aqueous 10% DMSO solution | 4 | 32.0 |
| Compound 28 | 0.3 | aqueous 10% DMSO solution | 4 | 19.6 |
| Compound 29 | 1.0 | physiological saline | 4 | 0.8 |
| Compound 30 | 3.0 | physiological saline | 4 | 2.3 |
| Compound 31 | 1.0 | physiological saline | 5 | 1.0 |
| Compound 33 | 3.0 | physiological saline | 4 | 2.1 |
| Compound 34 | 1.0 | physiological saline | 4 | 9.2 |
| Compound 35 | 0.3 | aqueous 5% xylitol solution | 6 | 29.9 |
| Compound 46 | 1.0 | aqueous 10% DMSO solution | 4 | 20.0 |
| Compound 47 | 1.0 | aqueous 10% DMSO solution | 4 | 21.8 |
| Compound 50 | 0.1 | aqueous 10% DMSO solution | 4 | 12.8 |
| Compound 55 | 0.1 | aqueous 10% DMSO solution | 4 | 15.0 |
| Compound 56 | 0.1 | aqueous 10% DMSO solution | 4 | 13.7 |
| Compound 57 | 0.1 | aqueous 10% DMSO solution | 4 | 24.2 |
| Compound 58 | 0.03 | aqueous 10% DMSO solution | 4 | 19.3 |
| Compound 59 | 0.1 | aqueous 10% DMSO solution | 4 | 6.1 |
| Compound 60 | 0.03 | aqueous 10% DMSO solution | 4 | 19.7 |
| Compound 61 | 0.03 | aqueous 10% DMSO solution | 4 | 22.6 |
| Compound 62 | 0.01 | aqueous 10% DMSO solution | 4 | 15.3 |
| Compound 63 | 0.005 | aqueous 10% DMSO solution | 4 | 16.1 |
| Compound 64 | 0.01 | aqueous 10% DMSO solution | 4 | 20.8 |
| Compound 65 | 0.01 | aqueous 10% DMSO solution | 4 | 18.6 |
| Compound 66 | 0.003 | aqueous 10% DMSO solution | 5 | 27.4 |
| Compound 67 | 0.003 | aqueous 20% DMSO solution | 5 | 27.3 |
| Compound 68 | 0.001 | aqueous 10% DMSO solution | 4 | 18.0 |
| Compound 69 | 0.1 | aqueous 10% DMSO solution | 4 | 15.7 |
| Compound 70 | 0.1 | aqueous 10% DMSO solution | 4 | 8.9 |
| Compound 71 | 0.1 | aqueous 10% DMSO solution | 4 | 24.9 |
| Compound 72 | 0.003 | aqueous 10% DMSO solution | 4 | 26.7 |
| Compound 73 | 0.03 | aqueous 10% DMSO solution | 4 | 13.4 |
| Compound 74 | 0.03 | aqueous 10% DMSO solution | 4 | 24.0 |
| Compound 75 | 0.1 | physiological saline | 4 | 20.2 |
| Compound 76 | 0.01 | physiological saline | 4 | 16.7 |
| Compound 77 | 0.01 | aqueous 10% DMSO solution | 4 | 16.6 |
| Compound 78 | 0.1 | aqueous 10% DMSO solution | 4 | 13.4 |
| Compound 79 | 0.1 | physiological saline | 4 | 2.1 |
| Compound 80 | 0.1 | physiological saline | 5 | 1.1 |
| Compound 81 | 0.03 | physiological saline | 4 | 16.1 |
| Compound 82 | 0.03 | physiological saline | 6 | 19.9 |
| Compound 83 | 0.1 | aqueous 10% DMSO solution | 4 | 10.6 |

TABLE 6-continued

| Test Compound | Dose (mg/kg body Weight) | Vehicle | Number of Cases | Mean Inhibitory Time of Rhythmic Bladder Contractions (min) |
|---|---|---|---|---|
| Compound 84 | 0.1 | physiological saline | 4 | 9.3 |
| Compound 85 | 0.1 | aqueous 10% DMSO solution | 4 | 6.9 |
| Compound 86 | 0.1 | aqueous 10% DMSO solution | 4 | 12.1 |
| Compound 87 | 0.1 | aqueous 10% DMSO solution | 4 | 6.4 |
| Compound 88 | 0.03 | aqueous 10% DMSO solution | 4 | 10.7 |
| Compound 89 | 0.1 | physiological saline | 4 | 12.5 |
| Compound 90 | 0.1 | physiological saline | 4 | 17.6 |
| Compound 91 | 0.03 | physiological saline | 5 | 14.7 |
| Compound 92 | 0.1 | aqueous 10% DMSO solution | 4 | 16.0 |
| Compound 93 | 0.1 | physiological saline | 4 | 16.0 |
| Compound 94 | 0.1 | physiological saline | 4 | 11.9 |
| Compound 95 | 0.1 | physiological saline | 4 | 15.0 |
| Compound 96 | 0.1 | aqueous 10% DMSO solution | 5 | 12.9 |
| Compound 97 | 0.1 | aqueous 10% DMSO solution | 5 | 11.2 |
| Compound 98 | 0.1 | aqueous 10% DMSO solution | 4 | 7.2 |
| Compound 99 | 0.1 | aqueous 10% DMSO solution | 5 | 16.9 |
| Compound 100 | 0.1 | aqueous 10% DMSO solution | 4 | 14.0 |
| Compound 101 | 0.3 | aqueous 20% DMSO solution | 4 | 15.1 |
| Compound 102 | 0.1 | aqueous 10% DMSO solution | 4 | 15.6 |
| Compound 103 | 0.1 | aqueous 10% DMSO solution | 4 | 13.1 |
| Compound 104 | 0.1 | aqueous 10% DMSO solution | 4 | 13.5 |
| Compound 105 | 0.1 | aqueous 10% DMSO solution | 4 | 7.3 |
| Compound 106 | 0.01 | aqueous 10% DMSO solution | 4 | 12.9 |
| Compound 107 | 0.01 | aqueous 10% DMSO solution | 5 | 14.1 |
| Compound 108 | 0.01 | aqueous 10% DMSO solution | 4 | 25.6 |
| Compound 109 | 0.1 | aqueous 10% DMSO solution | 4 | 18.1 |
| Compound 110 | 0.1 | physiological saline | 4 | 12.6 |
| Compound 111 | 1.0 | physiological saline | 3 | 2.8 |
|  | 1 ml/kg | aqueous 10% DMSO solution | 4 | 3.5 |
|  | 1 ml/kg | aqueous 20% DMSO solution | 4 | 6.5 |
|  | 1 ml/kg | aqueous 5% xylitol solution | 4 | 1.3 |

From the above, it was proved that the compounds have excellent therapeutic or prophylactic effects against urinary frequency or urinary incontinence.

INDUSTRIAL AVAILABILITY

The compounds are useful as novel therapeutic or prophylactic agents for urinary frequency or urinary incontinence, from which side effects are diminished.

The invention claimed is:

1. A method of treating urinary frequency, urinary urgency or urinary incontinence, comprising administering a therapeutically effective amount of a morphinan derivative having a nitrogen-containing heterocyclic group of the Formula (I):

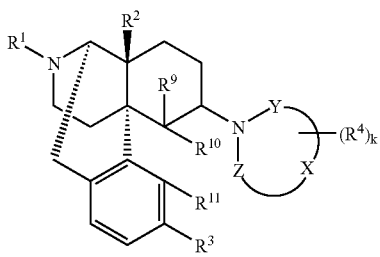

wherein $R^1$ is hydrogen, $C_1$-$C_5$ alkyl, $C_4$-$C_7$ cycloalkylalkyl, $C_6$-$C_8$ cycloalkenylalkyl, $C_6$-$C_{12}$ aryl, $C_7$-$C_{13}$ aralkyl, $C_3$-$C_7$ alkenyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5), $R^2$ and $R^3$ independently are hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy; Y and Z independently represent valence bond or —C(=O)—; —X— represents a $C_2$-$C_7$ carbon chain (one or more of the carbon atoms therein may be replaced by nitrogen, oxygen or sulfur atom(s), and the carbon chain may contain an unsaturated bond) constituting a part of the ring structure; k is an integer of 0 to 8; $R^4$ is(are) (a) substituent(s) in the number of k on the nitrogen-containing ring, which independently represent(s) fluorine, chlorine, bromine, iodine, nitro, hydroxy, $C_1$-$C_5$ alkyl, benzylidene, ethylidene, cyclohexylmethylidene, butylidene, phenethylidene, $C_7$-$C_{13}$ cycloalkylalkyl, $C_6$-$C_{12}$ aryl, $C_7$-$C_{13}$ aralkyl, $C_7$-$C_{13}$ aralkyloxy, $C_1$-$C_5$ alkoxy, trifluoromethyl, trifluoromethoxy, cyano, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)pNR^7R^8$ or $(CH_2)pN(R^7)COR^8$, or among the $R^4$s in the number of k, two $R^4$s bound to the same carbon atom or to the same sulfur atom cooperatively represent one oxygen atom to form carbonyl or sulfoxide (with the proviso that in cases where Y and Z is a valence bond, the formed carbonyl is not bound directly to the nitrogen atom which is bound to the morphinan structure), or two $R^4$s bound to the same carbon atom cooperatively represent one sulfur atom to form thiocarbonyl, or four $R^4$s bound to the same sulfur atom cooperatively represent two oxygen atoms to form sulfone, or among the $R^4$s in the number of k, two $R^4$s bound to adjacent carbon atoms, respectively, cooperatively form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of said fused rings is non-substituted or substituted by 1 or more R⁵s, wherein R⁵(s) independently represent(s) fluorine, chlorine, bromine, iodine, nitro, hydroxy, $C_1$-$C_5$ alkyl, $C_1$-$C_5$ alkoxy, trifluoromethyl, trifluoro-methoxy, cyano, $C_6$-$C_{12}$ aryl, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)pN(R^7)COR^8$; $R^9$ is hydrogen, $C_1$-$C_5$ alkyl, $C_1$-$C_5$ alkenyl, $C_7$-$C_{13}$ aralkyl, $C_1$-$C_3$ hydroxyalkyl, $(CH_2)pOR^6$ or $(CH_2)pCO_2R^6$; $R^{10}$ and $R^{11}$ are bound to form —O—, —S— or —$CH_2$—, or $R^{10}$ is hydrogen and $R^{11}$ is hydrogen, hydroxy, $C_1$-$C_5$ alkoxy or $C_1$-$C_5$ alkanoyloxy; p is an integer of 0 to 5; $R^6$ is hydrogen, $C_1$-$C_5$ alkyl, $C_3$-$C_7$ alkenyl, $C_6$-$C_{12}$ aryl or $C_7$-$C_{13}$ aralkyl; and $R^7$ and $R^8$ independently are hydrogen, $C_1$-$C_5$ alkyl or $C_7$-$C_{13}$ aralkyl;

or a pharmaceutically acceptable acid addition salt thereof to a patient.

2. The method according to claim 1, wherein in said Formula (I), only one of Y and Z is —C(=O)— and the other is valence bond.

3. The method according to claim 1, wherein in said Formula (I), both Y and Z are —C(=O)—.

4. The method according to claim 3, wherein in said Formula (I), $R^1$ is hydrogen, $C_4$-$C_7$ cycloalkylalkyl, $C_6$-$C_8$ cycloalkenylalkyl, $C_6$-$C_{12}$ aryl or $C_3$-$C_7$ alkenyl; k is an integer of 2 to 8; and two $R^4$s bound to adjacent carbon atoms, respectively, cooperatively form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of said fused rings is non-substituted or substituted by 1 or more $R^5$s.

5. The method according to claim 3, wherein in said Formula (I), $R^1$ is hydrogen, cyclopropylmethyl, cyclobutylmethyl, cyclopentylmethyl, cyclohexylmethyl, allyl or prenyl; $R^2$ is hydrogen, hydroxy, methoxy, ethoxy, allyloxy, benzyloxy, acetoxy or propionoxy; $R^3$ is hydrogen, hydroxy, methoxy, ethoxy, benzyloxy, acetoxy or propionoxy; k is an integer of 2 to 6, two $R^4$s cooperatively form benzene fused ring which is non-substituted or substituted by 1 to 4 $R^5$s; $R^5$(s) independently is(are) fluorine, chlorine, bromine, iodine, nitro, methyl, ethyl, propyl, hydroxy, methoxy, ethoxy, trifluoromethyl, trifluoromethoxy, cyano, phenyl, isothiocyanato, $SR^6$, $SOR^6$, $SO_2R^6$, $(CH_2)_pOR^6$, $(CH_2)_p COR^6$, $(CH_2)pCO_2R^6$, $SO_2NR^7R^8$, $CONR^7R^8$, $(CH_2)pNR^7R^8$ or $(CH_2)pN(R^7)COR^8$; p is an integer of 0 to 5; $R^6$ is hydrogen, methyl, ethyl, propyl or phenyl; $R^7$ and $R^8$ independently are hydrogen, methyl, ethyl, propyl or benzyl; $R^9$ is hydrogen or methyl; $R^{10}$ and R" are bound to form —O—, or $R^{10}$ is hydrogen and $R^{11}$ is hydrogen, hydroxy or methoxy.

6. The method according to claim 1, wherein in said Formula (I), both Y and Z are valence bonds.

7. The method according to claim 6, wherein in said Formula (I), $R^1$ is hydrogen, $C_1$-$C_5$ alkyl, $C_7$-$C_{13}$ aralkyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5); k is an integer of 2 to 8; two $R^4$s bound to adjacent carbon atoms, respectively, cooperatively form benzene fused ring, pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of said fused rings is non-substituted or substituted by 1 or more $R^5$s.

8. The method according to claim 6, wherein in said Formula (I), $R^1$ is hydrogen, methyl, ethyl, propyl, benzyl, phenethyl, phenylpropyl, 2-furanylmethyl, 2-furanylethyl, 2-furanylpropyl, 3-furanylmethyl, 3-furanylethyl, 3-furanylprofyl, 2-thienylmethyl, 2-thienylethyl, 2-thienylpropyl, 3-thienylmethyl, 3-thienylethyl, 3-thienylpropyl, 2-pyridynylmethyl, 2-pyridynylethyl, 2-pyridynylpropyl, 3-pyridynylmethyl, 3-pyridynylethyl, 3-pyridynylpropyl, 4-pyridynylmethyl, 4-pyridynylethyl, or 4-pyridynylpropyl; $R^2$ is hydrogen, hydroxy, methoxy, ethoxy, allyloxy, benzyloxy, acetoxy or propionoxy; $R^3$ is hydrogen, hydroxy, methoxy, ethoxy, benzyloxy, acetoxy or propionoxy; k is an integer of 2 to 6; two $R^4$s cooperatively form benzene fused ring which is non-substituted or substituted by 1 to 4 $R^5$s and other $R^4$(s) independently is(are) methyl, ethyl, propyl or benzyl, or two $R^4$s bound to the same carbon atom represent one oxygen atom to form carbonyl, $R^5$(s) independently is(are) fluorine, chlorine, bromine, iodine, nitro, methyl, ethyl, propyl, hydroxy, methoxy, ethoxy, trifluoromethyl, trifluoromethoxy, cyano, phenyl, isothiocyanato, $SR^6$, $SOR^6$, $SO_2R^6$, $(CH_2)_pOR^6$, $(CH_2)_pCOR^6$, $(CH_2)_pCO_2R^6$, $SO_2NR^7R^8$, $CONR^7R^8$, $(CH_2)_pNR^7R^8$ or $(CH_2)pN(R^7)COR^8$; p is an integer of 0 to 5; $R^6$ is hydrogen, methyl, ethyl, propyl or phenyl; $R^7$ and $R^8$ independently are hydrogen, methyl, ethyl, propyl or benzyl; $R^9$ is hydrogen or methyl; $R^{10}$ and $R^{11}$ are bound to form —O—, or $R^{10}$ is hydrogen and $R^{11}$ is hydrogen, hydroxy or methoxy.

9. A morphinan derivative of the Formula (II) having a nitrogen-containing heterocyclic group:

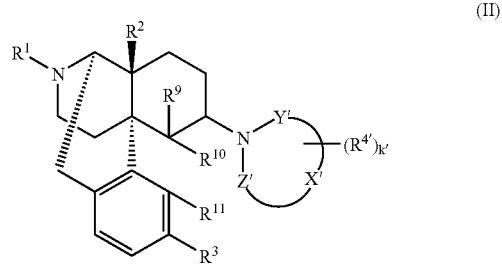

(II)

wherein $R^1$, $R^2$, $R^3$, $R^9$, $R^{10}$ and $R^{11}$ are the same as in claim 1, $R^{4'}$, X', Y', Z' and k' are the same as $R^4$, X, Y, Z and k in claim 1 with the proviso that Y' and Z' are not simultaneously valence bonds, in cases where Y' and Z' are simultaneously —C(=O)— and X' is a chain comprising a part of a ring structure, k' must be not less than 1, and in particular, in cases where $(R^{4'})k'$ is a benzene fused ring, the benzene ring must be substituted by the $R^5$;

or a pharmaceutically acceptable acid addition salt thereof.

10. The morphinan derivative or the pharmaceutically acceptable acid addition salt thereof according to claim 9, wherein in said Formula (II), only one of Y' and Z' is —C(=O)— and the other is valence bond.

11. The morphinan derivative or the pharmaceutically acceptable acid addition salt thereof according to claim 9, wherein in said Formula (II), both Y' and Z' are —C(=O)—.

12. The morphinan derivative or the pharmaceutically acceptable acid addition salt thereof according to claim 11, wherein in said Formula (II), $R^1$ is hydrogen, $C_4$-$C_7$ cycloalkylalkyl, $C_6$-$C_8$ cycloalkenylalkyl, $C_6$-$C_{12}$ aryl or $C_3$-$C_7$ alkenyl; k' is an integer of 2 to 8 and two $R^4$s bound to adjacent carbon atoms, respectively, cooperatively form benzene fused ring substituted by 1 or more $R^5$s, or cooperatively form a pyridine fused ring, naphthalene fused ring, cyclopropane fused ring, cyclobutane fused ring, cyclopentane fused ring, cyclopentene fused ring, cyclohexane fused ring, cyclohexene fused ring, cycloheptane fused ring or cycloheptene fused ring, each of said fused rings is non-substituted or substituted by 1 or more $R^5$s.

13. The morphinan derivative or the pharmaceutically acceptable acid addition salt thereof according to claim 11, wherein in said Formula (II), $R^1$ is hydrogen, cyclopropylmethyl, cyclobutylmethyl, cyclopentylmethyl, cyclohexylmethyl, allyl or prenyl; $R^2$ is hydrogen, hydroxy, methoxy, ethoxy, allyloxy, benzyloxy, acetoxy or propionoxy; $R^3$ is hydrogen, hydroxy, methoxy, ethoxy, benzyloxy, acetoxy or propionoxy; k' is an integer of 2 to 6, two $R^{4'}$s cooperatively form benzene fused ring which is substituted by 1 to 4 $R^5$s; $R^5$(s) independently is(are) fluorine, chlorine, bromine, iodine, nitro, methyl, ethyl, propyl, hydroxy, methoxy, ethoxy, trifluoromethyl, trifluoromethoxy, cyano, phenyl, isothiocyanato, $SR^6$, $SOR^6$, $SO_2R^6$, $(CH_2)_pOR^6$, $(CH_2)pCOR^6$, $(CH_2)_pCO_2R^6$, $SO_2NR^7R^8$, $CONR^7R^8$, $(CH_2)_pNR^7R^8$ or $(CH_2)_pN(R^7)COR^8$; p is an integer of 0 to 5; $R^6$ is hydrogen, methyl, ethyl, propyl or phenyl; $R^7$ and $R^8$ independently are hydrogen, methyl, ethyl, propyl or benzyl; $R^9$ is hydrogen or methyl; $R^{10}$ and $R^{11}$ are bound to form —O—, or $R^{10}$ is hydrogen and $R^{11}$ is hydrogen, hydroxy or methoxy.

14. A pharmaceutical composition comprising the morphinan derivative or the pharmaceutically acceptable acid addition salt thereof according to claim 9.

\* \* \* \* \*

UNITED STATES PATENT AND TRADEMARK OFFICE
CERTIFICATE OF CORRECTION

PATENT NO. : 7,320,984 B2  
APPLICATION NO. : 10/530664  
DATED : January 22, 2008  
INVENTOR(S) : Izumimoto et al.

Page 1 of 1

It is certified that error appears in the above-identified patent and that said Letters Patent is hereby corrected as shown below:

In Column 2:  
At line 21, please insert --aryl,-- after "$C_{12}$".  
At line 22, please change "furanylalkyl]" to --furanylalkyl--.

Signed and Sealed this

Eleventh Day of November, 2008

JON W. DUDAS  
*Director of the United States Patent and Trademark Office*